United States Patent
Ito et al.

(10) Patent No.: US 9,551,931 B2
(45) Date of Patent: Jan. 24, 2017

(54) METHOD OF FORMING PATTERN, ACTINIC-RAY- OR RADIATION-SENSITIVE RESIN COMPOSITION, ACTINIC-RAY- OR RADIATION-SENSITIVE FILM, PROCESS FOR MANUFACTURING ELECTRONIC DEVICE AND ELECTRONIC DEVICE

(71) Applicant: FUJIFILM CORPORATION, Tokyo (JP)

(72) Inventors: Junichi Ito, Shizuoka (JP); Akinori Shibuya, Shizuoka (JP); Akiyoshi Goto, Shizuoka (JP); Michihiro Shirakawa, Shizuoka (JP); Kei Yamamoto, Shizuoka (JP); Fumihiro Yoshino, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/853,574

(22) Filed: Sep. 14, 2015

(65) Prior Publication Data
US 2016/0004157 A1    Jan. 7, 2016

Related U.S. Application Data

(63) Continuation of application No. PCT/JP2014/057940, filed on Mar. 14, 2014.

(60) Provisional application No. 61/792,682, filed on Mar. 15, 2013.

(30) Foreign Application Priority Data

Mar. 15, 2013    (JP) .................. 2013-054259

(51) Int. Cl.
| | | |
|---|---|---|
| *G03F 7/004* | (2006.01) | |
| *G03F 7/038* | (2006.01) | |
| *C08F 220/36* | (2006.01) | |
| *H01L 21/027* | (2006.01) | |
| *C08F 220/18* | (2006.01) | |
| *C07C 381/12* | (2006.01) | |
| *C08F 220/30* | (2006.01) | |
| *G03F 7/20* | (2006.01) | |
| *C08F 220/14* | (2006.01) | |
| *C08F 220/28* | (2006.01) | |
| *C08F 220/26* | (2006.01) | |
| *C08F 232/08* | (2006.01) | |
| *G03F 7/32* | (2006.01) | |
| *G03F 7/039* | (2006.01) | |

(52) U.S. Cl.
CPC ............ *G03F 7/038* (2013.01); *C07C 381/12* (2013.01); *C08F 220/14* (2013.01); *C08F 220/18* (2013.01); *C08F 220/26* (2013.01); *C08F 220/28* (2013.01); *C08F 220/30* (2013.01); *C08F 220/36* (2013.01); *C08F 232/08* (2013.01); *G03F 7/0045* (2013.01);
*G03F 7/0397* (2013.01); *G03F 7/20* (2013.01); *G03F 7/2041* (2013.01); *G03F 7/325* (2013.01); *H01L 21/0274* (2013.01)

(58) Field of Classification Search
CPC .......... G03F 7/004; G03F 7/2041; G03F 7/32; G03F 7/0045; G03F 7/0046; G03F 7/0397; G03F 7/325; C08F 220/14; C08F 220/26; C08F 220/18; C08F 220/28; C08F 220/30; C08F 220/24; C08F 220/36; C07C 381/12; H01L 21/0274
USPC .... 430/270.1, 913, 435, 322, 325, 329, 330; 526/270, 268, 281, 256; 560/149
See application file for complete search history.

(56) References Cited

U.S. PATENT DOCUMENTS

| | | |
|---|---|---|
| 8,227,183 B2 | 7/2012 | Tsubaki et al. |
| 8,440,386 B2 | 5/2013 | Hatakeyama et al. |
| 8,951,718 B2 | 2/2015 | Tsubaki et al. |
| 9,213,237 B2 * | 12/2015 | Ito .......................... G03F 7/0388 |
| 2008/0187860 A1 | 8/2008 | Tsubaki et al. |
| 2011/0236826 A1 | 9/2011 | Hatakeyama et al. |
| 2011/0262864 A1 | 10/2011 | Hirano et al. |

(Continued)

FOREIGN PATENT DOCUMENTS

| | | |
|---|---|---|
| JP | 4-39665 A | 2/1992 |
| JP | 2008-281975 A | 11/2008 |

(Continued)

OTHER PUBLICATIONS

International Search Report of PCT/JP2014/057940, dated Apr. 15, 2014. [PCT/ISA/210].

(Continued)

*Primary Examiner* — Amanda C Walke
(74) *Attorney, Agent, or Firm* — Sughrue Mion, PLLC

(57) ABSTRACT

A method of forming a pattern includes (a) forming a film of an actinic-ray- or radiation-sensitive resin composition, (b) exposing the film to light, and (c) developing the exposed film with a developer comprising an organic solvent to thereby form a negative pattern. The actinic-ray- or radiation-sensitive resin composition includes (A) a resin whose solubility in the developer comprising an organic solvent is lowered when acted on by an acid, which resin contains a repeating unit with any of lactone structures of general formula (1) below, and (B) a compound that when exposed to actinic rays or radiation, generates an acid.

(1)

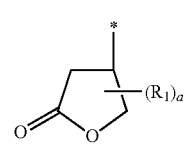

11 Claims, No Drawings

(56) References Cited

U.S. PATENT DOCUMENTS

| | | | |
|---|---|---|---|
| 2012/0009529 A1 | 1/2012 | Hatakeyama | |
| 2012/0015302 A1* | 1/2012 | Tango | C08F 220/18 |
| | | | 430/285.1 |
| 2012/0058436 A1 | 3/2012 | Tsubaki et al. | |
| 2012/0214101 A1* | 8/2012 | Shimizu | G03F 7/0045 |
| | | | 430/285.1 |
| 2012/0276481 A1 | 11/2012 | Shimizu et al. | |
| 2012/0282548 A1* | 11/2012 | Enomoto | G03F 7/0045 |
| | | | 430/284.1 |
| 2012/0315449 A1 | 12/2012 | Tsubaki et al. | |
| 2013/0065183 A1 | 3/2013 | Kobayashi et al. | |
| 2013/0202999 A1* | 8/2013 | Iwato | G03F 7/004 |
| | | | 430/270.1 |
| 2013/0316285 A1* | 11/2013 | Takaki | G03F 7/0045 |
| | | | 430/270.1 |
| 2014/0248556 A1* | 9/2014 | Kato | G03F 7/0392 |
| | | | 430/18 |
| 2014/0272692 A1* | 9/2014 | Yokokawa | G03F 7/0388 |
| | | | 430/18 |
| 2015/0079522 A1 | 3/2015 | Tsubaki et al. | |

FOREIGN PATENT DOCUMENTS

| | | |
|---|---|---|
| JP | 2008-292975 A | 12/2008 |
| JP | 2009-25707 A | 2/2009 |
| JP | 2009-25723 A | 2/2009 |
| JP | 2008-292975 A5 | 3/2010 |
| JP | 2010-139996 A | 6/2010 |
| JP | 2010-164958 A | 7/2010 |
| JP | 201 1-221513 A | 11/2011 |
| JP | 2012-32807 A | 2/2012 |
| JP | 2012-73565 A | 4/2012 |
| JP | 2012-128009 A | 7/2012 |
| JP | 2012-189982 A | 10/2012 |
| JP | 2012-208431 A | 10/2012 |
| JP | 2012-230328 A | 11/2012 |
| JP | 2013-29751 A | 2/2013 |

OTHER PUBLICATIONS

Written Opinion of PCT/JP2014/057940, dated Apr. 15, 2014. [PCT/ISA/237].

Office Action dated Mar. 8, 2016 from the Japanese Patent Office issued in corresponding Japanese Application No. 2013-054259.

Office Action dated Oct. 4, 2016, from the Japanese Patent Office in counterpart Japanese Application No. 2013-054259.

* cited by examiner

METHOD OF FORMING PATTERN, ACTINIC-RAY- OR RADIATION-SENSITIVE RESIN COMPOSITION, ACTINIC-RAY- OR RADIATION-SENSITIVE FILM, PROCESS FOR MANUFACTURING ELECTRONIC DEVICE AND ELECTRONIC DEVICE

CROSS-REFERENCE TO RELATED APPLICATIONS

This application is a Continuation Application of PCT Application No. PCT/JP2014/057940, filed Mar. 14, 2014, and based upon and claiming the benefit of priority from Japanese Patent Application No. 2013-054259, filed Mar. 15, 2013, and claiming the benefit of U.S. Provisional Application No. 61/792,682, filed Mar. 15, 2013, the entire contents of all of which are incorporated herein by reference.

BACKGROUND OF THE INVENTION

1. Field of the Invention

The present invention relates to a method of forming a pattern, which method finds appropriate application in a semiconductor production process for an IC or the like, a circuit board production process for a liquid crystal, a thermal head or the like and other photofabrication lithography processes, and also relates to an actinic-ray- or radiation-sensitive resin composition, an actinic-ray- or radiation-sensitive film, a process for manufacturing an electronic device and an electronic device.

2. Description of the Related Art

Since the development of the resist for a KrF excimer laser (248 nm), in semiconductor lithography, a pattern forming method based on chemical amplification has been employed.

Shortening of the wavelength of exposure light sources and realization of high numerical apertures (high NA) for projector lenses have been advanced in order to cope with the miniaturization of semiconductor elements. To now, an exposure unit using an ArF excimer laser of 193 nm wavelength as a light source has been developed. A method (known as a liquid-immersion method) in which the space between a projector lens and a sample is filled with a liquid of high refractive index (hereinafter also referred to as an "immersion liquid") has been proposed as a technology for enhancing the resolving power. Moreover, an EUV lithography in which the exposure is carried out using an ultraviolet of further shorter wavelength (13.5 nm) has been proposed.

In recent years, methods of forming a pattern with a developer comprising an organic solvent are being developed. For example, patent references 1 to 9 describe methods of forming a pattern, comprising the operation of developing a resist composition, in which a resin containing a repeating unit containing a group that when acted on by an acid, is decomposed to thereby produce a polar group is incorporated, with a developer comprising an organic solvent.

PRIOR ART LITERATURE

Patent Reference

Patent reference 1: Jpn. Pat. Appln. KOKAI Publication No. (hereinafter referred to as JP-A-) 2008-292975,
Patent reference 2: JP-A-2008-281975,
Patent reference 3: JP-A-2010-139996,
Patent reference 4: JP-A-2010-164958,
Patent reference 5: JP-A-2009-25707,
Patent reference 6: JP-A-2011-221513,
Patent reference 7: JP-A-2012-208431,
Patent reference 8: JP-A-H4-39665, and
Patent reference 9: JP-A-2009-25723.

SUMMARY OF THE INVENTION

Discovering an appropriate combination of resist composition, developer, rinse liquid, etc. required for the formation of a pattern of high comprehensive performance is extremely difficult, and the current situation is that further enhancement is demanded. For example, in the resist pattern forming process in which the resist film is treated with a developer and a rinse liquid, various conditions exist, depending upon a desired pattern shape, production equipment, etc., in the development and rinse operations, in particular, the system for supplying a developer and a rinse liquid, the rotating speed applied in the supply, the duration of treatment with the developer and rinse liquid, etc. Further, in the development with an organic-solvent-based developer, the solvent per se of employed developer may be varied. Therefore, a resist composition widely adaptable to such various conditions is versatile, and can be stated as ensuring wide production latitude and being excellent.

It is an object of the present invention to provide a method of forming a pattern, in which use is made of an actinic-ray- or radiation-sensitive resin composition adaptable to development and rinse operations conducted in various conditions. It is other objects of the present invention to provide an appropriate actinic-ray- or radiation-sensitive resin composition, actinic-ray- or radiation-sensitive film, process for manufacturing an electronic device and electronic device.

The present invention is, for example, as set forth below.

[1] A method of forming a pattern, comprising:
(a) forming a film of an actinic-ray- or radiation-sensitive resin composition,
(b) exposing the film to light, and
(c) developing the exposed film with a developer comprising an organic solvent to thereby form a negative pattern, wherein the actinic-ray- or radiation-sensitive resin composition comprises:
(A) a resin whose solubility in the developer comprising an organic solvent is lowered when acted on by an acid, which resin contains a repeating unit with any of lactone structures of general formula (1) below, and
(B) a compound that when exposed to actinic rays or radiation, generates an acid,

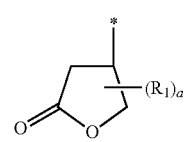

(1)

in which
$R_1$ represents an alkyl group, a cycloalkyl group, an alkoxy group, an aryloxy group, an aralkyloxy group, an alkoxycarbonyl group, a carboxyl group, a halogen atom, a hydroxyl group, a cyano group or an acid-decomposable group, provided that when there are a plurality of $R_1$s, they may be identical to or different from each other, and
a is an integer of 0 to 4.

[2] The method according to item [1], wherein the compound (B) contains any of anions of general formula (2) below, $$\ominus O-\underset{\underset{O}{\overset{O}{\|}}}{\overset{\overset{O}{\|}}{S}}-(\underset{Xf}{\overset{Xf}{C}})_x-(\underset{R_8}{\overset{R_7}{C}})_y-(L)_z-A \quad (2)$$

in which
each of Xf's independently represents a fluorine atom or an alkyl group substituted with at least one fluorine atom,
each of $R_7$ and $R_8$ independently represents a hydrogen atom, a fluorine atom, an alkyl group or an alkyl group substituted with at least one fluorine atom, provided that when there are a plurality of $R_7$s and $R_8$s, $R_7$s, and $R_8$s, may be identical to or different from each other,
L represents a bivalent connecting group, provided that when there are a plurality of L's, they may be identical to or different from each other,
A represents an organic group containing a cyclic structure, and
x is an integer of 1 to 20, y an integer of 0 to 10 and z an integer of 0 to 10.

[3] The method according to item [1] or [2], wherein the compound (B) contains an anion, the anion containing two or three fluorine atoms.

[4] The method according to any one of items [1] to [3], wherein the resin (A) contains any of repeating units of general formula (3) below in an amount of 0 to 5 mol % based on all repeating units, $$\text{(3)}$$

in which
m is an integer of 1 to 3, and R represents a hydrogen atom or an alkyl group.

[5] The method according to any one of items [1] to [4], wherein the resin (A) further contains a repeating unit (LC) with a lactone structure different from the lactone structures of general formula (1), or a repeating unit (SU) with a sultone structure.

[6] The method according to item [5], wherein the repeating unit (LC) contains a lactone-containing polycyclic structure, or the repeating unit (SU) contains a sultone-containing polycyclic structure.

[7] The method according to any one of items [1] to [6], wherein the resin (A) further contains any of repeating units of general formula (aI) below, $$\text{(aI)}$$

in which
$Xa_1$ represents a hydrogen atom, an alkyl group, a cyano group or a halogen atom,
T represents a single bond or a bivalent connecting group, and
each of $Rx_1$ to $Rx_3$ independently represents an alkyl group or a cycloalkyl group, provided that two of $Rx_1$ to $Rx_3$ may be bonded to each other to thereby form a cyclic structure.

[8] The method according to item [7], wherein any of repeating units of general formula (aI) is contained in an amount of 50 to 70 mol % based on all repeating units constituting the resin (A).

[9] An actinic-ray- or radiation-sensitive resin composition for use in a method of forming a pattern, comprising:
(a) forming a film of an actinic-ray- or radiation-sensitive resin composition,
(b) exposing the film to light, and
(c) developing the exposed film with a developer comprising an organic solvent to thereby form a negative pattern,
which actinic-ray- or radiation-sensitive resin composition comprises:
(A) a resin whose solubility in the developer comprising an organic solvent is lowered when acted on by an acid, which resin contains a repeating unit with any of lactone structures of general formula (1) below, and
(B) a compound that when exposed to actinic rays or radiation, generates an acid, $$\text{(1)}$$

in which
$R_1$ represents an alkyl group, a cycloalkyl group, an alkoxy group, an aryloxy group, an aralkyloxy group, an alkoxycarbonyl group, a carboxyl group, a halogen atom, a hydroxyl group, a cyano group or an acid-decomposable group, provided that when there are a plurality of $R_1$s, they may be identical to or different from each other, and
a is an integer of 0 to 4.

[10] The actinic-ray- or radiation-sensitive resin composition according to item [9], wherein the compound (B) contains any of anions of general formula (2) below, $$\ominus O-\underset{\underset{O}{\overset{O}{\|}}}{\overset{\overset{O}{\|}}{S}}-(\underset{Xf}{\overset{Xf}{C}})_x-(\underset{R_8}{\overset{R_7}{C}})_y-(L)_z-A \quad (2)$$

in which each of Xf's independently represents a fluorine atom or an alkyl group substituted with at least one fluorine atom, each of $R_7$ and $R_8$ independently represents a hydrogen atom, a fluorine atom, an alkyl group or an alkyl group substituted with at least one fluorine atom, provided that when there are a plurality of $R_7$s and $R_8$s, $R_7$s, and $R_8$s, may be identical to or different from each other, L represents a bivalent connecting group, provided that when there are a plurality of L's, they may be identical to or different from each other, A represents an organic group containing a cyclic structure, and x is an integer of 1 to 20, y an integer of 0 to 10 and z an integer of 0 to 10.

[11] The actinic-ray- or radiation-sensitive resin composition according to item [9] or [10], wherein the compound (B) contains an anion, the anion containing two or three fluorine atoms.

[12] The actinic-ray- or radiation-sensitive resin composition according to any one of items [9] to [11], wherein the resin (A) contains any of repeating units of general formula (3) below in an amount of 0 to 5 mol % based on all repeating units,

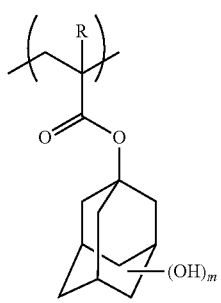

(3)

in which m is an integer of 1 to 3, and R represents a hydrogen atom or an alkyl group.

[13] The actinic-ray- or radiation-sensitive resin composition according to any one of items [9] to [12], wherein the resin (A) further contains a repeating unit (LC) with a lactone structure different from the lactone structures of general formula (1), or a repeating unit (SU) with a sultone structure.

[14] The actinic-ray- or radiation-sensitive resin composition according to item [13], wherein the repeating unit (LC) contains a lactone-containing polycyclic structure, or the repeating unit (SU) contains a sultone-containing polycyclic structure.

[15] The actinic-ray- or radiation-sensitive resin composition according to any one of items [9] to [14], wherein the resin (A) further contains any of repeating units of general formula (aI) below,

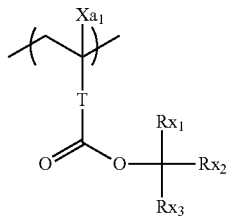

(aI)

in which $Xa_1$ represents a hydrogen atom, an alkyl group, a cyano group or a halogen atom, T represents a single bond or a bivalent connecting group, and each of $Rx_1$ to $Rx_3$ independently represents an alkyl group or a cycloalkyl group, provided that two of $Rx_1$ to $Rx_3$ may be bonded to each other to thereby form a cyclic structure.

[16] The actinic-ray- or radiation-sensitive resin composition according to item [15], wherein any of repeating units of general formula (aI) is contained in an amount of 50 to 70 mol % based on all repeating units constituting the resin (A).

[17] An actinic-ray- or radiation-sensitive film formed from the actinic-ray- or radiation-sensitive resin composition according to any one of items [9] to [16].

[18] A process for manufacturing an electronic device, comprising the method of forming a pattern according to any one of items [1] to [8].

[19] An electronic device manufactured by the process of item [18].

The present invention has made it feasible to provide a method of forming a pattern, in which use is made of an actinic-ray- or radiation-sensitive resin composition adaptable to development and rinse operations conducted in various conditions. Further, the present invention has made it feasible to provide an appropriate actinic-ray- or radiation-sensitive resin composition, actinic-ray- or radiation-sensitive film, process for manufacturing an electronic device and electronic device.

DESCRIPTION OF THE INVENTION

With respect to the expression of group (atomic group) used in this specification, the expression even when there is no mention of "substituted and unsubstituted" encompasses groups not only having no substituent but also having substituents. For example, the expression "alkyl groups" encompasses not only alkyls having no substituent (unsubstituted alkyls) but also alkyls having substituents (substituted alkyls).

In this specification, the term "actinic rays" or "radiation" means, for example, brightline spectra from a mercury lamp, far ultraviolet represented by an excimer laser, extreme ultraviolet (EUV light), X-rays, electron beams (EB) and the like. Further, in the present invention, the term "light" means actinic rays or radiation.

The term "exposure to light" used in this specification, unless otherwise specified, means not only irradiation with light, such as light from a mercury lamp, far ultraviolet represented by an excimer laser, X-rays or EUV light, but also lithography using particle beams, such as electron beams and ion beams.

The method of forming a negative pattern according to the present invention comprises the operations of forming a specified film of actinic-ray- or radiation-sensitive resin composition, exposing the film to light, and developing the exposed film with a developer comprising an organic solvent. First, the actinic-ray- or radiation-sensitive resin composition for use in the method of forming a negative pattern according to the present invention will be described. Next, the method of forming a negative pattern in which use is made of the composition will be described.

<Actinic-Ray- or Radiation-Sensitive Resin Composition>

The actinic-ray- or radiation-sensitive resin composition (hereinafter also referred to as "composition of the present invention" or the like) for use in the method of forming a negative pattern according to the present invention comprises (A) a resin whose solubility in a developer comprising an organic solvent is lowered when acted on by an acid, which resin contains a repeating unit with any of lactone structures of general formula (1) below, and (B) a compound that when exposed to actinic rays or radiation, generates an acid.

The composition of the present invention in its one form may further comprise at least one member selected from among a hydrophobic resin, a basic compound, a solvent, a surfactant and other additives.

Each of these components of the composition will be described below.

<Resin (A) Whose Solubility in a Developer Comprising an Organic Solvent is Lowered when Acted on by an Acid>

The composition of the present invention comprises a resin (hereinafter also referred to as "resin (A)" or "acid-decomposable resin") whose solubility in a developer comprising an organic solvent is lowered when acted on by an acid, which resin contains a repeating unit with any of lactone structures of general formula (1) below. The actinic-ray- or radiation-sensitive resin composition adaptable to development and rinse operations conducted in various conditions can be provided by introducing a repeating unit with the β-γ-butyrolactone structure of general formula (1) below in the acid-decomposable resin. This effect is especially striking when the resin is used in the negative pattern forming method comprising the operation of development with a developer comprising an organic solvent.

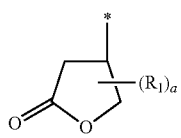

(1)

In the formula,
$R_1$ represents an alkyl group, a cycloalkyl group, an alkoxy group, an aryloxy group, an aralkyloxy group, an alkoxycarbonyl group, a carboxyl group, a halogen atom, a hydroxyl group, a cyano group or an acid-decomposable group, provided that when there are a plurality of $R_1$s, they may be identical to or different from each other, and a is an integer of 0 to 4, preferably 0 to 2.

A double bond may be introduced in the alkyl group represented by $R_1$. As the alkyl group, there can be mentioned, for example, a methyl group, an ethyl group, a propyl group, an isopropyl group, a butyl group, an isobutyl group, a t-butyl group, a vinyl group or the like.

As the cycloalkyl group represented by $R_1$, there can be mentioned, for example, a cyclopropyl group, a cyclobutyl group, a cyclopentyl group, a cyclohexyl group, or the like.

The alkyl group as a constituent of the alkoxy group represented by $R_1$ may be a linear, branched or cyclic alkyl group, and a double bond may be introduced therein. As the alkoxy group represented by $R_1$, there can be mentioned, for example, a methoxy group, an ethoxy group, a propoxy group, a t-butoxy group, a pentyloxy group, a cyclohexyloxy group, an allyloxy group or the like.

As the aryloxy group represented by $R_1$, there can be mentioned, for example, a phenoxy group, a 1-naphthyloxy group or the like.

As the aralkyloxy group represented by $R_1$, there can be mentioned, for example, a benzyloxy group or the like.

The alkyl group as a constituent of the alkoxycarbonyl group represented by $R_1$ is, for example, a linear, branched or cyclic alkyl group having 1 to 8 carbon atoms, preferably 1 to 4 carbon atoms. A double bond may be introduced therein.

As the halogen atom represented by $R_1$, there can be mentioned, for example, an F atom, a Cl atom, a Br atom or an I atom.

As the acid-decomposable group represented by $R_1$, there can be mentioned, for example, a tertiary ester group having 3 to 12 carbon atoms, an acetal group having 2 to 10 carbon atoms or the like.

In an aspect of the present invention, it is preferred for the repeating unit with the lactone structure of general formula (1) to be one expressed by general formula (III-A) below.

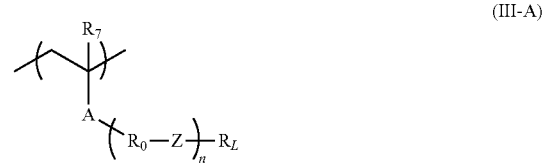

(III-A)

In general formula (III-A) above,
A represents an ester bond (group expressed by —COO—) or an amide bond (group expressed by —CONH—).

$R_0$, or each of $R_0$s independently, represents an alkylene group, a cycloalkylene group or a combination thereof.

Z, or each of Z's independently, represents a single bond, an ether bond, an ester bond, an amide bond, any of urethane bonds of the formula:

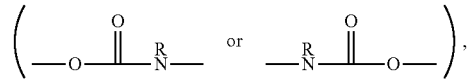

any of urea bonds of the formula:

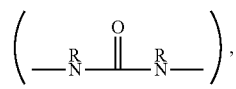

in which each of R's independently represents a hydrogen atom, an alkyl group, a cycloalkyl group or an aryl group.

$R_L$ represents a monovalent organic group with any of lactone structures of general formula (1).

In the formula, n is the number of repetitions of any of the structures of the formula —$R_0$—Z— and is an integer of 0 to 5, preferably 0 or 1 and more preferably 0. When n is 0, —R₀—Z— is not present, becoming a single bond.

R₇ represents a hydrogen atom, a halogen atom or an alkyl group.

Substituents may be introduced in the alkylene group and cycloalkylene group represented by R₀.

Z is preferably an ether bond or an ester bond, most preferably an ester bond.

The alkyl group represented by R₇ is preferably an alkyl group having 1 to 4 carbon atoms, more preferably a methyl group or an ethyl group and most preferably a methyl group.

Substituents may be introduced in the alkylene group and cycloalkylene group represented by R₀ and the alkyl group represented by R₇. As the substituents, there can be mentioned, for example, a halogen atom, such as a fluorine, chlorine or bromine atom; a mercapto group; a hydroxyl group; an alkoxy group, such as a methoxy group, an ethoxy group, an isopropoxy group, a t-butoxy group or a benzyloxy group; and an acyloxy group, such as an acetoxy group or a propionyloxy group.

R₇ is preferably a hydrogen atom, a methyl group, a trifluoromethyl group, or a hydroxymethyl group.

Preferred chain alkylene groups represented by R₀ are those having 1 to 10 carbon atoms, more preferably 1 to 5 carbon atoms. As such, there can be mentioned, for example, a methylene group, an ethylene group, a propylene group or the like. Preferred cycloalkylene groups represented by R₀ are those having 3 to 20 carbon atoms. As such, there can be mentioned, for example, a cyclohexylene group, a cyclopentylene group, a norbornylene group, an adamantylene group or the like. The chain alkylene groups are preferred from the viewpoint of the exertion of the effect of the present invention. A methylene group is most preferred.

As preferred repeating units of a form other than that of general formula (III-A), there can be mentioned those of general formula (III-B) below in which the principal chain has a norbornene structure.

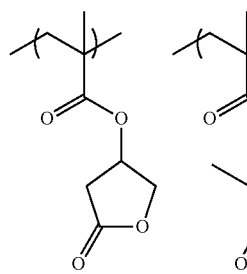

(III-B)

In general formula (III-B) above, A, R₀, Z, R_L and n are as defined above in connection with general formula (III-A).

Particular examples of the repeating units with lactone structures of general formula (1) above are shown below, which in no way limit the scope of the present invention.

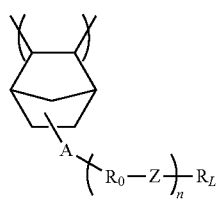

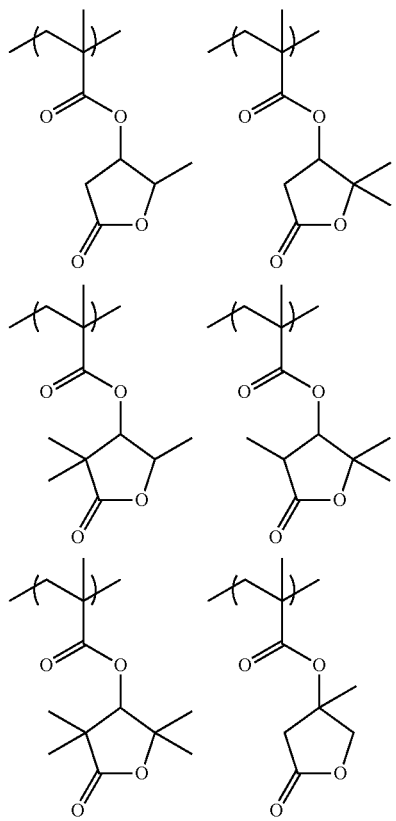

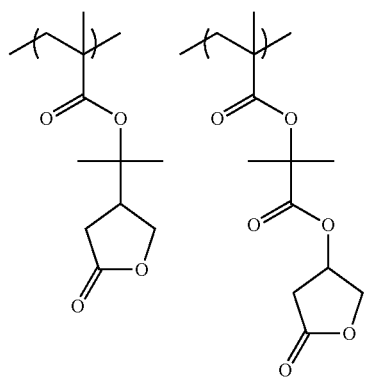

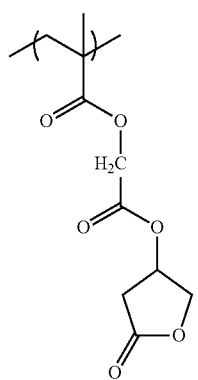

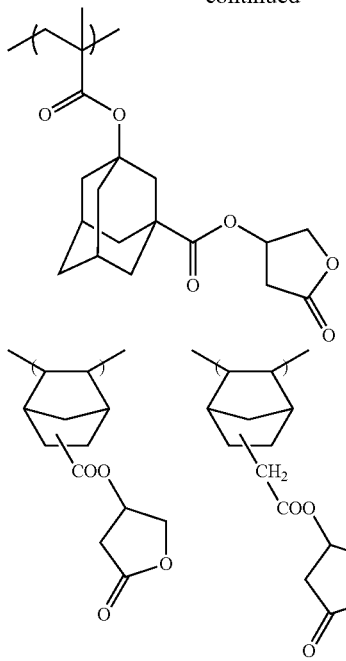

The resin (A) in its one form preferably further contains a repeating unit (LC) with a lactone structure other than that of general formula (1), or a repeating unit (SU) with a sultone structure. Fine regulation of solubility in developers and regulation of dry etching resistance can be achieved by the joint use of different lactone structure.

The lactone structures other than those of general formula (1) and sultone structures are not particularly limited as long as lactone and sultone structures are contained respectively. A 5- to 7-membered ring lactone structure and a 5- to 7-membered ring sultone structure are preferred. One resulting from the condensation of a 5- to 7-membered ring lactone structure with another cyclic structure effected in a fashion to form a bicyclo structure or spiro structure and one resulting from the condensation of a 5- to 7-membered ring sultone structure with another cyclic structure effected in a fashion to form a bicyclo structure or spiro structure are also preferred. The repeating unit with any of the lactone structures of general formulae (LC1-1) to (LC1-19) below and repeating unit with any of the sultone structures of general formulae (SL1-1) and (SL1-2) below are more preferred. The lactone structure or sultone structure may be directly bonded to the principal chain of the resin.

In an aspect of the present invention, it is preferred for the lactone structure contained in the repeating unit (LC) to be any of those of formulae (LC1-1), (LC1-4), (LC1-5), (LC1-8), (LC1-13), (LC1-14), (LC1-15), (LC1-18) and (LC1-19) below. The lactone structures of formulae (LC1-1) and (LC1-4) are especially preferred.

In another aspect of the present invention, the repeating unit (LC) preferably contains a lactone-containing polycyclic structure, and the repeating unit (SU) preferably contains a sultone-containing polycyclic structure.

The LWR and CDU (Critical Dimension Uniformity) performances can be enhanced by the joint use of repeating units with these specified lactone structures and sultone structures.

LC1-1
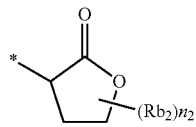

LC1-2
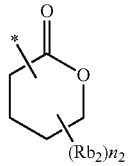

LC1-3
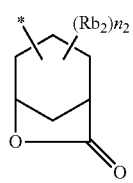

LC1-4
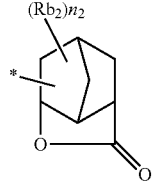

LC1-5
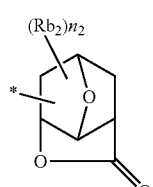

LC1-6
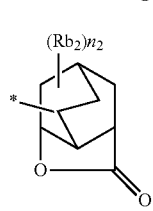

LC1-7
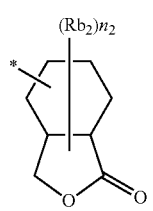

LC1-8
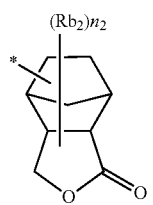

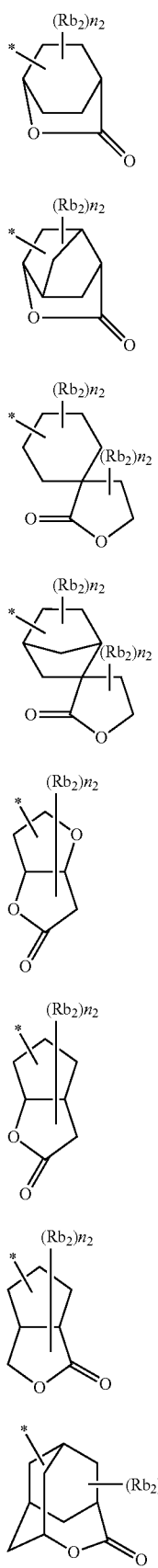

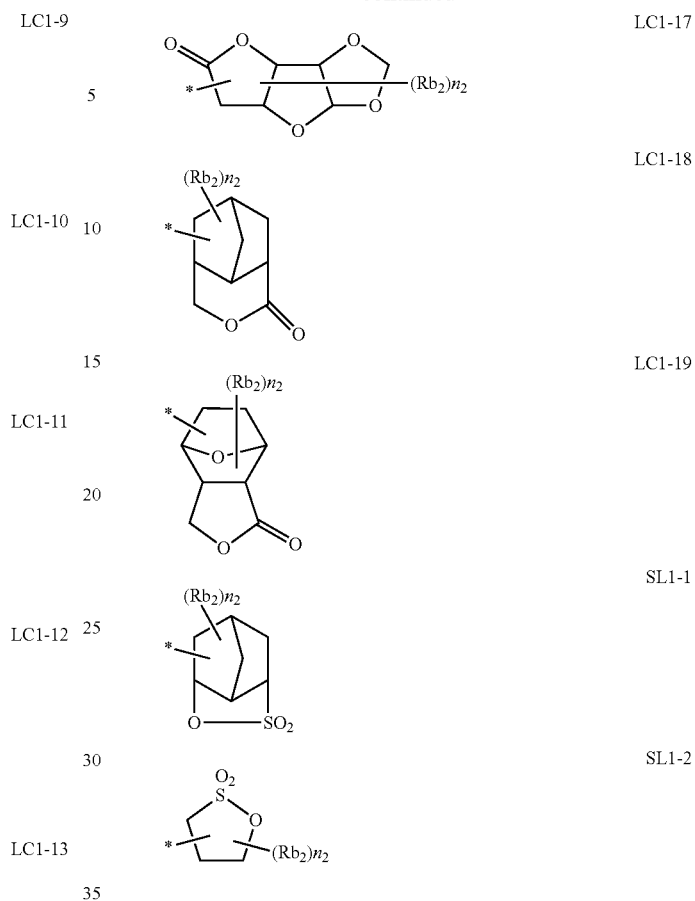

Substituents ($Rb_2$) are optionally introduced in the portion of the lactone structure other than that of general formula (1) and the portion of the sultone structure. As preferred substituents ($Rb_2$), there can be mentioned an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, an acid-decomposable group and the like. An alkyl group having 1 to 4 carbon atoms, a cyano group and an acid-decomposable group are more preferred. In the formulae, $n_2$ is an integer of 0 to 4. When $n_2$ is 2 or greater, the plurality of introduced substituents ($Rb_2$) may be identical to or different from each other. Further, the plurality of introduced substituents ($Rb_2$) may be bonded to each other to thereby form a ring.

The repeating unit with a lactone structure or sultone structure is generally present in the form of optical isomers. Any of the optical isomers may be used. It is both appropriate to use one type of optical isomer alone and to use a plurality of optical isomers in the form of a mixture. When one type of optical isomer is mainly used, the optical purity (ee) thereof is preferably 90% or higher, more preferably 95% or higher.

It is preferred for the repeating unit with a lactone structure other than that of general formula (1) or with a sultone structure to be any of repeating units of general formula (III) below.

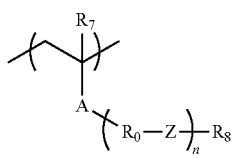
(III)

In general formula (III) above,

A represents an ester bond (group expressed by —COO—) or an amide bond (group expressed by —CONH—).

R₀, or each of R₀s independently, represents an alkylene group, a cycloalkylene group or a combination thereof.

Z, or each of Z's independently, represents a single bond, an ether bond, an ester bond, an amide bond, any of urethane bonds of the formula:

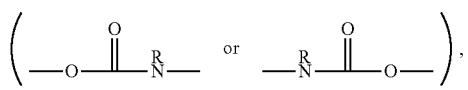

or any of urea bonds of the formula:

in which each of R's independently represents a hydrogen atom, an alkyl group, a cycloalkyl group or an aryl group.

R₈ represents a monovalent organic group with a lactone structure other than that of general formula (1) or with a sultone structure.

In the general formula, n is the number of repetitions of the structure —R₀—Z—, being an integer of 0 to 5.

R₇ represents a hydrogen atom, a halogen atom or an alkyl group.

In general formula (III) above, R₀, Z, R₇ and n are as defined above in connection with general formula (III-A). Detailed description thereof made in connection with general formula (III-A) apply to these.

The monovalent organic group with a lactone structure other than that of general formula (1) or a sultone structure represented by R₈ is not limited as long as a lactone structure or sultone structure is contained. As particular examples thereof, there can be mentioned the lactone structures and sultone structures of general formulae (LC1-1) to (LC1-19) and (SL1-1) and (SL1-2) above. Of these, the above-mentioned structures are especially preferred. In general formulae (LC1-1) to (LC1-19), n₂ is preferably 2 or less.

R₈ is preferably a monovalent organic group with an unsubstituted lactone structure or sultone structure, or a monovalent organic group with a lactone structure or sultone structure substituted with a methyl group, a cyano group or an alkoxycarbonyl group. More preferably, R₈ is a monovalent organic group with a lactone structure substituted with a cyano group (cyanolactone).

Particular examples of the repeating units (CL) and (SL) containing groups with a lactone structure other than that of general formula (1) or with a sultone structure are shown below, which in no way limit the scope of the present invention. In the formulae, Rx represents H, CH₃, CH₂OH or CF₃.

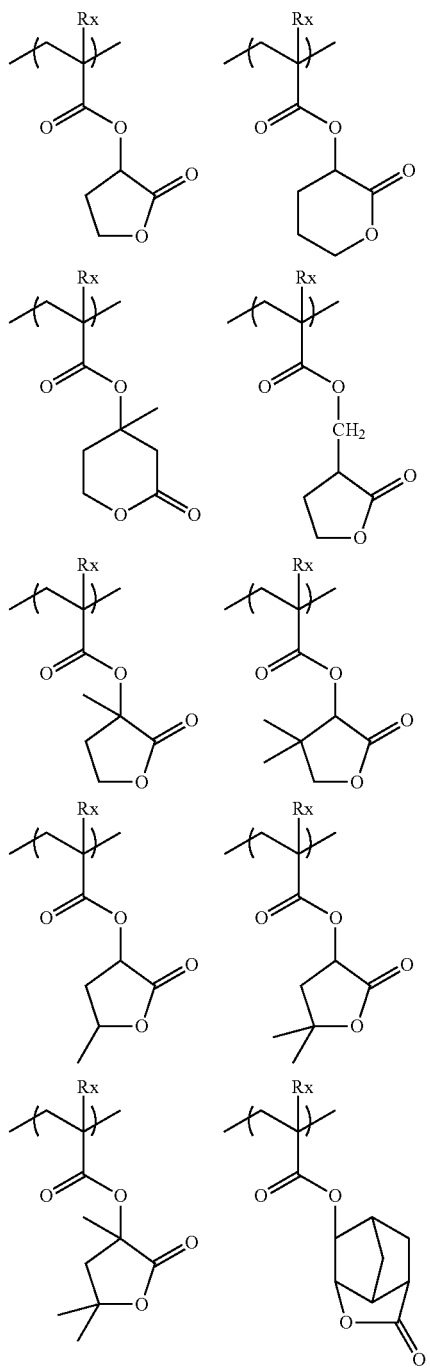

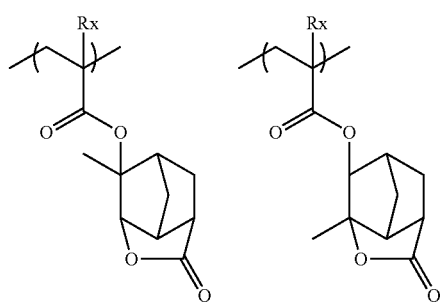

-continued
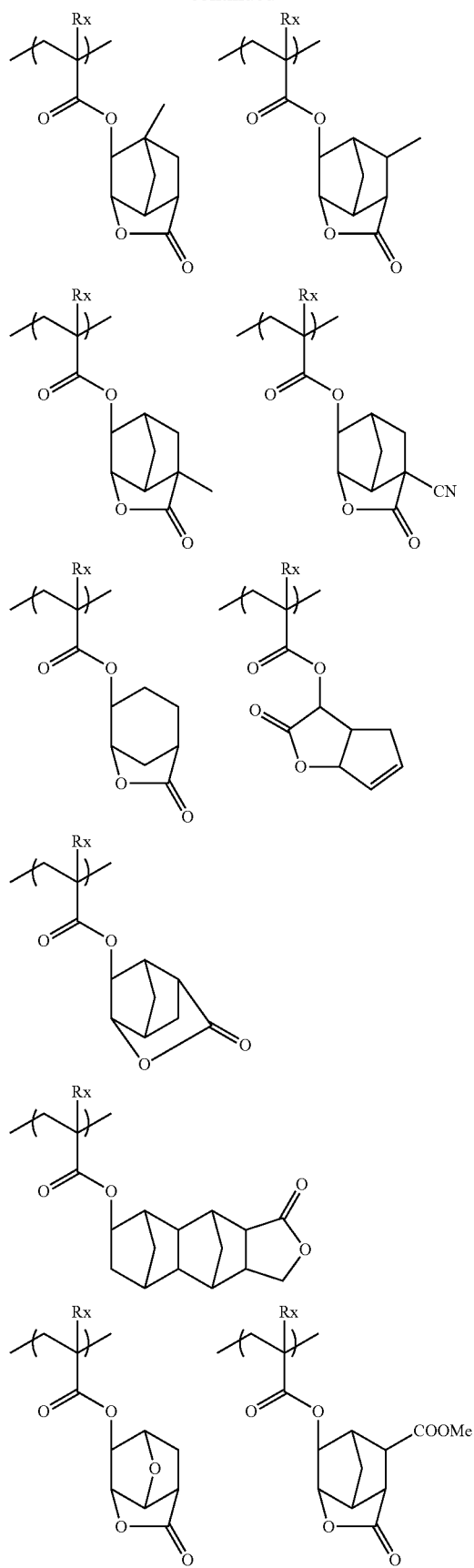
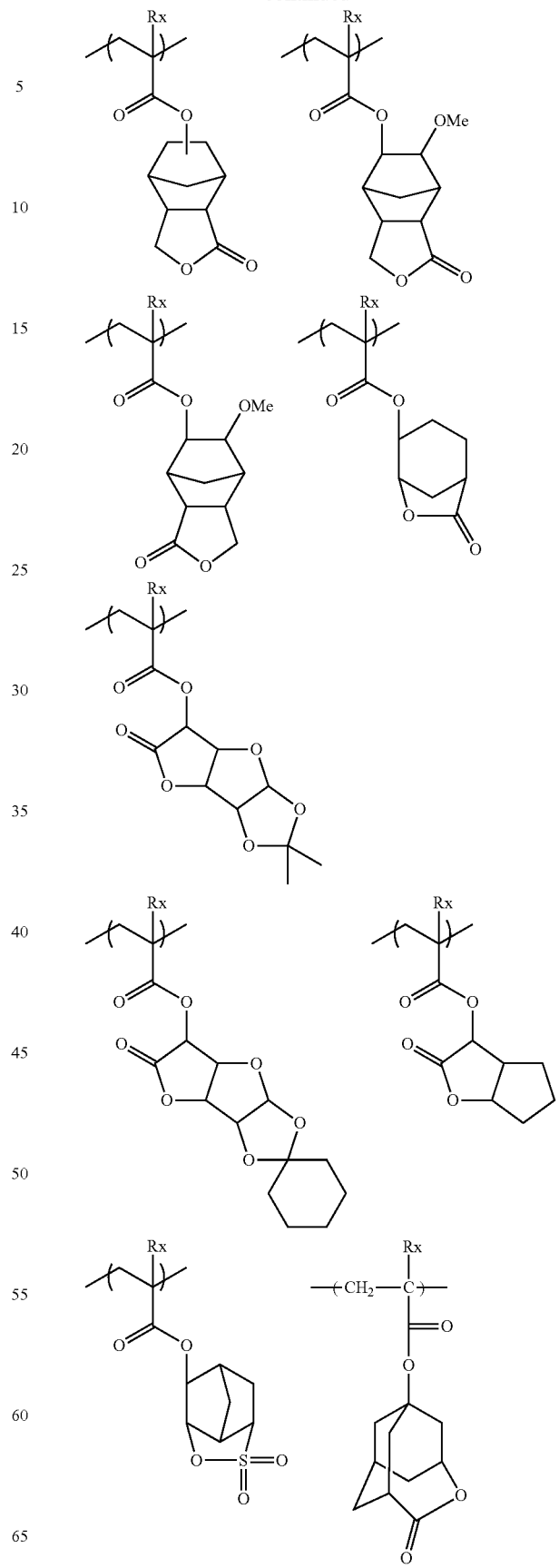

-continued

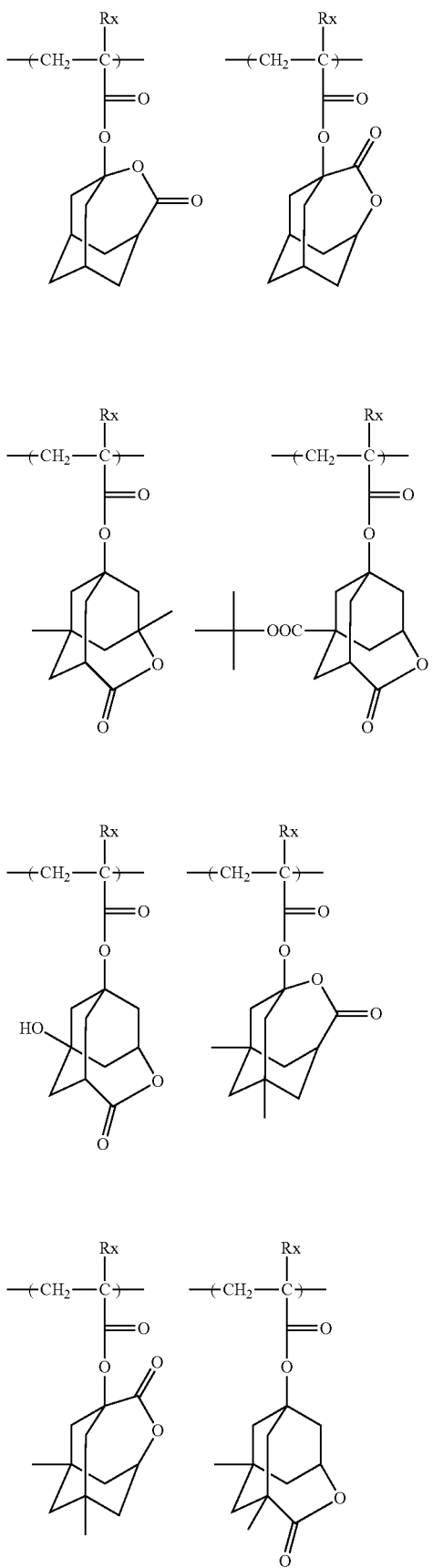

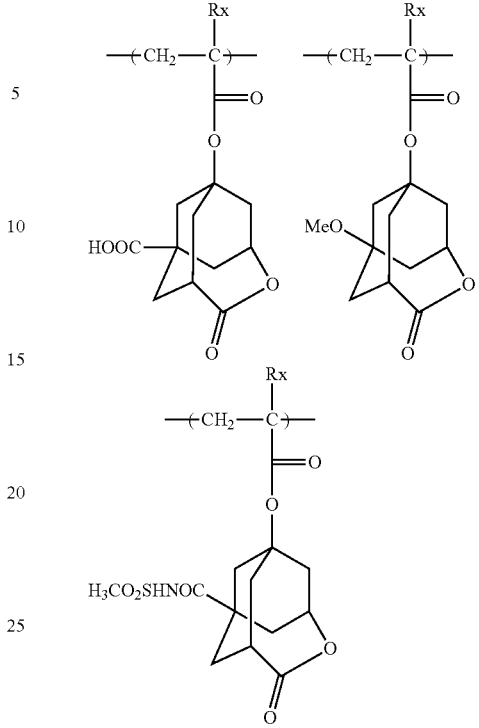

When the resin (A) contains neither a repeating unit (LC) nor a repeating unit (SL), the content of repeating unit with any of lactone structures of general formula (1) based on all the repeating units constituting the resin (A) is preferably in the range of 5 to 60 mol %, more preferably 10 to 50 mol % and most preferably 15 to 45 mol %.

When the resin (A) contains a repeating unit (LC) or a repeating unit (SL), the content of repeating unit with any of lactone structures of general formula (1) plus repeating unit (LC) or repeating unit (SL) based on all the repeating units constituting the resin (A) is preferably in the range of 5 to 50 mol %, more preferably 10 to 40 mol %.

The resin (A) is a resin whose solubility in a developer comprising an organic solvent is lowered when acted on by an acid. For example, the resin contains a group (hereinafter also referred to as an "acid-decomposable group") that when acted on by an acid, is decomposed to thereby produce a polar group in the principal chain or a side chain or in both the principal chain and a side chain of the resin.

It is preferred for the acid-decomposable group to have a structure in which a polar group is protected by a group that when acted on by an acid, is decomposed and leaves.

The polar group is not particularly limited as long as it is rendered poorly soluble or insoluble in a developer comprising an organic solvent. As polar groups, there can be mentioned an acid group (group dissociated in a 2.38 mass % aqueous tetramethylammonium hydroxide solution conventionally used as a resist developer), such as a phenolic hydroxyl group, a carboxyl group, a fluoroalcohol group (preferably a hexafluoroisopropanol group), a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group or a tris(alkylsulfonyl)methylene group; an alcoholic hydroxyl group; and the like.

The alcoholic hydroxyl group refers to a hydroxyl group bonded to a hydrocarbon group, which is one other than the hydroxyl group (phenolic hydroxyl group) directly bonded onto an aromatic ring. Any aliphatic alcohol substituted at its α-position with an electron withdrawing group, such as a fluorine atom, (for example, a fluorinated alcohol group (a hexafluoroisopropanol group, etc.)) is not included in the category of the alcoholic hydroxyl group. It is preferred for the alcoholic hydroxyl group to be a hydroxyl whose pKa value is in the range of 12 to 20.

Preferred polar groups include a carboxyl group, a fluoroalcohol group (preferably a hexafluoroisopropanol group) and a sulfonic acid group.

It is preferred for the acid-decomposable group to be a group whose hydrogen atom is replaced by a group leaving under the action of an acid.

As the group leaving under the action of an acid, there can be mentioned, for example, —C($R_{36}$)($R_{37}$)($R_{38}$), —C($R_{36}$)($R_{37}$)($OR_{39}$), —C($R_{01}$)($R_{02}$)($OR_{39}$) or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded to each other to thereby form a ring.

Each of $R_{01}$ and $R_{02}$ independently represents a hydrogen atom, an alkyl group, a cycloalkyl group, an aryl group, an aralkyl group or an alkenyl group.

Each of the alkyl groups represented by $R_{36}$ to $R_{39}$, $R_{01}$ and $R_{02}$ preferably has 1 to 8 carbon atoms. For example, there can be mentioned a methyl group, an ethyl group, a propyl group, an n-butyl group, a sec-butyl group, a hexyl group, an octyl group or the like.

The cycloalkyl groups represented by $R_{36}$ to $R_{39}$, $R_{01}$ and $R_{02}$ may be monocyclic or polycyclic. Each of the cycloalkyl groups preferably has 3 to 20 carbon atoms. Each of the aryl groups represented by $R_{36}$ to $R_{39}$, $R_{01}$ and $R_{02}$ is preferably one having 6 to 10 carbon atoms. For example, there can be mentioned a phenyl group, a naphthyl group, an anthryl group or the like.

Each of the aralkyl groups represented by $R_{36}$ to $R_{39}$, $R_{01}$ and $R_{02}$ is preferably one having 7 to 12 carbon atoms. For example, there can be mentioned a benzyl group, a phenethyl group, a naphthylmethyl group or the like.

Each of the alkenyl groups represented by $R_{36}$ to $R_{39}$, $R_{01}$ and $R_{02}$ preferably has 2 to 8 carbon atoms. For example, there can be mentioned a vinyl group, an allyl group, a butenyl group, a cyclohexenyl group or the like.

The ring formed by the mutual bonding of $R_{36}$ and $R_{37}$ is preferably a cycloalkyl group (monocyclic or polycyclic). The cycloalkyl group is preferably a monocycloalkyl group, such as a cyclopentyl group or a cyclohexyl group, or a polycycloalkyl group, such as a norbornyl group, a tetracyclodecanyl group, a tetracyclododecanyl group or an adamantyl group. A monocycloalkyl group having 5 or 6 carbon atoms is more preferred. A monocycloalkyl group having 5 carbon atoms is most preferred.

It is preferred for the acid-decomposable group to be a cumyl ester group, an enol ester group, an acetal ester group, a tertiary alkyl ester group or the like. A tertiary alkyl ester group is more preferred.

[Repeating Unit Containing an Acid-Decomposable Group]

It is preferred for the resin (A) to contain a repeating unit containing an acid-decomposable group.

The resin (A) in its one form preferably contains a repeating unit (AI) (hereinafter also referred to as "repeating unit (AI)") that when acted on by an acid, is decomposed to thereby produce a carboxyl group as the repeating unit containing an acid-decomposable group, more preferably any of repeating units of general formula (aI) or (aI') below,

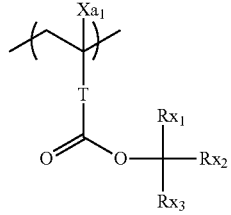

(aI)

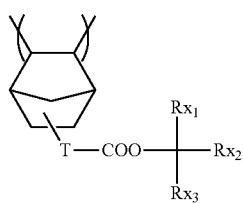

(aI')

In general formulae (aI) and (aI'), $Xa_1$ represents a hydrogen atom, an alkyl group, a cyano group or a halogen atom.

T represents a single bond or a bivalent connecting group.

Each of $Rx_1$ to $Rx_3$ independently represents an alkyl group or a cycloalkyl group, provided that two of $Rx_1$ to $Rx_3$ may be bonded to each other to thereby form a cyclic structure.

As the bivalent connecting group represented by T, there can be mentioned an alkylene group, any of groups of the formula —COO—Rt-, any of groups of the formula —O—Rt-, a phenylene group or the like. In the formulae, Rt represents an alkylene group or a cycloalkylene group.

T is preferably a single bond or any of groups of the formula —COO—Rt-. Rt is preferably an alkylene group having 1 to 5 carbon atoms, more preferably a —$CH_2$— group, a —$(CH_2)_2$— group or a —$(CH_2)_3$— group. T is more preferably a single bond.

A substituent may be introduced in the alkyl group represent by $Xa_1$. As the substituent, there can be mentioned, for example, a hydroxyl group or a halogen atom (preferably a fluorine atom).

The alkyl group represent by $Xa_1$ preferably has 1 to 4 carbon atoms. For example, there can be mentioned a methyl group, an ethyl group, a propyl group, a hydroxymethyl group, a trifluoromethyl group or the like. A methyl group is preferred.

It is preferred for $Xa_1$ to be a hydrogen atom or a methyl group.

The alkyl group represented by each of $Rx_1$, $Rx_2$ and $Rx_3$ may be linear or branched, which is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of $Rx_1$, $Rx_2$ and $Rx_3$ is preferably a monocycloalkyl group, such as a cyclopentyl group or a cyclohexyl group, or a polycycloalkyl group, such as a norbornyl group, a tetracyclodecanyl group, a tetracyclododecanyl group or an adamantyl group.

The cyclic structure formed by the mutual bonding of two of $Rx_1$, $Rx_2$ and $Rx_3$ is preferably a monocycloalkane ring, such as a cyclopentyl ring or a cyclohexyl ring, or a polycycloalkyl group, such as a norbornane ring, a tetracyclodecane ring, a tetracyclododecane ring or an adamantane ring. A monocycloalkane ring having 5 or 6 carbon atoms is especially preferred.

Each of $Rx_1$, $Rx_2$ and $Rx_3$ independently preferably represents an alkyl group, more preferably a linear or branched alkyl group having 1 to 4 carbon atoms.

Substituents may be introduced in these groups. As the substituents, there can be mentioned, for example, an alkyl group (1 to 4 carbon atoms), a cycloalkyl group (3 to 8 carbon atoms), a halogen atom, an alkoxy group (1 to 4 carbon atoms), a carboxyl group, an alkoxycarbonyl group (2 to 6 carbon atoms) and the like. The number of carbon atoms of each of these substituents is preferably up to 8. From the viewpoint of enhancing the contrast of dissolution in a developer comprising an organic solvent between before and after acid decomposition, it is preferred for the substituent to be one not containing any heteroatom, such as an oxygen atom, a nitrogen atom or a sulfur atom (for example, an alkyl group substituted with a hydroxyl group and the like not preferred). The substituent is more preferably a group comprised only of hydrogen and carbon atoms, most preferably a linear or branched alkyl group or a cycloalkyl group.

Particular examples of the repeating units of general formulae (aI) and (aI') are shown below, which in no way limit the scope of the present invention.

In the particular examples, Rx represents a hydrogen atom, $CH_3$, $CF_3$ or $CH_2OH$. Each of Rxa and Rxb represents an alkyl group having 1 to 4 carbon atoms. $Xa_1$ represents a hydrogen atom, $CH_3$, $CF_3$ or $CH_2OH$. Z represents a substituent. When there are a plurality of Z's, they may be identical to or different from each other. In the formulae, p is 0 or a positive integer. Particular examples and preferred examples of Z are the same as those of the substituents introducible in the $Rx_1$ to $Rx_3$ groups.

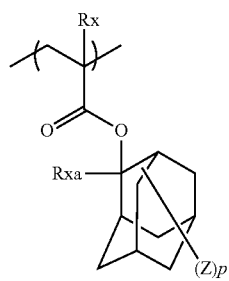

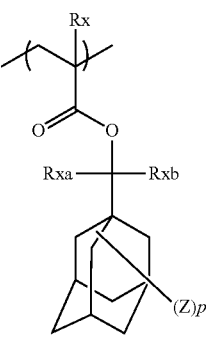

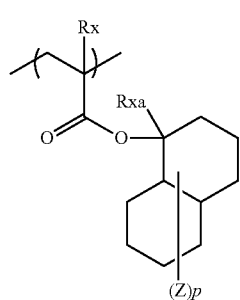

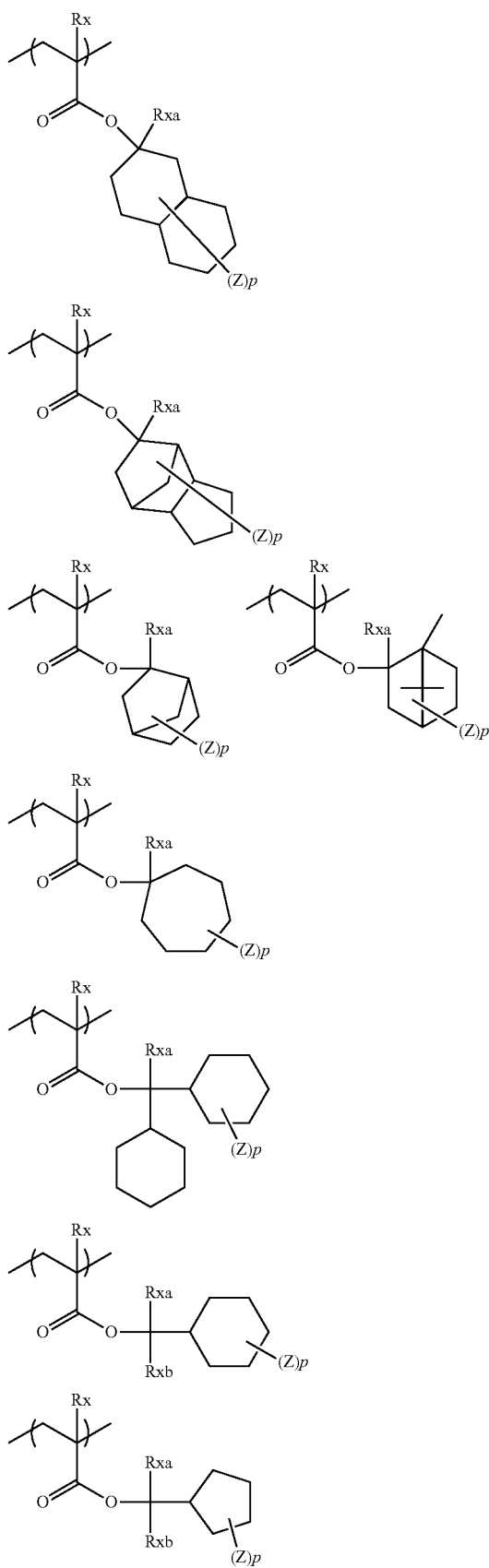

-continued
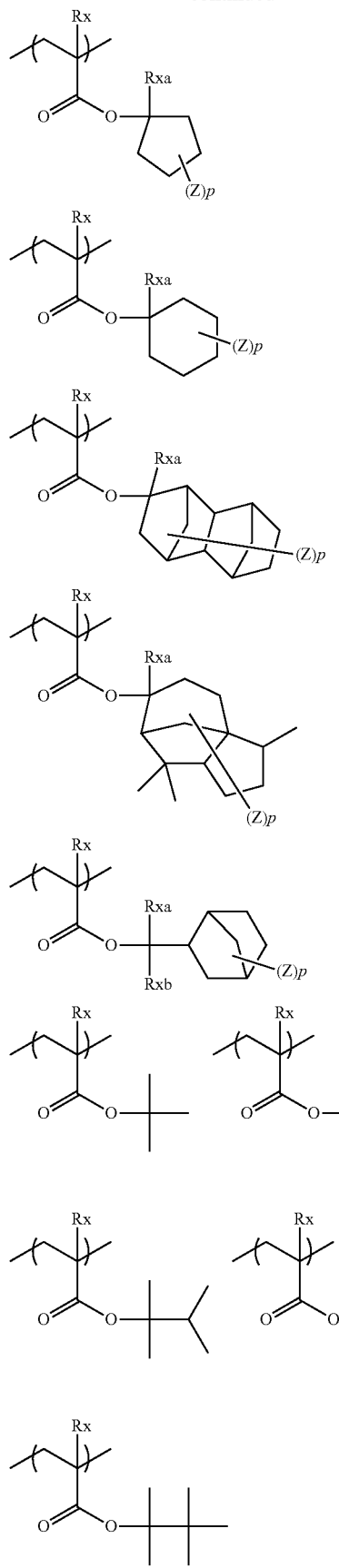
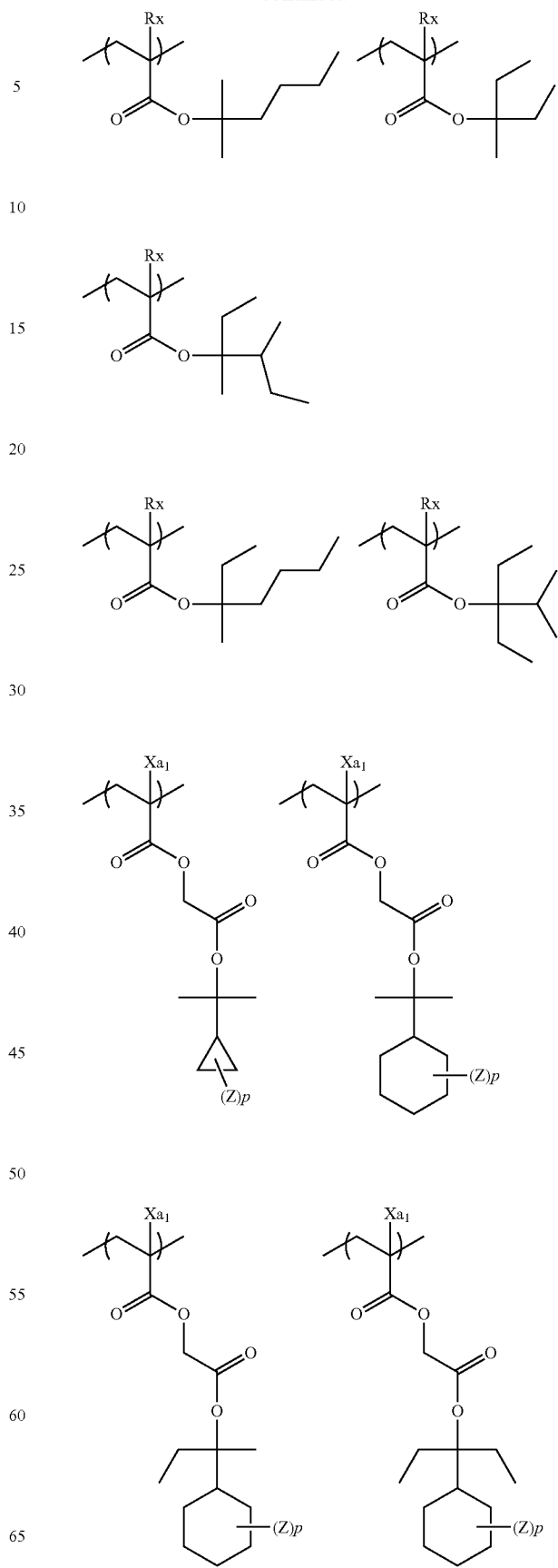

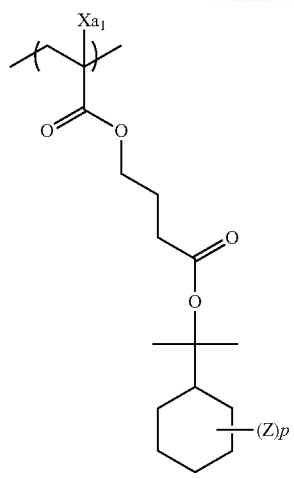
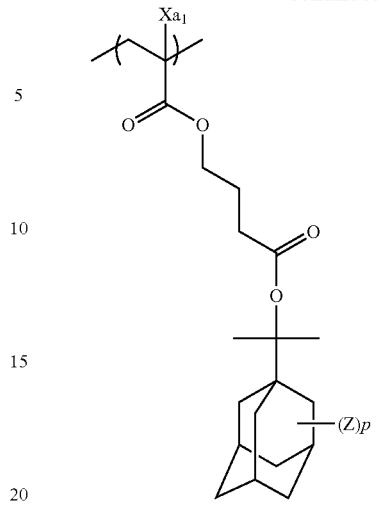
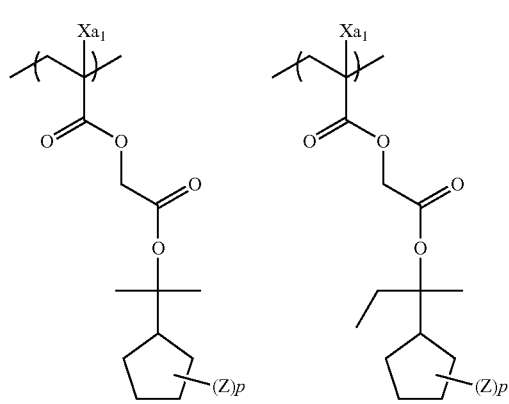
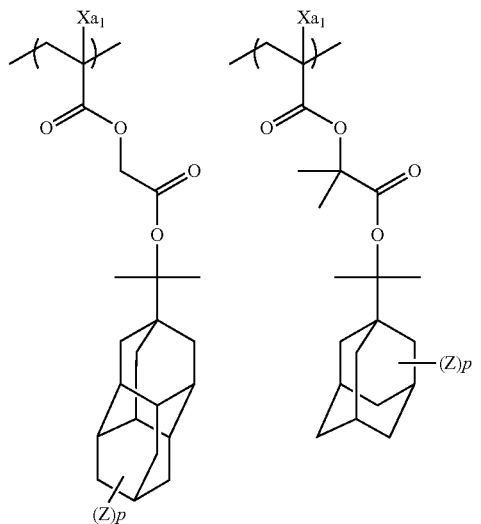
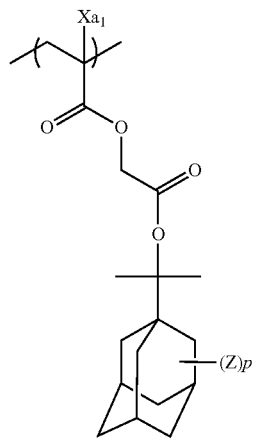
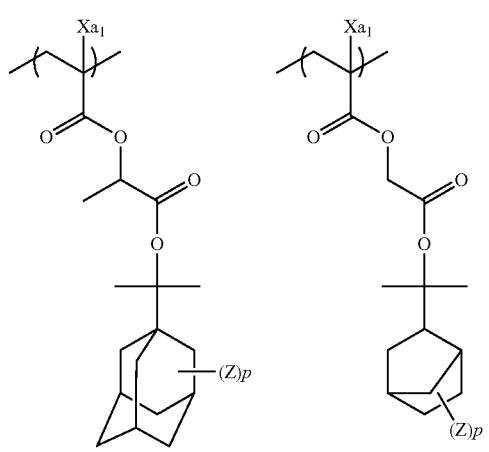

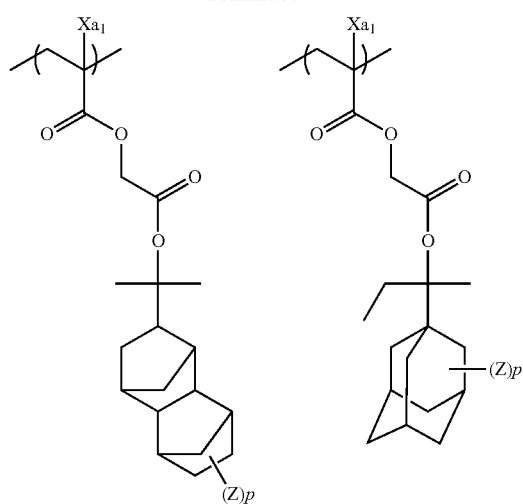
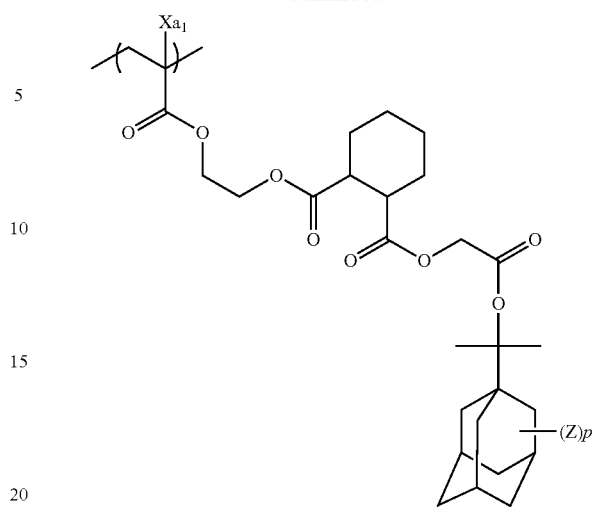
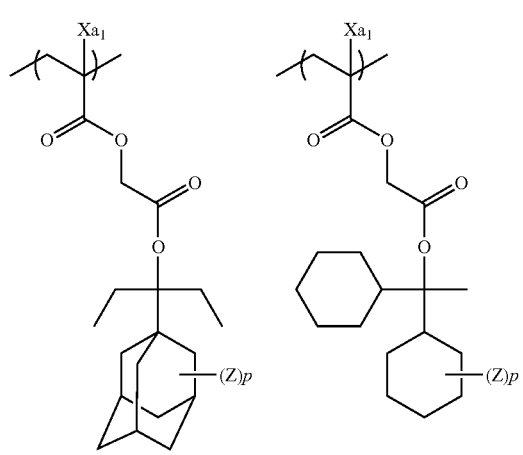
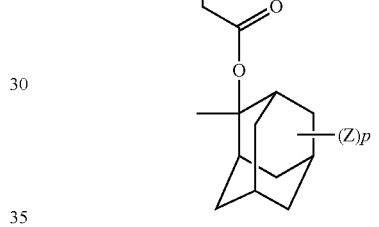
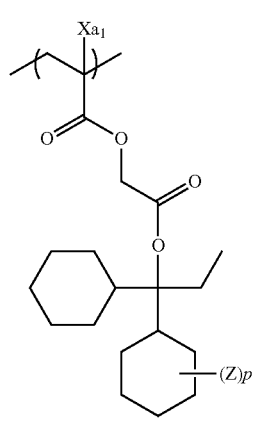
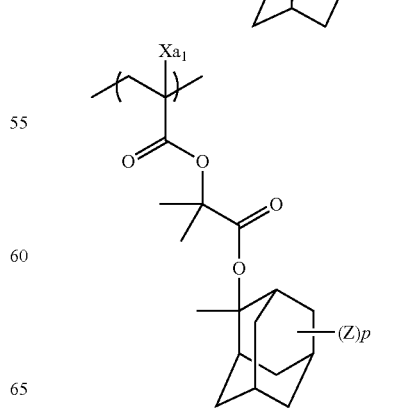

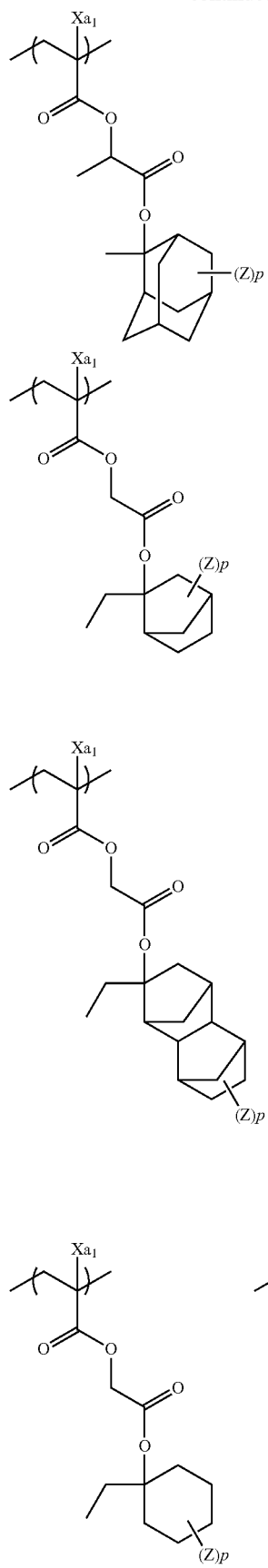
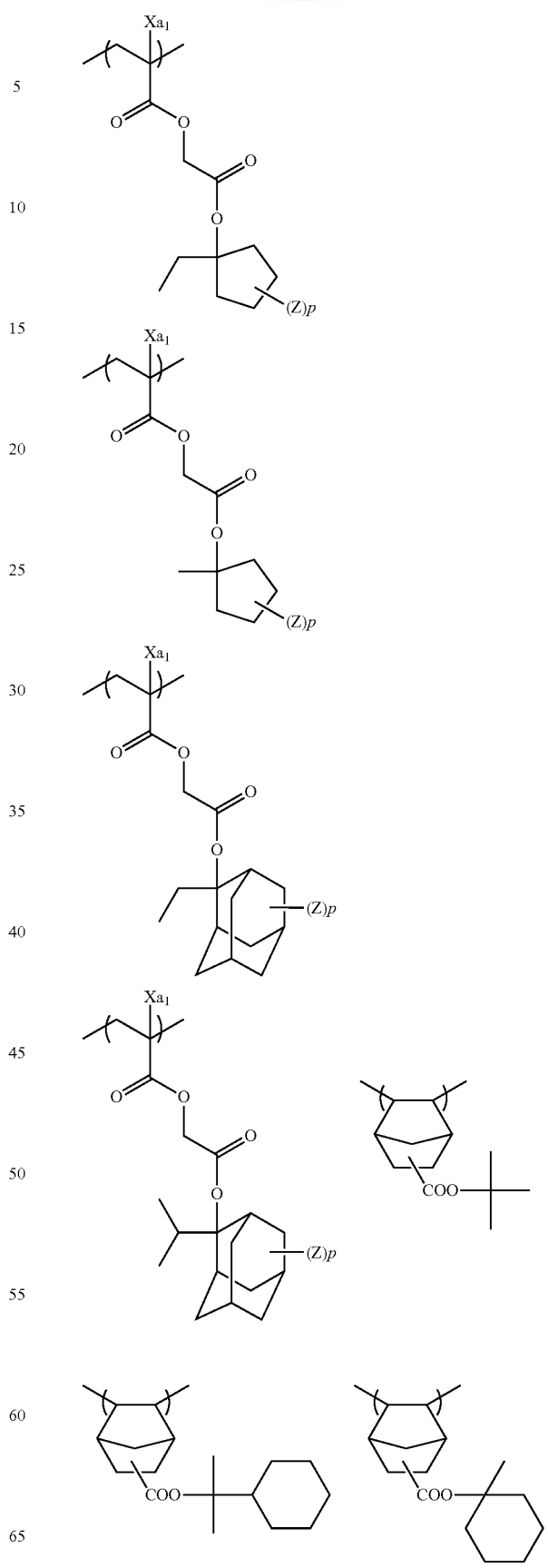

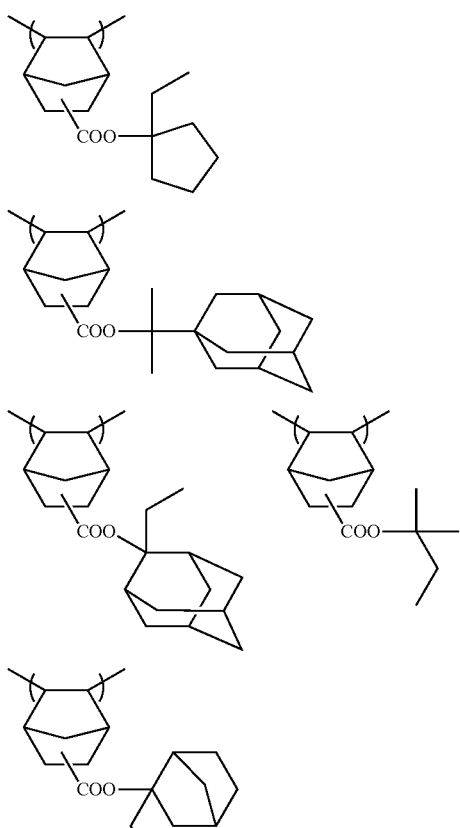
In the following particular examples, Xa represents a hydrogen atom, an alkyl group, a cyano group or a halogen atom.
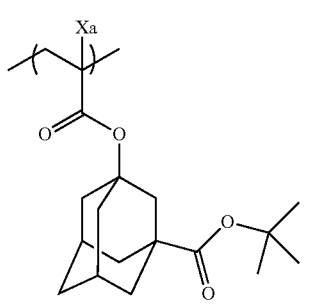
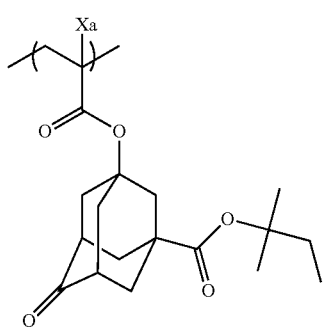
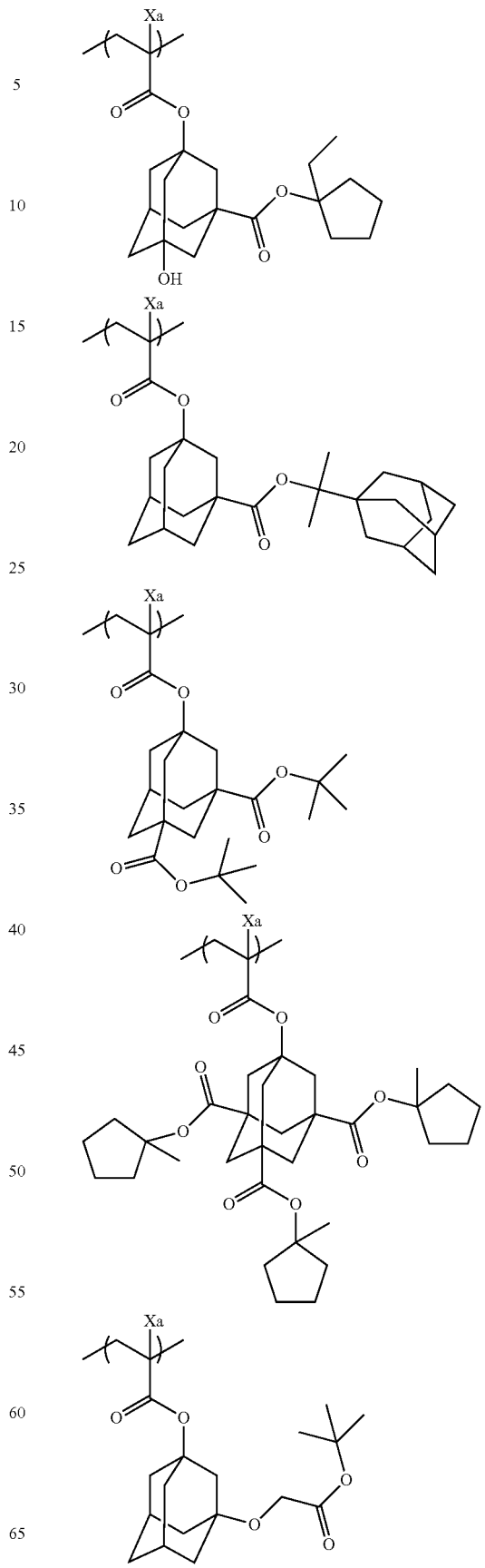

35
-continued
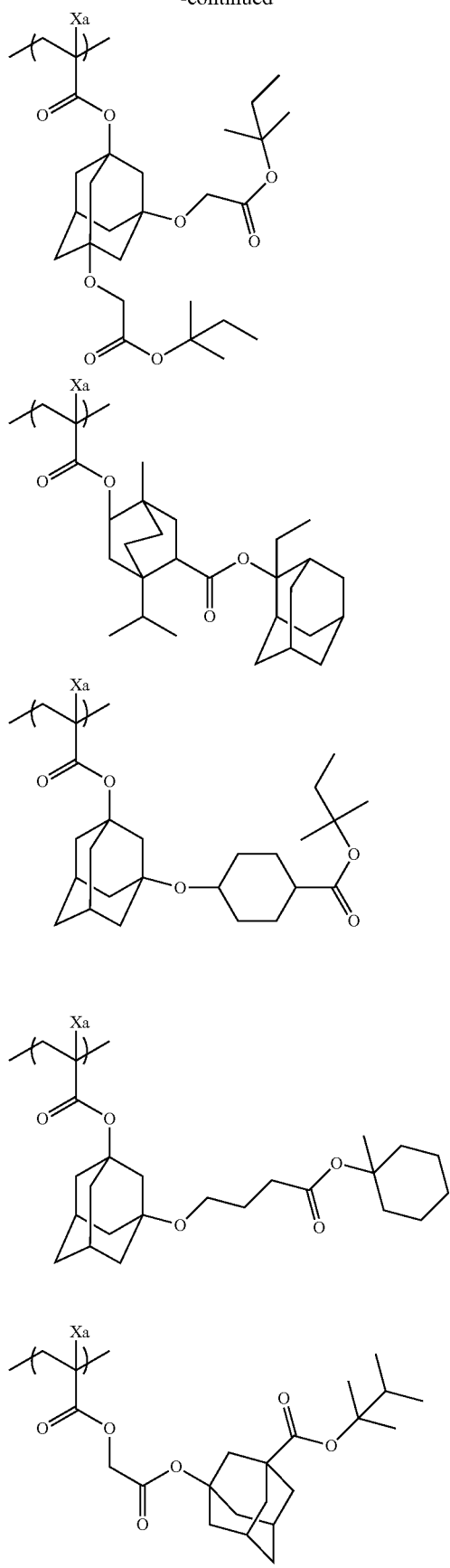
36
-continued
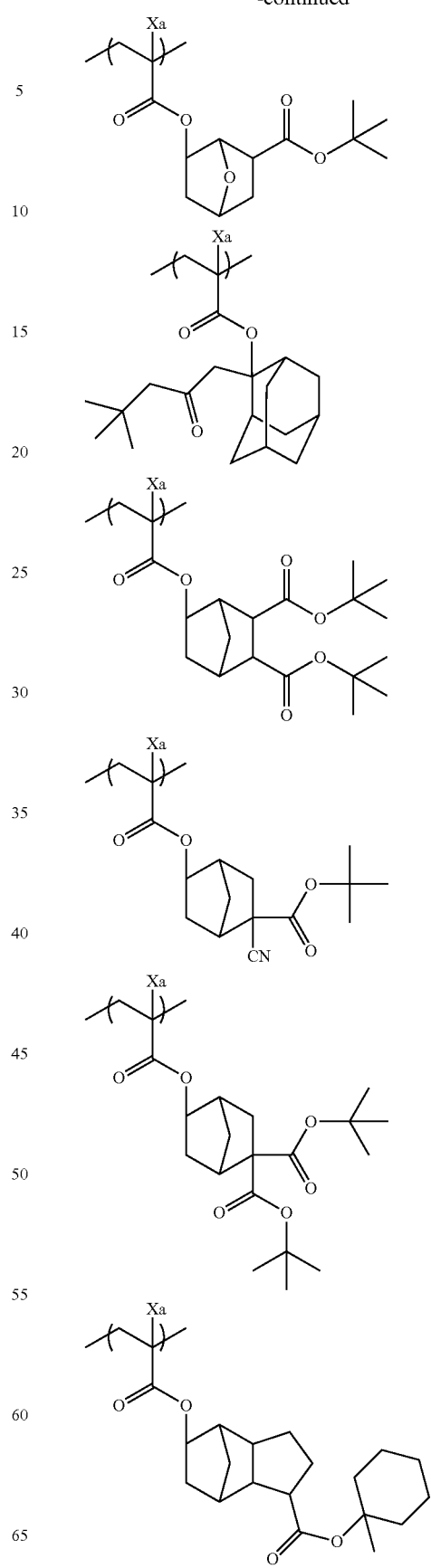

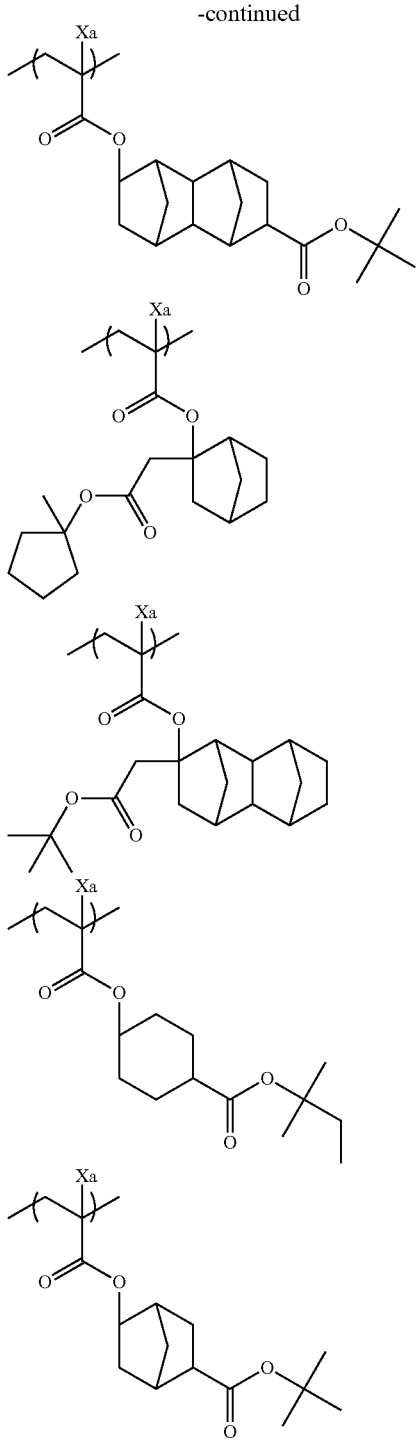

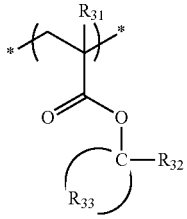

(aII)

In general formula (aII), $R_{31}$ represents a hydrogen atom or an alkyl group.

$R_{32}$ represents a methyl group, an ethyl group, an n-propyl group, an isopropyl group, an n-butyl group, an isobutyl group or a sec-butyl group.

$R_{33}$ represents an atomic group required for forming a monoalicyclic hydrocarbon structure in cooperation with the carbon atom to which $R_{32}$ is bonded. In the alicyclic hydrocarbon structure, the carbon atoms constructing the ring may partially be replaced by a heteroatom or a group containing a heteroatom.

The sum of carbon atoms in $R_{32}$ and $R_{33}$ is up to 8.

A substituent may be introduced in the alkyl group represented by $R_{31}$. The substituent is, for example, a fluorine atom or a hydroxyl group.

$R_{31}$ is preferably a hydrogen atom, a methyl group, a trifluoromethyl group or a hydroxymethyl group.

$R_{32}$ is preferably a methyl group, an ethyl group, an n-propyl group or an isopropyl group. $R_{32}$ is more preferably a methyl group or an ethyl group.

The monoalicyclic hydrocarbon structure formed by $R_{33}$ in cooperation with the carbon atom is preferably a 3- to 8-membered ring, more preferably a 5- or 6-membered ring.

In the monoalicyclic hydrocarbon structure formed by $R_{33}$ in cooperation with the carbon atom, the heteroatom as a constituent of the ring is, for example, an oxygen atom or a sulfur atom. As the group containing a heteroatom, there can be mentioned a carbonyl group or the like. Preferably, the group containing a heteroatom is not an ester group (ester bond).

It is preferred for the monoalicyclic hydrocarbon structure formed by $R_{33}$ in cooperation with the carbon atom to be comprised only of a carbon atom and a hydrogen atom.

The resin (A) in its other form may contain a repeating unit (aIII) containing an acid-decomposable moiety containing a polycyclic structure, in which the moiety to be decomposed under the action of an acid has 10 to 20 carbon atoms, as a repeating unit containing an acid-decomposable group.

The repeating unit (aIII) containing an acid-decomposable moiety containing a polycyclic structure, in which the acid-decomposable moiety has 10 to 20 carbon atoms, preferably has a form in which one of $Rx_1$, $Rx_2$ and $Rx_3$ in general formula (aI) above is a group with an adamantane skeleton while the other two are linear or branched alkyl groups, or a form in which two of $Rx_1$, $Rx_2$ and $Rx_3$ in general formula (aI) above are bonded to each other to thereby produce an adamantane structure while the other one is a linear or branched alkyl group.

The resin (A) may further contain any of repeating units of formulae below that when acted on by an acid, are decomposed to thereby produce an alcoholic hydroxyl group as a repeating unit containing an acid-decomposable group.

In the following particular examples, $Xa_1$ represents a hydrogen atom, $CH_3$, $CF_3$ or $CH_2OH$.

The resin (A) in its one form preferably contains a repeating unit in which the sum of carbon atoms in a moiety to be decomposed under the action of an acid is in the range of 4 to 9 as a repeating unit containing an acid-decomposable group. The resin (A) in its more preferred form contains any of repeating units of general formula (aI) above in which the sum of carbon atoms in a —C($Rx_1$)($Rx_2$)($Rx_3$) is in the range of 4 to 9.

In a further more preferred form, all of $Rx_1$, $Rx_2$ and $Rx_3$ in general formula (aI) are methyl or ethyl groups, or the general formula is expressed by general formula (aII) below.

-continued
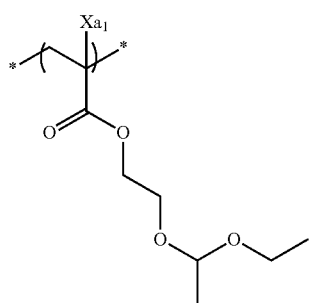
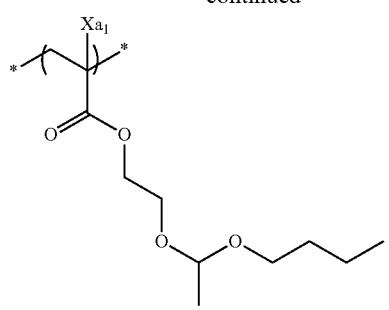
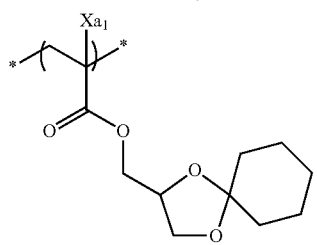
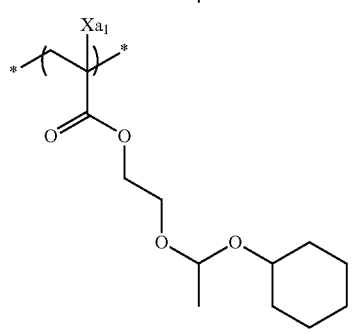
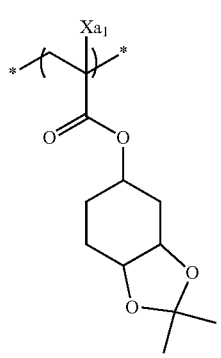
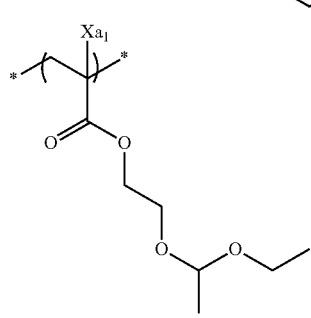
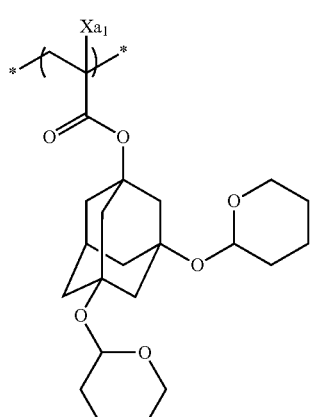
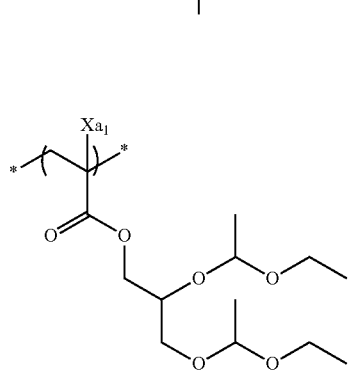
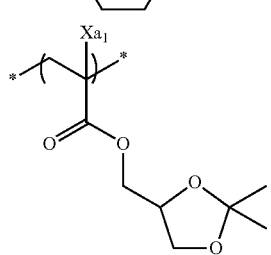
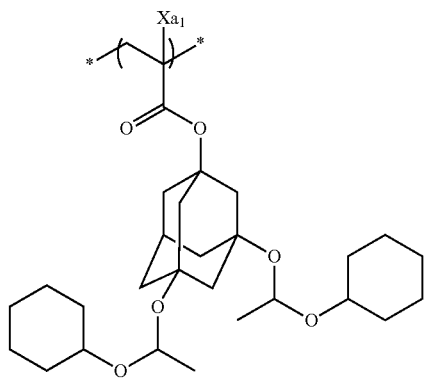

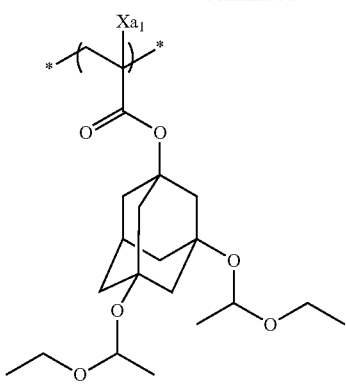
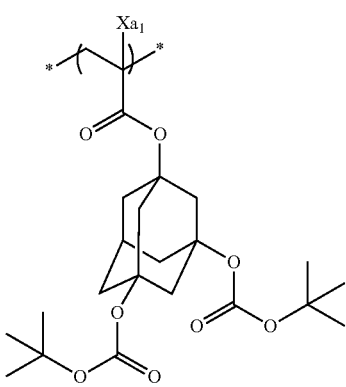
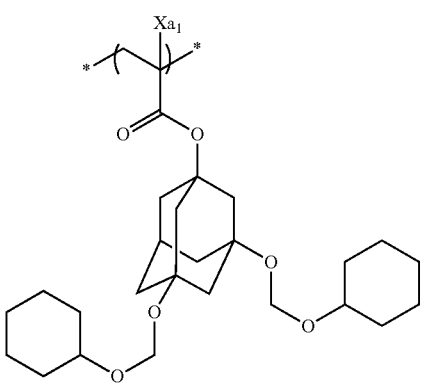
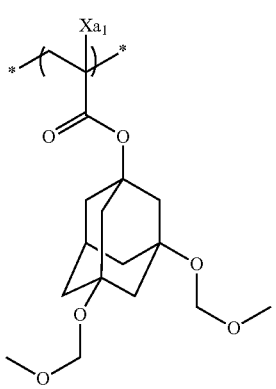

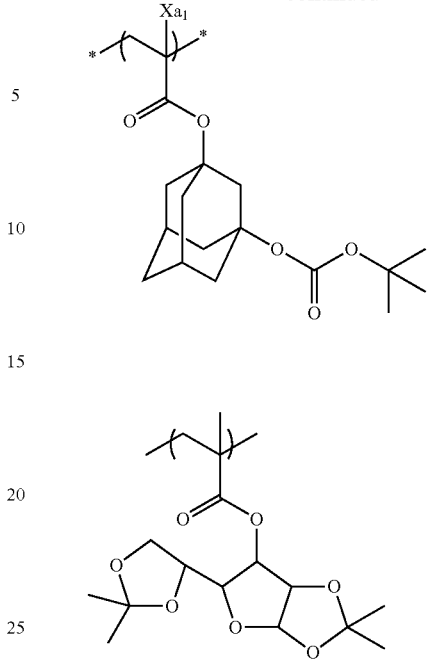
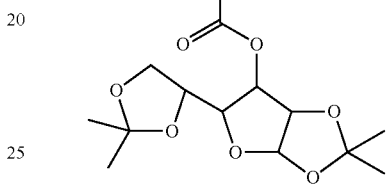

With respect to the repeating unit containing an acid-decomposable group, one type thereof may be introduced, or two or more types thereof may be jointly introduced in the resin (A).

When two or more types of repeating units each containing an acid-decomposable group are jointly introduced in the resin (A), in a particular preferred form, all of $Rx_1$, $Rx_2$ and $Rx_3$ in general formula (aI) above are methyl or ethyl groups. In a particular other preferred form, the above-mentioned repeating unit with a structure of general formula (aII) is combined with the above-mentioned repeating unit (aIII) containing an acid-decomposable moiety containing a polycyclic structure, in which the acid-decomposable moiety has 10 to 20 carbon atoms.

The total amount of repeating units each containing an acid-decomposable group, based on all the repeating units constituting the resin (A), is preferably in the range of 30 to 80 mol %, more preferably 40 to 75 mol %, further more preferably 45 to 70 mol % and most preferably 50 to 70 mol %.

The content of any of repeating units of general formula (aI), based on all the repeating units constituting the resin (A), is preferably in the range of 30 to 80 mol %, more preferably 40 to 75 mol %, further more preferably 45 to 70 mol % and most preferably 50 to 70 mol %.

The ratio of repeating unit (aIII) to all the repeating units each containing an acid-decomposable group is preferably in the range of 3 to 50 mol %, more preferably 5 to 40 mol % and most preferably 5 to 30 mol %.

[Repeating Unit with Cyclic Carbonic Acid Ester Structure]

The resin (A) may contain a repeating unit with a cyclic carbonic acid ester structure.

It is preferred for the repeating unit with a cyclic carbonic acid ester structure to be any of repeating units of general formula (A-1) below.

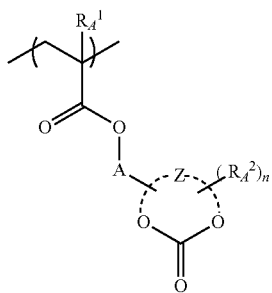

(A-1)

In general formula (A-1), $R_A^1$ represents a hydrogen atom or an alkyl group.

$R_A^2$, each independently when n is 2 or greater, represents a substituent.

A represents a single bond or a bivalent connecting group.

Z represents an atomic group forming a mono- or polycyclic structure in cooperation with a group expressed by —O—C(=O)—O— in the formula; and n is an integer of 0 or greater.

General formula (A-1) will be described in detail below.

A substituent, such as a fluorine atom, may be introduced in the alkyl group represented by $R_A^1$. $R_A^1$ is preferably a hydrogen atom, a methyl group or a trifluoromethyl group, more preferably a methyl group.

Examples of the substituents represented by $R_A^2$ include an alkyl group, a cycloalkyl group, a hydroxyl group, an alkoxy group, an amino group and an alkoxycarbonylamino group. The substituent represented by $R_A^2$ is preferably an alkyl group having 1 to 5 carbon atoms. As such, there can be mentioned, for example, a linear alkyl group having 1 to 5 carbon atoms, or a branched alkyl group having 3 to 5 carbon atoms. A substituent, such as a hydroxyl group, may be introduced in the alkyl group.

In the formula, n is an integer of 0 or greater, representing the number of substituents. For example, n is preferably 0 to 4, more preferably 0.

As the bivalent connecting group represented by A, there can be mentioned, for example, an alkylene group, a cycloalkylene group, an ester bond, an amide bond, an ether bond, a urethane bond, a urea bond, a combination of these or the like. The alkylene group is preferably an alkylene group having 1 to 10 carbon atoms, more preferably an alkylene group having 1 to 5 carbon atoms.

In an aspect of the present invention, A is preferably a single bond or an alkylene group.

As the monocycle containing —O—C(=O)—O—, involving Z, there can be mentioned, for example, any of 5- to 7-membered rings of cyclic carbonic acid esters of general formula (a) below in which $n_A$ is 2 to 4. The monocycle is preferably a 5- or 6-membered ring ($n_A$ is 2 or 3), more preferably a 5-membered ring ($n_A$ is 2).

As the polycycle containing —O—C(=O)—O—, involving Z, there can be mentioned, for example, a structure in which a condensed ring, or a spiro ring, is formed by any of cyclic carbonic acid esters of general formula (a) below in cooperation with one, or two, or more other ring structures. The "other ring structure" capable of forming a condensed ring or a spiro ring may be an alicyclic hydrocarbon group, or an aromatic hydrocarbon group, or a heterocycle.

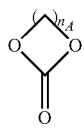

(a)

In the resin (A), one of the repeating units of general formula (A-1) may be contained alone, or two or more thereof may be contained.

The content of repeating unit with a cyclic carbonic acid ester structure (preferably any of repeating units of general formula (A-1)) in the resin (A), based on all the repeating units of the resin (A), is preferably in the range of 3 to 80 mol %, more preferably 3 to 60 mol %, further more preferably 3 to 30 mol % and most preferably 10 to 15 mol %. The resist satisfying this content can achieve enhanced developability, low defect occurrence, low LWR, low PEB temperature dependence, profile, etc.

Particular examples of the repeating units of general formula (A-1) are shown below, which in no way limit the scope of the present invention.

In the following particular examples, $R_A^1$ is as defined above in connection with general formula (A-1).

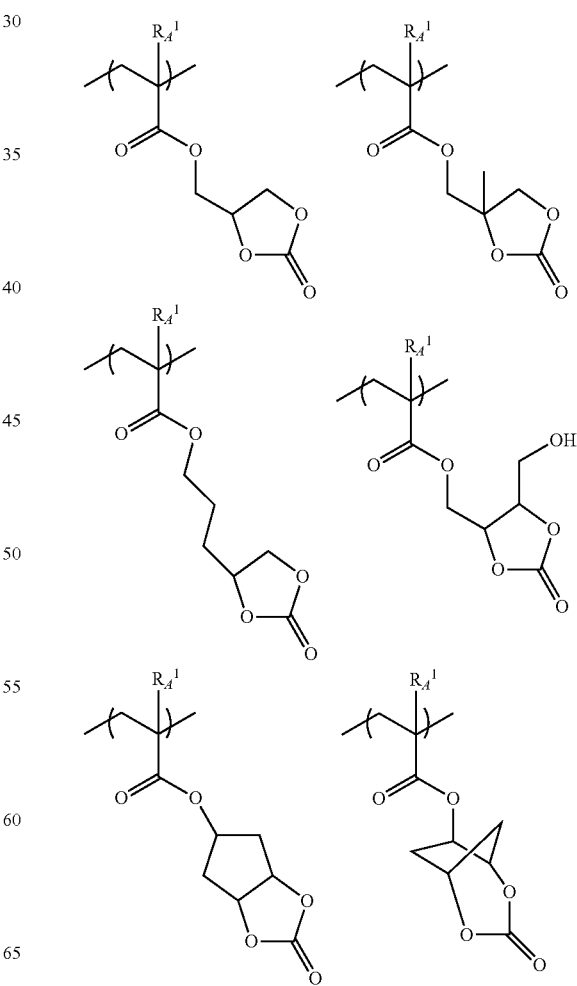

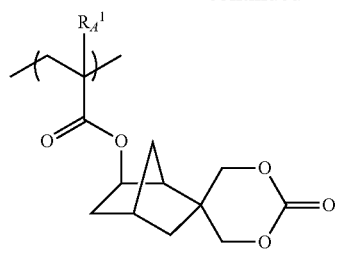
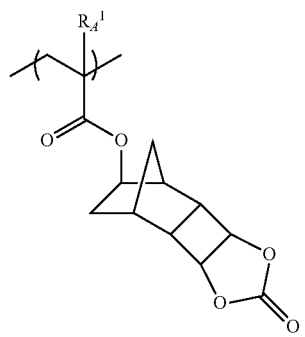
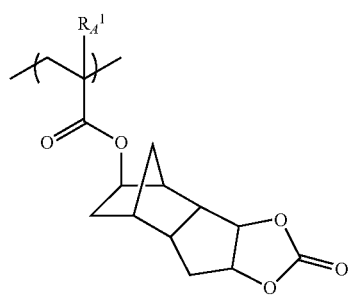
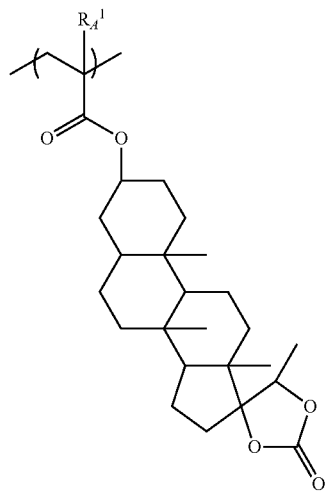
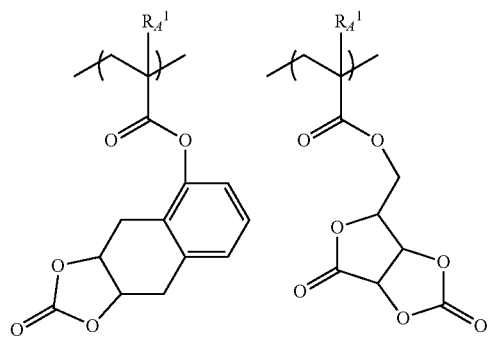
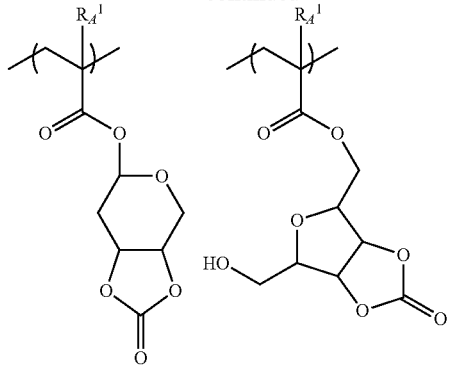
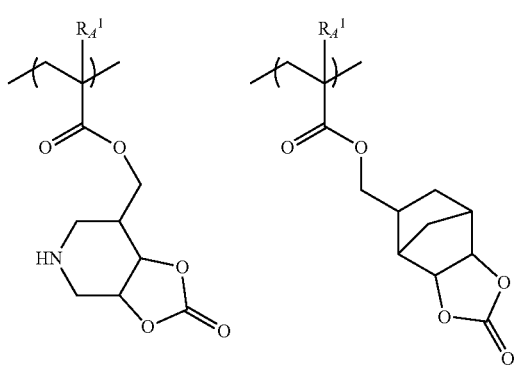
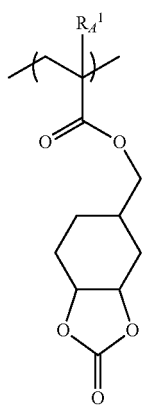

[Repeating unit containing a hydroxyl group, a cyano group or a carbonyl group]

The resin (A) may contain a repeating unit containing a hydroxyl group, a cyano group or a carbonyl group. This enhances the adhesion to substrate and developer affinity.

From the viewpoint of the effect of the present invention, it is preferred for the resin (A) to contain none of repeating units of general formula (3) below. For example, the content of any of repeating units of general formula (3), based on all the repeating units constituting the resin (A), is preferably 0 to 5 mol %, more preferably 0 to 3 mol % and most preferably 0 mol %.

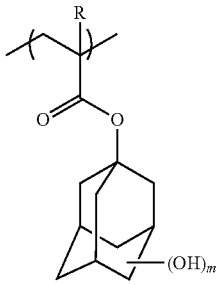

(3)

In the formula, m is an integer of 1 to 3, and R represents a hydrogen atom or an alkyl group.

A substituent may be introduced in the alkyl group represented by R. The substituent is a hydroxyl group, an alkoxy group, a carboxyl group, an alkoxycarbonyl group, an aminocarbonyl group, a sulfonyl group, a sulfoxyl group, a nitrile group, a nitro group or a sulfonic acid group.

The repeating unit containing a hydroxyl group, a cyano group or a carbonyl group is preferably a repeating unit having an alicyclic hydrocarbon structure substituted with a hydroxyl group, a cyano group or a carbonyl group, which repeating unit preferably contains no acid-decomposable group.

It is preferred for the repeating unit containing an alicyclic hydrocarbon structure substituted with a hydroxyl group, a cyano group or a carbonyl group to be different from the repeating units containing an acid-decomposable group (namely, repeating unit being stable against acids preferred).

In the alicyclic hydrocarbon structure substituted with a hydroxyl group, a cyano group or a carbonyl group, the alicyclic hydrocarbon structure is preferably an adamantyl group, a diadamantyl group or a norbornane group.

More preferably, there can be mentioned the repeating units of general formulae (AIIa) to (AIIc) below, which exclude the repeating units of general formula (3) above.

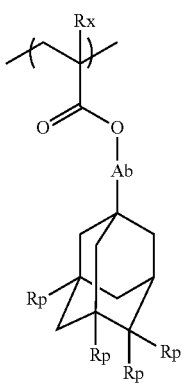

(AIIa)

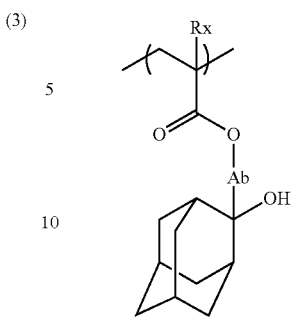

(AIIb)

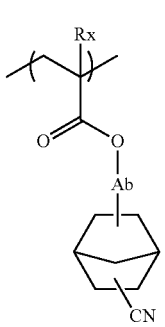

(AIIc)

In the formulae, Rx represents a hydrogen atom, a methyl group, a hydroxymethyl group or a trifluoromethyl group.

Ab represents a single bond or a bivalent connecting group.

As the bivalent connecting group represented by Ab, there can be mentioned, for example, an alkylene group, a cycloalkylene group, an ester bond, an amide bond, an ether bond, a urethane bond, a urea bond, a combination of these or the like. The alkylene group is preferably an alkylene group having 1 to 10 carbon atoms, more preferably an alkylene group having 1 to 5 carbon atoms. For example, there can be mentioned a methylene group, an ethylene group, a propylene group or the like.

In an aspect of the present invention, Ab is preferably a single bond or an alkylene group.

Rp represents a hydrogen atom, a hydroxyl group or a hydroxyalkyl group. Two or more Rp's may be identical to or different from each other, provided that at least one of two or more Rp's is a hydroxyl group or a hydroxyalkyl group.

It is optional for the resin (A) to contain the repeating unit containing a hydroxyl group, a cyano group or a carbonyl group. When the resin (A) contains the repeating unit containing a hydroxyl group, a cyano group or a carbonyl group, the content of repeating unit containing a hydroxyl group, a cyano group or a carbonyl group (excluding the repeating units of general formula (3) above), based on all the repeating units of the resin (A), is preferably in the range of 1 to 40 mol %, more preferably 3 to 30 mol % and further more preferably 5 to 25 mol %.

Particular examples of the repeating units each containing a hydroxyl group or a cyano group are shown below, which in no way limit the scope of the present invention.

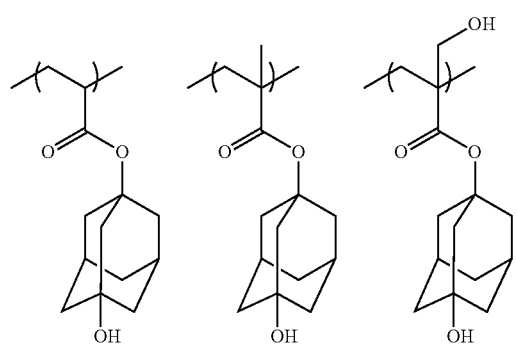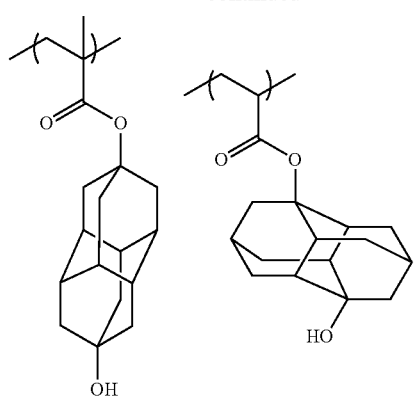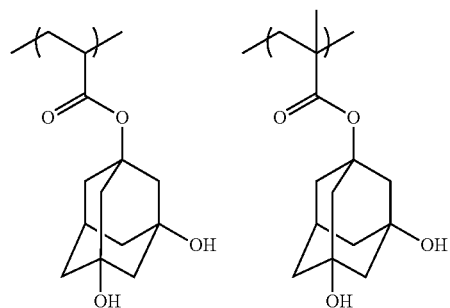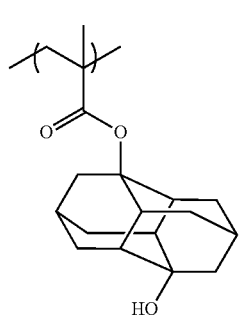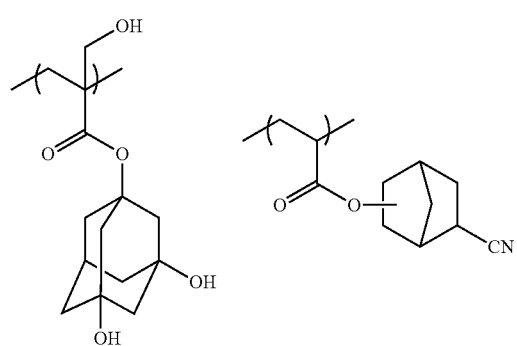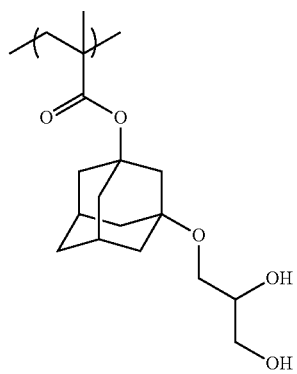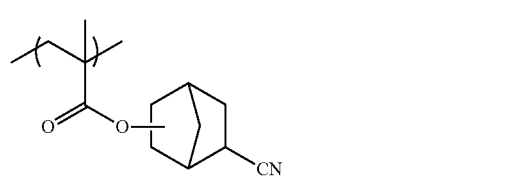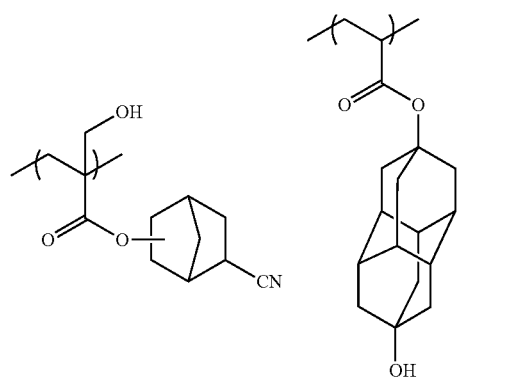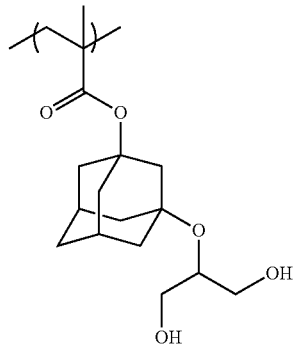

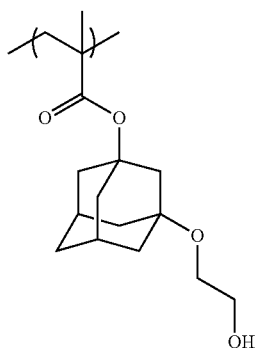

The repeating unit containing a hydroxyl group, a cyano group or a carbonyl group is more preferably any of carbonyl-group-containing repeating units of general formulae (AIIIa) and (AIIIb) below.

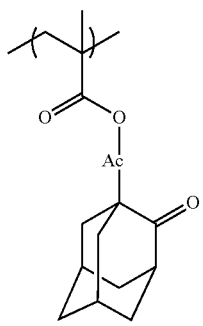

(AIIIa)

(AIIIb)

In general formulae (AIIIa) and (AIIIb) above, Ac represents a single bond or a bivalent connecting group. Preferred examples thereof are the same as those of Ab set forth above in connection with the repeating units of (AIIa) to (AIIc).

Particular examples of the repeating units of general formulae (AIIIa) and (AIIIb) above are shown below, which in no way limit the scope of the present invention.

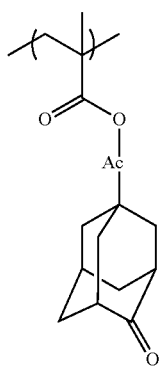

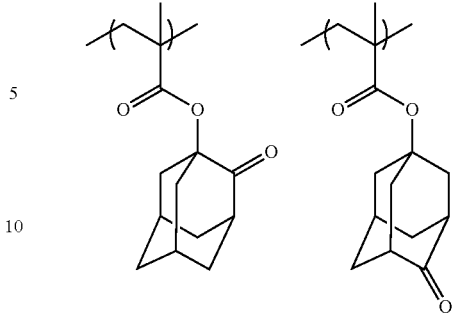

In addition, appropriate use can be made of the monomers, and repeating units corresponding thereto, set forth in section [0011] et seq. of International Publication No. 2011/122336.

[Repeating Unit Containing an Acid Group]

The resin (A) may contain a repeating unit containing an acid group. As the acid group, there can be mentioned a carboxyl group, a sulfonamido group, a sulfonylimido group, a bissulfonylimido group, a naphthol structure, or an aliphatic alcohol substituted at its α-position with an electron-withdrawing group (for example, a hexafluoroisopropanol group). It is preferred to contain a repeating unit containing a carboxyl group. The incorporation of the repeating unit containing an acid group enhances the resolution in, for example, contact hole usage. The repeating unit containing an acid group is preferably any of a repeating unit wherein the acid group is directly bonded to the principal chain of a resin such as a repeating unit of acrylic acid or methacrylic acid, a repeating unit wherein the acid group is bonded via a connecting group to the principal chain of a resin and a repeating unit wherein the acid group is introduced in a terminal of a polymer chain by the use of a chain transfer agent or polymerization initiator containing the acid group in the stage of polymerization. The connecting group may have a mono- or polycyclohydrocarbon structure. The repeating unit of acrylic acid or methacrylic acid is especially preferred.

It is optional for the resin (A) to contain the repeating unit containing an acid group. When the repeating unit containing an acid group is contained in the resin (A), the content thereof based on all the repeating units of the resin (A) is preferably up to 25 mol %, more preferably up to 20 mol %. When the repeating unit containing an acid group is contained in the resin (A), the content thereof is generally 1 mol % or greater.

Particular examples of the repeating units each containing an acid group are shown below, which in no way limit the scope of the present invention.

In the particular examples, Rx represents H, $CH_3$, $CH_2OH$ or $CF_3$.

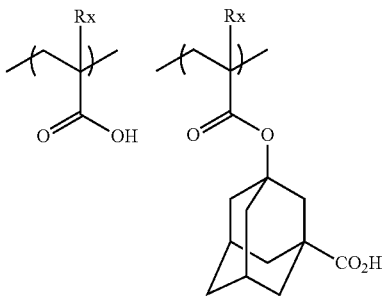

-continued

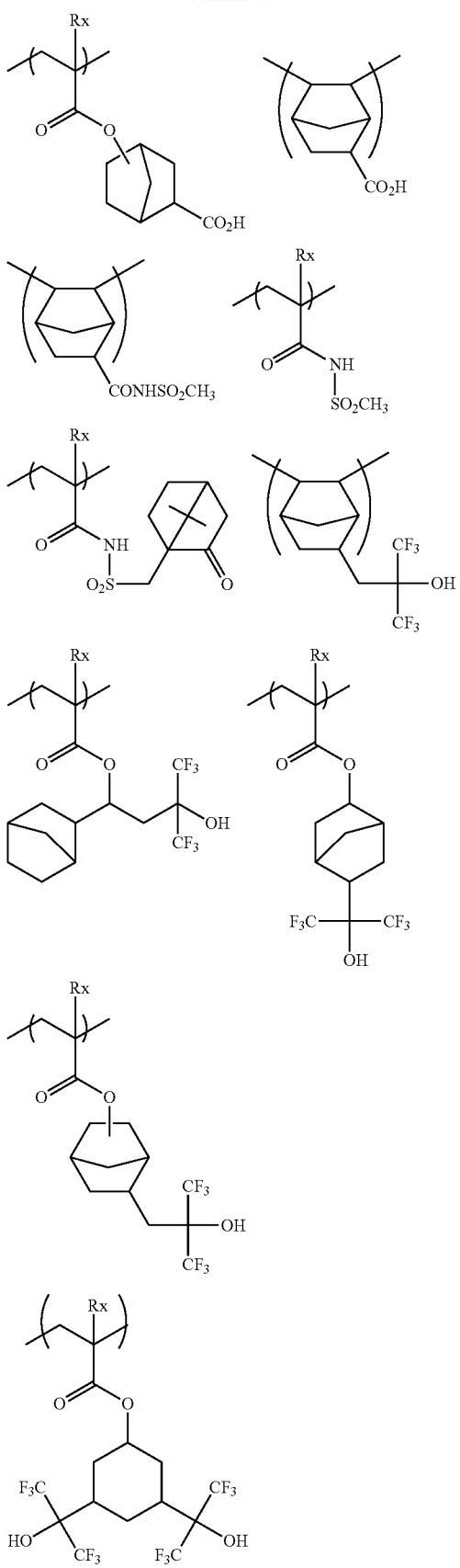

-continued

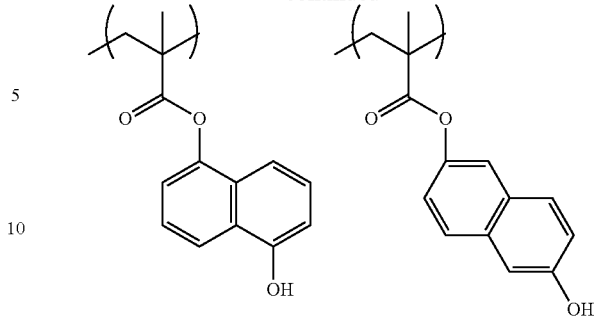

[Repeating Unit Having an Alicyclic Hydrocarbon Structure in which No Polar Group is Introduced and Exhibiting No Acid-Decomposability]

The resin (A) according to the present invention can further contain a repeating unit having an alicyclic hydrocarbon structure in which no polar group (for example, the above acid group, hydroxyl group or cyano group) is introduced and exhibiting no acid-decomposability. This makes it feasible to reduce any leaching of low-molecular components from the resist film into the immersion liquid in the stage of liquid-immersion exposure and further to appropriately regulate the solubility of the resin in the stage of development using a developer comprising an organic solvent. As such a repeating unit, there can be mentioned any of repeating units of general formula (IV) below.

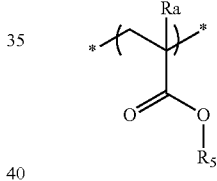

(IV)

In general formula (IV) above, $R_5$ represents a hydrocarbon group having at least one cyclic structure in which no polar group is introduced.

Ra represents a hydrogen atom, an alkyl group or a group of the formula —$CH_2$—O—$Ra_2$. In this formula, $Ra_2$ represents a hydrogen atom, an alkyl group or an acyl group. Ra is preferably a hydrogen atom, a methyl group, a hydroxymethyl group or a trifluoromethyl group, most preferably a hydrogen atom or a methyl group.

The cyclic structures introduced in $R_5$ include a monocyclic hydrocarbon group and a polycyclic hydrocarbon group. As the monocyclic hydrocarbon group, there can be mentioned, for example, a cycloalkyl group having 3 to 12 carbon atoms, such as a cyclopentyl group, a cyclohexyl group, a cycloheptyl group or a cyclooctyl group, or a cycloalkenyl group having 3 to 12 carbon atoms, such as a cyclohexenyl group. Preferably, the monocyclic hydrocarbon group is a monocyclic hydrocarbon group having 3 to 7 carbon atoms. A cyclopentyl group and a cyclohexyl group are more preferred.

The polycyclic hydrocarbon groups include ring-assembly hydrocarbon groups and crosslinked-ring hydrocarbon groups. Examples of the ring-assembly hydrocarbon groups include a bicyclohexyl group and a perhydronaphthalenyl group. As the crosslinked-ring hydrocarbon rings, there can be mentioned, for example, bicyclic hydrocarbon rings, such as pinane, bornane, norpinane, norbornane and bicyclooctane rings (e.g., bicyclo[2.2.2]octane ring or bicyclo[3.2.1]octane ring); tricyclic hydrocarbon rings, such as homobledane, adamantane, tricyclo[5.2.1.0$^{2,6}$]decane and tricyclo[4.3.1.1$^{2,5}$]undecane rings; and tetracyclic hydrocarbon rings, such as tetracyclo[4.4.0.1$^{2,5}$. 1$^{7,10}$]dodecane and perhydro-1,4-methano-5,8-methanonaphthalene rings. Further, the crosslinked-ring hydrocarbon rings include condensed-ring hydrocarbon rings, for example, condensed rings resulting from the condensation of a plurality of 5- to 8-membered cycloalkane rings, such as perhydronaphthalene (decalin), perhydroanthracene, perhydrophenanthrene, perhydroacenaphthene, perhydrofluorene, perhydroindene and perhydrophenalene rings.

As preferred crosslinked-ring hydrocarbon rings, there can be mentioned a norbornyl group, an adamantyl group, a bicyclooctanyl group, a tricyclo[5,2,1,0$^{2,6}$]decanyl group and the like. As more preferred crosslinked-ring hydrocarbon rings, there can be mentioned a norbornyl group and an adamantyl group.

Substituents may be introduced in these alicyclic hydrocarbon groups. As preferred substituents, there can be mentioned a halogen atom, an alkyl group, a hydroxyl group having its hydrogen atom replaced, an amino group having its hydrogen atom replaced and the like.

It is optional for the resin (A) to contain the repeating unit having an alicyclic hydrocarbon structure in which no polar group is introduced and exhibiting no acid-decomposability. When this repeating unit is contained, the content thereof based on all the repeating units of the resin (A) is preferably in the range of 1 to 50 mol %, more preferably 5 to 50 mol %.

Particular examples of the repeating units each having an alicyclic hydrocarbon structure in which no polar group is introduced and exhibiting no acid-decomposability are shown below, which in no way limit the scope of the present invention. In the formulae, Ra represents H, CH$_3$, CH$_2$OH or CF$_3$.

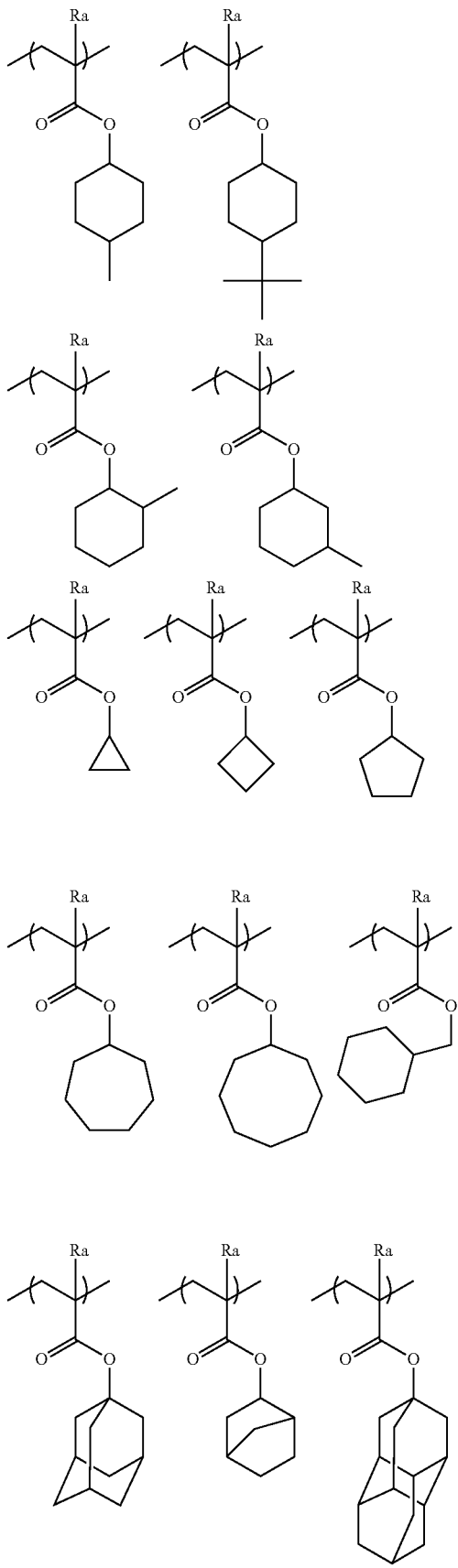

-continued

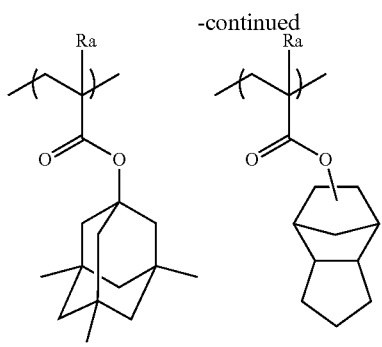

[Repeating Unit Containing an Aromatic Ring]

When the composition of the present invention is exposed to a KrF excimer laser light, electron beams, X-rays or high-energy rays of wavelength 50 nm or shorter (for example, EUV), it is preferred for the resin (A) to contain a repeating unit containing an aromatic ring, typified by a hydroxystyrene repeating unit.

Particular examples of the resins (A) each containing a repeating unit containing an aromatic ring are shown below.

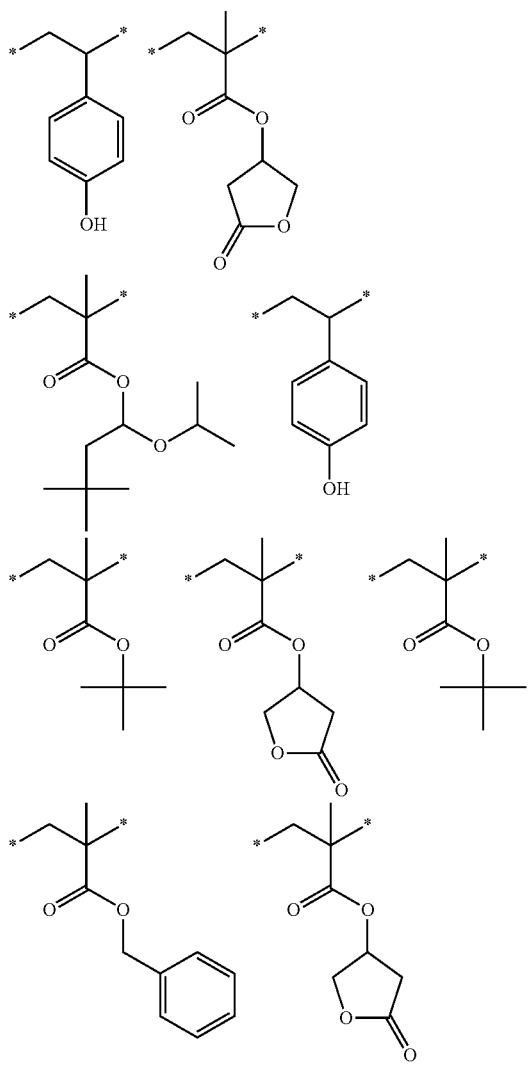

-continued

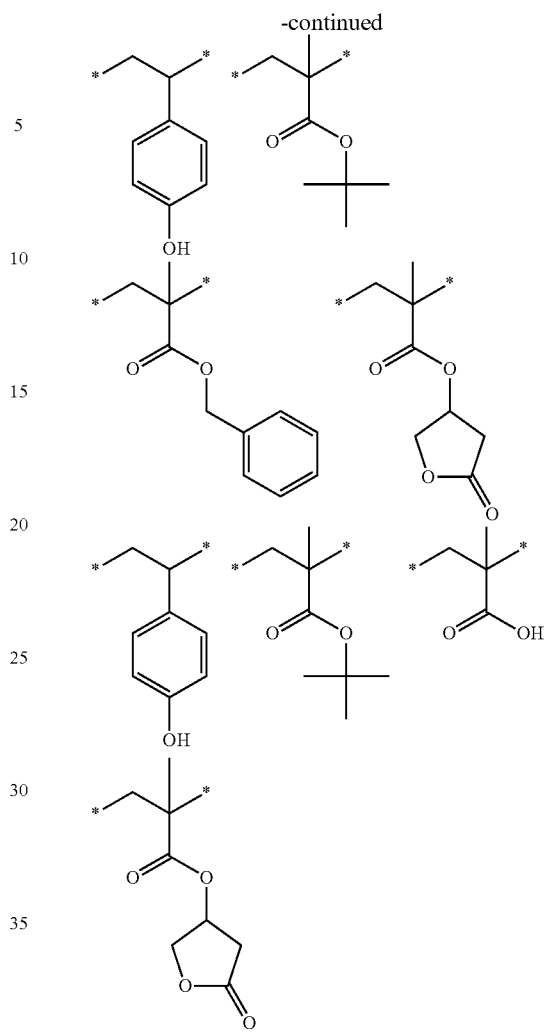

The resin (A) for use in the composition of the present invention can contain, in addition to the foregoing repeating structural units, various repeating structural units for the purpose of regulating the dry etching resistance, standard developer adaptability, substrate adhesion, resist profile and generally required properties of the actinic-ray- or radiation-sensitive resin composition such as resolving power, heat resistance and sensitivity.

As such repeating structural units, there can be mentioned those corresponding to the following monomers, which are nonlimiting.

The incorporation of such repeating structural units attains fine regulation of the required properties of the resin for use in the composition of the present invention, especially:

(1) solubility in application solvents,
(2) film forming easiness (glass transition point),
(3) alkali developability,
(4) film thinning (selections of hydrophilicity/hydrophobicity and alkali-soluble group),
(5) adhesion of unexposed area to substrate,
(6) dry etching resistance, etc.

As appropriate monomers, there can be mentioned, for example, compounds each having one unsaturated bond capable of addition polymerization, selected from among acrylic esters, methacrylic esters, acrylamides, methacrylamides, allyl compounds, vinyl ethers, vinyl esters and the like.

In addition, any unsaturated compound capable of addition polymerization that is copolymerizable with monomers corresponding to the above various repeating structural units may be copolymerized therewith.

In the resin (A) for use in the composition of the present invention, the molar ratios of individual repeating structural units contained are appropriately determined from the viewpoint of regulating the dry etching resistance, standard developer adaptability, substrate adhesion and resist profile of the actinic-ray- or radiation-sensitive resin composition and generally required properties of the actinic-ray- or radiation-sensitive resin composition such as resolving power, heat resistance and sensitivity.

When the composition of the present invention is one for ArF exposure, from the viewpoint of transparency to ArF light, it is preferred for the resin (A) for use in the composition of the present invention to contain substantially no aromatic ring (in particular, the ratio of repeating unit containing an aromatic group in the resin is preferably 5 mol % or less, more preferably 3 mol % or less, and ideally 0 mol %, namely, containing no aromatic group). It is preferred for the resin (A) to have a mono- or polyalicyclic hydrocarbon structure.

The resin (A) according to the present invention may have any of the random, block, comb and star forms. The resin (A) can be synthesized by, for example, the radical, cation or anion polymerization of unsaturated monomers corresponding to given structures. Alternatively, the intended resin can be obtained by first polymerizing unsaturated monomers corresponding to the precursors of given structures and thereafter carrying out a polymer reaction.

When the composition of the present invention contains a hydrophobic resin (HR) to be described hereinafter, it is preferred for the resin (A) to contain neither a fluorine atom nor a silicon atom (in particular, the ratio of repeating unit containing a fluorine atom or a silicon atom in the resin is preferably 5 mol % or less, more preferably 3 mol % or less, and ideally 0 mol %) from the viewpoint of the compatibility with the hydrophobic resin (HR).

In the resin (A) for use in the composition of the present invention, preferably, all the repeating units thereof are comprised of (meth)acrylate repeating units. In that instance, use can be made of any of a resin wherein all the repeating units are comprised of methacrylate repeating units, a resin wherein all the repeating units are comprised of acrylate repeating units and a resin wherein all the repeating units are comprised of methacrylate repeating units and acrylate repeating units. However, it is preferred for the acrylate repeating units to account for 50 mol % or less of all the repeating units.

The resin (A) according to the present invention can be synthesized in accordance with routine methods (for example, methods conventionally employed in the field of polymer synthesis, such as radical polymerization, living radical polymerization, anion polymerization and cation polymerization). As general synthesizing methods, there can be mentioned, for example, a batch polymerization method in which a monomer species and an initiator are dissolved in a solvent and heated to thereby carry out polymerization, a dropping polymerization method in which a solution of monomer species and initiator is dropped into a heated solvent over a period of 1 to 10 hours, and the like. The dropping polymerization method is preferred. As a reaction solvent, there can be mentioned, for example, an ether such as tetrahydrofuran, 1,4-dioxane or diisopropyl ether, a ketone such as methyl ethyl ketone or methyl isobutyl ketone, an ester solvent such as ethyl acetate, an amide solvent such as dimethylformamide or dimethylacetamide, or the solvent capable of dissolving the composition of the present invention, such as propylene glycol monomethyl ether acetate, propylene glycol monomethyl ether or cyclohexanone, to be described hereinafter. Preferably, the polymerization is carried out with the use of the same solvent as that used in the photosensitive composition of the present invention. This inhibits any particle generation during storage.

The polymerization reaction is preferably carried out in an atmosphere comprised of an inert gas, such as nitrogen or argon. The polymerization is initiated by use of a commercially available radical initiator (azo initiator, peroxide, etc.) as a polymerization initiator. Among the radical initiators, an azo initiator is preferred, and azo initiators containing an ester group, a cyano group and a carboxyl group are especially preferred. As specific preferred initiators, there can be mentioned azobisisobutyronitrile, azobisdimethylvaleronitrile, dimethyl 2,2'-azobis(2-methylpropionate) and the like. If desirable, the initiator may be supplemented, or may be added in fractional amounts. After the completion of the reaction, the reaction liquid is poured into a solvent, and the intended polymer is recovered by a method of powder or solid recovery or the like. The reaction concentration is in the range of 5 to 50 mass %, preferably 10 to 30 mass %. The reaction temperature is generally in the range of 10 to 150° C., preferably 30 to 120° C. and more preferably 60 to 100° C.

After the completion of the reaction, the reaction mixture is allowed to stand still to cool to room temperature and purified. In the purification, use can be made of routine methods, such as a liquid-liquid extraction method in which residual monomers and oligomer components are removed by water washing or by the use of a combination of appropriate solvents, a method of purification in solution form such as ultrafiltration capable of extraction removal of only components of a given molecular weight or below, a re-precipitation method in which a resin solution is dropped into a poor solvent to thereby coagulate the resin in the poor solvent and thus remove residual monomers, etc., and a method of purification in solid form such as washing of a resin slurry obtained by filtration with the use of a poor solvent.

For example, the reaction solution is brought into contact with a solvent wherein the resin is poorly soluble or insoluble (poor solvent) amounting to 10 or less, preferably 10 to 5 times the volume of the reaction solution to thereby precipitate the resin as a solid.

The solvent for use in the operation of precipitation or re-precipitation from a polymer solution (precipitation or re-precipitation solvent) is not limited as long as the solvent is a poor solvent for the polymer. Use can be made of any solvent appropriately selected from among a hydrocarbon, a halogenated hydrocarbon, a nitro compound, an ether, a ketone, an ester, a carbonate, an alcohol, a carboxylic acid, water, a mixed solvent containing these solvents and the like, according to the type of the polymer. Among these, a solvent containing at least an alcohol (especially, methanol, etc.) or water is preferably used as the precipitation or re-precipitation solvent.

The amount of precipitation or re-precipitation solvent used can be appropriately selected taking efficiency, yield, etc. into account. Generally, the amount is in the range of 100 to 10,000 parts by mass, preferably 200 to 2000 parts by mass and more preferably 300 to 1000 parts by mass per 100 parts by mass of polymer solution.

The temperature at which the precipitation or re-precipitation is carried out can be appropriately selected taking efficiency and operation easiness into account. Generally, the temperature is in the range of about 0 to 50° C., preferably about room temperature (for example, about 20 to 35° C.). The operation of precipitation or re-precipitation can be carried out by a routine method, such as a batch or continuous method, with the use of a customary mixing container, such as an agitation vessel.

The polymer resulting from the precipitation or re-precipitation is generally subjected to customary solid/liquid separation, such as filtration or centrifugal separation, and dried before use. The filtration is carried out with the use of a filter medium ensuring solvent resistance, preferably under pressure. The drying is performed at about 30 to 100° C., preferably about 30 to 50° C. under ordinary pressure or reduced pressure (preferably reduced pressure).

Alternatively, after the precipitation and separation of the resin, the resultant resin may be once more dissolved in a solvent and brought into contact with a solvent in which the resin is poorly soluble or insoluble. Specifically, the method may include the operations of, after the completion of the radical polymerization reaction, bringing the polymer into contact with a solvent wherein the polymer is poorly soluble or insoluble to thereby attain resin precipitation (operation a), separating the resin from the solution (operation b), re-dissolving the resin in a solvent to thereby obtain a resin solution A (operation c), thereafter bringing the resin solution A into contact with a solvent wherein the resin is poorly soluble or insoluble amounting to less than 10 times (preferably 5 times or less) the volume of the resin solution A to thereby precipitate a resin solid (operation d) and separating the precipitated resin (operation e).

Further, the operation of dissolving a synthesized resin in a solvent to thereby obtain a solution and heating the solution at about 30 to 90° C. for about 30 minutes to 4 hours as described in, for example, JP-A-2009-037108 may be added in order to inhibit any aggregation, etc. of the resin after the preparation of the composition.

It is preferred to minimize the amount of unreacted low-molecular components (monomer and oligomer) through these precipitation operations.

The weight average molecular weight of the resin (A) according to the present invention, in terms of polystyrene-equivalent value measured by GPC, is preferably in the range of 6000 to 50,000. It is more preferably in the range of 8000 to 30,000, and most preferably 10,000 to 25,000. By regulating the weight average molecular weight so as to fall within these ranges, it can be expected to realize an appropriate value of solubility in an organic developer.

The polydispersity index (molecular weight distribution) of the resin is generally in the range of 1.0 to 3.0, preferably 1.0 to 2.6, more preferably 1.0 to 2.0 and most preferably 1.4 to 2.0. The narrower the molecular weight distribution, the more excellent the resolution and resist shape. Further, the side wall of the resist pattern can be smooth to thereby ensure excellent roughness characteristics.

In the actinic-ray- or radiation-sensitive resin composition of the present invention, the content of resin (A) in the whole composition is preferably in the range of 30 to 99 mass %, more preferably 60 to 95 mass %, based on the total solids of the composition.

In the present invention, one type of rein (A) may be used alone, or two or more types thereof may be used in combination.

Moreover, in the present invention, a resin other than the resin (A), namely, a resin whose solubility in a developer comprising an organic solvent is lowered when acted on by an acid, which resin does not contain any of lactone structures of general formula (1), may be contained in addition to the resin (A). It is preferred for this resin other than the resin (A) to be a copolymer comprising any of the repeating units other than repeating units with lactone structures of general formula (1) as described above in connection with the resin (A). From the viewpoint of the satisfactory exertion of the effect of the present invention, it is preferred for the ratio of resin (A) added, based on the total amount of resins whose solubility in a developer comprising an organic solvent is lowered when acted on by an acid, to be 50 mass % or greater, especially 80 mass % or greater.

Nonlimiting particular examples of the resins (A) are shown below.

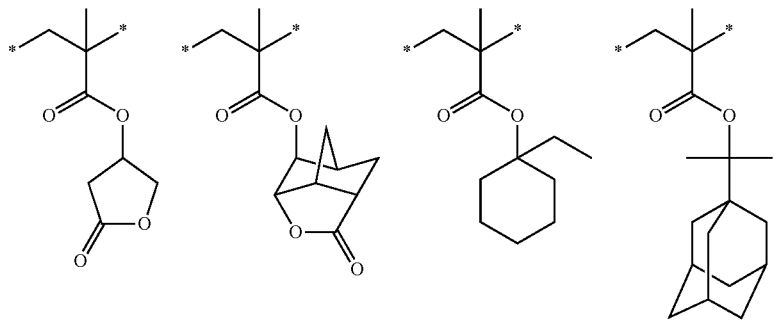

-continued
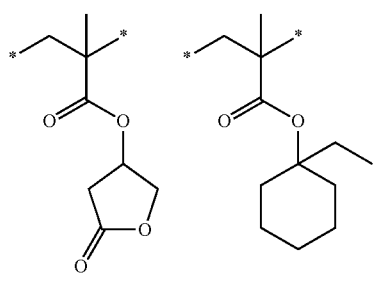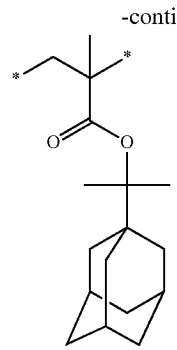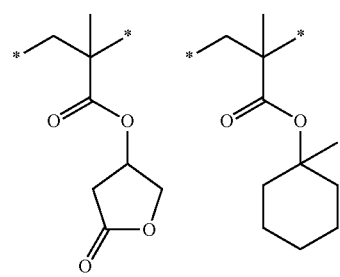
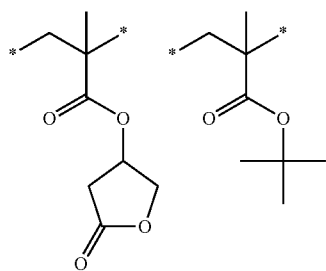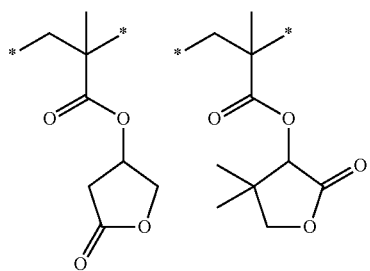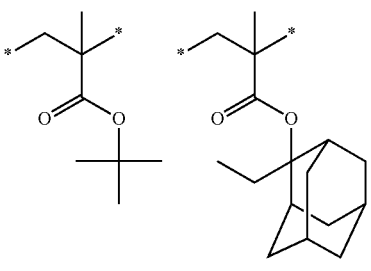
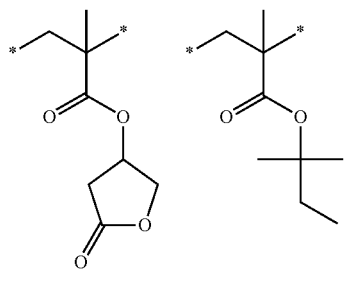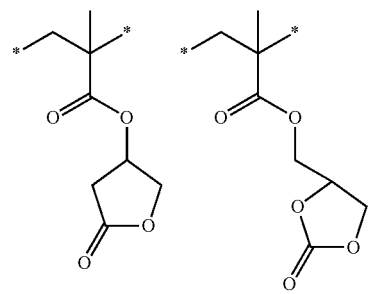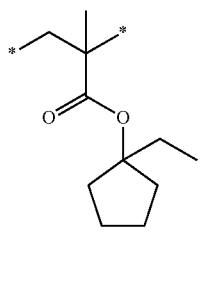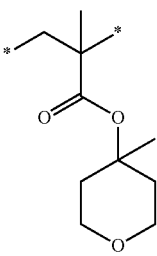
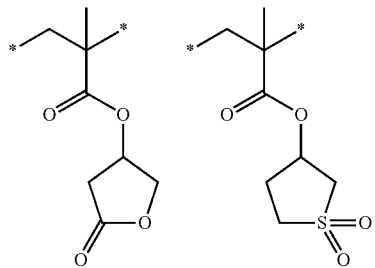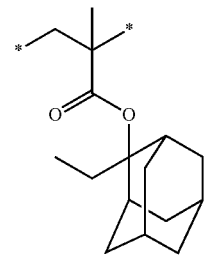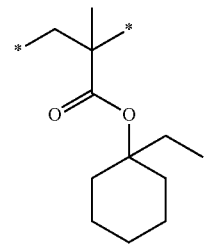
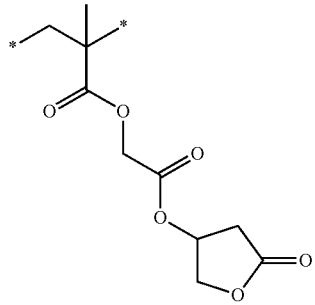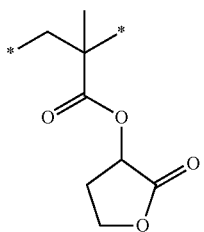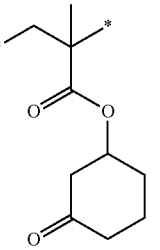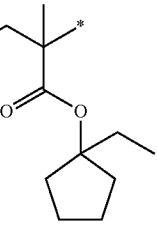

-continued
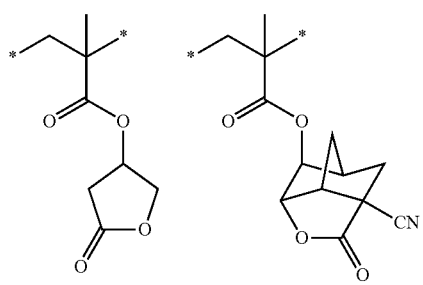
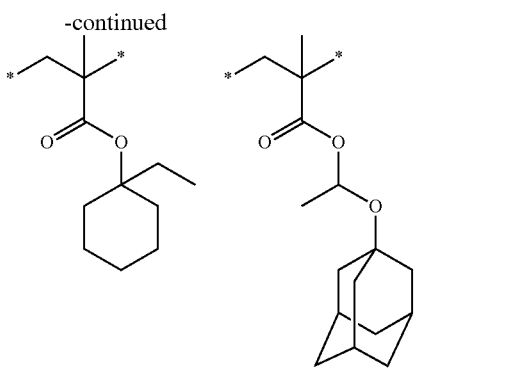
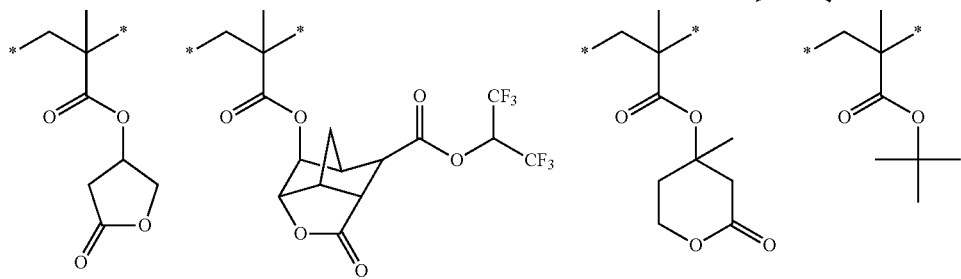
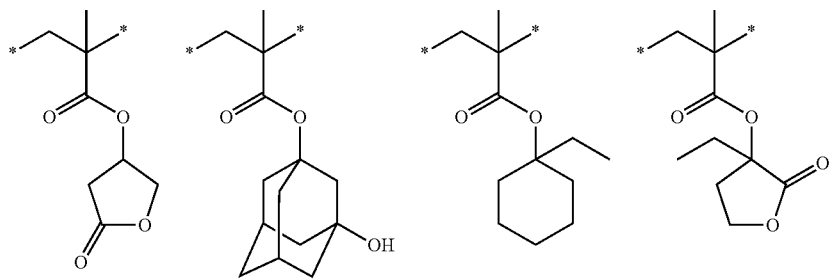
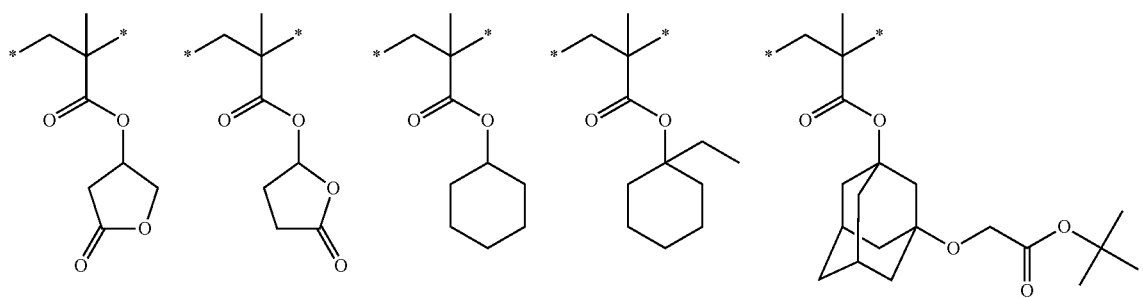
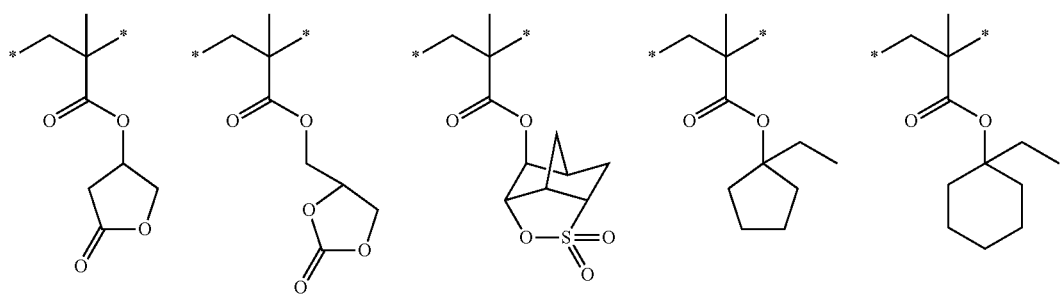

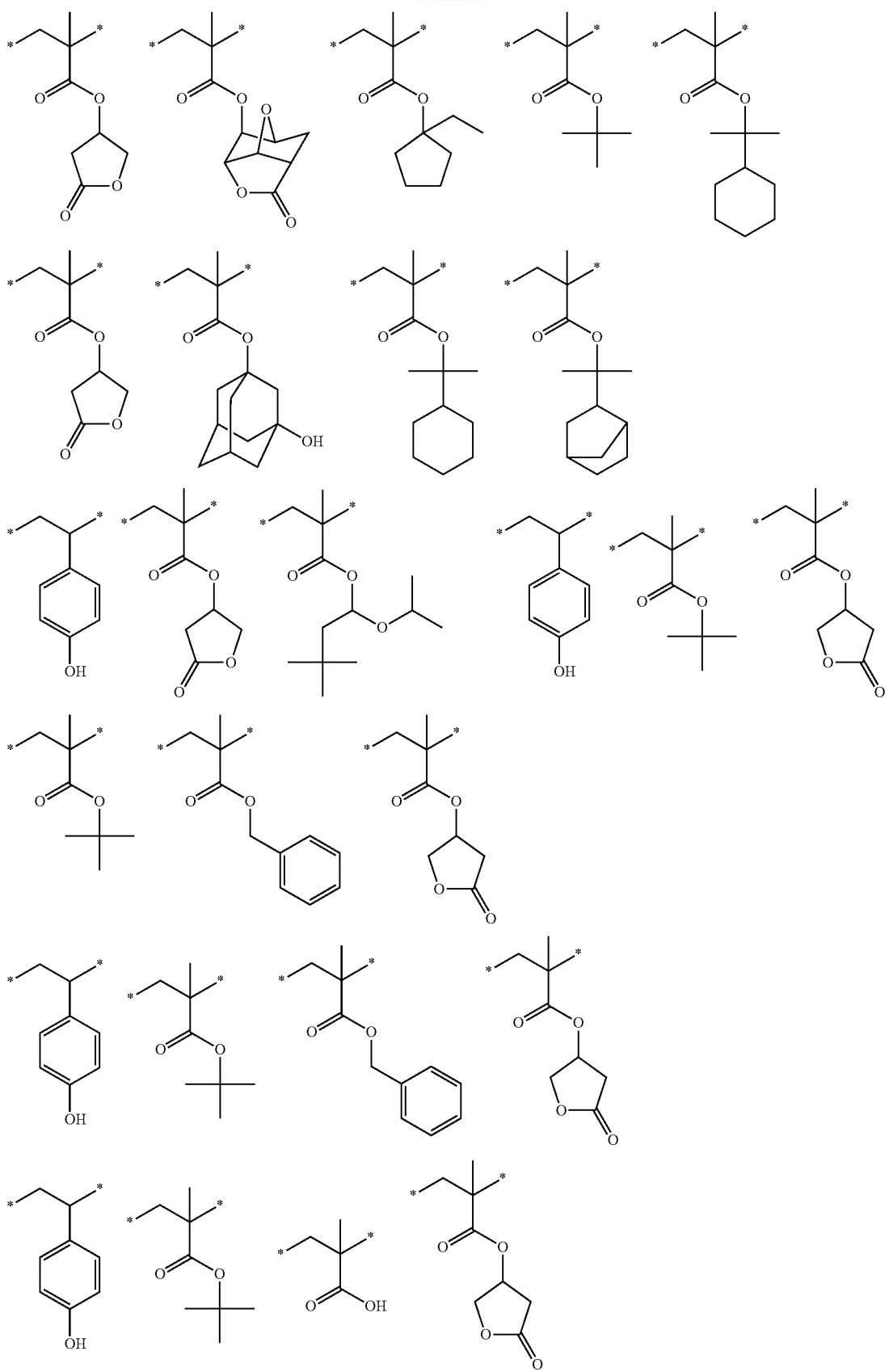

-continued

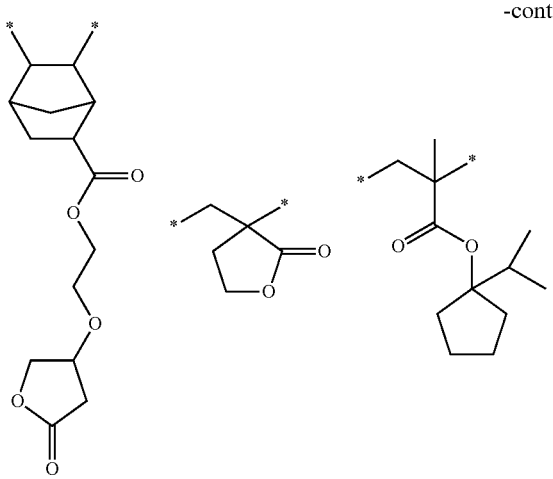
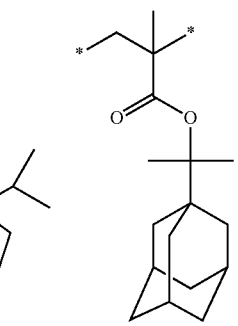

<Compound (B) that when Exposed to Actinic Rays or Radiation, Generates an Acid>

The composition of the present invention comprises a compound (hereinafter also referred to as "compound (B)" or "acid generator") that when exposed to actinic rays or radiation, generates an acid.

In an aspect of the present invention, it is preferred for the acid generator to be a compound with any of anion structures of general formula (2) to be described hereinafter. The joint use of this compound with the foregoing resin (A) preferably makes it feasible to provide a method of forming a pattern widely adaptable to various production conditions including development conditions and rinse conditions.

In another aspect of the present invention, the acid generator can be any of compounds of general formulae (ZI), (ZII) and (ZIII) below.

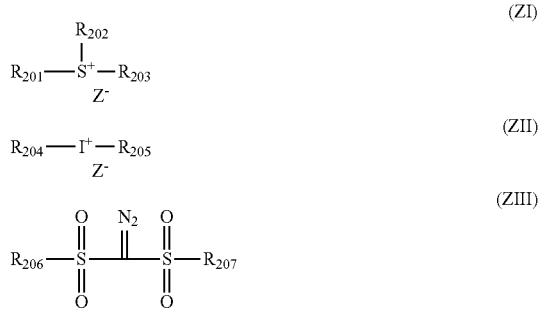

In general formula (ZI) above, each of $R_{201}$, $R_{202}$ and $R_{203}$ independently represents an organic group.

The number of carbon atoms of each of the organic groups represented by $R_{201}$, $R_{202}$ and $R_{203}$ is generally in the range of 1 to 30, preferably 1 to 20.

Any two of $R_{201}$ to $R_{203}$ may be bonded to each other to thereby form a ring structure, and the ring within the same may contain an oxygen atom, a sulfur atom, an ester bond, an amide bond or a carbonyl group. As the group formed by the bonding of two of $R_{201}$ to $R_{203}$, there can be mentioned an alkylene group (for example, a butylene group or a pentylene group).

Use can be made of a compound containing a plurality of structures of general formula (ZI). For example, use can be made of a compound with a structure in which at least one of $R_{201}$ to $R_{203}$ of a compound expressed by general formula (ZI) is bonded through a single bond or a connecting group to at least one of $R_{201}$ to $R_{203}$ of another compound expressed by general formula (ZI).

$Z^-$ represents a nonnucleophilic anion (anion whose capability of inducing a nucleophilic reaction is markedly low).

As $Z^-$, there can be mentioned, for example, a sulfonate anion (an aliphatic sulfonate anion, an aromatic sulfonate anion, a camphor sulfonate anion or the like), a carboxylate anion (an aliphatic carboxylate anion, an aromatic carboxylate anion, an aralkyl carboxylate anion or the like), a sulfonylimide anion, a bis(alkylsulfonyl)imide anion, a tris(alkylsulfonyl)methide anion or the like.

The aliphatic moiety in the aliphatic sulfonate anion and aliphatic carboxylate anion may be an alkyl group or a cycloalkyl group, being preferably a linear or branched alkyl group having 1 to 30 carbon atoms or a cycloalkyl group having 3 to 30 carbon atoms.

As a preferred aromatic group in the aromatic sulfonate anion and aromatic carboxylate anion, there can be mentioned an aryl group having 6 to 14 carbon atoms, for example, a phenyl group, a tolyl group, a naphthyl group or the like.

Substituents may be introduced in the above-mentioned alkyl group, cycloalkyl group and aryl group. As particular examples of the substituents, there can be mentioned a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), a cycloalkylalkyloxyalkyloxy group (preferably having 8 to 20 carbon atoms) and the like. With respect to the aryl group or ring structure of each of these groups, as its substituent, there can further be mentioned an alkyl group (preferably having 1 to 15 carbon atoms).

As a preferred aralkyl group in the aralkyl carboxylate anion, there can be mentioned an aralkyl group having 7 to 12 carbon atoms, for example, a benzyl group, a phenethyl group, a naphthylmethyl group, a naphthylethyl group, a naphthylbutyl group or the like.

As the sulfonylimide anion, there can be mentioned, for example, a saccharin anion.

Each of the alkyl groups in the bis(alkylsulfonyl)imide anion and tris(alkylsulfonyl)methide anion is preferably an alkyl group having 1 to 5 carbon atoms. As substituents introducible in these alkyl groups, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group and the like. Among these, a fluorine atom and an alkyl group substituted with a fluorine atom are preferred.

As other $Z^-$, there can be mentioned, for example, phosphorus fluoride (e.g., $PF_6^-$), boron fluoride (e.g., $BF_4^-$), antimony fluoride (e.g., $SbF_6^-$) and the like.

$Z^-$ is preferably an aliphatic sulfonate anion substituted at its at least α-position of sulfonic acid with a fluorine atom, an aromatic sulfonate anion substituted with a fluorine atom or a group containing a fluorine atom, a bis(alkylsulfonyl)imide anion whose alkyl group is substituted with a fluorine atom, or a tris(alkylsulfonyl)methide anion whose alkyl group is substituted with a fluorine atom.

In an aspect of the present invention, the number of fluorine atoms contained in the anion represented by $Z^-$ is preferably 2 or 3. This enhances the effect of the joint use with the foregoing resin (A).

From the viewpoint of acid strength, it is preferred for the pKa value of generated acid to be −1 or less so as to ensure a sensitivity enhancement.

As the organic groups represented by $R_{201}$, $R_{202}$ and $R_{203}$, there can be mentioned an aryl group (preferably having 6 to 15 carbon atoms), a linear or branched alkyl group (preferably having 1 to 10 carbon atoms), a cycloalkyl group (preferably having 3 to 15 carbon atoms) and the like.

Preferably, at least one of $R_{201}$, $R_{202}$ and $R_{203}$ is an aryl group. More preferably, these three are simultaneously aryl groups. The aryl groups include not only a phenyl group, a naphthyl group and the like but also heteroaryl groups, such as an indole residue and a pyrrole residue.

Substituents may further be introduced in these aryl, alkyl and cycloalkyl groups represented by $R_{201}$, $R_{202}$ and $R_{203}$. As the substituents, there can be mentioned a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms) and the like. The appropriate substituents are not limited to these.

Any two selected from among $R_{201}$, $R_{202}$ and $R_{203}$ may be bonded via a single bond or a connecting group to each other. The connecting group may be any of an alkylene group (preferably having 1 to 3 carbon atoms), —O—, —S—, —CO—, —SO$_2$— and the like. These are however nonlimiting.

As preferred structures in which at least one of $R_{201}$, $R_{202}$ and $R_{203}$ is not an aryl group, there can be mentioned the cation structures of the compounds set forth in Sections 0046 and 0047 of JP-A-2004-233661, compounds set forth in Sections 0040 to 0046 of JP-A-2003-35948, compounds of formulae (I-1) to (I-70) shown as examples in US Patent Application Publication No. 2003/0224288 A1, compounds of formulae (IA-1) to (IA-54) and (IB-1) to (IB-24) shown as examples in US Patent Application Publication No. 2003/0077540 A1 and the like.

As further preferred examples among the compounds of general formula (ZI), there can be mentioned compounds of general formulae (ZI-3) and (ZI-4) below. First, the compounds of general formula (ZI-3) will be described.

(ZI-3)

In general formula (ZI-3) above, $R_1$ represents an alkyl group, a cycloalkyl group, an alkoxy group, a cycloalkoxy group, an aryl group or an alkenyl group.

Each of $R_2$ and $R_3$ independently represents a hydrogen atom, an alkyl group, a cycloalkyl group or an aryl group, provided that $R_2$ and $R_3$ may be connected to each other to thereby form a ring.

$R_1$ and $R_2$ may be connected to each other to thereby form a ring.

Each of Rx and Ry independently represents an alkyl group, a cycloalkyl group, an alkenyl group, an aryl group, a 2-oxoalkyl group, a 2-oxocycloalkyl group, an alkoxycarbonylalkyl group or an alkoxycarbonylcycloalkyl group, provided that Rx and Ry may be connected to each other to thereby form a ring structure, in which an oxygen atom, a nitrogen atom, a sulfur atom, a ketone group, an ether bond, an ester bond and/or an amide bond may be contained.

$Z^-$ represents a nonnucleophilic anion.

The alkyl group represented by $R_1$ is preferably a linear or branched alkyl group having 1 to 20 carbon atoms. The alkyl group in its chain may contain an oxygen atom, a sulfur atom or a nitrogen atom. For example, there can be mentioned a linear alkyl group, such as a methyl group, an ethyl group, an n-propyl group, an n-butyl group, an n-pentyl group, an n-hexyl group, an n-octyl group, an n-dodecyl group, an n-tetradecyl group or an n-octadecyl group, and a branched alkyl group, such as an isopropyl group, an isobutyl group, a t-butyl group, a neopentyl group or a 2-ethylhexyl group. A substituent may be introduced in the alkyl group represented by $R_1$. As substituted alkyl groups, there can be mentioned a cyanomethyl group, a 2,2,2-trifluoroethyl group, a methoxycarbonylmethyl group, an ethoxycarbonylmethyl group and the like.

The cycloalkyl group represented by $R_1$ is preferably one having 3 to 20 carbon atoms. The cycloalkyl group in its ring may contain an oxygen atom or a sulfur atom. As examples thereof, there can be mentioned a cyclopropyl group, a cyclopentyl group, a cyclohexyl group, a norbornyl group, an adamantyl group and the like. A substituent may be introduced in the cycloalkyl group represented by $R_1$. As the substituent, there can be mentioned, for example, an alkyl group or an alkoxy group.

The alkoxy group represented by $R_1$ is preferably one having 1 to 20 carbon atoms. As examples thereof, there can be mentioned a methoxy group, an ethoxy group, an isopropoxy group, a t-butoxy group, a t-amyloxy group and an n-butoxy group. A substituent may be introduced in the alkoxy group represented by $R_1$. As the substituent, there can be mentioned, for example, an alkyl group or a cycloalkyl group.

The cycloalkoxy group represented by $R_1$ is preferably one having 3 to 20 carbon atoms. As examples thereof, there can be mentioned a cyclohexyloxy group, a norbornyloxy group, an adamantyloxy group and the like. A substituent may be introduced in the cycloalkoxy group represented by $R_1$. As the substituent, there can be mentioned, for example, an alkyl group or a cycloalkyl group.

The aryl group represented by $R_1$ is preferably one having 6 to 14 carbon atoms. As examples thereof, there can be mentioned a phenyl group, a naphthyl group, a biphenyl group and the like. A substituent may be introduced in the aryl group represented by $R_1$. As preferred substituents, there can be mentioned an alkyl group, a cycloalkyl group, an alkoxy group, a cycloalkoxy group, an aryloxy group, an alkylthio group and an arylthio group. The alkyl group, cycloalkyl group, alkoxy group and cycloalkoxy group as the substituents can be the same as set forth above in connection with $R_1$.

As the alkenyl group represented by $R_1$, there can be mentioned a vinyl group or an allyl group.

Each of $R_2$ and $R_3$ represents a hydrogen atom, an alkyl group, a cycloalkyl group or an aryl group, provided that $R_2$ and $R_3$ may be connected to each other to thereby form a ring, and that at least one of $R_2$ and $R_3$ is an alkyl group, a cycloalkyl group or an aryl group. Particular examples and preferred examples of the alkyl groups, cycloalkyl groups and aryl groups represented by $R_2$ and $R_3$ can be the same as those set forth above in connection with $R_1$. When $R_2$ and $R_3$ are connected to each other to thereby form a ring, the sum of carbon atoms contributing to ring formation contained in $R_2$ and $R_3$ is preferably in the range of 4 to 7, most preferably 4 or 5.

$R_1$ and $R_2$ may be connected to each other to thereby form a ring. When $R_1$ and $R_2$ are connected to each other to thereby form a ring, preferably, $R_1$ is an aryl group (preferably an optionally substituted phenyl group or naphthyl group) while $R_2$ is an alkylene group having 1 to 4 carbon atoms (preferably a methylene group or an ethylene group). As preferred introducible substituents, there can be mentioned those set forth above as being introducible in the aryl group represented by $R_1$. In another preferred form of the ring formed by the mutual connection of $R_1$ and $R_2$, $R_1$ is a vinyl group while $R_2$ is an alkylene group having 1 to 4 carbon atoms.

Each of the alkyl groups represented by Rx and Ry is preferably an alkyl group having 1 to 15 carbon atoms. As such, there can be mentioned, for example, a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group or the like.

Each of the cycloalkyl groups represented by Rx and Ry is preferably one having 3 to 20 carbon atoms. As examples thereof, there can be mentioned a cyclopropyl group, a cyclopentyl group, a cyclohexyl group, a norbornyl group, an adamantyl group and the like.

Each of the alkenyl groups represented by Rx and Ry is preferably one having 2 to 30 carbon atoms. As examples thereof, there can be mentioned a vinyl group, an allyl group and a styryl group.

Each of the aryl groups represented by Rx and Ry is preferably, for example, one having 6 to 20 carbon atoms. As such, there can be mentioned, for example, a phenyl group, a naphthyl group, an azulenyl group, an acenaphthylenyl group, a phenanthrenyl group, a penalenyl group, a phenanthracenyl group, a fluorenyl group, an anthracenyl group, a pyrenyl group, a benzopyrenyl group or the like. A phenyl group and a naphthyl group are preferred. A phenyl group is more preferred.

The alkyl group moieties in the 2-oxoalkyl groups and alkoxycarbonylalkyl groups represented by Rx and Ry are, for example, those set forth above as being represented by Rx and Ry.

The cycloalkyl group moieties in the 2-oxocycloalkyl groups and alkoxycarbonylcycloalkyl groups represented by Rx and Ry are, for example, those set forth above as being represented by Rx and Ry.

$Z^-$ is, for example, any of those set forth above as being represented by $Z^-$ in general formula (ZI).

The compounds of general formula (ZI-3) are preferably those of general formulae (ZI-3a) and (ZI-3b) below.

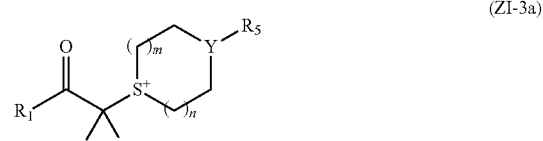

(ZI-3a)

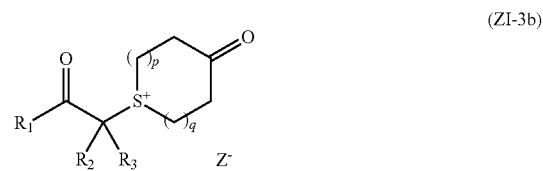

(ZI-3b)

In general formulae (ZI-3a) and (ZI-3b), $R_1$, $R_2$ and $R_3$ are as defined above in connection with general formula (ZI-3).

Y represents an oxygen atom, a sulfur atom or a nitrogen atom, preferably an oxygen atom or a nitrogen atom. Each of m, n, p and q is an integer of, preferably 0 to 3, more preferably 1 or 2 and most preferably 1. A substituent may be introduced in the alkylene group for the mutual connection of $S^+$ and Y. As a preferred substituent, there can be mentioned an alkyl group.

$R_5$ represents a monovalent organic group when Y is a nitrogen atom, being nil when Y is an oxygen atom or a sulfur atom. $R_5$ is preferably a group containing an electron withdrawing group, most preferably any of groups of general formulae (ZI-3a-1) to (ZI-3a-4) below.

(ZI-3a-1)

(ZI-3a-2)

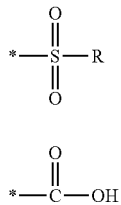

(ZI-3a-3)

(ZI-3a-4)

In general formulae (ZI-3a-1) to (ZI-3a-3) above, R represents a hydrogen atom, an alkyl group, a cycloalkyl group or an aryl group, preferably an alkyl group. Particular examples and preferred examples of the alkyl, cycloalkyl and aryl groups represented by R are the same as those set forth above in connection with $R_1$ in general formula (ZI-3).

In general formulae (ZI-3a-1) to (ZI-3a-4) above, * represents a bonding hand linked to the nitrogen atom as Y in the compounds of general formula (ZI-3a).

When Y is a nitrogen atom, it is most preferred for $R_5$ to be any of groups of the formula —$SO_2$—$R_4$. $R_4$ represents an alkyl group, a cycloalkyl group or an aryl group, preferably an alkyl group. Particular examples and preferred examples of the alkyl group, cycloalkyl group and aryl group represented by $R_4$ can be the same as set forth above in connection with $R_1$.

$Z^-$ is, for example, as set forth above in connection with general formula (ZI).

The compounds of general formula (ZI-3) are most preferably those of general formulae (ZI-3a') and (ZI-3b') below.

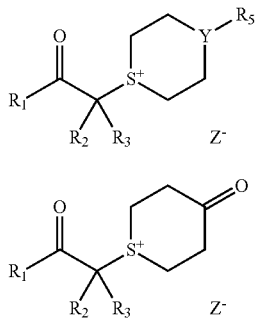

In general formulae (ZI-3a') and (ZI-3b'), $R_1$, $R_2$, $R_3$, Y and $R_5$ are as defined above in connection with general formulae (ZI-3a) and (ZI-3b).

$Z^-$ is, for example, as set forth above in connection with general formula (ZI).

Specific examples of the cation moieties of the compounds of general formula (ZI-3) are shown below.

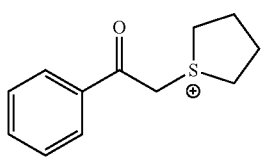

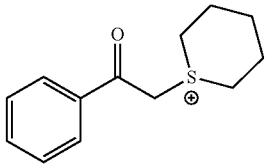

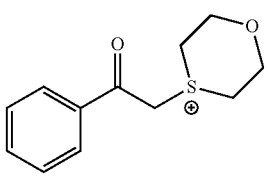

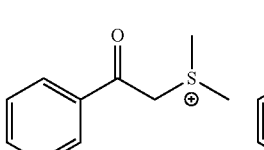

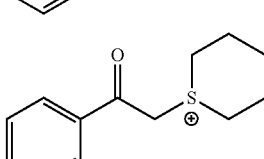

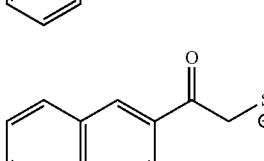

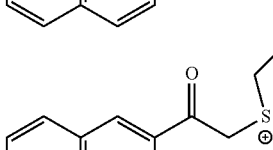

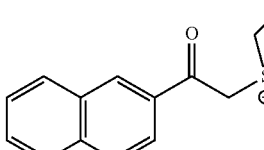

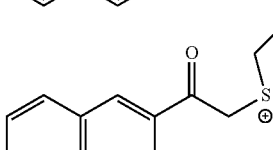

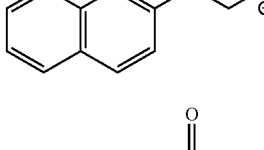

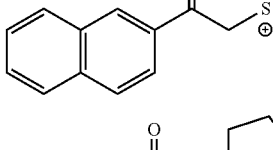

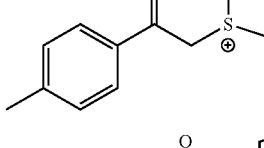

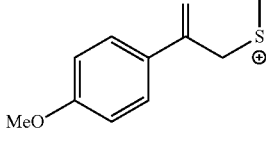

77
-continued
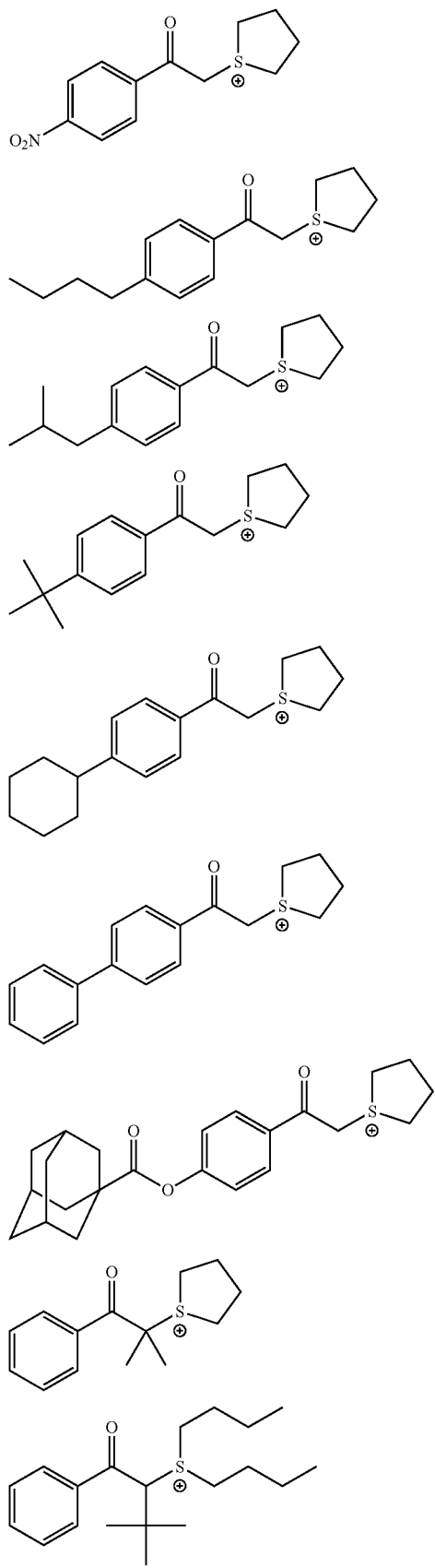
78
-continued
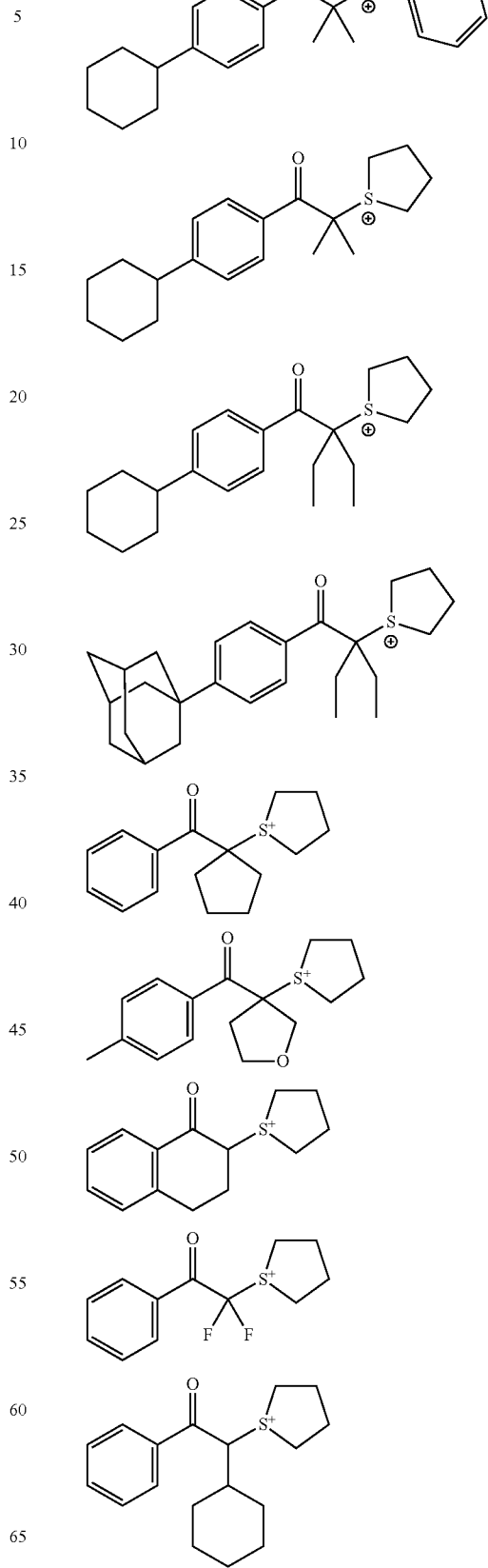

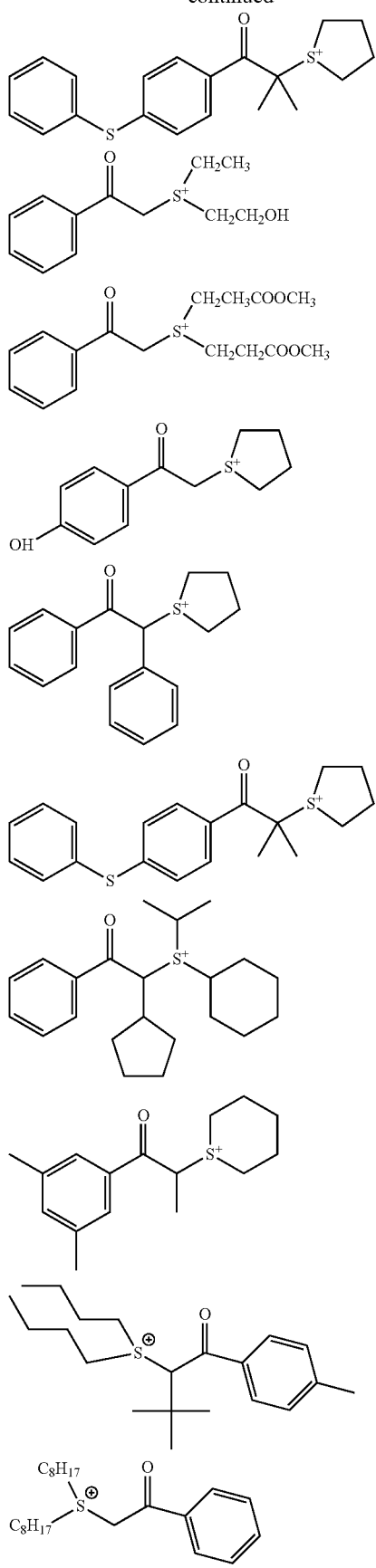
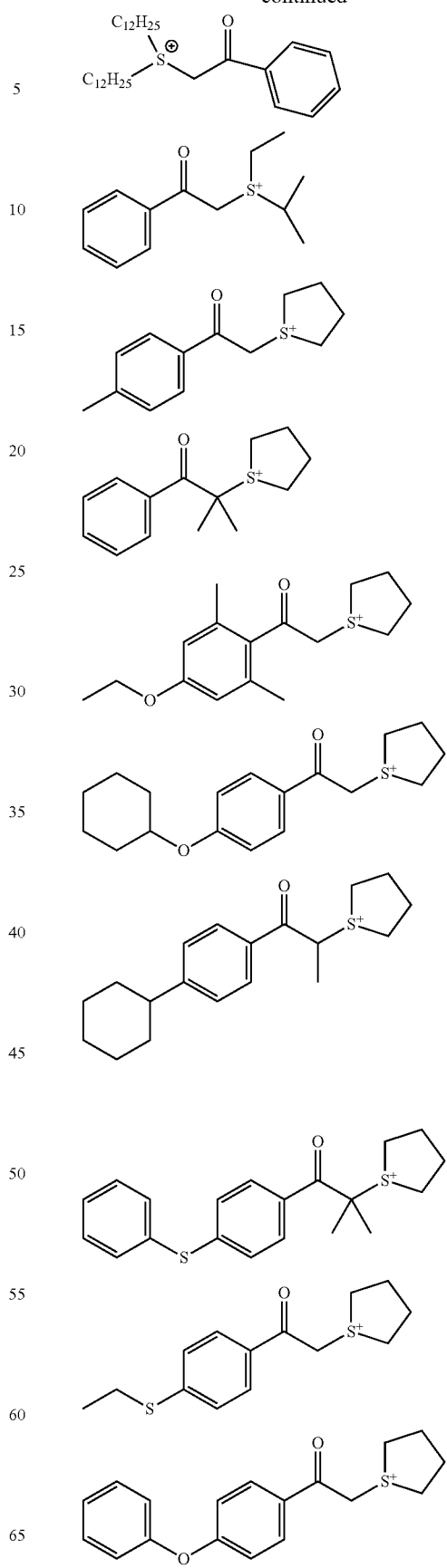

-continued

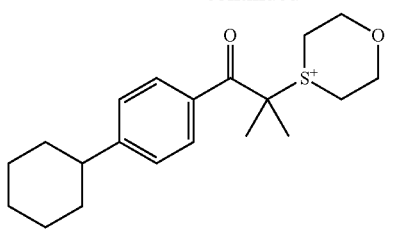
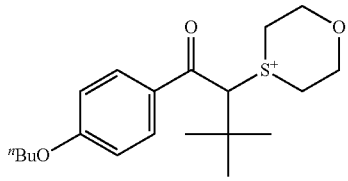
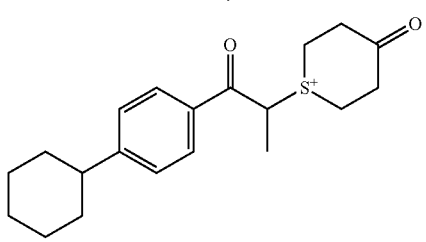
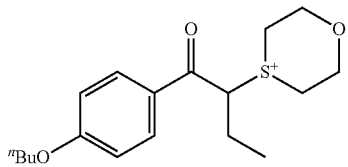
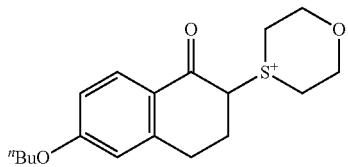
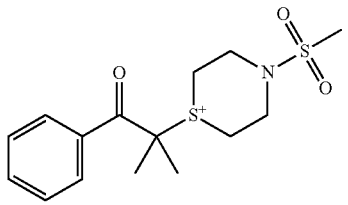
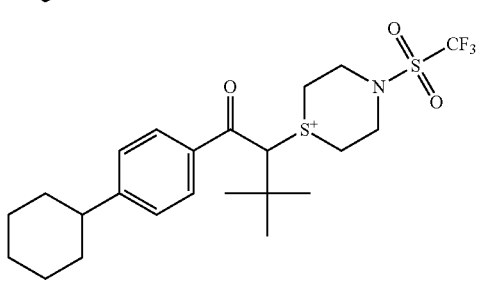
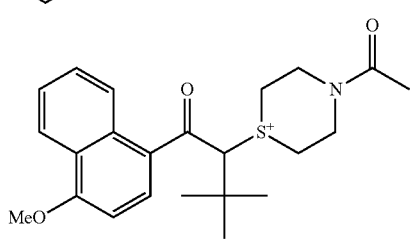

-continued

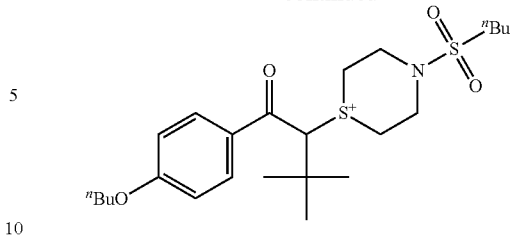

The compounds of general formula (ZI-4) will be described below.

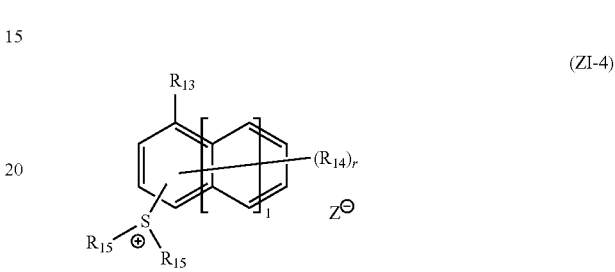

(ZI-4)

In general formula (ZI-4), $R_{13}$ represents a hydrogen atom, a fluorine atom, a hydroxyl group, an alkyl group, a cycloalkyl group, an alkoxy group, an alkoxycarbonyl group or a group containing a cycloalkyl group. Substituents may be introduced in these groups.

$R_{14}$, or each of $R_{14}$s independently, represents a hydroxyl group, an alkyl group, a cycloalkyl group, an alkoxy group, an alkoxycarbonyl group, an alkylcarbonyl group, an alkylsulfonyl group, a cycloalkylsulfonyl group or a group containing a cycloalkyl group. Substituents may be introduced in these groups.

Each of $R_{15}$s independently represents an alkyl group, a cycloalkyl group or a naphthyl group, provided that two $R_{15}$s may be bonded to each other to thereby form a ring. A heteroatom, such as an oxygen atom, a sulfur atom or a nitrogen atom, may be contained as an atom constituting the ring. Substituents may be introduced in these groups.

In the formula, l is an integer of 0 to 2, and r is an integer of 0 to 8.

$Z^-$ represents a nonnucleophilic anion, which is the same as set forth above in connection with $Z^-$ in general formula (ZI).

Each of the alkyl groups represented by $R_{13}$, $R_{14}$ and $R_{15}$ in general formula (ZI-4) is linear or branched, preferably having 1 to 10 carbon atoms.

As the cycloalkyl groups represented by $R_{13}$, $R_{14}$ and $R_{15}$, there can be mentioned mono- and polycycloalkyl groups.

Each of the alkoxy groups represented by $R_{13}$ and $R_{14}$ is linear or branched, preferably having 1 to 10 carbon atoms.

Each of the alkoxycarbonyl groups represented by $R_{13}$ and $R_{14}$ is linear or branched, preferably having 2 to 11 carbon atoms.

As the groups containing a cycloalkyl group represented by $R_{13}$ and $R_{14}$, there can be mentioned groups each containing a mono- or polycycloalkyl group. Substituents may be introduced in these groups.

With respect to the alkyl group in the alkylcarbonyl group represented by $R_{14}$, there can be mentioned the same particular examples as mentioned above with respect to the alkyl groups represented by $R_{13}$ to $R_{15}$.

Each of the alkylsulfonyl group and cycloalkylsulfonyl group represented by $R_{14}$ may be linear, branched or cyclic and preferably has 1 to 10 carbon atoms.

As substituents that may be introduced in these groups, there can be mentioned a halogen atom (e.g., a fluorine atom), a hydroxyl group, a carboxyl group, a cyano group, a nitro group, an alkoxy group, an alkoxyalkyl group, an alkoxycarbonyl group, an alkoxycarbonyloxy group and the like.

As the ring structure that may be formed by the mutual bonding of two $R_{15}$s, there can be mentioned a 5- or 6-membered ring, most preferably a 5-membered ring (namely, a tetrahydrothiophene ring or a 2,5-dihydrothiophene ring), formed by two $R_{15}$s in cooperation with the sulfur atom in general formula (ZI-4). The ring structure may be condensed with an aryl group or a cycloalkyl group. Substituents may be introduced in bivalent $R_{15}$s. As such substituents, there can be mentioned, for example, a hydroxyl group, a carboxyl group, a cyano group, a nitro group, an alkyl group, a cycloalkyl group, an alkoxy group, an alkoxyalkyl group, an alkoxycarbonyl group, an alkoxycarbonyloxy group and the like. A plurality of substituents may be introduced in the ring structure. The substituents may be bonded to each other to thereby form a ring.

$R_{15}$ in general formula (ZI-4) is preferably a methyl group, an ethyl group, a naphthyl group, a bivalent group occurring at the formation of a tetrahydrothiophene ring structure upon the mutual bonding of two $R_{15}$s in cooperation with the sulfur atom, or the like. A bivalent group occurring at the formation of a tetrahydrothiophene ring structure upon the mutual bonding of two $R_{15}$s in cooperation with the sulfur atom is most preferred.

Preferred substituents that can be introduced in $R_{13}$ and $R_{14}$ are a hydroxyl group, an alkoxy group, an alkoxycarbonyl group and a halogen atom (especially, a fluorine atom).

In the formula, 1 is preferably 0 or 1, more preferably 1; and r is preferably from 0 to 2.

As particular examples of the cation structures contained in the compounds of general formulae (ZI-3) and (ZI-4) described above, there can be mentioned not only the above-mentioned cation structures of compounds shown as examples in JP-A-2004-233661, JP-A-2003-35948, US Patent Application Publication No. 2003/0224288 A1 and US Patent Application Publication No. 2003/0077540 A1 and the like but also, for example, the cation structures of the chemical structures shown as examples in sections [0046], [0047], [0072] to [0077] and [0107] to [0110] of JP-A-2011-53360 and the like and the cation structures of the chemical structures shown as examples in sections [0135] to [0137], [0151] and [0196] to [0199] of JP-A-2011-53430 and the like.

In general formulae (ZII) and (ZIII), each of $R_{204}$ to $R_{207}$ independently represents an aryl group, an alkyl group or a cycloalkyl group.

The aryl groups, alkyl groups and cycloalkyl groups represented by $R_{204}$ to $R_{207}$ are the same as those set forth above in connection with $R_{201}$ to $R_{203}$ in the compounds (ZI).

Substituents may be introduced in the aryl groups, alkyl groups and cycloalkyl groups represented by $R_{204}$ to $R_{207}$. The substituents are also the same as those set forth above in connection with $R_{201}$ to $R_{203}$ in the compounds (ZI).

$Z^-$ is, for example, as set forth above in connection with $Z^-$ in general formula (ZI).

Apart from the compounds of general formulae (ZI-3) and (ZI-4), the compounds of general formula (ZI-5) below can also preferably used as acid generators. The use of According to one preferred embodiment of the present invention, the acid generator is expressed by general formula (I') below. The use of the compounds of general formula (ZI-5) below enhances the transmission of exposure light, thereby contributing to the improvement of LWR and DOF.

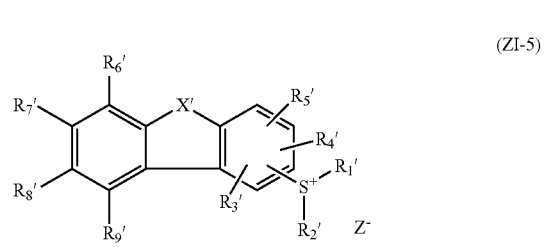

(ZI-5)

In general formula (ZI-5) above,

X' represents an oxygen atom, a sulfur atom or —N(Rx)-.

Each of $R_1'$ and $R_2'$ independently represents an alkyl group, a cycloalkyl group or an aryl group.

Each of $R_3'$ to $R_9'$ independently represents a hydrogen atom, an alkyl group, a cycloalkyl group, an alkoxy group, an alkoxycarbonyl group, an acyl group, an alkylcarbonyloxy group, an aryl group, an aryloxy group, an aryloxycarbonyl group or an arylcarbonyloxy group.

Rx represents a hydrogen atom, an alkyl group, a cycloalkyl group, an acyl group, an alkenyl group, an alkoxycarbonyl group, an aryl group, an arylcarbonyl group or an aryloxycarbonyl group.

$R_1'$ and $R_2'$ may be connected to each other to thereby form a ring. Any two or more of $R_6'$ to $R_9'$, $R_3'$ and $R_9'$, $R_4'$ and $R_5'$, $R_5'$ and Rx, and $R_6'$ and Rx may be connected to each other to thereby form a ring.

From the viewpoint of lowering the light absorption (for example, absorbance at a wavelength of 193 nm), it is preferred for X' to be a sulfur atom or —N(Rx)-.

$Z^-$ is, for example, as set forth above in connection with $Z^-$ in general formula (ZI).

Substituents may be introduced in the alkyl groups represented by to $R_1'$ to $R_9'$ and Rx. A linear or branched alkyl group having 1 to 20 carbon atoms is a preferred substituent. An oxygen atom, a sulfur atom or a nitrogen atom may be introduced in the alkyl chain.

As the substituted alkyl group represented by Rx, there can be mentioned a cyanomethyl group, a 2,2,2-trifluoroethyl group, a methoxycarbonylmethyl group, an ethoxycarbonylmethyl group or the like.

As the substituted alkyl groups represented by $R_1'$ and $R_2'$, there can be mentioned a methoxyethyl group and the like.

Further, in particular, there can be mentioned a linear or branched alkyl group substituted with a cycloalkyl group (for example, an adamantylmethyl group, an adamantylethyl group, a cyclohexylethyl group, a camphor residue or the like) or the like.

Substituents may be introduced in the cycloalkyl groups represented by $R_1'$ to $R_9'$ and Rx. A cycloalkyl group having 3 to 20 carbon atoms is preferred, and an oxygen atom may be introduced in the ring.

Substituents may be introduced in the acyl groups represented by $R_3'$ to $R_9'$ and Rx. An acyl group having 1 to 10 carbon atoms is preferred.

The alkenyl group represented by Rx is preferably one having 2 to 8 carbon atoms. For example, there can be mentioned a vinyl group, an allyl group, a butenyl group or the like.

Substituents may be introduced in the alkoxy groups represented by $R_3'$ to $R_9'$. An alkoxy group having 1 to 20 carbon atoms is preferred.

Substituents may be introduced in the alkoxycarbonyl groups represented by $R_3'$ to $R_9'$. An alkoxycarbonyl group having 2 to 20 carbon atoms is preferred.

Substituents may be introduced in the alkylcarbonyloxy groups represented by $R_3'$ to $R_9'$. An alkylcarbonyloxy group having 2 to 20 carbon atoms is preferred.

Substituents may be introduced in the aryl groups represented by $R_1'$ to $R_9'$ and Rx. An aryl group having 6 to 14 carbon atoms is preferred.

Substituents may be introduced in the aryloxy groups represented by $R_3'$ to $R_9'$. An aryloxy group having 6 to 14 carbon atoms is preferred.

Substituents may be introduced in the groups represented by $R_3'$ to $R_9'$ and Rx. An aryloxycarbonyl group having 7 to 15 carbon atoms is preferred.

Substituents may be introduced in the arylcarbonyloxy groups represented by $R_3'$ to $R_9'$. An arylcarbonyloxy group having 7 to 15 carbon atoms is preferred.

A substituent may be introduced in the arylcarbonyl group represented by Rx. An arylcarbonyloxy group having 7 to 15 carbon atoms is preferred.

As substituents that may further be introduced in the alkyl groups represented by $R_3'$ to $R_9'$, cycloalkyl groups represented by $R_1'$ to $R_9'$ and Rx, acyl group represented by Rx, alkoxy groups represented by $R_3'$ to $R_9'$, alkoxycarbonyl groups represented by $R_3'$ to $R_9'$, alkylcarbonyloxy groups represented by $R_3'$ to $R_9'$, aryl groups represented by $R_1'$ to $R_9'$ and Rx, aryloxy groups represented by $R_3'$ to $R_9'$, aryloxycarbonyl groups represented by $R_3'$ to $R_9'$ and Rx, arylcarbonyloxy groups represented by $R_3'$ to $R_9'$ and arylcarbonyl group represented by Rx, there can be mentioned an alkyl group (may be linear, branched or cyclic, preferably having 1 to 12 carbon atoms), an aryl group (preferably having 6 to 14 carbon atoms), a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an acyl group (preferably having 2 to 12 carbon atoms) and the like.

As the ring structure that may be formed by the mutual bonding of $R_1'$ and $R_2'$, there can be mentioned a 5-membered or 6-membered ring, most preferably a 5-membered ring (namely, a tetrahydrothiophene ring), formed by bivalent $R_1'$ and $R_2'$ (for example, an ethylene group, a propylene group, a 1,2-cyclohexylene group or the like) in cooperation with the sulfur atom in general formula (ZI-5) above. From the viewpoint of decomposition efficiency for acid anion generation, it is preferred not to realize the mutual bonding of $R_1'$ and $R_2'$ to form a ring.

The ring structure that may be formed by the mutual bonding of any two or more of $R_6'$ to $R_9'$, $R_3'$ and $R_9'$, $R_4'$ and $R_5'$, $R_5'$ and Rx, and $R_6'$ and Rx is preferably a 5-membered or 6-membered ring, most preferably a 6-membered ring.

Each of $R_1'$ and $R_2'$ is most preferably an alkyl group or an aryl group.

As most preferred examples of the groups represented by $R_3'$ to $R_9'$, there can be mentioned optionally substituted alkyl groups and a hydrogen atom. A hydrogen atom is most preferred from the viewpoint of absorption intensity at 193 nm in the use as an ArF resist.

Rx is most preferably an alkyl group or an acyl group.

Now, preferred structures of the nonnucleophilic anions $Z^-$ will be described.

It is preferred for the nonnucleophilic anion $Z^-$ to be any of sulfonate anions of general formula (2).

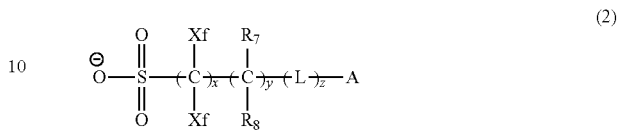

(2)

In general formula (2), each of Xf's independently represents a fluorine atom or an alkyl group substituted with at least one fluorine atom.

Each of $R_7$ and $R_8$ independently represents a hydrogen atom, a fluorine atom, an alkyl group or an alkyl group substituted with at least one fluorine atom, provided that when there are a plurality of $R_7$s and $R_8$s, $R_7$s, and $R_8$s, may be identical to or different from each other.

L represents a bivalent connecting group, provided that when there are a plurality of L's, they may be identical to or different from each other.

A represents an organic group containing a cyclic structure, and x is an integer of 1 to 20, y an integer of 0 to 10 and z an integer of 0 to 10.

The anions of general formula (2) will be described in detail below.

Xf represents a fluorine atom or an alkyl group substituted with at least one fluorine atom, as mentioned above. The alkyl group in the alkyl group substituted with at least one fluorine atom is preferably one having 1 to 10 carbon atoms, more preferably 1 to 4 carbon atoms. It is preferred for the alkyl group substituted with at least one fluorine atom to be a perfluoroalkyl group.

Xf is preferably a fluorine atom or a perfluoroalkyl group having 1 to 4 carbon atoms. In particular, there can be mentioned a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$. Of these, a fluorine atom and $CF_3$ are preferred. Both Xf's being fluorine atoms is most preferred.

As mentioned above, each of $R_7$ and $R_8$ represents a hydrogen atom, a fluorine atom, an alkyl group or an alkyl group substituted with at least one fluorine atom. The alkyl group preferably has 1 to 4 carbon atoms, more preferably being a perfluoroalkyl group having 1 to 4 carbon atoms. As particular examples of the alkyl groups each substituted with at least one fluorine atom represented by $R_7$ and $R_8$, there can be mentioned $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$. Of these, $CF_3$ is preferred.

L represents a bivalent connecting group. As the bivalent connecting group, there can be mentioned —COO—, —OCO—, —CO—, —O—, —S—, —SO—, —SO$_2$—, —N(Ri)- (in which Ri represents a hydrogen atom or an alkyl), an alkylene group (preferably 1 to 6 carbon atoms), a cycloalkylene group (preferably 3 to 10 carbon atoms), an alkenylene group (preferably 2 to 6 carbon atoms), a bivalent connecting group comprised of a combination of two or more of these, or the like. L is preferably —COO—, —OCO—, —CO—, —SO$_2$—, —CON(Ri)-, —SO$_2$N(Ri)-, —CON(Ri)-alkylene-, —N(Ri)CO-alkylene-, —COO-alkylene- or —OCO-alkylene-. More preferably, L is —COO—, —OCO—, —SO$_2$—, —CON(Ri)- or —SO$_2$N(Ri)-. When there are a plurality of L's, they may be identical to or different from each other.

The alkyl group represented by Ri is preferably a linear or branched alkyl group having 1 to 20 carbon atoms. The alkyl group in its chain may contain an oxygen atom, a sulfur atom or a nitrogen atom. For example, there can be mentioned a linear alkyl group, such as a methyl group, an ethyl group, an n-propyl group, an n-butyl group, an n-pentyl group, an n-hexyl group, an n-octyl group, an n-dodecyl group, an n-tetradecyl group or an n-octadecyl group, and a branched alkyl group, such as an isopropyl group, an isobutyl group, a t-butyl group, a neopentyl group or a 2-ethylhexyl group. As substituted alkyl groups, there can be mentioned a cyanomethyl group, a 2,2,2-trifluoroethyl group, a methoxycarbonylmethyl group, an ethoxycarbonylmethyl group and the like.

The organic group containing a cyclic structure represented by A is not particularly limited as long as a cyclic structure is contained. There can be mentioned an alicyclic group, an aryl group, a heterocyclic group (including not only one exhibiting aromaticity but also one exhibiting no aromaticity; including, for example, a tetrahydropyran ring and a lactone ring structure), or the like.

The alicyclic group may be monocyclic or polycyclic. As preferred alicyclic groups, there can be mentioned a monocycloalkyl group, such as a cyclopentyl group, a cyclohexyl group or a cyclooctyl group, and a polycycloalkyl group, such as a norbornyl group, a norbornenyl group, a tricyclodecanyl group (for example, a tricyclo[5.2.1.0 (2,6)]decanyl group), a tetracyclodecanyl group, a tetracyclododecanyl group or an adamantyl group. Also, preferred use is made of a nitrogen-atom-containing alicyclic group, such as a piperidine group, a decahydroquinoline group or a decahydroisoquinoline group. Of these, alicyclic groups with a bulky structure having 7 or more carbon atoms, selected from among a norbornyl group, a tricyclodecanyl group, a tetracyclodecanyl group, a tetracyclododecanyl group, an adamantyl group, a decahydroquinoline group and a decahydroisoquinoline group, are preferred from the viewpoint of inhibiting any in-film diffusion in the PEB (post-exposure bake) operation, thereby attaining an enhancement of exposure latitude.

As the aryl groups, there can be mentioned a benzene ring, a naphthalene ring, a phenanthrene ring and an anthracene ring. Of these, naphthalene ensuring a low absorbance is preferred from the viewpoint of the light absorbance at 193 nm.

As the heterocyclic groups, there can be mentioned a furan ring, a thiophene ring, a benzofuran ring, a benzothiophene ring, a dibenzofuran ring, a dibenzothiophene ring and a pyridine ring. Of these, a furan ring, a thiophene ring and a pyridine ring are preferred.

Substituents may be introduced in the above cyclic organic groups. As the substituents, there can be mentioned an alkyl group (any of linear, branched and cyclic forms, preferably having 1 to 12 carbon atoms), an aryl group (preferably having 6 to 14 carbon atoms), a hydroxyl group, an alkoxy group, an ester group, an amido group, a urethane group, a ureido group, a thioether group, a sulfonamido group, a sulfonic ester group, a cyano group and the like.

The carbon as a constituent of the organic group containing a cyclic structure (carbon contributing to ring formation) may be a carbonyl carbon.

In the formula, x is preferably 1 to 8, more preferably 1 to 4 and most preferably 1; y is preferably 0 to 4, more preferably 0 or 1 and further more preferably 0; and z is preferably 0 to 8, more preferably 0 to 4 and further more preferably 1.

In an aspect of the present invention, it is preferred for each of the anions of general formula (2) to contain 2 or 3 fluorine atoms. This enhances the effect of the joint use with resin (A).

Specific examples of the sulfonate anion structures of general formula (2) are shown below, which in no way limit the scope of the present invention.

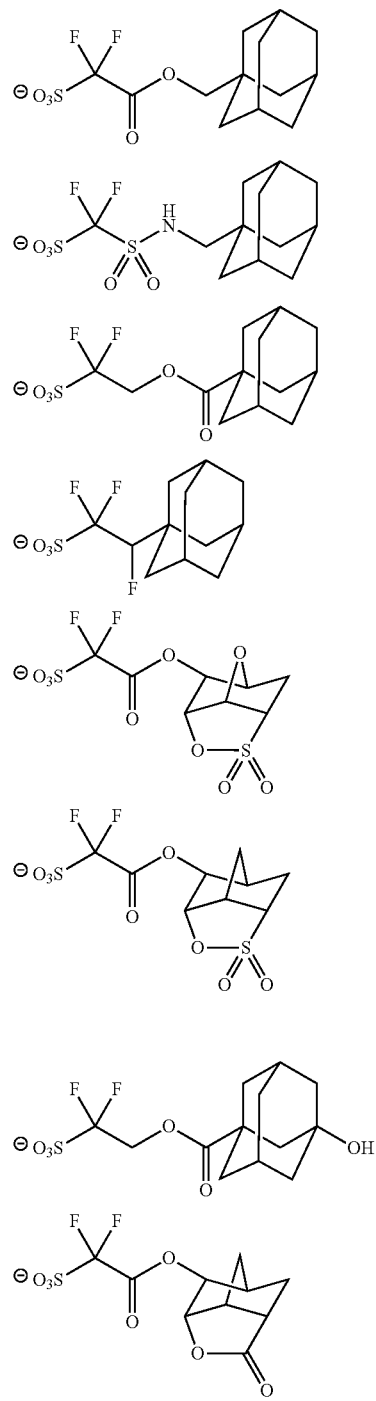

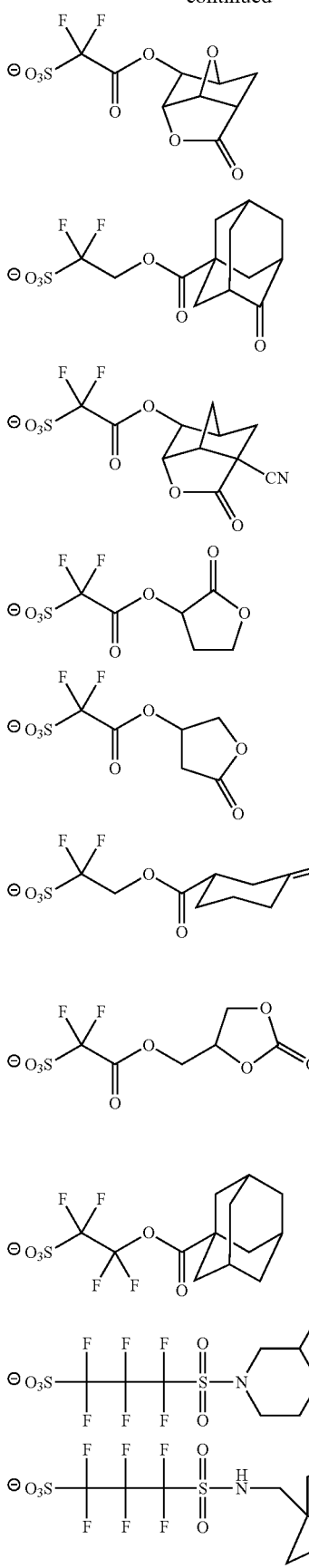

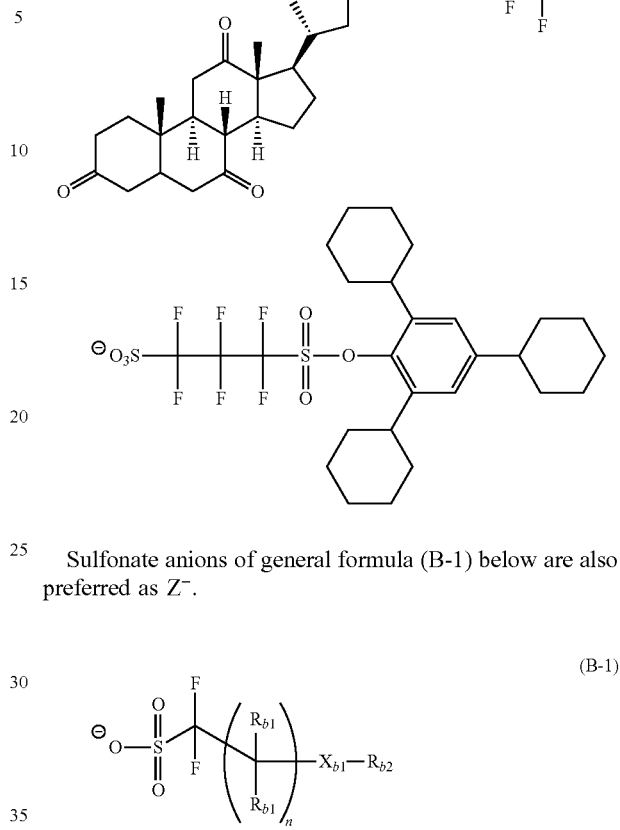

Sulfonate anions of general formula (B-1) below are also preferred as $Z^-$.

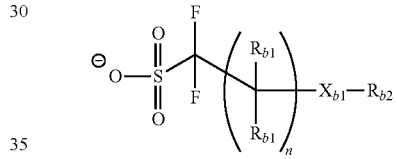

(B-1)

In general formula (B-1) above,

Each of $R_{b1}$s independently represents a hydrogen atom, a fluorine atom or a trifluoromethyl group ($CF_3$); and n is an integer of 0 to 4.

Preferably, n is an integer of 0 to 3. More preferably, n is 0 or 1.

$X_{b1}$ represents a single bond, an alkylene group, an ether bond, an ester bond (—OCO— or —COO—), a sulfonic ester bond (—OSO$_2$— or —SO$_3$—) or a combination of these.

$X_{b1}$ is preferably an ester bond (—OCO— or —COO—) or a sulfonic ester bond (—OSO$_2$— or —SO$_3$—). An ester bond (—OCO— or —COO—) is more preferred.

$R_{b2}$ represents an organic group having 6 or more carbon atoms.

It is preferred for the organic group having 6 or more carbon atoms represented by $R_{b2}$ to be a bulky group. As examples thereof, there can be mentioned an alkyl group, an alicyclic group, an aryl group and a heterocyclic group each having 6 or more carbon atoms.

The alkyl group having 6 or more carbon atoms represented by $R_{b2}$ may be linear or branched. A linear or branched alkyl group having 6 to 20 carbon atoms is preferred. As examples thereof, there can be mentioned a linear or branched hexyl group, a linear or branched heptyl group and a linear or branched octyl group. From the viewpoint of bulkiness, branched alkyl groups are preferred.

The alicyclic group having 6 or more carbon atoms represented by $R_{b2}$ may be monocyclic or polycyclic. The monoalicyclic group is, for example, a monocycloalkyl group, such as a cyclohexyl group or a cyclooctyl group. The polyalicyclic group is, for example, a polycycloalkyl group, such as a norbornyl group, a tricyclodecanyl group, a tetracyclodecanyl group, a tetracyclododecanyl group or an adamantyl group. Of the mentioned groups, alicyclic groups each with a bulky structure having 7 or more carbon atoms, such as a norbornyl group, a tricyclodecanyl group, a tetracyclodecanyl group, a tetracyclododecanyl group and an adamantyl group, are preferred from the viewpoint of inhibiting any in-film diffusion in the operation of post-exposure bake (PEB) and enhancing MEEF (mask error enhancement factor).

The aryl group having 6 or more carbon atoms represented by $R_{b2}$ may be monocyclic or polycyclic. As the aryl group, there can be mentioned, for example, a phenyl group, a naphthyl group, a phenanthryl group or an anthryl group. Of these, a naphthyl group exhibiting a relatively low light absorbance at 193 nm is preferred.

The heterocyclic group having 6 or more carbon atoms represented by $R_{b2}$ may be monocyclic or polycyclic. The polycyclic structure is superior in the inhibition of any acid diffusion. It is optional for the heterocyclic group to have aromaticity. As the heterocycle having aromaticity, there can be mentioned, for example, a benzofuran ring, a benzothiophene ring, a dibenzofuran ring or a dibenzothiophene ring. As the heterocycle having no aromaticity, there can be mentioned, for example, a tetrahydropyran ring, a lactone ring, a sultone ring or a decahydroisoquinoline ring.

A further substituent may be introduced in the organic group having 6 or more carbon atoms represented by $R_{b2}$. As the further substituent, there can be mentioned, for example, an alkyl group (may be linear or branched, preferably having 1 to 12 carbon atoms), a cycloalkyl group (may be any of a monocycle, a polycycle and a spiro ring, preferably having 3 to 20 carbon atoms), an aryl group (preferably having 6 to 14 carbon atoms), a hydroxyl group, an alkoxy group, an ester group, an amido group, a urethane group, a ureido group, a thioether group, a sulfonamido group or a sulfonic ester group. The carbon (carbon contributing to ring formation) as a constituent of the above alicyclic group, aryl group and heterocyclic group may be a carbonyl carbon.

Particular examples of the sulfonate anion structures of general formula (B-1) are shown below, which in no way limit the scope of the present invention. The following particular examples include those corresponding to sulfonate anions of general formula (2) above.

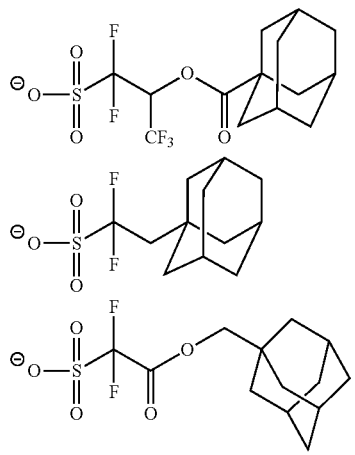

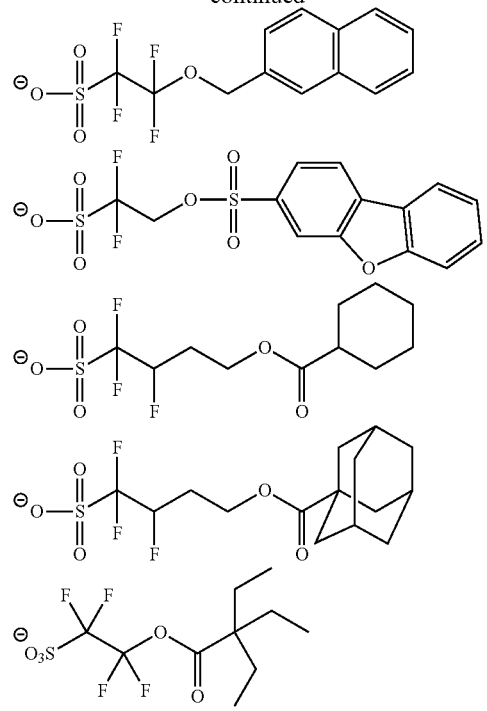

Further, sulfonate anions of general formula (A-I) below are also preferred as $Z^-$.

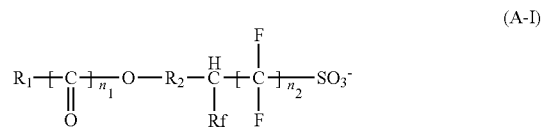

(A-I)

In general formula (A-I) above, $R_1$ represents an alkyl group, a monovalent alicyclic hydrocarbon group, an aryl group or a heteroaryl group.]

$R_2$ represents a bivalent connecting group.

Rf represents a fluorine atom or an alkyl group substituted with at least one fluorine atom.

Each of $n_1$ and $n_2$ is independently 0 or 1.

The alkyl group represented by $R_1$ is preferably one having 1 to 20 carbon atoms, more preferably 1 to 10 carbon atoms, further more preferably 1 to 5 carbon atoms and most preferably 1 to 4 carbon atoms.

A substituent (preferably a fluorine atom) may be introduced in this alkyl group. The substituted alkyl group is preferably an alkyl group having 1 to 5 carbon atoms substituted with at least one fluorine atom, more preferably a perfluoroalkyl group having 1 to 5 carbon atoms.

The alkyl group represented by $R_1$ is preferably a methyl group, an ethyl group or a trifluoromethyl group, more preferably a methyl group or an ethyl group.

The monovalent alicyclic hydrocarbon group represented by $R_1$ preferably has 5 or more carbon atoms. The number of carbon atoms of this monovalent alicyclic hydrocarbon group is preferably up to 20, more preferably up to 15. The monovalent alicyclic hydrocarbon group may be monocyclic or polycyclic. The —$CH_2$— moiety of the alicyclic hydrocarbon group may be partially replaced by —O— or —C(=O)—.

The monoalicyclic hydrocarbon group preferably has 5 to 12 carbon atoms and is preferably a cyclopentyl group, a cyclohexyl group or a cyclooctyl group.

The polyalicyclic hydrocarbon group preferably has 10 to 20 carbon atoms and is preferably a norbornyl group, an adamantyl group or a noradamantyl group.

The aryl group represented by $R_1$ preferably has 6 or more carbon atoms. The number of carbon atoms of this aryl group is preferably up to 20, more preferably up to 15.

The heteroaryl group represented by $R_1$ preferably has 2 or more carbon atoms. The number of carbon atoms of this heteroaryl group is preferably up to 20, more preferably up to 15.

The aryl group and heteroaryl group may be both monocyclic or polycyclic.

The monocyclic aryl group is, for example, a phenyl group.

The polycyclic aryl group is, for example, a naphthyl group or an anthracenyl group.

The monocyclic heteroaryl group is, for example, a pyridyl group, a thienyl group or a furanyl group.

The polycyclic heteroaryl group is, for example, a quinolyl group or an isoquinolyl group.

Substituents may further be introduced in the monovalent alicyclic hydrocarbon group, aryl group and heteroaryl group represented by $R_1$. As the further substituents, there can be mentioned a hydroxyl group, a halogen atom (a fluorine atom, a chlorine atom, a bromine atom, an iodine atom, etc.), a nitro group, a cyano group, an amido group, a sulfonamido group, an alkyl group, an alkoxy group, an alkoxycarbonyl group, an acyl group, an acyloxy group, and a carboxyl group.

$R_1$ is most preferably a cyclohexyl group or an adamantyl group.

The bivalent connecting group represented by $R_2$ is not particularly limited. As the bivalent connecting group, there can be mentioned —COO—, —OCO—, —CO—, —O—, —S—, —SO—, —SO$_2$—, an alkylene group (preferably 1 to 30 carbon atoms), a cycloalkylene group (preferably 3 to 30 carbon atoms), an alkenylene group (preferably 2 to 30 carbon atoms), an arylene group (preferably 6 to 30 carbon atoms), a heteroarylene group (preferably 2 to 30 carbon atoms) or a group comprised of a combination of two or more of these. Further substituents may be introduced in these alkylene, cycloalkylene, alkenylene, arylene and heteroarylene groups. Particular examples of such substituents are the same as set forth above in connection with the substituents further introducible in the monovalent alicyclic hydrocarbon group, aryl group and heteroaryl group represented by $R_1$.

The bivalent connecting group represented by $R_2$ is preferably an alkylene group, a cycloalkylene group, an alkenylene group, an arylene group or a heteroarylene group. An alkylene group is more preferred. An alkylene group having 1 to 10 carbon atoms is furthermore preferred, and an alkylene group having 1 to 5 carbon atoms is most preferred.

Rf represents a fluorine atom or an alkyl group substituted with at least one fluorine atom. This alkyl group preferably has 1 to 30 carbon atoms, more preferably 1 to 10 carbon atoms and further more preferably 1 to 4 carbon atoms. It is preferred for the alkyl group substituted with at least one fluorine atom to be a perfluoroalkyl group.

Rf is preferably a fluorine atom or a perfluoroalkyl group having 1 to 4 carbon atoms. In particular, it is preferred for Rf to be a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ or $CH_2CH_2C_4F_9$. Of these, a fluorine atom and $CF_3$ are more preferred.

Preferably, $n_1$ is 1.

Preferably, $n_2$ is 1.

Particular examples of the sulfonate anion structures of general formula (A-I) are shown below, which in no way limit the scope of the present invention. The following particular examples include those corresponding to sulfonate anions of general formula (2) above.

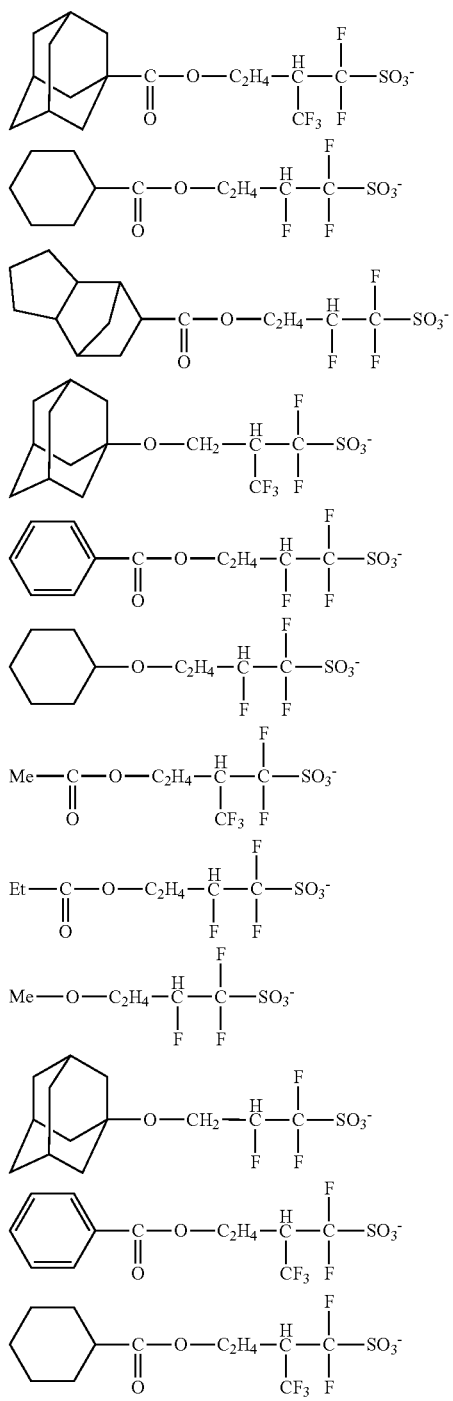

-continued

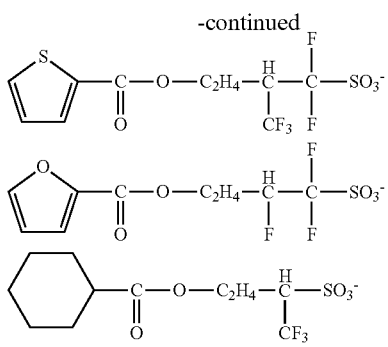

The nonnucleophilic anion $Z^-$ may be any of disulfonylimidate anions of general formula (2') below.

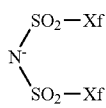

(2')

In general formula (2'), Xf's are as defined above in connection with general formula (2), and preferred examples thereof are also the same as mentioned above. In general formula (2'), two Xf's may be connected to each other to thereby form a ring structure.

It is preferred for the disulfonylimidate anion represented by $Z^-$ to be a bis(alkylsulfonyl)imide anion.

Each of the alkyl groups in the bis(alkylsulfonyl)imide anion is preferably an alkyl group having 1 to 5 carbon atoms.

In the bis(alkylsulfonyl)imide anion, two alkyl groups may be connected to each other to thereby form an alkylene group (preferably 2 to 4 carbon atoms), which may form a ring in cooperation with the imide group and two sulfonyl groups. The ring structure that may be formed in the bis(alkylsulfonyl)imide anion is preferably a 5- to 7-membered ring, more preferably a 6-membered ring.

As substituents that can be introduced in the above alkyl groups and alkylene group formed by the mutual connection of two alkyl groups, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group and the like. A fluorine atom and an alkyl group substituted with a fluorine atom are preferred.

Moreover, as an acid generator, there can be mentioned compounds of general formula (ZV) above.

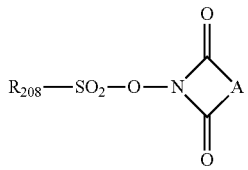

(ZV)

In general formula (ZV),
$R_{208}$ represents an alkyl group, a cycloalkyl group or an aryl group.
A represents an alkylene group, an alkenylene group or an arylene group.

Particular examples of the aryl groups represented by $R_{208}$ can be the same as those set forth above in connection with $R_{201}$ to $R_{203}$ in general formula (ZI).

Particular examples of the alkyl and cycloalkyl groups represented by $R_{208}$ can be the same as those set forth above in connection with $R_{201}$ to $R_{203}$ in general formula (ZI).

As the alkylene group represented by A, there can be mentioned an alkylene group having 1 to 12 carbon atoms (for example, a methylene group, an ethylene group, a propylene group, an isopropylene group, a butylene group, an isobutylene group or the like). As the alkenylene group represented by A, there can be mentioned an alkenylene group having 2 to 12 carbon atoms (for example, a vinylene group, a propenylene group, a butenylene group or the like). As the arylene group represented by A, there can be mentioned an arylene group having 6 to 10 carbon atoms (for example, a phenylene group, a tolylene group, a naphthylene group or the like).

In each of the compounds (B), the fluorine content expressed by (sum of the masses of all fluorine atoms contained in the compound)/(sum of the masses of all atoms contained in the compound) is preferably 0.30 or less, more preferably 0.25 or less, further more preferably 0.20 or less, still further preferably 0.15 or less and most preferably 0.10 or less.

Particular examples of the acid generators are shown below, which in no way limit the scope of the present invention.

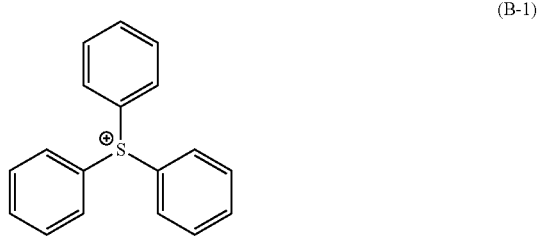

(B-1)

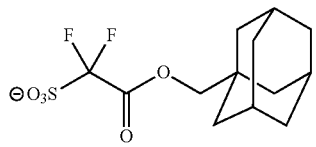

(B-2)

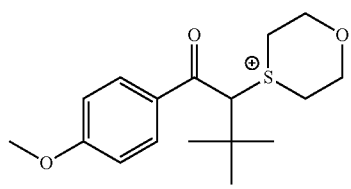

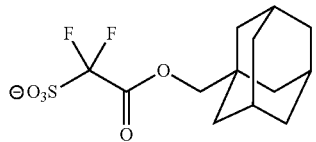

(B-3)
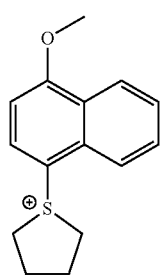 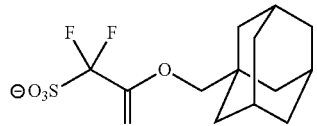
(B-4)
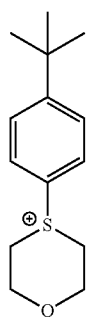 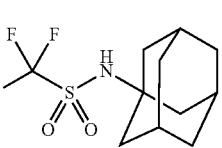
(B-5)
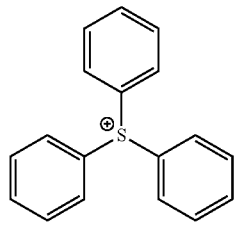
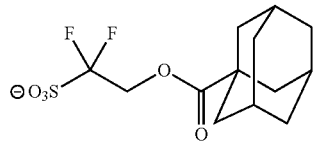
(B-6)
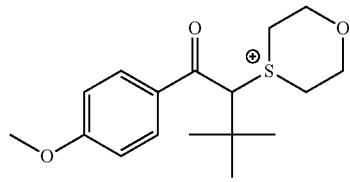
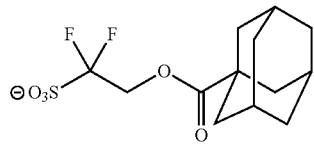
(B-7)
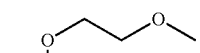
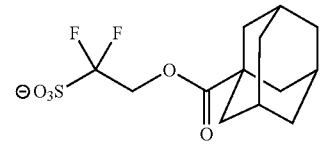
(B-8)
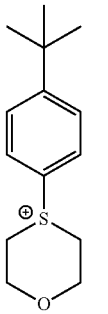 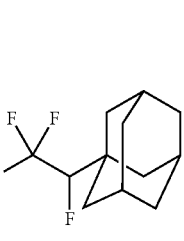
(B-9)
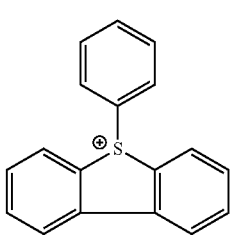 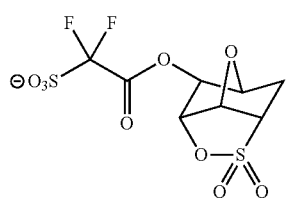
(B-10)
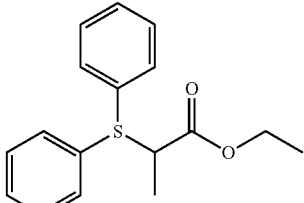
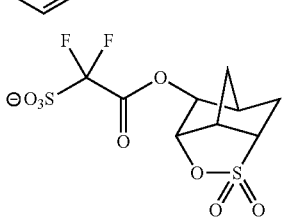
(B-11)
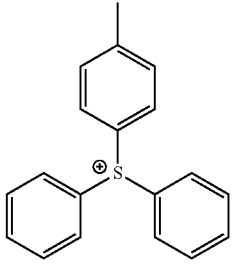
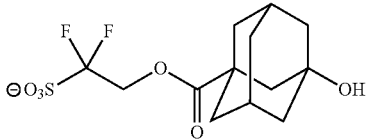
(B-12)
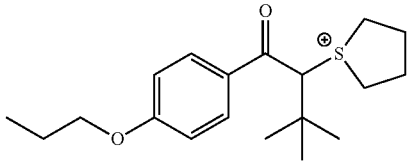

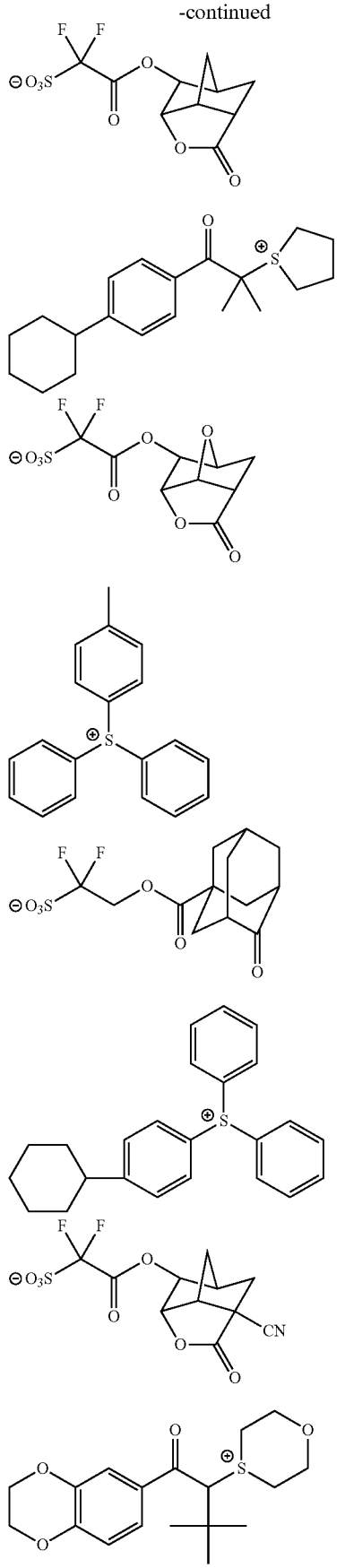
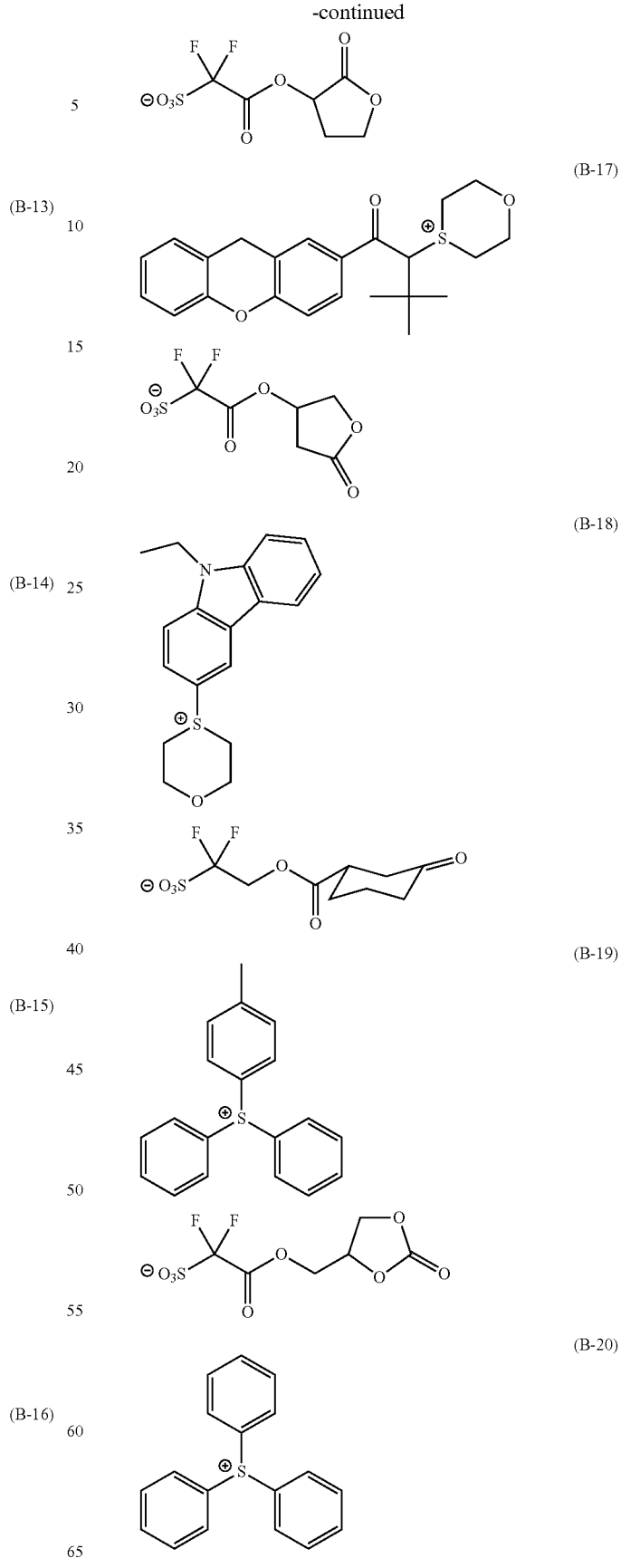

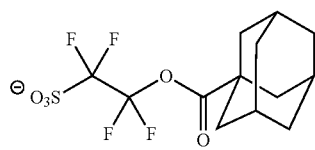
(B-21)
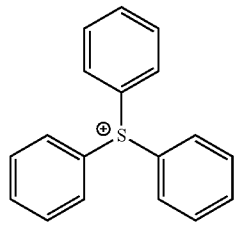
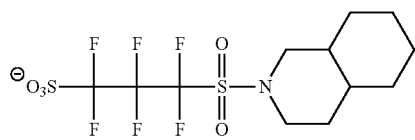
(B-22)
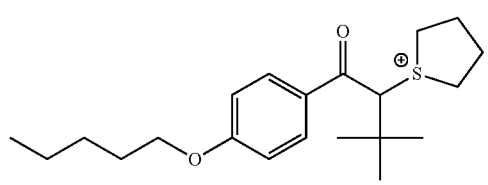
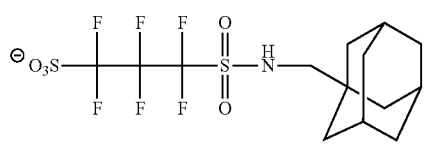
(B-23)
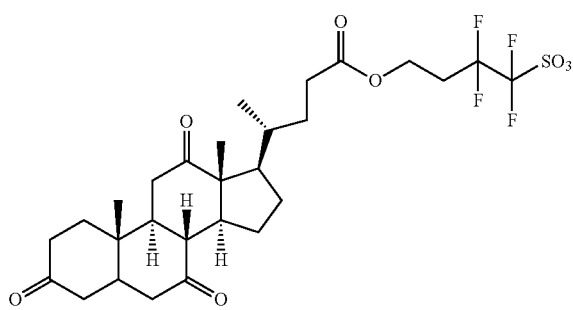
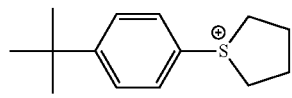
(B-24)
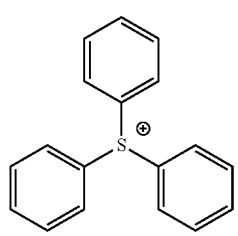
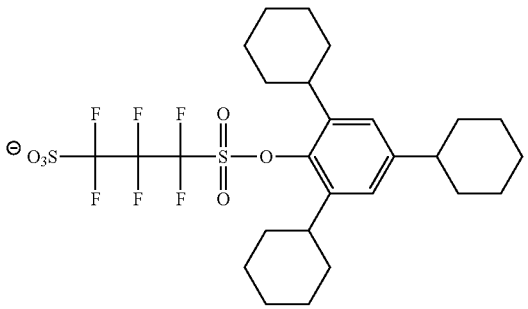
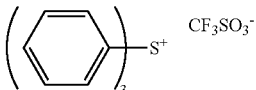 (z1)
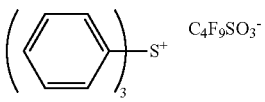 (z2)
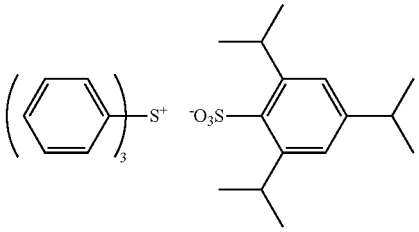 (z3)
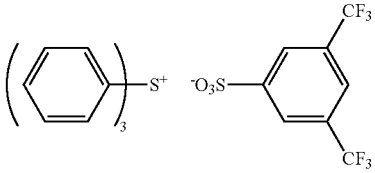 (z4)
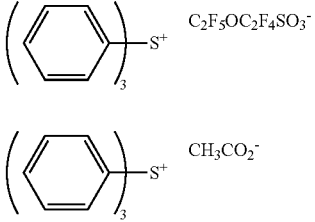 (z5)
(z6)
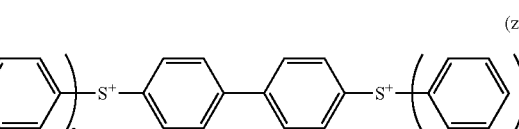 (z7)
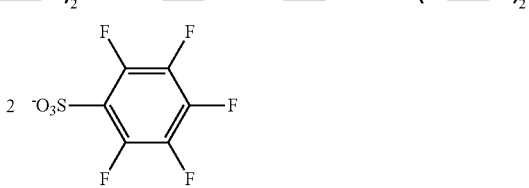 (z8)

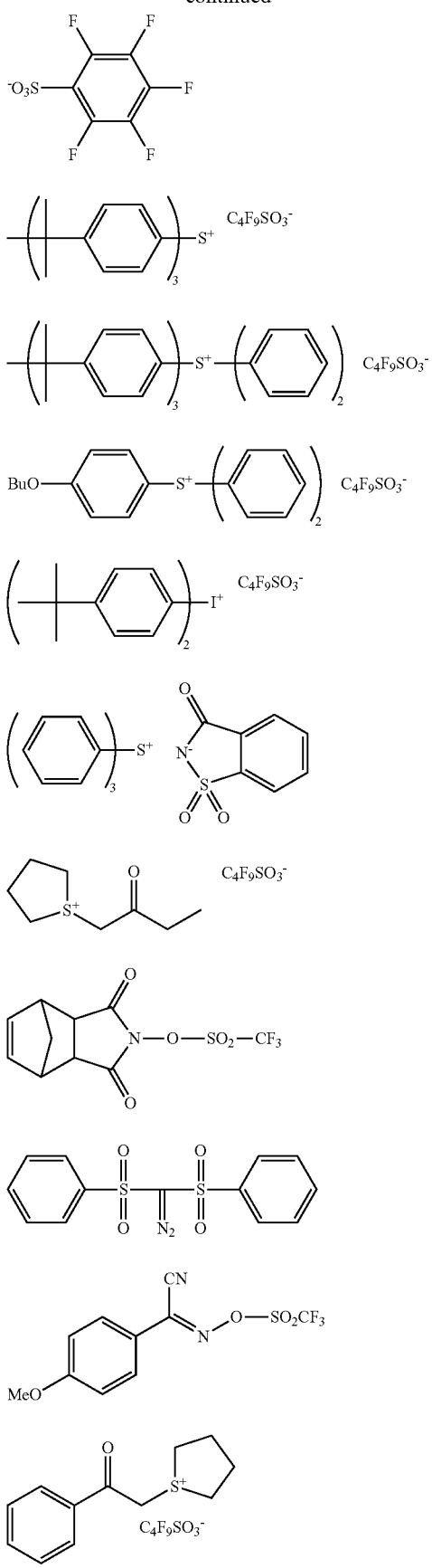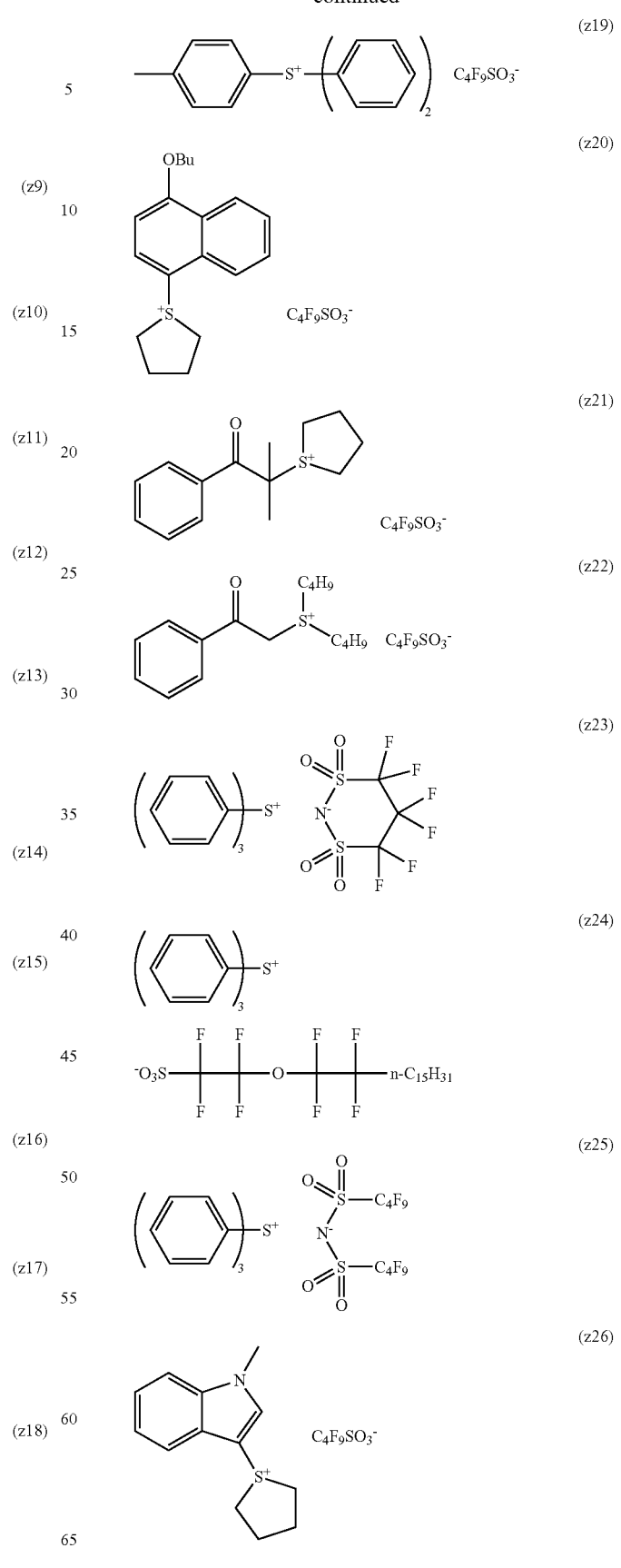

(z27) 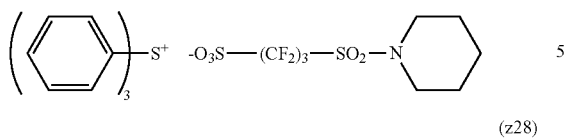
(z28) 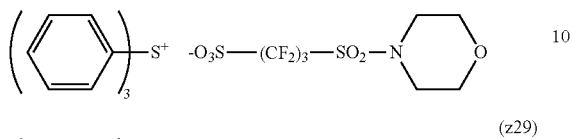
(z29) 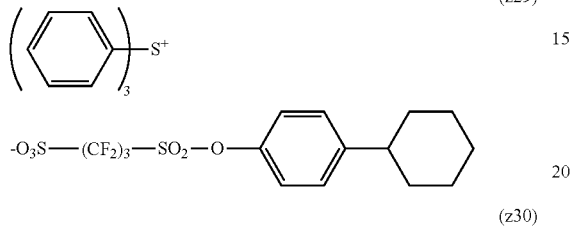
(z30) 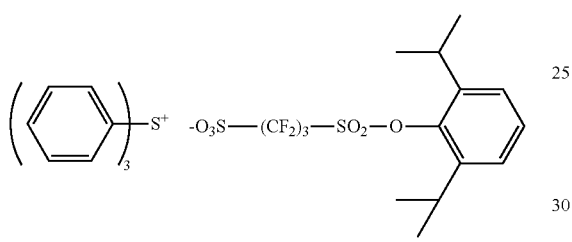
(z31) 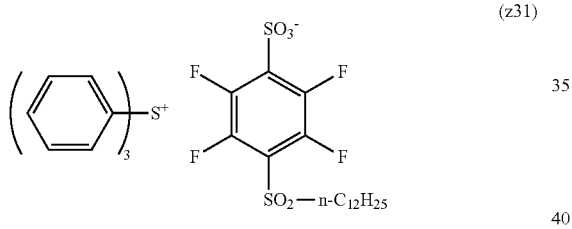
(z32) 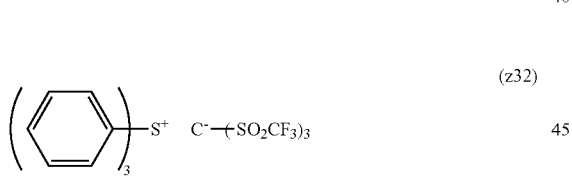
(z33) 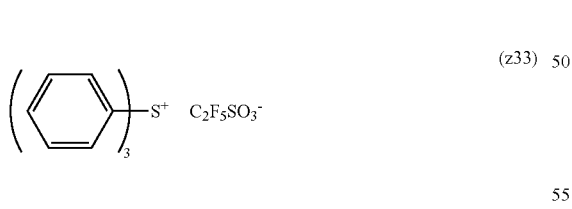
(z34) 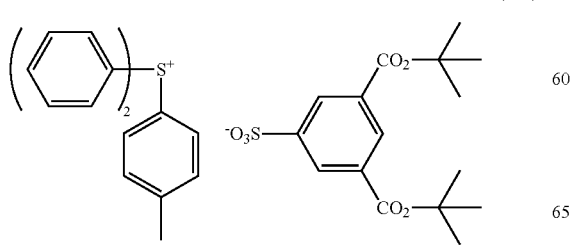
(z35) 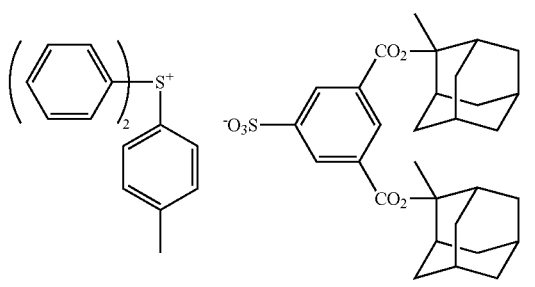
(z36) 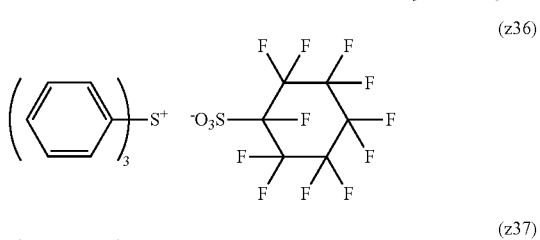
(z37) 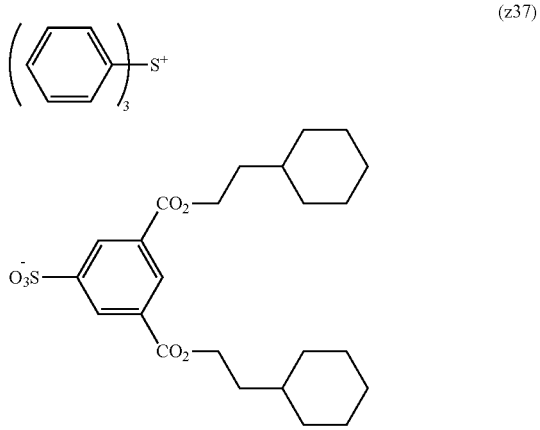
(z38) 
(z39) 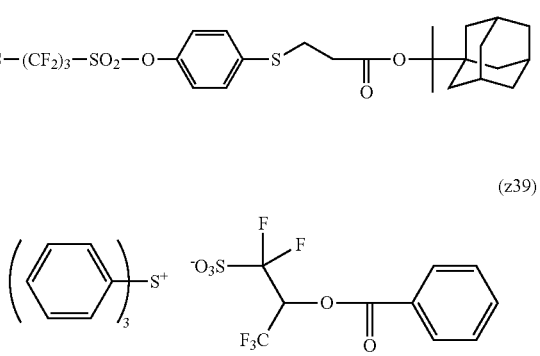
(z40) 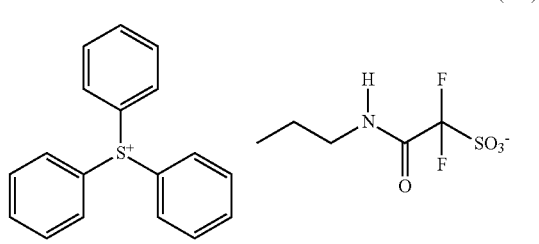

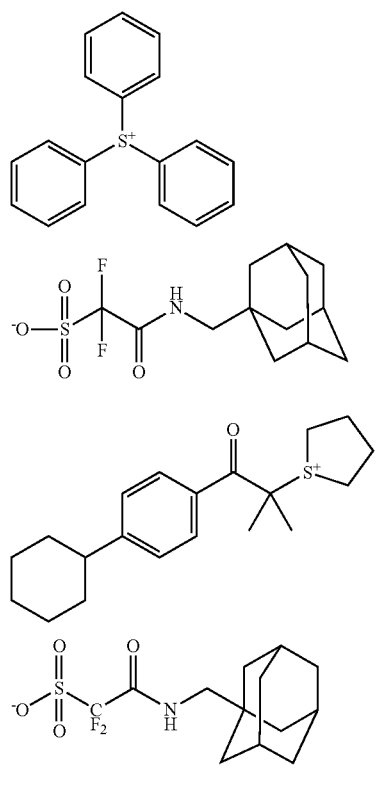
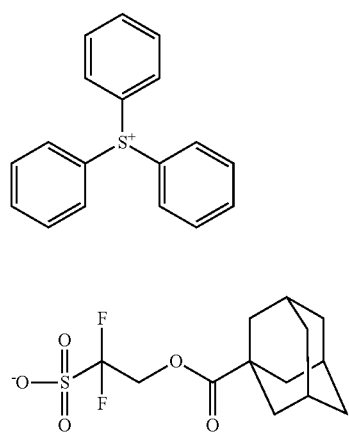
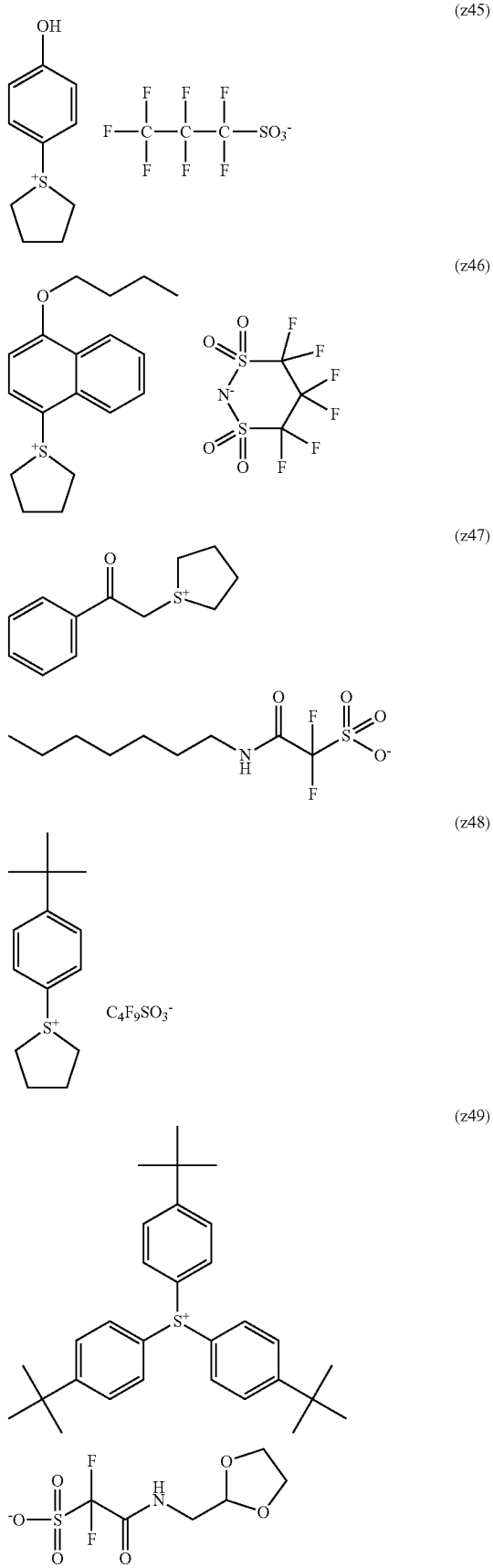

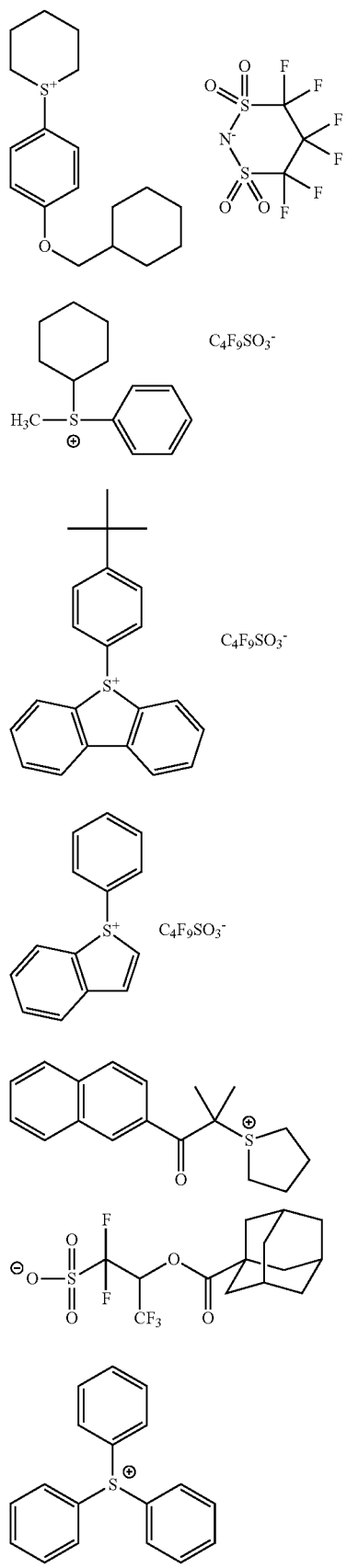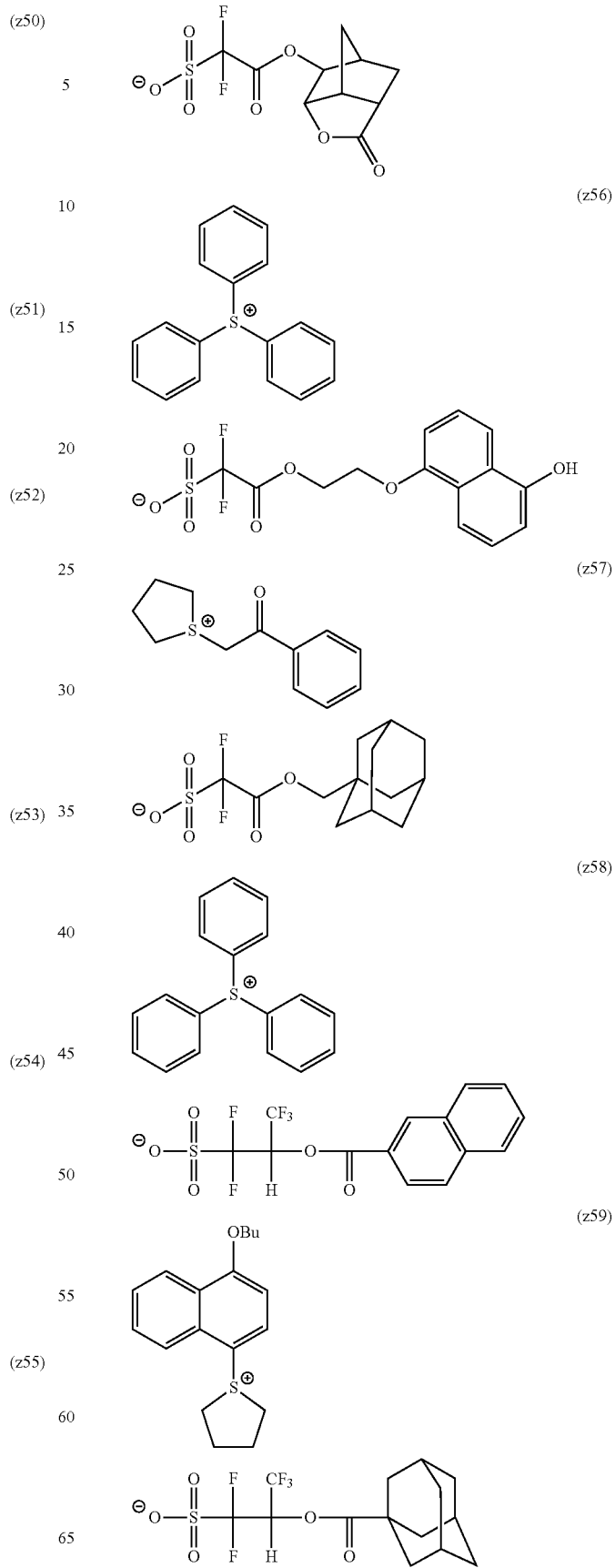

(z60) 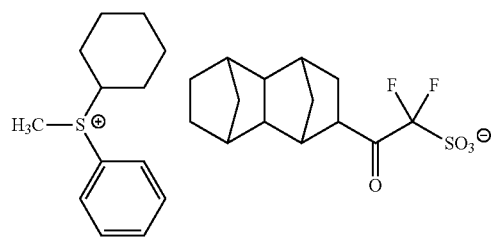
(z61) 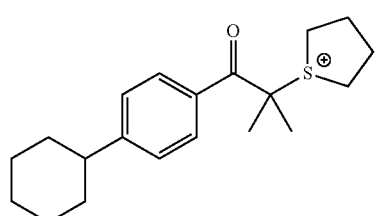
(z62) 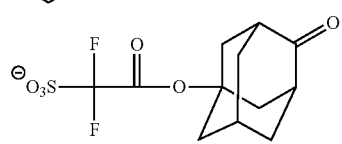
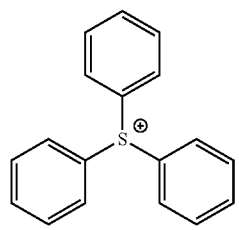
(z63) 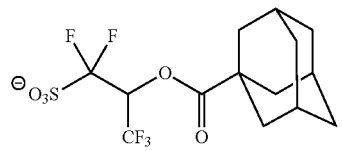
(z64) 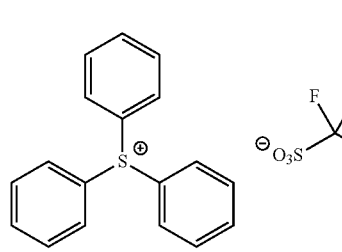
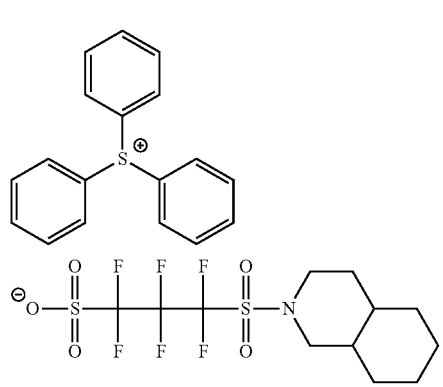
(z65) 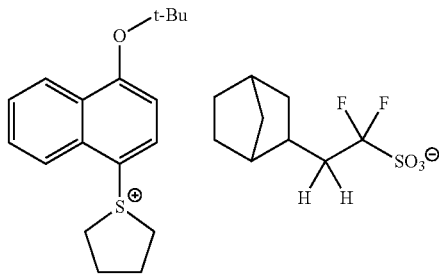
(z66) 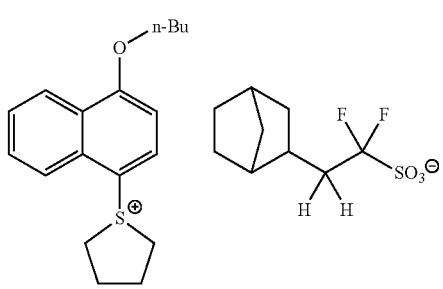
(z67) 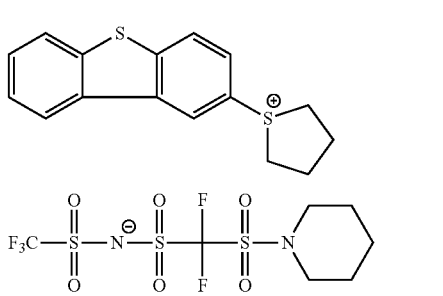
(z68) 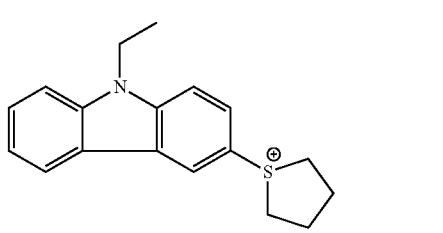
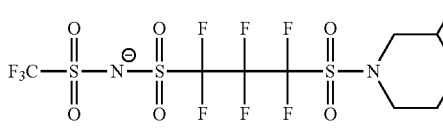
(z69) 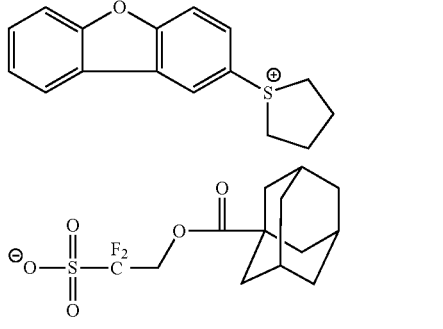

(z70) 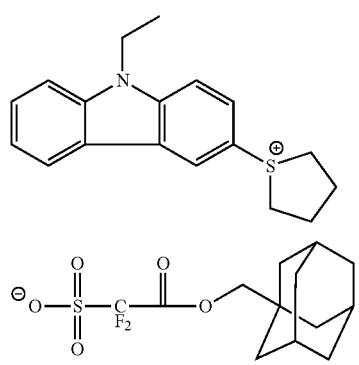
(z71) 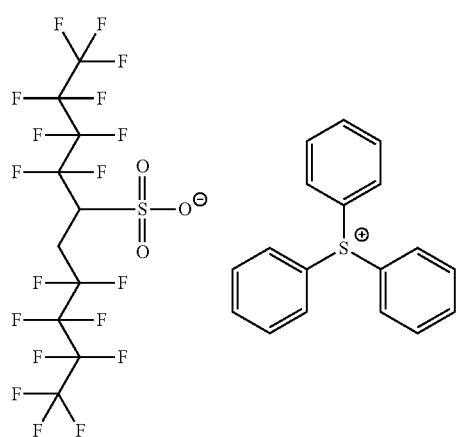
(z72) 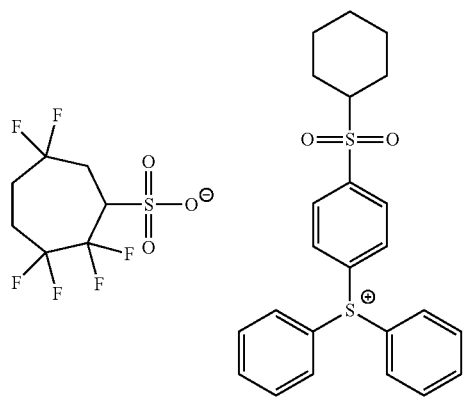
(z73) 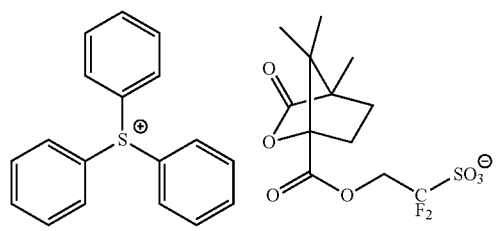
(z74) 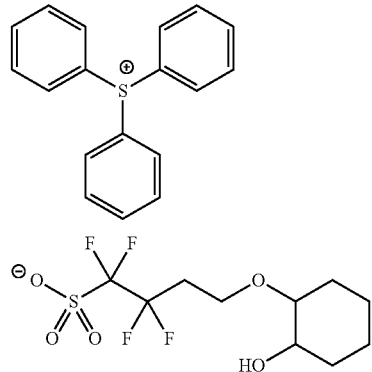
(z75) 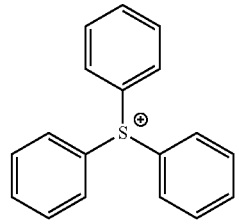
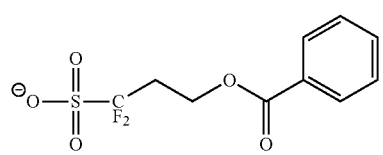
(z76) 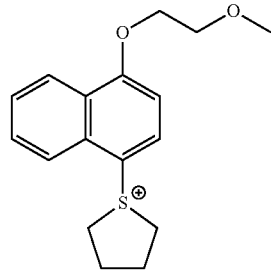
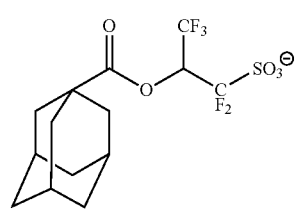
(z77) 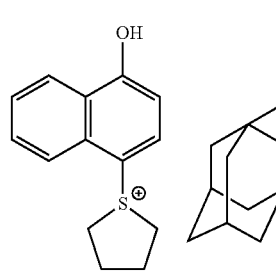

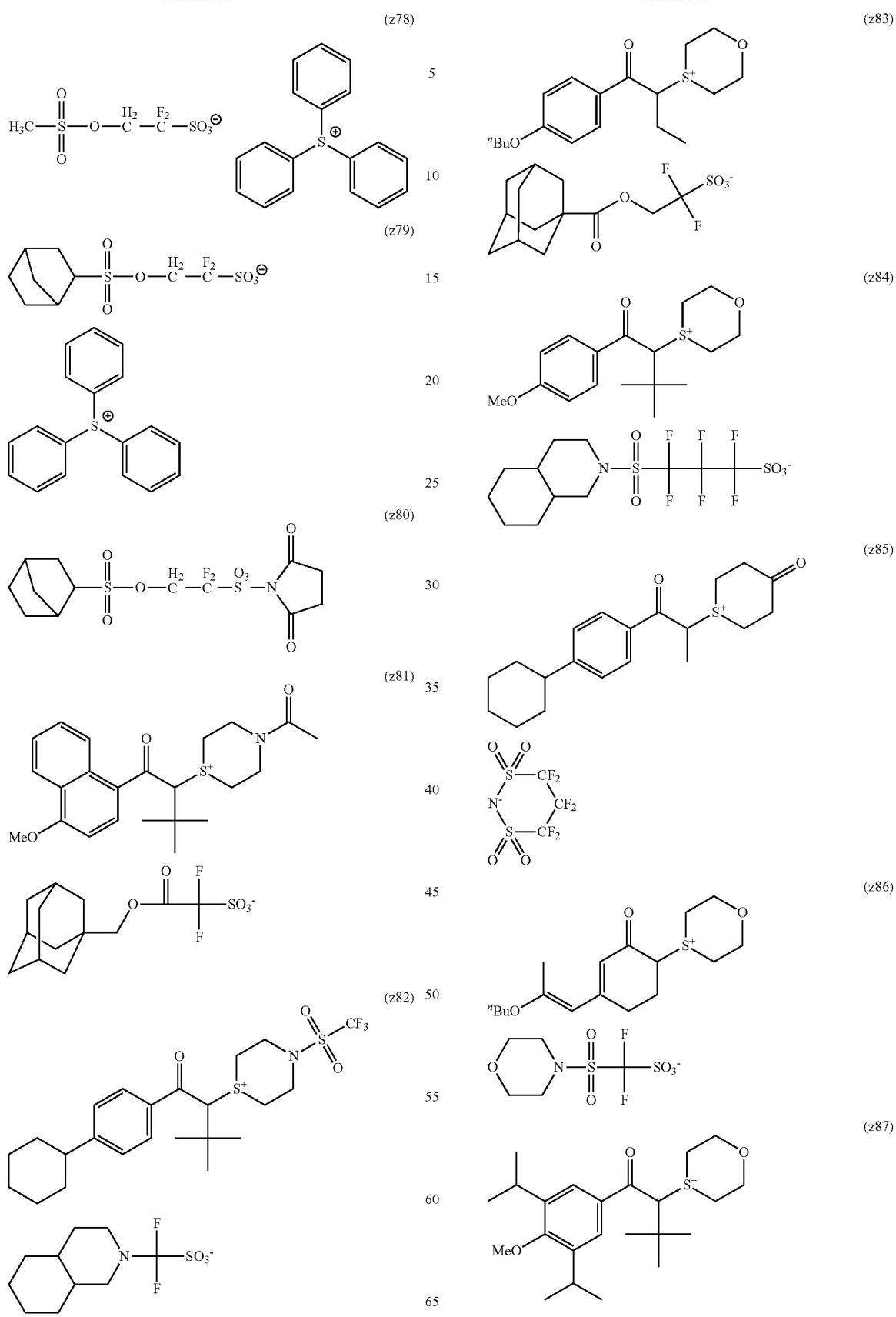

117
-continued
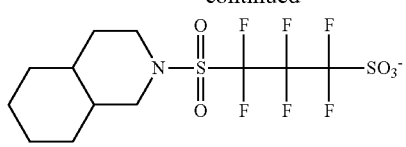
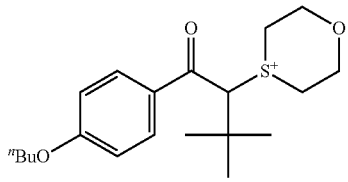
(z88)
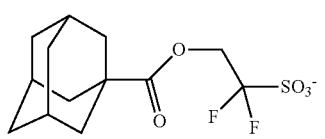
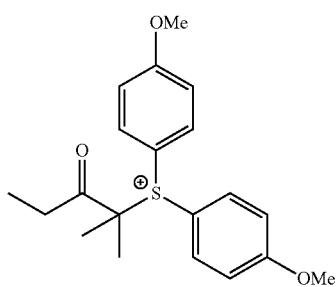
(z89)
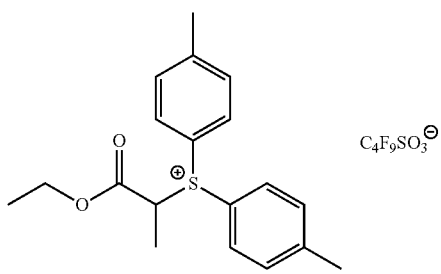
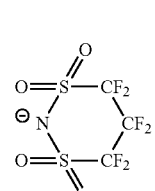
(z90)
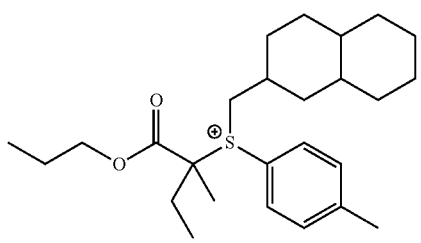
(z91)
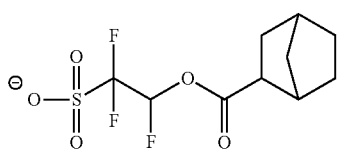
118
-continued
(z92)
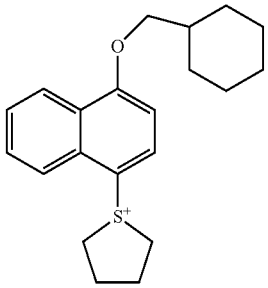
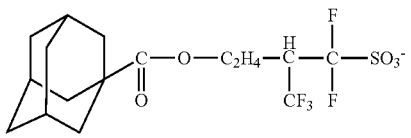
(z93)
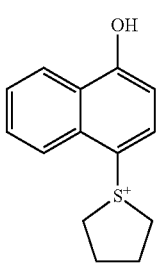
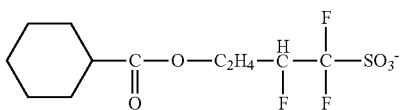
(z94)
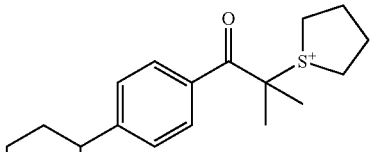
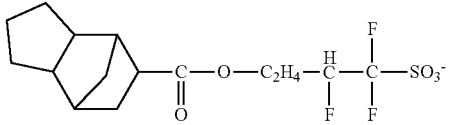
(z95)
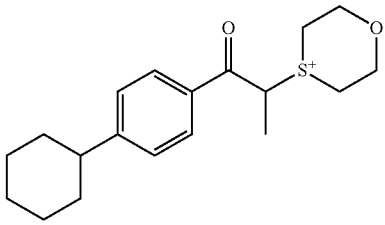
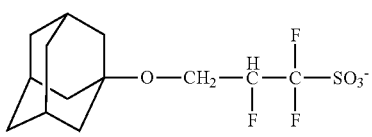

-continued
(z96) 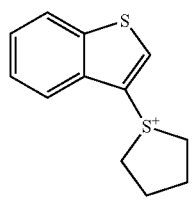 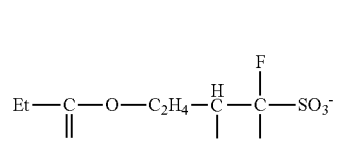
(z97) 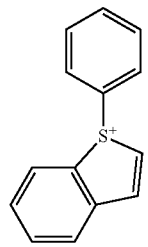 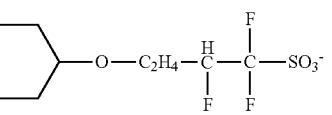
(z98) 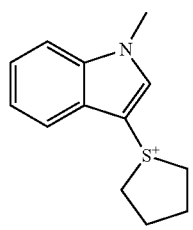 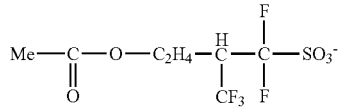
(z99) 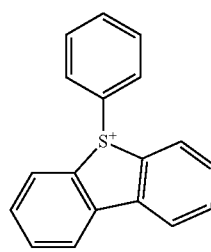
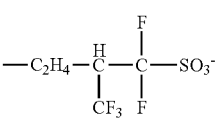
(z100) 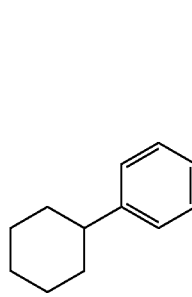
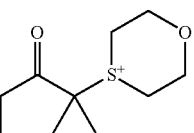
(z101) 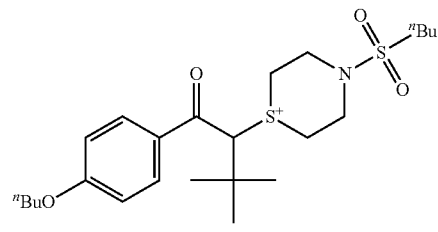
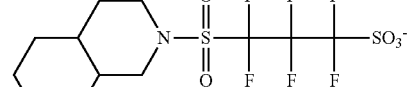
(z102) 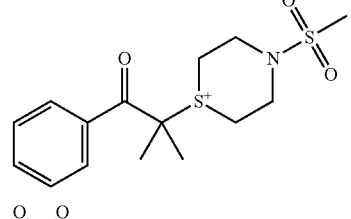
(z103) 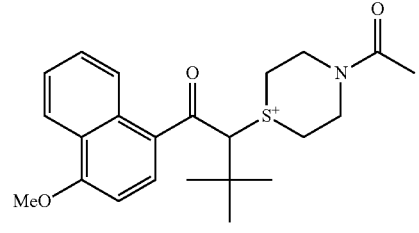
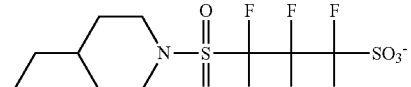
(z104) 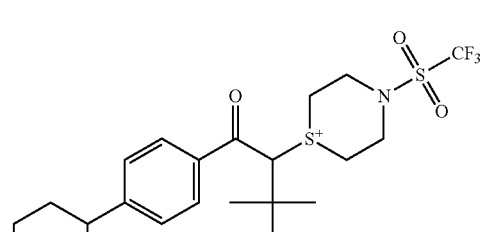
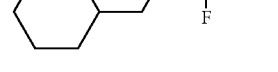

-continued (z105)
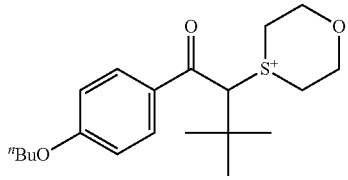

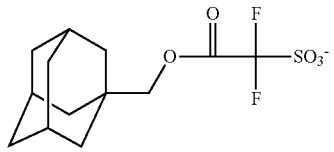

(z106)
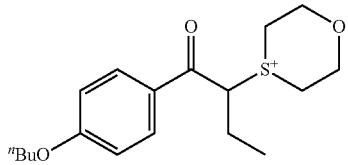

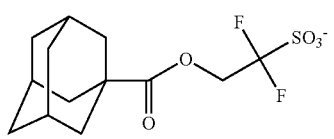

(z107)
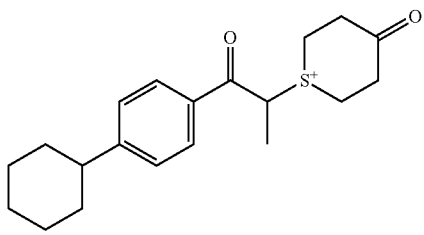

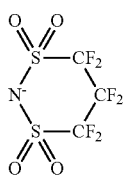

(z108)
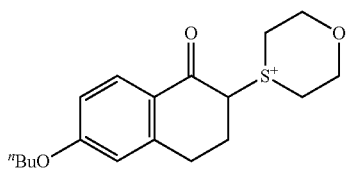

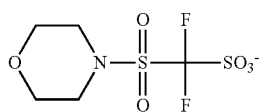

(z109)
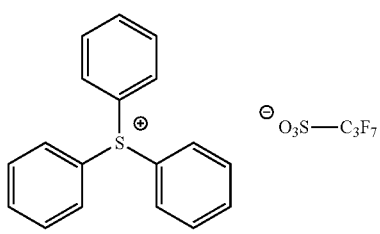

-continued (z110)
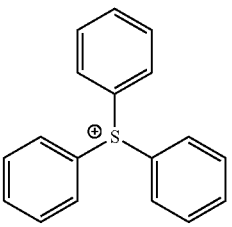

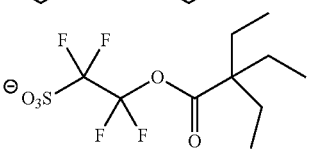

One type of acid generator may be used alone, or two or more types thereof may be used in combination.

The content of acid generator(s) in the composition is preferably in the range of 0.1 to 30 mass %, more preferably 5 to 28 mass % and further more preferably 10 to 25 mass %, based on the total solids of the composition.

<Hydrophobic Resin (HR)>

The actinic-ray- or radiation-sensitive resin composition of the present invention may further comprise a hydrophobic resin (hereinafter also referred to as "hydrophobic resin (HR)" or simply "resin (HR)") especially when a liquid immersion exposure is applied thereto. It is preferred for the hydrophobic resin (HR) to be different from the above-described resins (A).

This localizes the hydrophobic resin (HR) in the surface layer of the film. Accordingly, when the immersion medium is water, the static/dynamic contact angle of the surface of the resist film with respect to water can be increased, thereby enhancing the immersion liquid tracking property.

Although the hydrophobic resin (HR) is preferably designed so as to be localized in the interface as mentioned above, as different from surfactants, the hydrophobic resin does not necessarily have to contain a hydrophilic group in its molecule and does not need to contribute toward uniform mixing of polar/nonpolar substances.

From the viewpoint of localization in the surface layer of the film, it is preferred for the hydrophobic resin (HR) to contain at least one member selected from among a "fluorine atom," a "silicon atom" and a "$CH_3$ partial structure introduced in a side chain portion of the resin." More preferably, two or more members are contained.

When the hydrophobic resin (HR) contains a fluorine atom and/or a silicon atom, in the hydrophobic resin (HR), the fluorine atom and/or silicon atom may be introduced in the principal chain of the resin, or a side chain thereof.

When the hydrophobic resin (HR) contains a fluorine atom, it is preferred for the resin to comprise, as a partial structure containing a fluorine atom, an alkyl group containing a fluorine atom, a cycloalkyl group containing a fluorine atom or an aryl group containing a fluorine atom.

The alkyl group containing a fluorine atom (preferably having 1 to 10 carbon atoms, more preferably 1 to 4 carbon atoms) is a linear or branched alkyl group having at least one hydrogen atom thereof replaced by a fluorine atom. Further, non-fluorine-atom substituents may be introduced therein.

The cycloalkyl group containing a fluorine atom is a mono- or polycycloalkyl group having at least one hydrogen atom thereof replaced by a fluorine atom. Further, non-fluorine-atom substituents may be introduced therein.

As the aryl group containing a fluorine atom, there can be mentioned an aryl group, such as a phenyl or naphthyl group, having at least one hydrogen atom thereof replaced by a fluorine atom. Further, non-fluorine-atom substituents may be introduced therein.

As preferred alkyl groups containing a fluorine atom, cycloalkyl groups containing a fluorine atom and aryl groups containing a fluorine atom, there can be mentioned groups of general formulae (F2) to (F4) below, which however in no way limit the scope of the present invention.

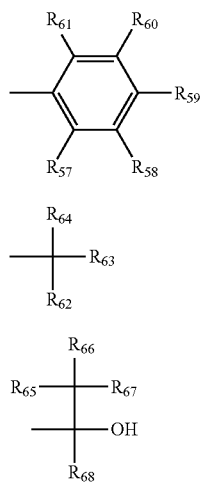

In general formulae (F2) to (F4), each of $R_{57}$ to $R_{68}$ independently represents a hydrogen atom, a fluorine atom or an alkyl group (linear or branched), provided that each of at least one of $R_{57}$-$R_{61}$, at least one of $R_{62}$-$R_{64}$ and at least one of $R_{65}$-$R_{68}$ independently represents a fluorine atom or an alkyl group (preferably having 1 to 4 carbon atoms) having at least one hydrogen atom thereof replaced by a fluorine atom.

It is preferred for all of $R_{57}$-$R_{61}$ and $R_{65}$-$R_{67}$ to represent fluorine atoms. Each of $R_{62}$, $R_{63}$ and $R_{68}$ preferably represents an alkyl group (especially having 1 to 4 carbon atoms) having at least one hydrogen atom thereof replaced by a fluorine atom, more preferably a perfluoroalkyl group having 1 to 4 carbon atoms. $R_{62}$ and $R_{63}$ may be connected to each other to thereby form a ring.

Specific examples of the groups of general formula (F2) include a p-fluorophenyl group, a pentafluorophenyl group, a 3,5-di(trifluoromethyl)phenyl group and the like.

Specific examples of the groups of general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, a perfluorocyclohexyl group and the like. Of these, a hexafluoroisopropyl group, a heptafluoroisopropyl group, a hexafluoro(2-methyl) isopropyl group, an octafluoroisobutyl group, a nonafluoro-t-butyl group and a perfluoroisopentyl group are preferred. A hexafluoroisopropyl group and a heptafluoroisopropyl group are more preferred.

Specific examples of the groups of general formula (F4) include —C(CF$_3$)$_2$OH, —C(C$_2$F$_5$)$_2$OH, —C(CF$_3$)(CH$_3$) OH, —CH(CF$_3$) OH and the like. —C(CF$_3$)$_2$OH is preferred.

Each of the partial structures containing a fluorine atom may be directly bonded to the principal chain, or may be bonded to the principal chain via a group selected from the group consisting of an alkylene group, a phenylene group, an ether bond, a thioether bond, a carbonyl group, an ester bond, an amide bond, a urethane bond and a ureylene bond, or via a group composed of a combination of two or more of these.

Particular examples of the repeating units containing a fluorine atom are shown below, which in no way limit the scope of the present invention.

In the particular examples, $X_1$ represents a hydrogen atom, —CH$_3$, —F or —CF$_3$. $X_2$ represents —F or —CF$_3$.

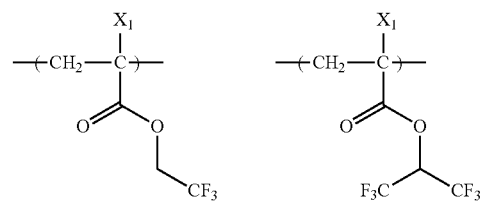

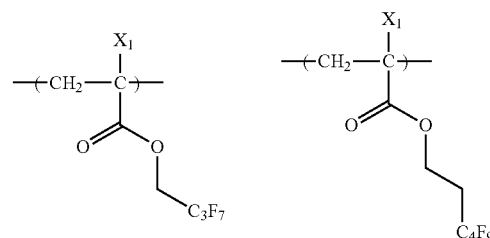

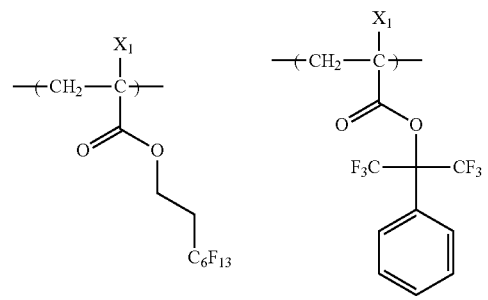

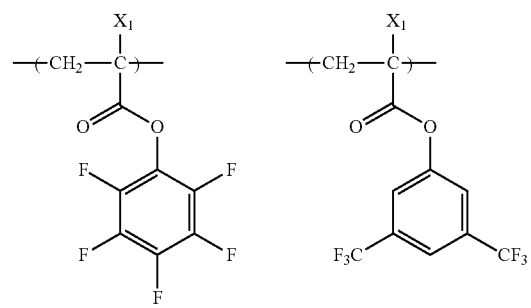

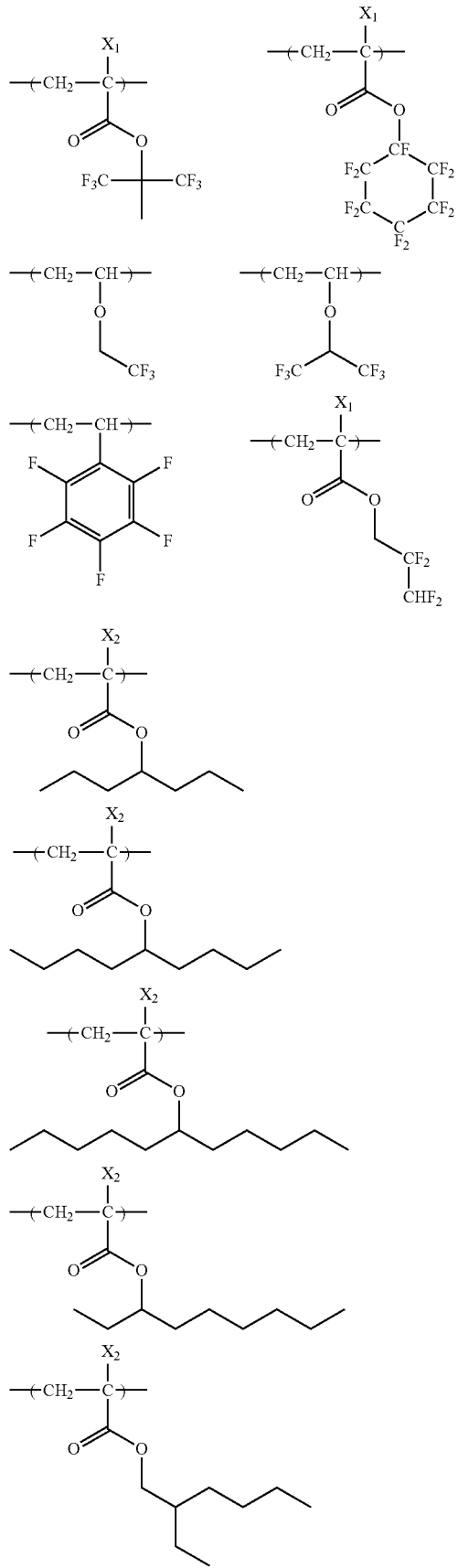
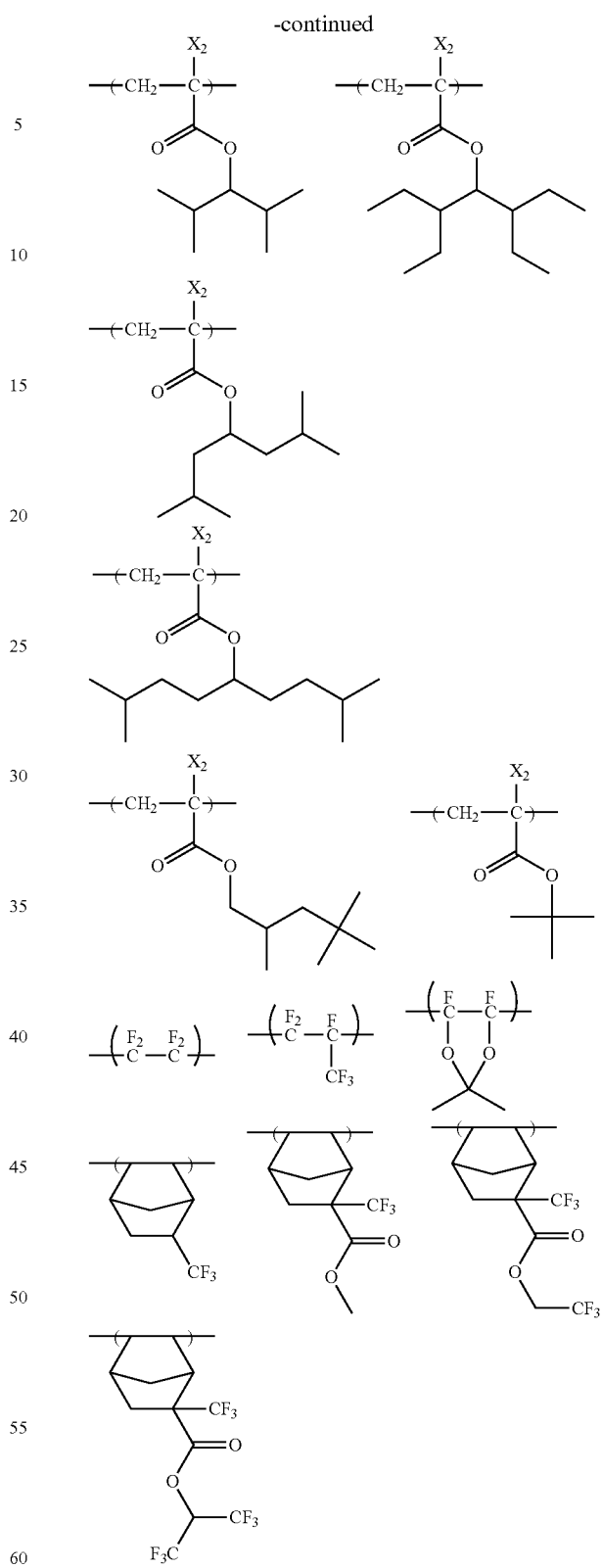
The hydrophobic resin (HR) may contain a silicon atom. It is preferred for the hydrophobic resin (HR) to be a resin with an alkylsilyl structure (preferably a trialkylsilyl group) or a cyclosiloxane structure as a partial structure containing a silicon atom.

As the alkylsilyl structure or cyclosiloxane structure, there can be mentioned, for example, any of the groups of general formulae (CS-1) to (CS-3) below or the like.

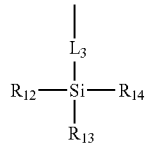
(CS-1)

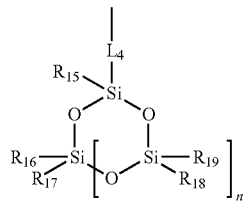
(CS-2)

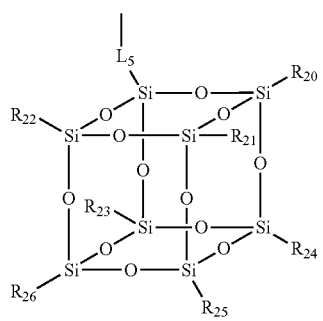
(CS-3)

In general formulae (CS-1) to (CS-3), each of $R_{12}$ to $R_{26}$ independently represents a linear or branched alkyl group (preferably having 1 to 20 carbon atoms) or a cycloalkyl group (preferably having 3 to 20 carbon atoms).

Each of $L_3$ to $L_5$ represents a single bond or a bivalent connecting group. As the bivalent connecting group, there can be mentioned any one, or a combination (preferably up to 12 carbon atoms in total) of two or more members, selected from the group consisting of an alkylene group, a phenylene group, an ether bond, a thioether bond, a carbonyl group, an ester bond, an amide bond, a urethane bond and a urea bond.

In the formulae, n is an integer of 1 to 5, preferably an integer of 2 to 4.

Particular examples of the repeating units each containing any of groups of general formulae (CS-1) to (CS-3) are shown below, which in no way limit the scope of the present invention. In the particular examples, $X_1$ represents a hydrogen atom, —$CH_3$, —F or —$CF_3$.

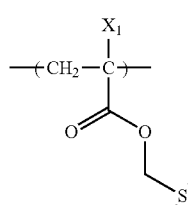 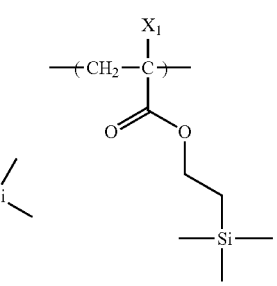

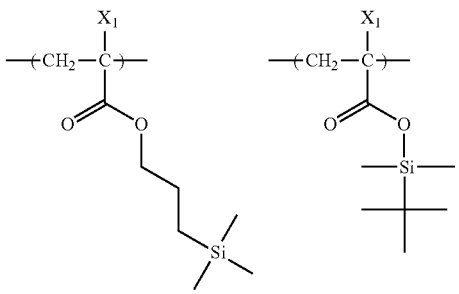

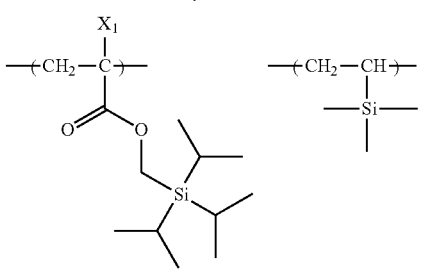

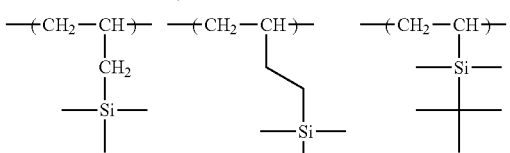

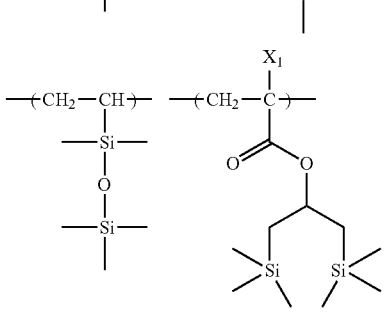

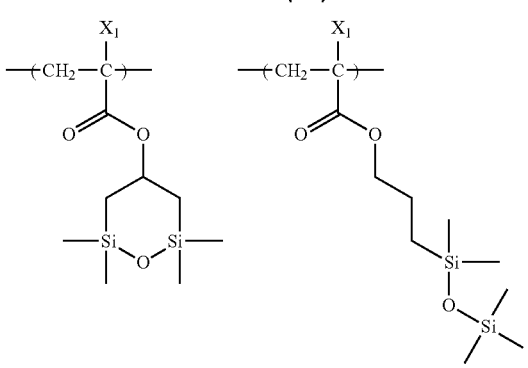

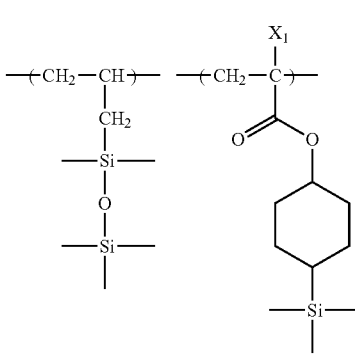

-continued

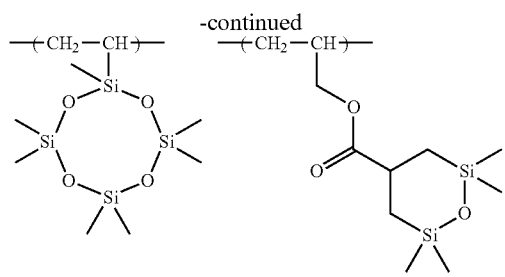

R = CH₃, C₂H₅, C₃H₇, C₄H₉

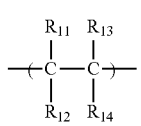

As mentioned above, it is also preferred for the hydrophobic resin (HR) to contain a CH₃ partial structure in its side chain portion.

Herein, the CH₃ partial structure (hereinafter also simply referred to as "side-chain CH₃ partial structure") contained in a side chain portion of the resin (HR) includes a CH₃ partial structure contained in an ethyl group, a propyl group or the like.

In contrast, a methyl group (for example, an α-methyl group in the repeating unit with a methacrylic acid structure) directly bonded to the principal chain of the resin (HR) is not included in the CH₃ partial structure according to the present invention, since the contribution thereof to the surface localization of the resin (HR) is slight due to the influence of the principal chain.

In particular, when the resin (HR) comprises, for example, a repeating unit derived from a monomer containing a polymerizable moiety having a carbon-carbon double bond, such as any of repeating units of general formula (M) below, and when each of $R_{11}$ to $R_{14}$ is CH₃ "per se," the CH₃ is not included in the CH₃ partial structure contained in a side chain portion according to the present invention.

In contrast, a CH₃ partial structure arranged via some atom apart from the C—C principal chain corresponds to the side-chain CH₃ partial structure according to the present invention. For example, when $R_{11}$ is an ethyl group (CH₂CH₃), it is deemed that "one" CH₃ partial structure according to the present invention is contained.

$$\begin{array}{c} R_{11} \quad R_{13} \\ | \quad\quad | \\ -(\!-\!C\!-\!-\!C\!-\!)\!- \\ | \quad\quad | \\ R_{12} \quad R_{14} \end{array} \quad (M)$$

In general formula (M) above,
each of $R_{11}$ to $R_{14}$ independently represents a side-chain portion.

As the side chain portion $R_{11}$ to $R_{14}$, there can be mentioned a hydrogen atom, a monovalent organic group and the like.

As the monovalent organic group represented by each of $R_{11}$ to $R_{14}$, there can be mentioned an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, an arylaminocarbonyl group or the like. Substituents may further be introduced in these groups.

It is preferred for the hydrophobic resin (HR) to be a resin comprising a repeating unit containing a CH₃ partial structure in its side chain portion. More preferably, the hydrophobic resin (HR) comprises, as such a repeating unit, at least one repeating unit (x) selected from among the repeating units of general formula (II) below and repeating units of general formula (V) below.

The repeating units of general formula (II) will be described in detail below.

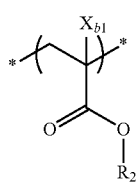

In general formula (II) above, $X_{b1}$ represents a hydrogen atom, an alkyl group, a cyano group or a halogen atom. $R_2$ represents an organic group having at least one CH₃ partial structure and being stable against acids. Herein, in particular, it is preferred for the organic group stable against acids to be an organic group not containing "any group that when acted on by an acid, is decomposed to thereby produce a polar group" described above in connection with the resin (A).

The alkyl group represented by $X_{b1}$ is preferably one having 1 to 4 carbon atoms, such as a methyl group, an ethyl group, a propyl group, a hydroxymethyl group or a trifluoromethyl group. A methyl group is preferred.

Preferably, $X_{b1}$ is a hydrogen atom or a methyl group.

As $R_2$, there can be mentioned an alkyl group, a cycloalkyl group, an alkenyl group, a cycloalkenyl group, an aryl group and an aralkyl group each containing at least one CH₃ partial structure. An alkyl group as a substituent may further be introduced in each of the above cycloalkyl group, alkenyl group, cycloalkenyl group, aryl group and aralkyl group.

$R_2$ is preferably an alkyl group or alkyl-substituted cycloalkyl group containing at least one CH₃ partial structure.

The organic group stable against acids containing at least one $CH_3$ partial structure represented by $R_2$ preferably contains 2 to 10 $CH_3$ partial structures, more preferably 2 to 8 $CH_3$ partial structures.

The alkyl group containing at least one $CH_3$ partial structure represented by $R_2$ is preferably a branched alkyl group having 3 to 20 carbon atoms.

The cycloalkyl group containing at least one $CH_3$ partial structure represented by $R_2$ may be monocyclic or polycyclic. In particular, there can be mentioned groups with, for example, monocyclo, bicyclo, tricyclo and tetracyclo structures each having 5 or more carbon atoms. The cycloalkyl group preferably has 6 to 30 carbon atoms, most preferably 7 to 25 carbon atoms. As preferred cycloalkyl groups, there can be mentioned a norbornyl group, a cyclopentyl group and a cyclohexyl group.

The alkenyl group containing at least one $CH_3$ partial structure represented by $R_2$ is preferably a linear or branched alkenyl group having 1 to 20 carbon atoms. A branched alkenyl group is more preferred.

The aryl group containing at least one $CH_3$ partial structure represented by $R_2$ is preferably an aryl group having 6 to 20 carbon atoms, such as a phenyl group or a naphthyl group. A phenyl group is more preferred.

The aralkyl group containing at least one $CH_3$ partial structure represented by $R_2$ is preferably one having 7 to 12 carbon atoms. For example, there can be mentioned a benzyl group, a phenethyl group, a naphthylmethyl group or the like.

Examples of hydrocarbon groups each containing two or more $CH_3$ partial structures represented by $R_2$ include an isobutyl group, a t-butyl group, a 2-methyl-3-butyl group, a 2,3-dimethyl-2-butyl group, a 2-methyl-3-pentyl group, a 3-methyl-4-hexyl group, a 3,5-dimethyl-4-pentyl group, a 2,4,4-trimethylpentyl group, a 2-ethylhexyl group, a 2,6-dimethylheptyl group, a 1,5-dimethyl-3-heptyl group, a 2,3,5,7-tetramethyl-4-heptyl group, a 3,5-dimethylcyclohexyl group, a 3,5-di-tert-butylcyclohexyl group, a 4-isopropylcyclohexyl group, a 4-t-butylcyclohexyl group and an isobornyl group.

Preferred particular examples of the repeating units of general formula (II) are shown below, which in no way limit the scope of the present invention.

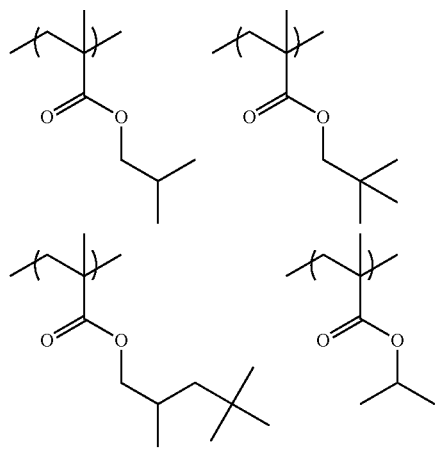

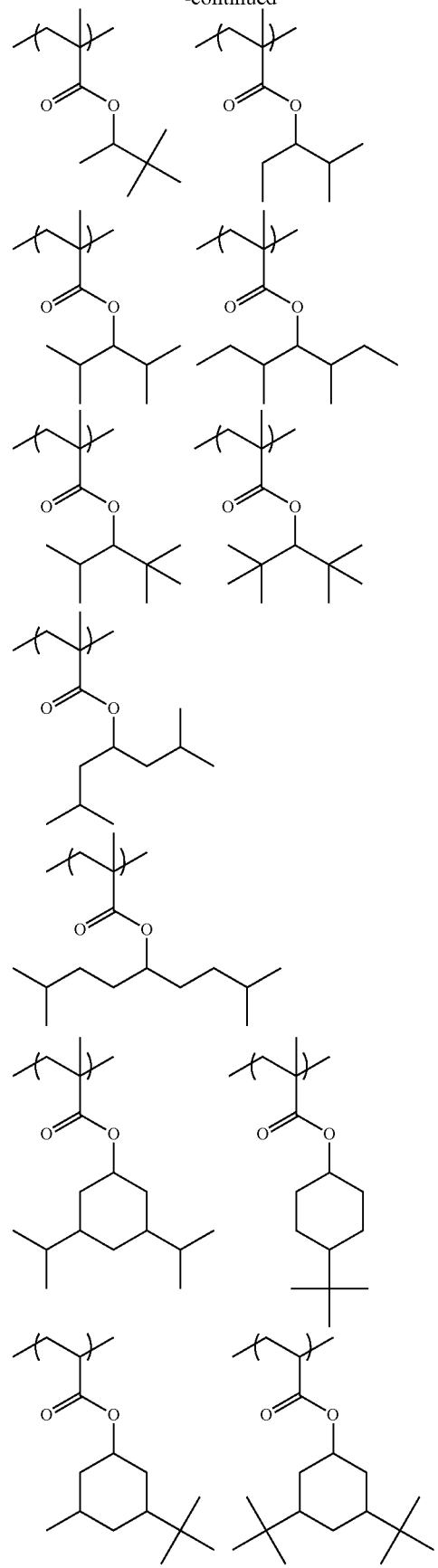
-continued

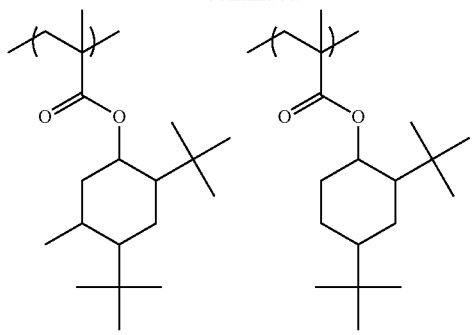

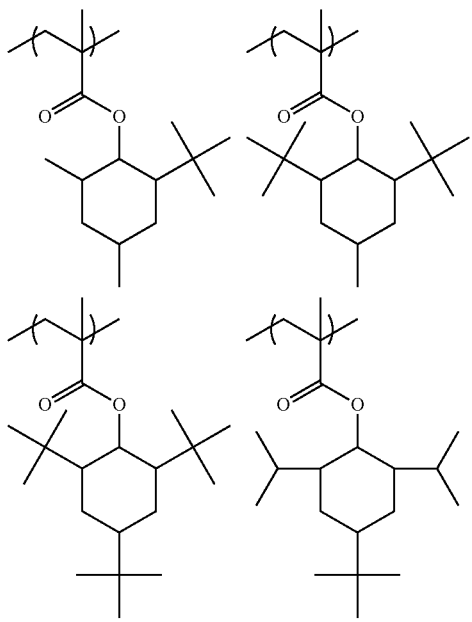

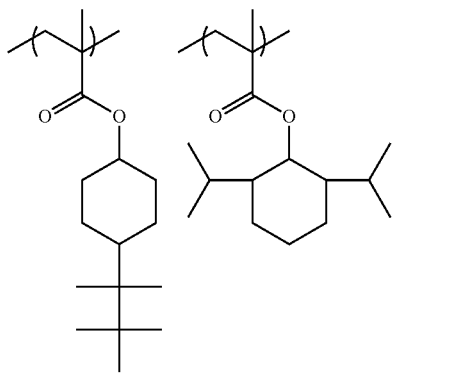

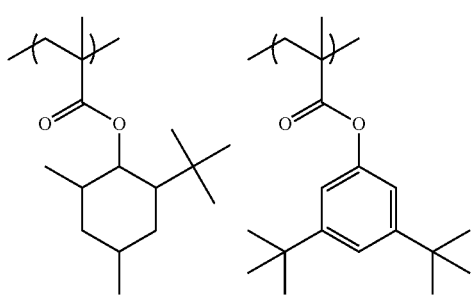

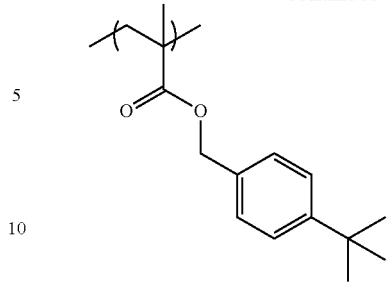

It is preferred for the repeating units of general formula (II) to be those stable against acids (non-acid-decomposable), in particular, repeating units containing none of groups that are decomposed under the action of an acid to thereby produce polar groups.

The repeating units of general formula (V) will be described in detail below.

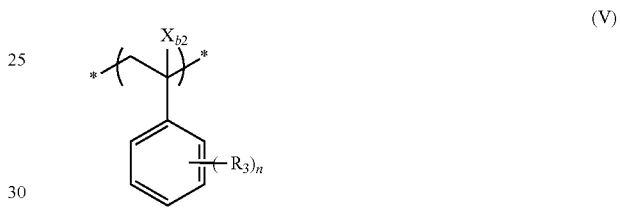

(V)

In general formula (V) above, $X_{b2}$ represents a hydrogen atom, an alkyl group, a cyano group or a halogen atom. $R_3$ represents an organic group having at least one $CH_3$ partial structure and being stable against acids; and n is an integer of 1 to 5.

The alkyl group represented by $X_{b2}$ is preferably one having 1 to 4 carbon atoms, such as a methyl group, an ethyl group, a propyl group, a hydroxymethyl group or a trifluoromethyl group. A methyl group is more preferred.

Preferably, $X_{b2}$ is a hydrogen atom.

$R_3$ is an organic group stable against acids. In particular, $R_3$ is preferably an organic group not containing "any group that when acted on by an acid, is decomposed to thereby produce a polar group" described above in connection with the resin (A).

As $R_3$, there can be mentioned an alkyl group containing at least one $CH_3$ partial structure.

The organic group stable against acids containing at least one $CH_3$ partial structure represented by $R_3$ preferably contains 1 to 10 $CH_3$ partial structures, more preferably 1 to 8 $CH_3$ partial structures and further more preferably 1 to 4 $CH_3$ partial structures.

The alkyl group containing at least one $CH_3$ partial structure represented by $R_3$ is preferably a branched alkyl group having 3 to 20 carbon atoms.

As alkyl groups each containing two or more $CH_3$ partial structures represented by $R_3$, there can be mentioned, for example, an isopropyl group, a t-butyl group, a 2-methyl-3-butyl group, a 2-methyl-3-pentyl group, a 3-methyl-4-hexyl group, a 3,5-dimethyl-4-pentyl group, a 2,4,4-trimethylpentyl group, a 2-ethylhexyl group, a 2,6-dimethylheptyl group, a 1,5-dimethyl-3-heptyl group and a 2,3,5,7-tetramethyl-4-heptyl group.

In the formula, n is an integer of 1 to 5, preferably an integer of 1 to 3, and more preferably 1 or 2.

Preferred particular examples of the repeating units of general formula (V) are shown below, which in no way limit the scope of the present invention.

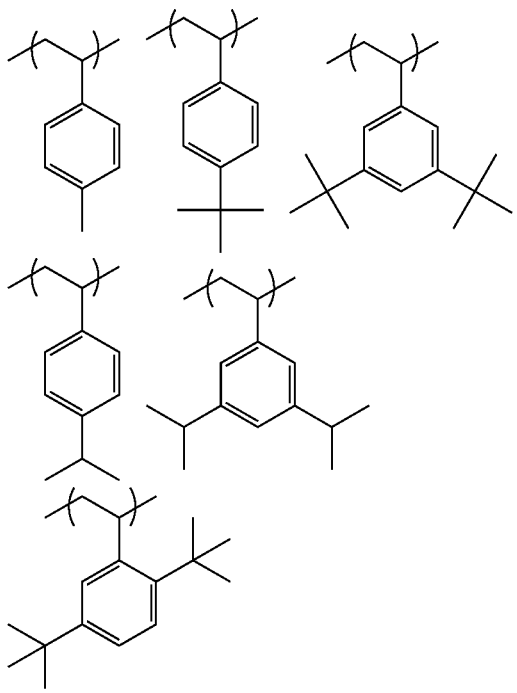

It is preferred for the repeating units of general formula (V) to be those stable against acids (non-acid-decomposable), in particular, repeating units not containing any groups that are decomposed under the action of an acid to thereby produce polar groups.

When the resin (HR) contains a $CH_3$ partial structure in its side chain portion and, in particular, contains neither a fluorine atom nor a silicon atom, the content of at least one repeating unit (x) selected from among the repeating units of general formula (II) and repeating units of general formula (V) based on all the repeating units of the resin (HR) is preferably 90 mol % or more, more preferably 95 mol % or more. The above content based on all the repeating units of the resin (HR) is generally up to 100 mol %.

When the resin (HR) contains at least one repeating unit (x) selected from among the repeating units of general formula (II) and repeating units of general formula (V) in an amount of 90 mol % or more based on all the repeating units of the resin (HR), the surface free energy of the resin (HR) is increased. As a result, the localization of the resin (HR) in the surface of the resist film is promoted, so that the static/dynamic contact angle of the resist film with respect to water can be securely increased, thereby enhancing the immersion liquid tracking property.

In the instance of containing a fluorine atom and/or a silicon atom (i) and also in the instance of containing a $CH_3$ partial structure in its side chain (ii), the hydrophobic resin (HR) may contain at least one group selected from among the following groups (x) to (z).

Namely, (x) an acid group, (y) a group with a lactone structure, an acid anhydride group or an acid imido group, and (z) a group decomposed under the action of an acid.

As the acid group (x), there can be mentioned a phenolic hydroxyl group, a carboxylic acid group, a fluoroalcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl) imido group, a bis(alkylsulfonyl)methylene group, a bis(alkylsulfonyl)imido group, a tris(alkylcarbonyl)methylene group, a tris(alkylsulfonyl)methylene group or the like.

As preferred acid groups, there can be mentioned a fluoroalcohol group (preferably hexafluoroisopropanol), a sulfonimido group and a bis(alkylcarbonyl)methylene group.

The repeating unit containing an acid group (x) is, for example, a repeating unit wherein the acid group is directly bonded to the principal chain of a resin, such as a repeating unit derived from acrylic acid or methacrylic acid. Alternatively, this repeating unit may be a repeating unit wherein the acid group is bonded via a connecting group to the principal chain of a resin. Still alternatively, this repeating unit may be a repeating unit wherein the acid group is introduced in a terminal of polymer chain by using a chain transfer agent or polymerization initiator containing the acid group in the stage of polymerization. Any of these repeating units are preferred. The repeating unit containing an acid group (x) may contain at least either a fluorine atom or a silicon atom.

The content of repeating unit containing an acid group (x) based on all the repeating units of the hydrophobic resin (HR) is preferably in the range of 1 to 50 mol %, more preferably 3 to 35 mol % and further more preferably 5 to 20 mol %.

Particular examples of the repeating units each containing an acid group (x) are shown below, which in no way limit the scope of the present invention. In the formulae, Rx represents a hydrogen atom, $CH_3$, $CF_3$ or $CH_2OH$.

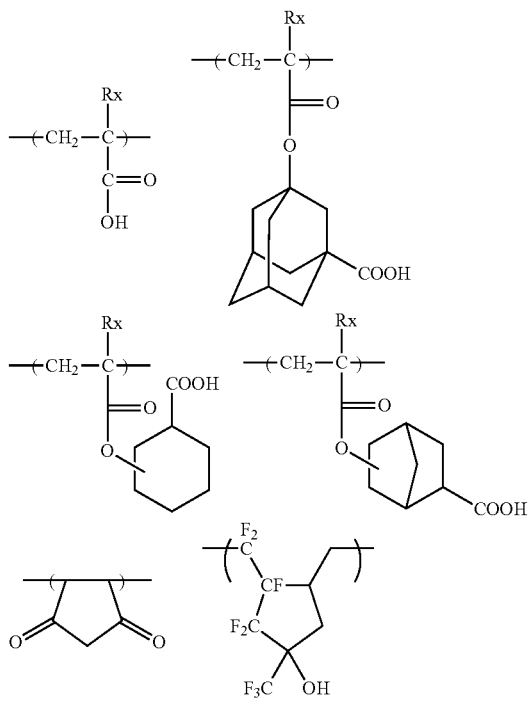

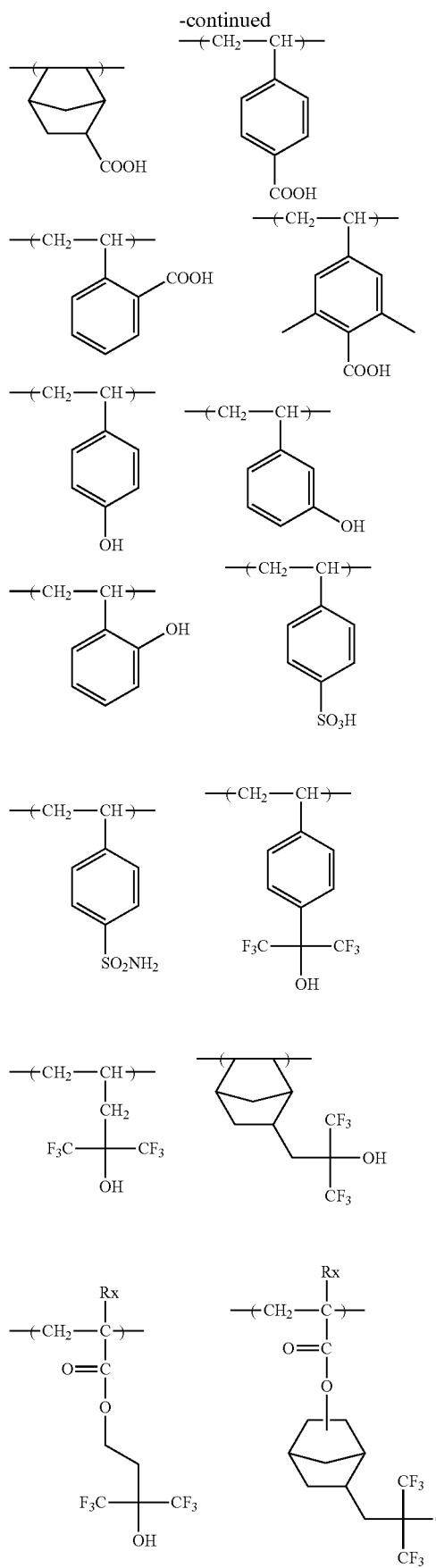
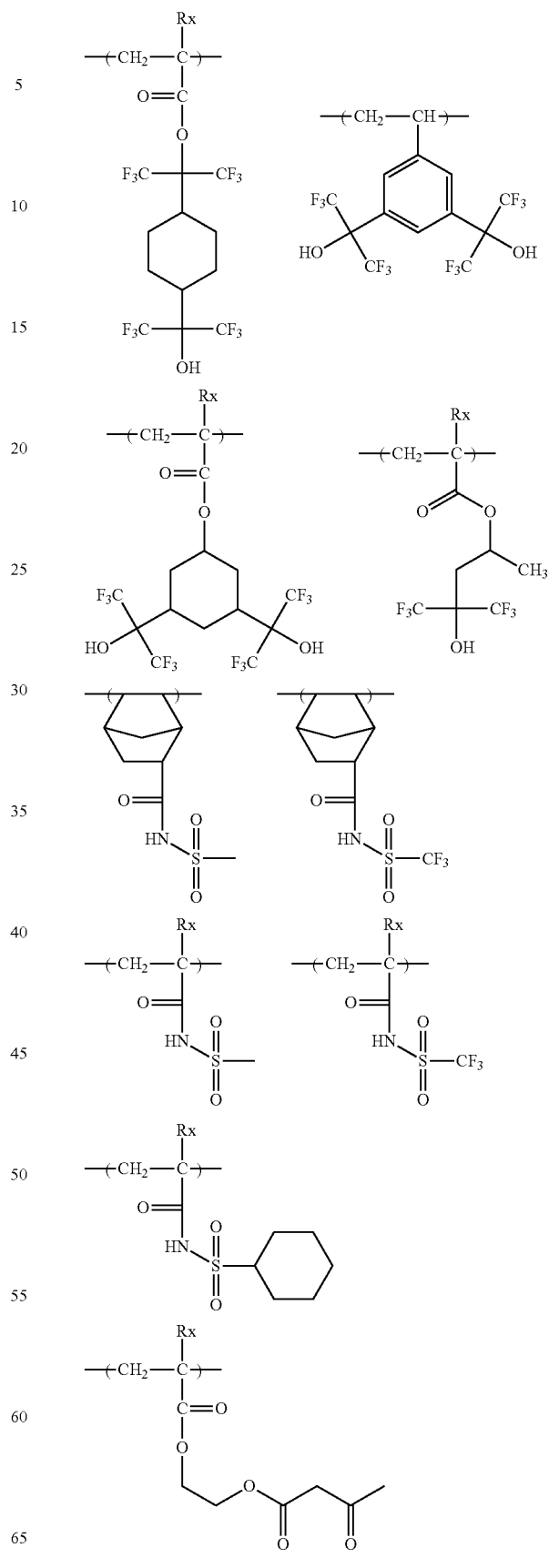

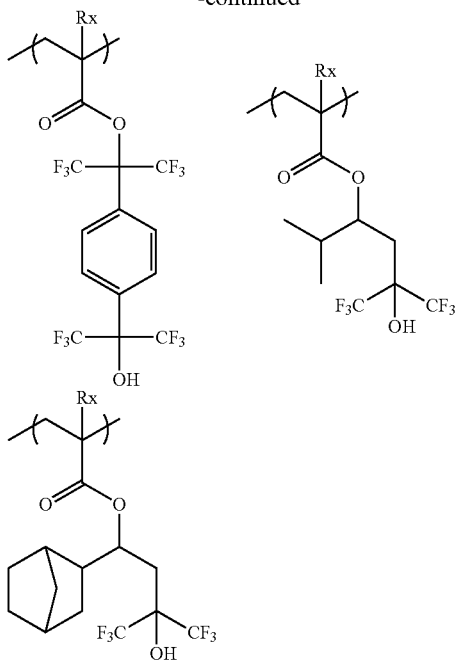

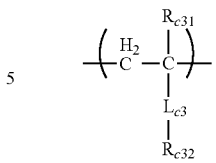

Among the group with a lactone structure, acid anhydride group and acid imido group (y), the group with a lactone structure is most preferred.

The repeating unit containing any of these groups is, for example, a repeating unit wherein the group is directly bonded to the principal chain of a resin, such as a repeating unit derived from an acrylic ester or a methacrylic ester. Alternatively, this repeating unit may be a repeating unit wherein the group is bonded via a connecting group to the principal chain of a resin. Still alternatively, this repeating unit may be a repeating unit wherein the group is introduced in a terminal of the resin by using a chain transfer agent or polymerization initiator containing the group in the stage of polymerization.

The repeating units each containing a group with a lactone structure can be, for example, the same as the repeating units each with a lactone structure described above in the section of the acid-decomposable resin (A).

The content of repeating unit containing a group with a lactone structure, an acid anhydride group or an acid imido group, based on all the repeating units of the hydrophobic resin (HR), is preferably in the range of 1 to 100 mol %, more preferably 3 to 98 mol % and further more preferably 5 to 95 mol %.

The repeating unit containing the group (z) decomposable under the action of an acid in the hydrophobic resin (HR) can be the same as any of the repeating units each containing an acid-decomposable group set forth above in connection with the resin (A). The repeating unit containing the group (z) decomposable under the action of an acid may contain at least either a fluorine atom or a silicon atom. The content of repeating unit containing the group (z) decomposable under the action of an acid in the hydrophobic resin (HR), based on all the repeating units of the resin (HR), is preferably in the range of 1 to 80 mol %, more preferably 10 to 80 mol % and furthermore preferably 20 to 60 mol %.

The hydrophobic resin (HR) may further comprise any of the repeating units of general formula (VI) below.

(VI)

In general formula (VI), $R_{c31}$ represents a hydrogen atom, an alkyl group (optionally substituted with a fluorine atom or the like), a cyano group or any of groups of the formula —$CH_2$—O—$Rac_2$ in which $Rac_2$ represents a hydrogen atom, an alkyl group or an acyl group. $R_{c31}$ is preferably a hydrogen atom, an methyl group, a hydroxymethyl group or a trifluoromethyl group, most preferably a hydrogen atom or a methyl group.

$R_{c32}$ represents a group containing an alkyl group, cycloalkyl group, alkenyl group, cycloalkenyl group or aryl group. This group may be substituted with a group containing a fluorine atom or silicon atom.

$L_{c3}$ represents a single bond or a bivalent connecting group.

In general formula (VI), the alkyl group in $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably an aryl group having 6 to 20 carbon atoms. A phenyl group and a naphthyl group are more preferred. Substituents may be introduced therein.

Preferably, $R_{c32}$ is an unsubstituted alkyl group or an alkyl group substituted with a fluorine atom.

The bivalent connecting group represented by $L_{c3}$ is preferably an alkylene group (preferably having 1 to 5 carbon atoms), an ether bond, a phenylene group or an ester bond (group of the formula —COO—).

The content of repeating unit expressed by general formula (VI), based on all the repeating units of the hydrophobic resin, is preferably in the range of 1 to 100 mol %, more preferably 10 to 90 mol % and further more preferably 30 to 70 mol %.

Preferably, the hydrophobic resin (HR) further comprises any of the repeating units of general formula (CII-AB) below.

(CII-AB)

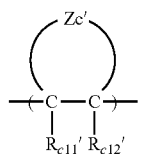

In general formula (CII-AB), each of $R_{c11}'$ and $R_{c12}'$ independently represents a hydrogen atom, a cyano group, a halogen atom or an alkyl group.

Zc' represents an atomic group for forming an alicyclic structure containing two mutually bonded carbon atoms (C—C).

The content of repeating unit expressed by general formula (CII-AB), based on all the repeating units of the hydrophobic resin, is preferably in the range of 1 to 100 mol %, more preferably 10 to 90 mol % and further more preferably 30 to 70 mol %.

Particular examples of the repeating units of general formula (VI) and general formula (CII-AB) are shown below, which in no way limit the scope of the present invention. In the formulae, Ra represents H, CH$_3$, CH$_2$OH, CF$_3$ or CN.

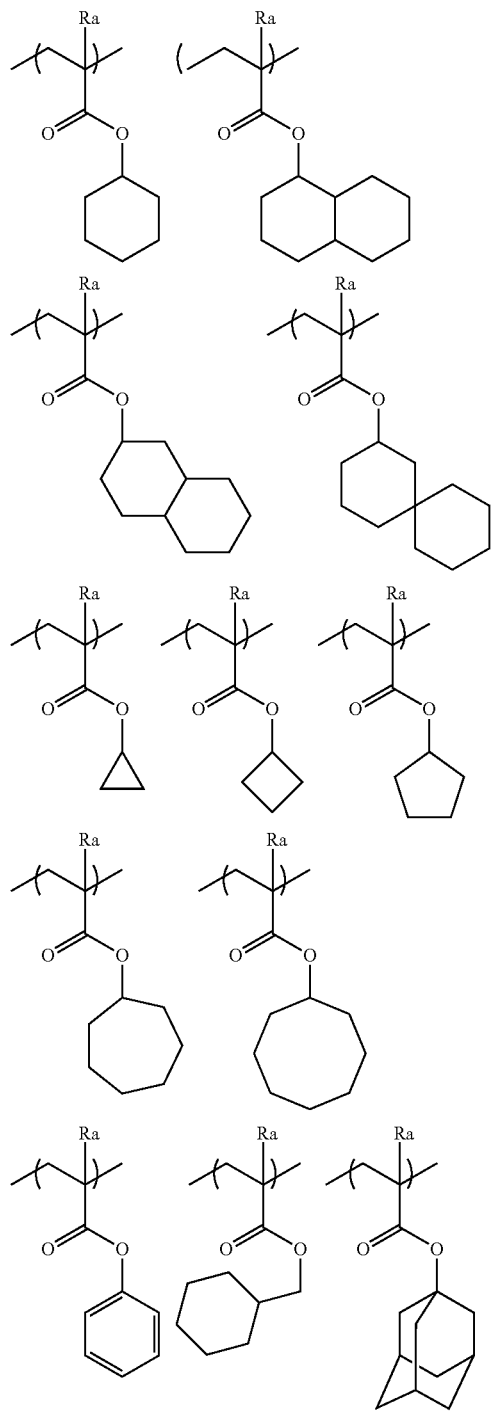

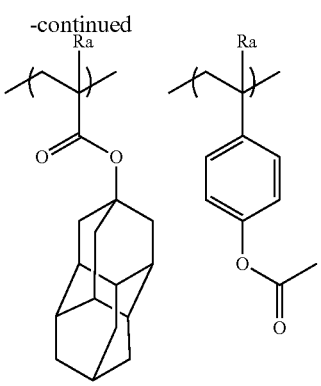

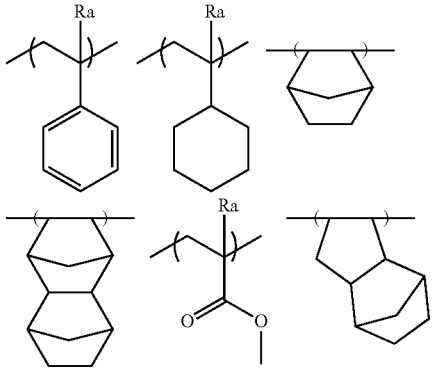

When the hydrophobic resin (HR) contains a fluorine atom, the content of fluorine atom is preferably in the range of 5 to 80 mass %, more preferably 10 to 80 mass %, based on the weight-average molecular weight of the hydrophobic resin (HR). The repeating unit containing a fluorine atom preferably accounts for 10 to 100 mol %, more preferably 30 to 100 mol %, in all the repeating units contained in the hydrophobic resin (HR).

When the hydrophobic resin (HR) contains a silicon atom, the content of silicon atom is preferably in the range of 2 to 50 mass %, more preferably 2 to 30 mass %, based on the weight-average molecular weight of the hydrophobic resin (HR). The repeating unit containing a silicon atom preferably accounts for 10 to 100 mol %, more preferably 20 to 100 mol %, in all the repeating units contained in the hydrophobic resin (HR).

In contrast, especially when the resin (HR) contains a CH$_3$ partial structure in its side-chain portion, a form of the resin (HR) in which substantially neither a fluorine atom nor a silicon atom is contained is also preferred. In that instance, in particular, the content of repeating unit containing a fluorine atom or a silicon atom, based on all the repeating units of the resin (HR), is preferably 5 mol % or less, more preferably 3 mol % or less, further more preferably 1 mol % or less, and ideally 0 mol %, namely, containing neither a fluorine atom nor a silicon atom. It is preferred for the resin (HR) to be comprised substantially only of a repeating unit comprised only of atoms selected from among a carbon atom, an oxygen atom, a hydrogen atom, a nitrogen atom and a sulfur atom. In particular, the content of repeating unit comprised only of atoms selected from among a carbon atom, an oxygen atom, a hydrogen atom, a nitrogen atom and a sulfur atom, based on all the repeating units of the resin (HR), is preferably 95 mol % or greater, more preferably 97 mol % or greater, further more preferably 99 mol % or less, and ideally 100 mol %.

The standard-polystyrene-equivalent weight average molecular weight of the hydrophobic resin (HR) is preferably in the range of 1000 to 100,000, more preferably 1000 to 50,000 and further more preferably 2000 to 15,000.

One type of hydrophobic resin (HR) may be used alone, or two or more thereof may be used in combination.

The content of hydrophobic resin (HR) in the composition, based on the total solids of the composition of the present invention, is preferably in the range of 0.01 to 10 mass %, more preferably 0.05 to 8 mass % and further more preferably 0.1 to 7 mass %.

Impurities, such as metals, should naturally be in low quantities in the hydrophobic resin (HR), as in the resin (A). Further, the amount of residual monomers and oligomer components is preferably 0.01 to 5 mass %, more preferably 0.01 to 3 mass % and further more preferably 0.05 to 1 mass %. Accordingly, there can be obtained an actinic-ray- or radiation-sensitive resin composition that is free from any change over time of in-liquid foreign matter, sensitivity, etc. From the viewpoint of resolution, resist shape, side wall of resist pattern, roughness, etc., the molecular weight distribution (Mw/Mn, also referred to as polydispersity index) thereof is preferably in the range of 1 to 5, more preferably 1 to 3 and further more preferably 1 to 2.

A variety of commercially available products can be used as the hydrophobic resin (HR). Alternatively, the hydrophobic resin (HR) can be synthesized in accordance with routine methods (for example, radical polymerization). As general synthesizing methods, there can be mentioned, for example, a batch polymerization method in which a monomer species and an initiator are dissolved in a solvent and heated to thereby carry out polymerization, a dropping polymerization method in which a solution of monomer species and initiator is dropped into a heated solvent over a period of 1 to 10 hours, etc. The dropping polymerization method is preferred.

The reaction solvent, polymerization initiator, reaction conditions (temperature, concentration, etc.) and purification method after reaction are the same as described above in connection with the resin (A). In the synthesis of the hydrophobic resin (HR), it is preferred for the concentration at reaction to range from 30 to 50 mass %.

Specific examples of the hydrophobic resins (HR) are shown below. The following Tables list the molar ratios of individual repeating units (corresponding to individual repeating units in order from left), weight average molecular weight and polydispersity index with respect to each of the resins.

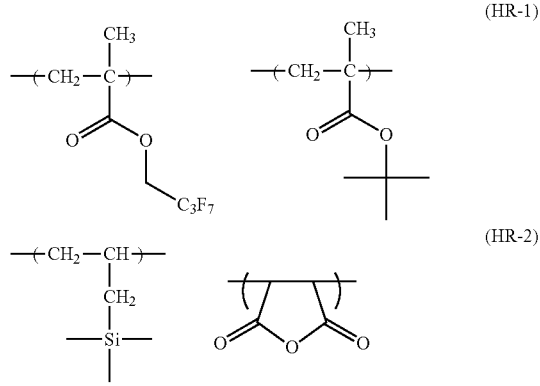

(HR-1)

(HR-2)

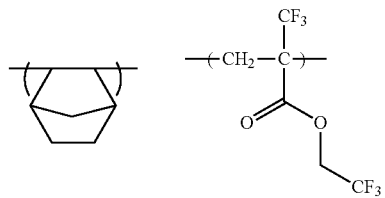

(HR-3)

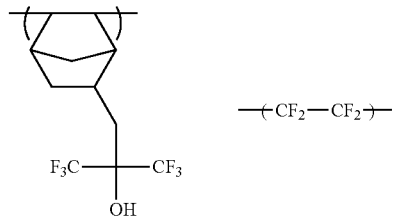

(HR-4)

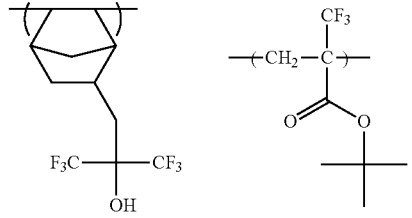

(HR-5)

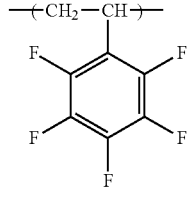

(HR-6)

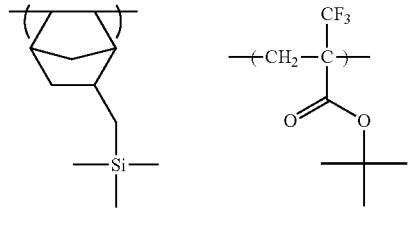

(HR-7)

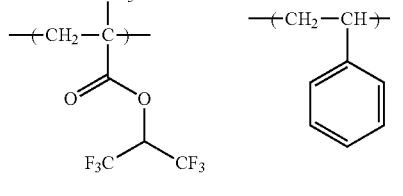

(HR-8)

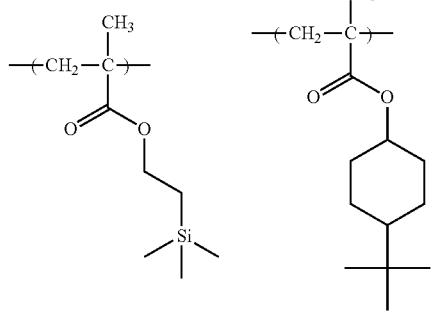

(HR-9)

(HR-10) 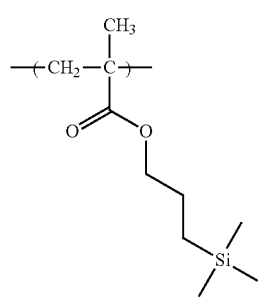 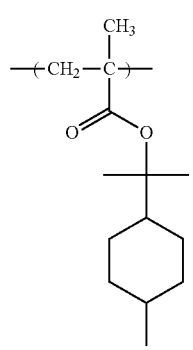
(HR-11) 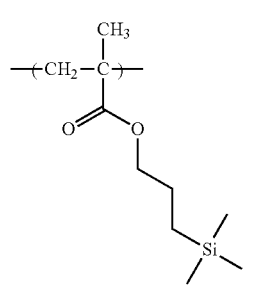 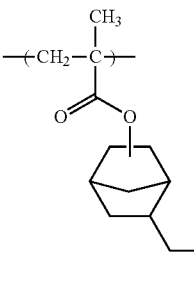
(HR-12) 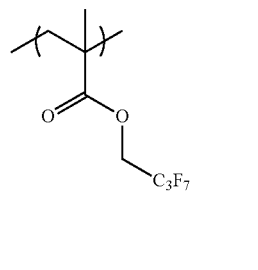 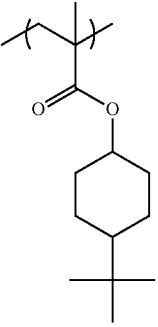
(HR-13) 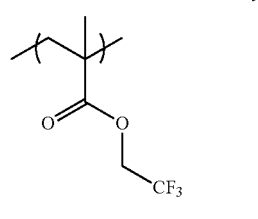 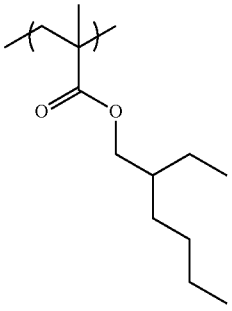
(HR-14) 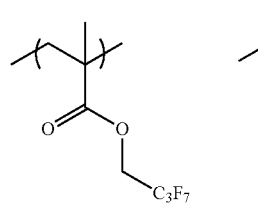 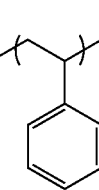
(HR-15) 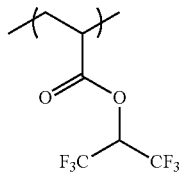
(HR-16) 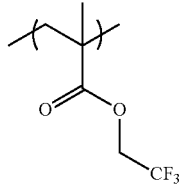
(HR-17) 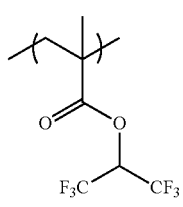
(HR-18) 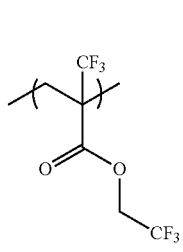 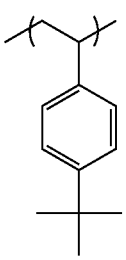
(HR-19)  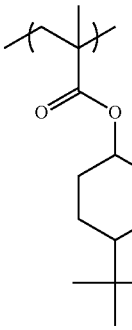
(HR-20) 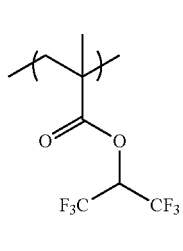 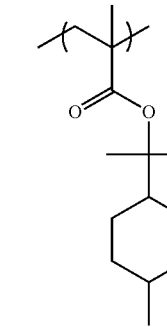

(HR-21) 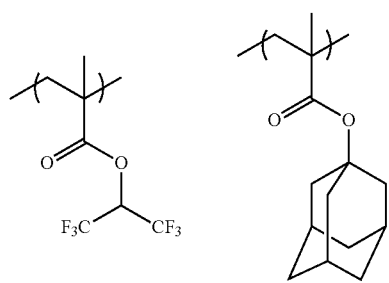
(HR-22) 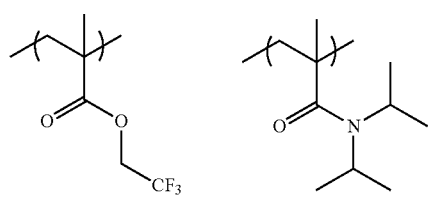
(HR-23) 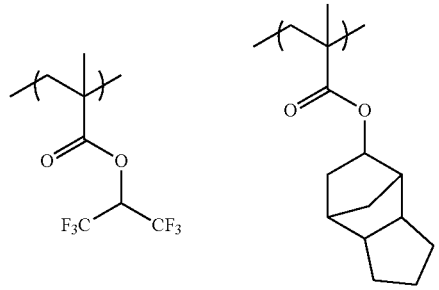
(HR-24) 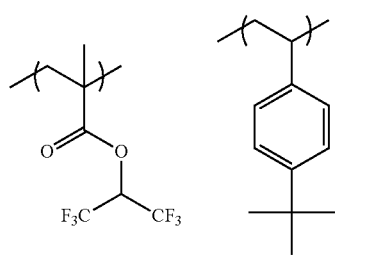
(HR-25) 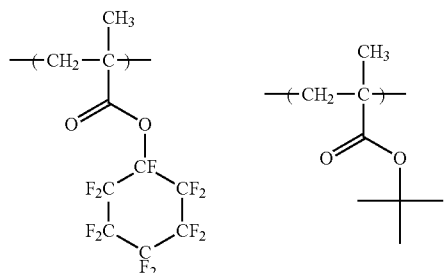
(HR-26) 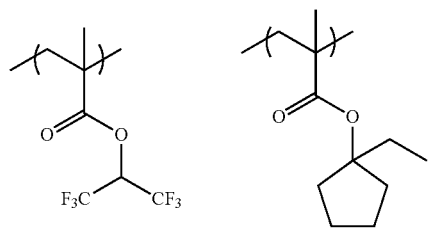
(HR-27) 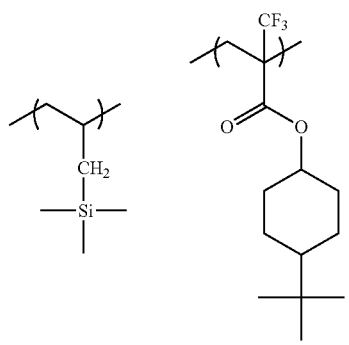
(HR-28) 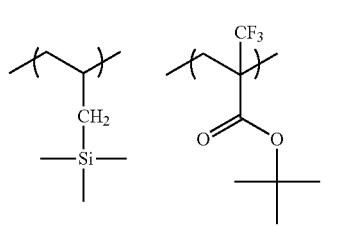
(HR-29) 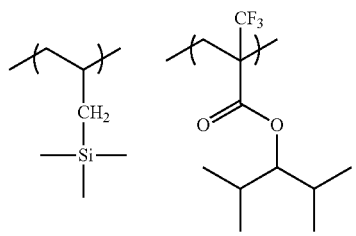
(HR-30) 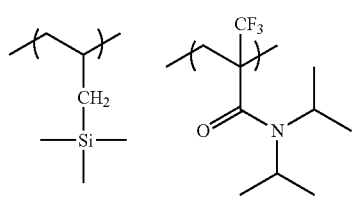
(HR-31) 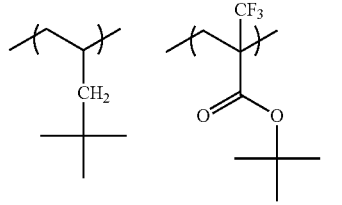
(HR-32) 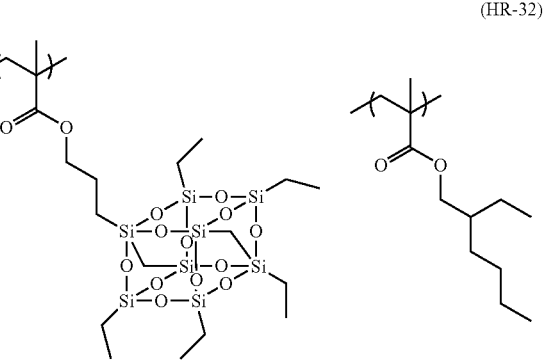

(HR-33)
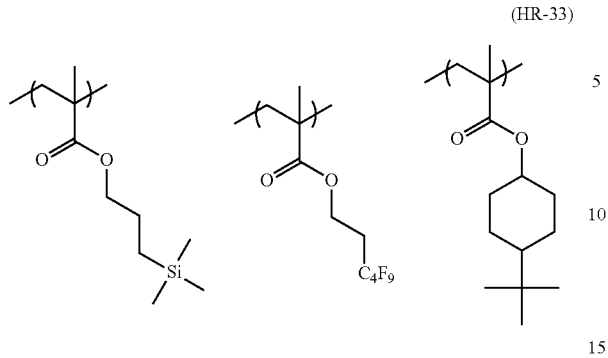
(HR-38)
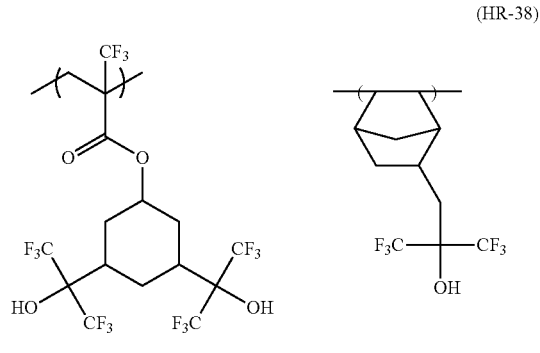
(HR-34)
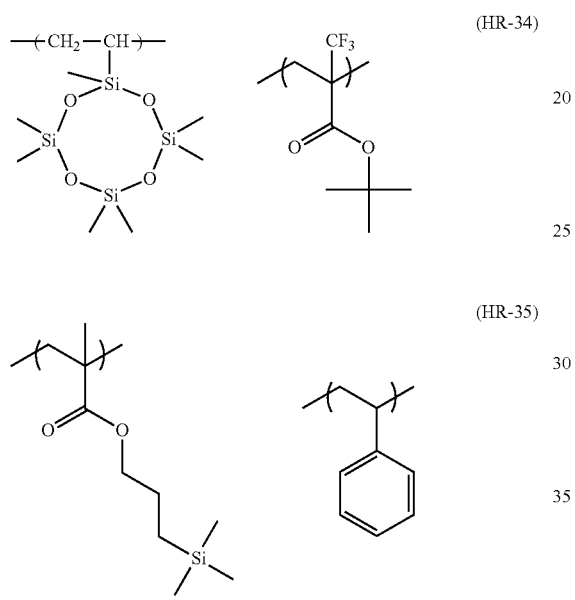
(HR-39)
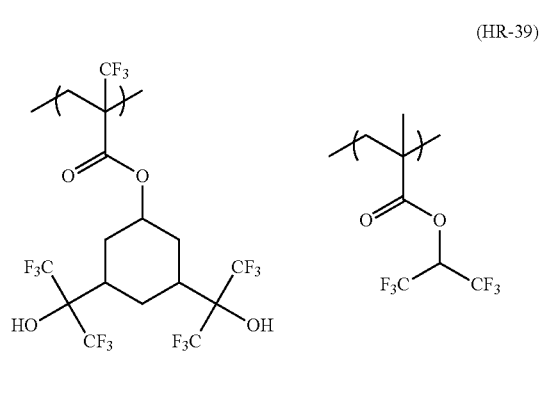
(HR-35)
(HR-40)
(HR-36)
(HR-41)
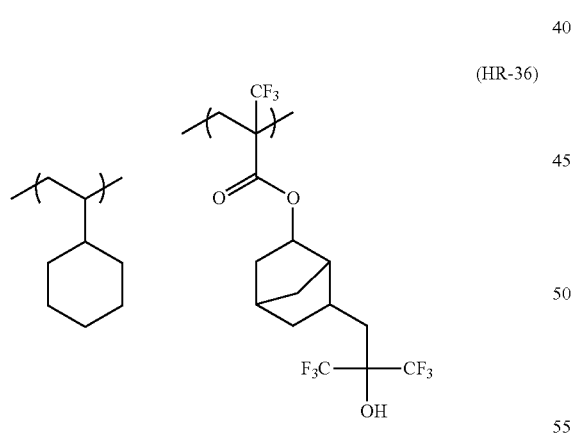
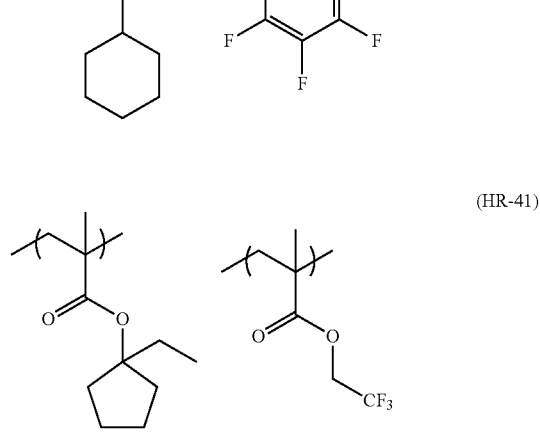
(HR-37)
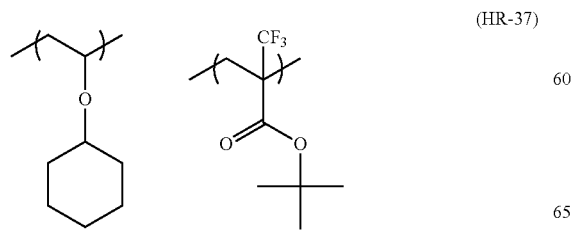
(HR-42)
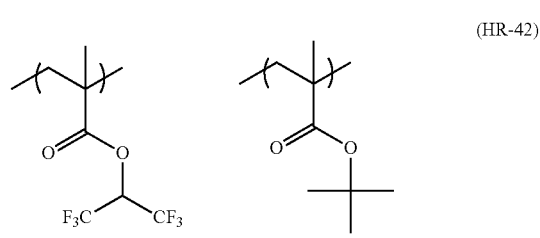

(HR-43)
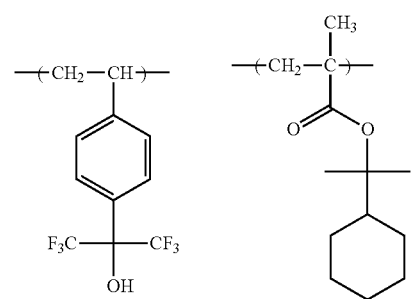
(HR-44)
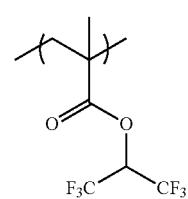 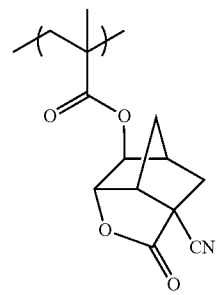
(HR-45)
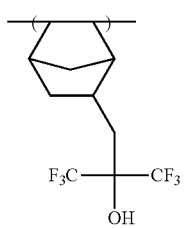 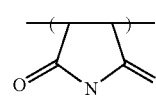 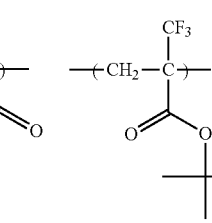
(HR-46)
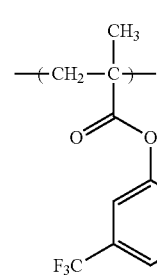 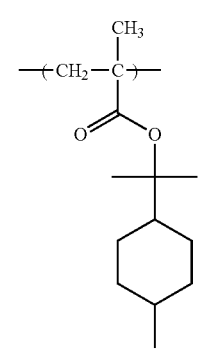
(HR-47)
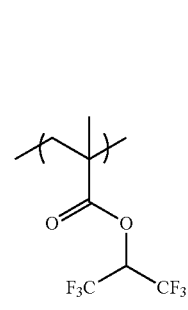 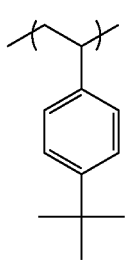 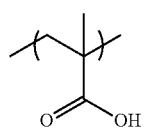
(HR-48)
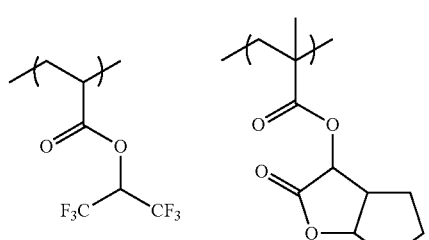
(HR-49)
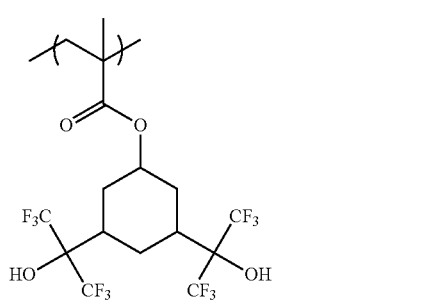
(HR-50)
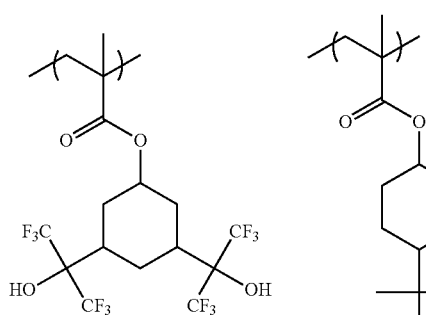
(HR-51)
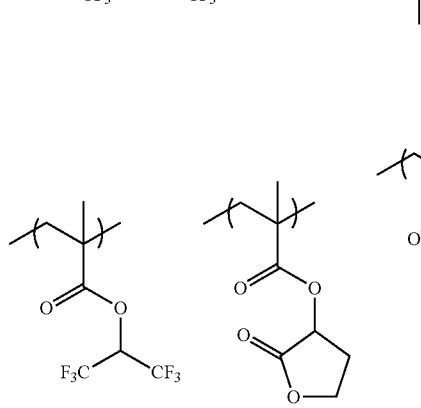
(HR-52)
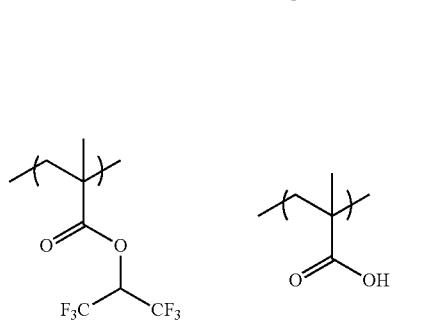

153
-continued
(HR-53)
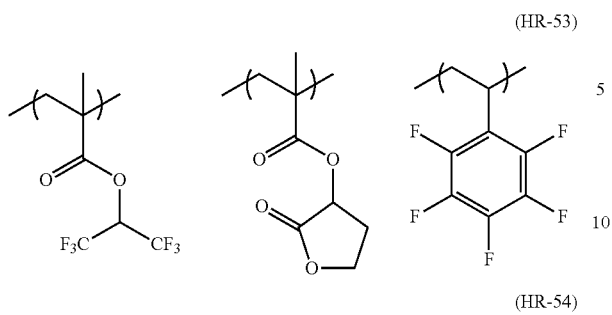
(HR-54)
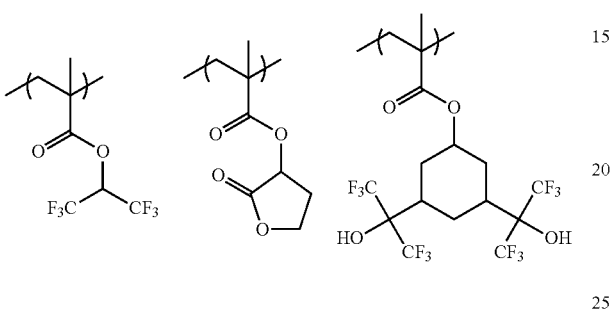
(HR-55)
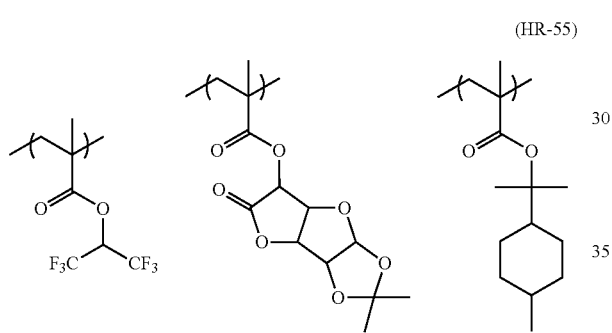
(HR-56)
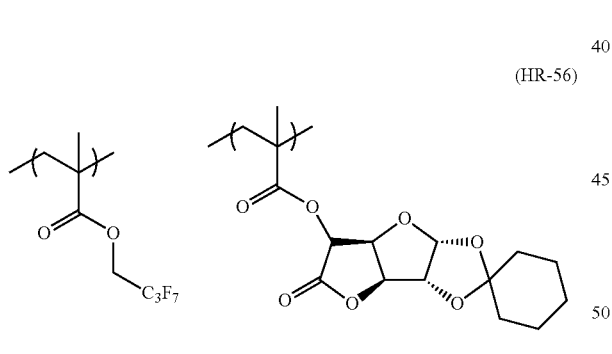
(HR-57)
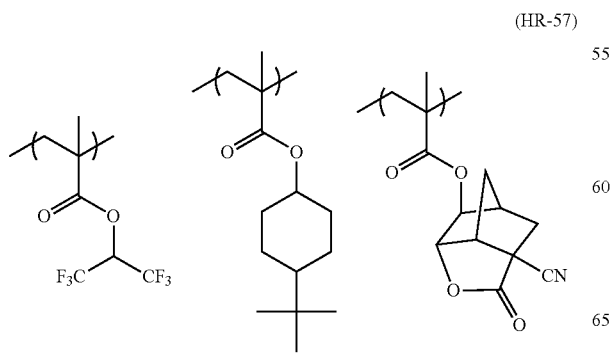
154
-continued
(HR-58)
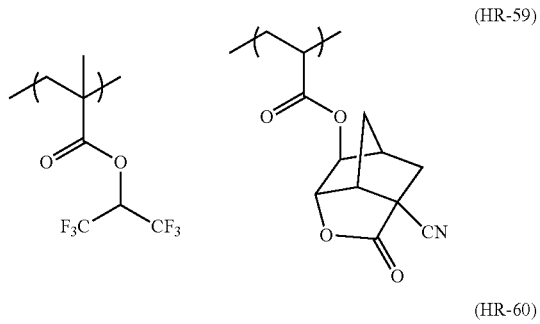
(HR-59)
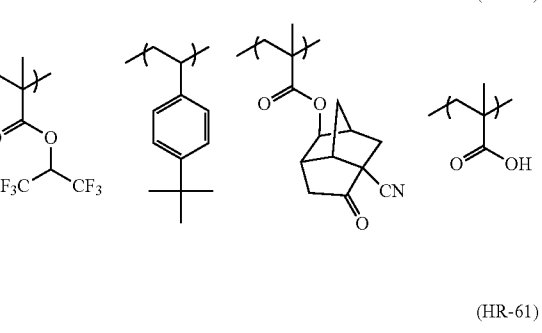
(HR-60)
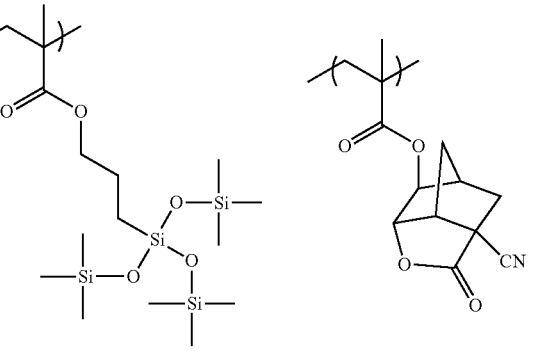
(HR-61)
(HR-62)
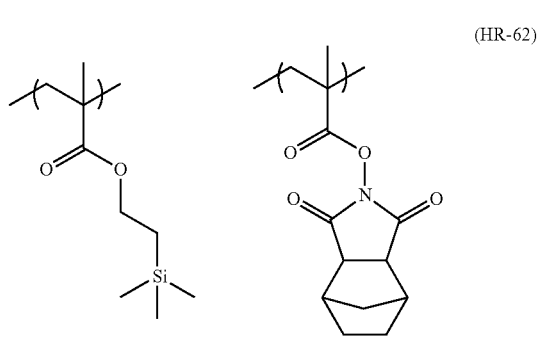

-continued
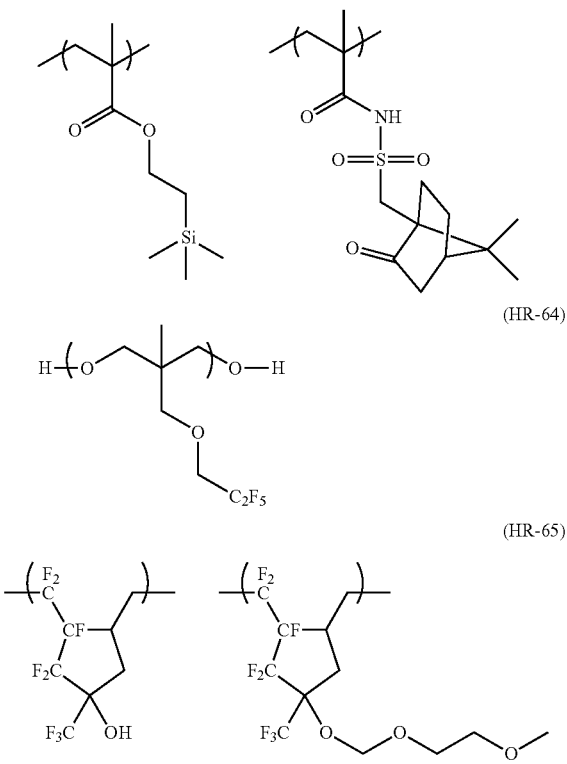
(HR-63)
(HR-64)
(HR-65)
TABLE 1
| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
TABLE 1-continued
| Resin | Composition | Mw | Mw/Mn |
|---|---|---|---|
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 12.1 |
| HR-63 | 80/20 | 7000 | 1.7 |
| HR-64 | 100 | 5500 | 1.8 |
| HR-65 | 50/50 | 9500 | 1.9 |
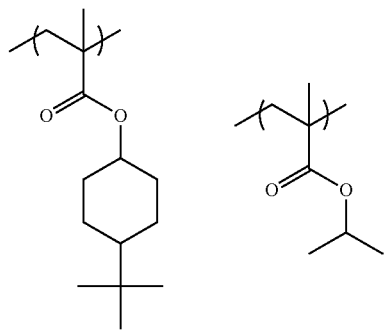
(C-1)
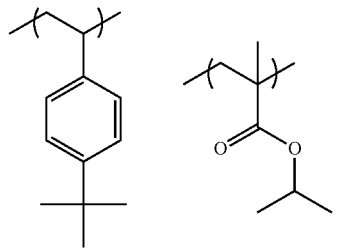
(C-2)
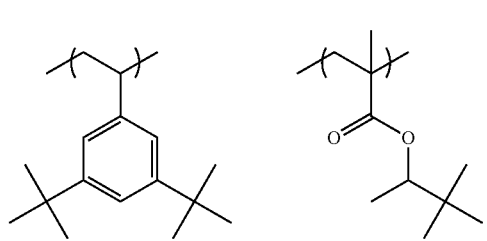
(C-3)

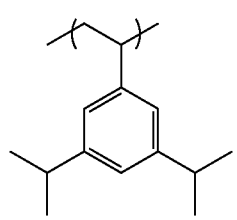 (C-4)
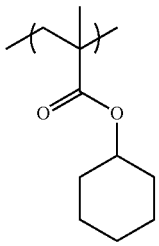
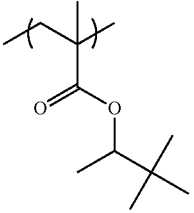 (C-10)
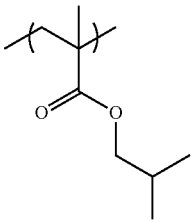
(C-5)
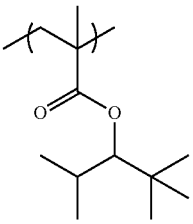 (C-11)
(C-6)
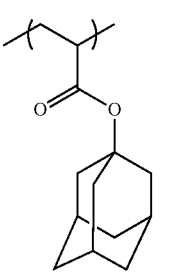 (C-12)
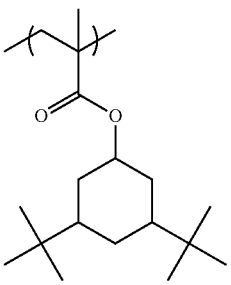
(C-7)
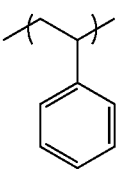 (C-13)
(C-8)
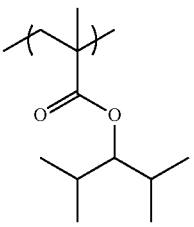 (C-14)
(C-9)
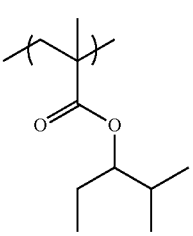 (C-15)

(C-16) 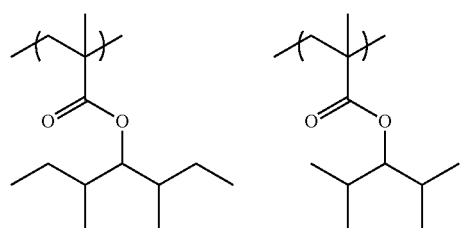
(C-17) 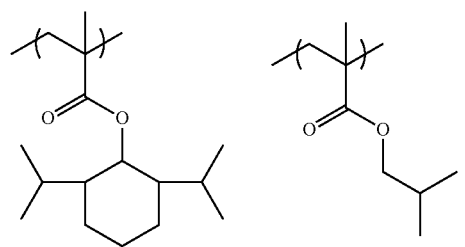
(C-18) 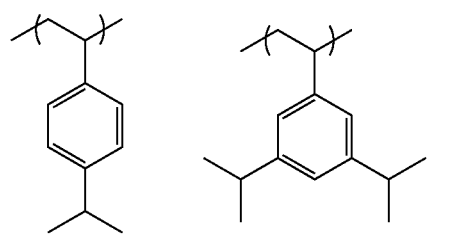
(C-19) 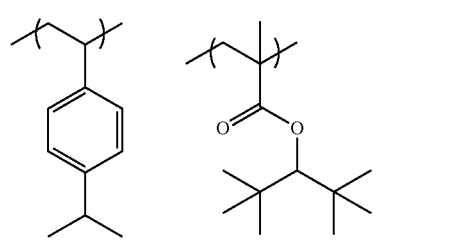
(C-20) 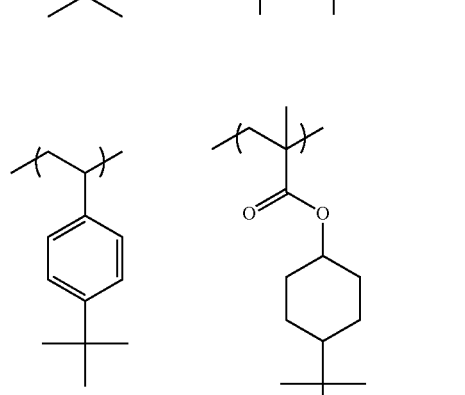
(C-21) 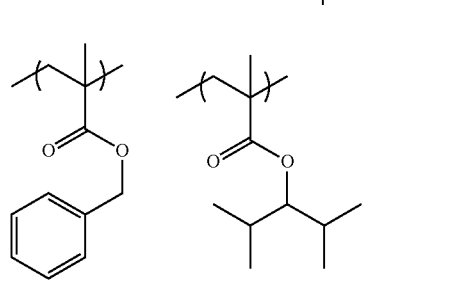
(C-22) 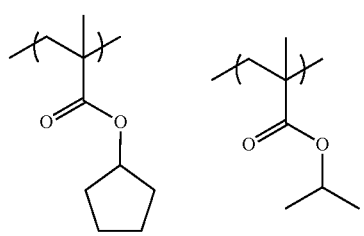
(C-23) 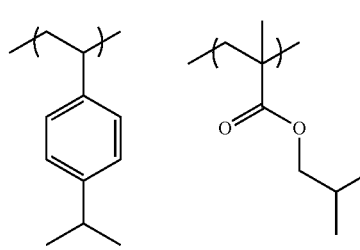
(C-24) 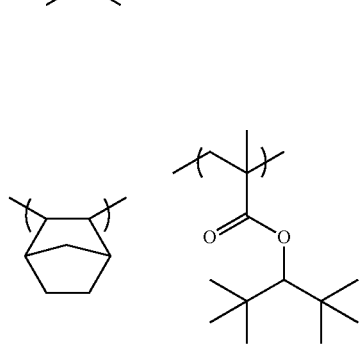
(C-25) 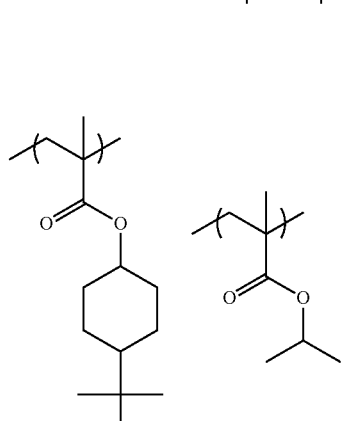
(C-26) 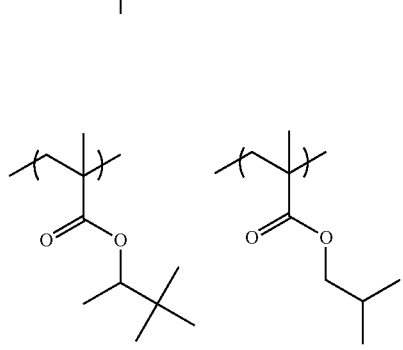

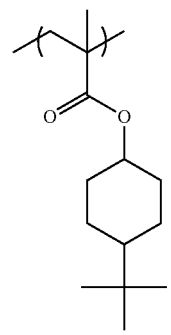 (C-27)
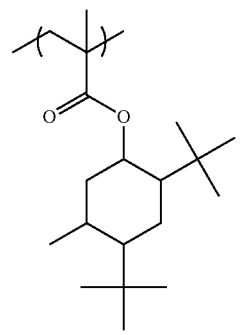
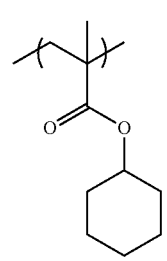 (C-28)
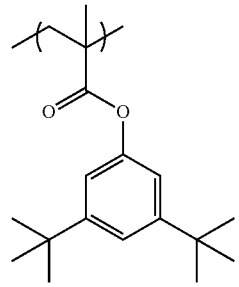
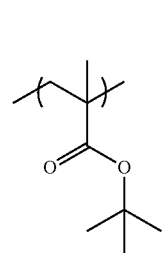 (D-1)
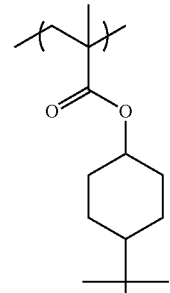
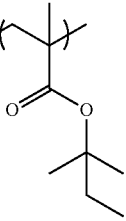 (D-2)
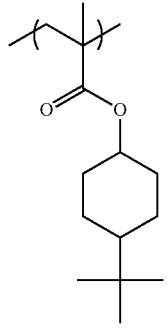
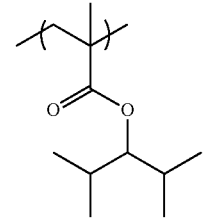
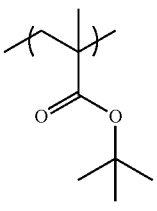 (D-3)
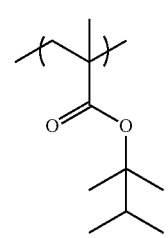
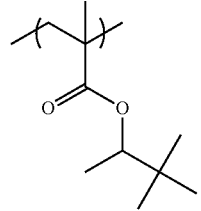
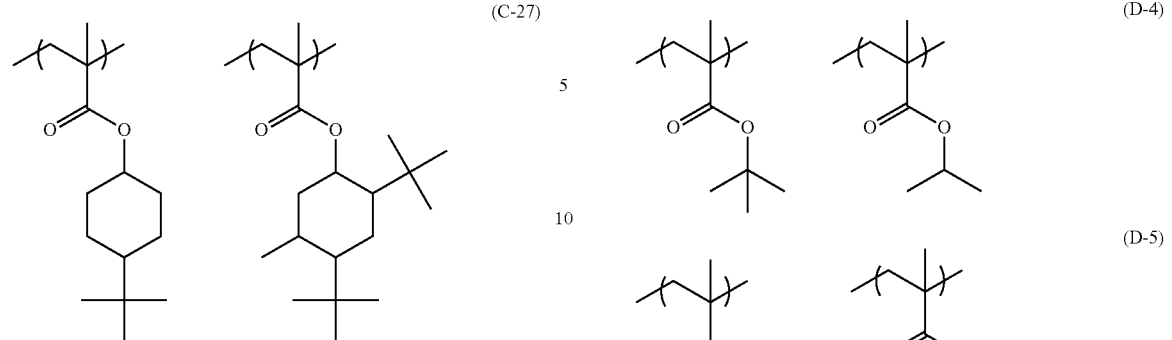 (D-4)
(D-5)
(D-6)
(D-7)
(D-8)
(D-9)

-continued
(D-10)
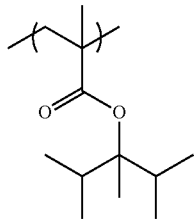 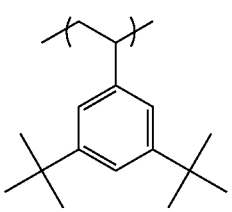
(D-11)
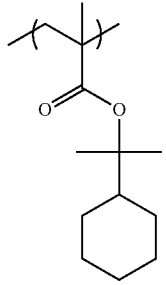 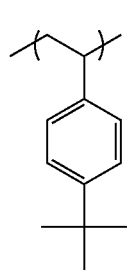
(D-12)
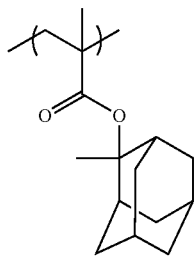 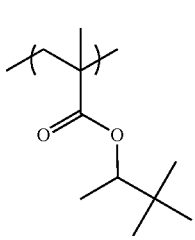
(D-13)
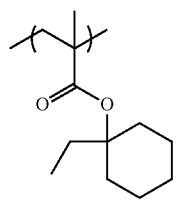 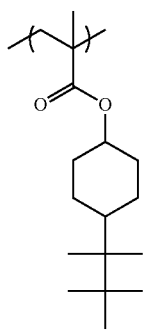 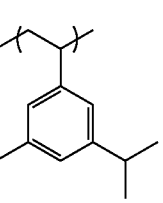
(D-14)
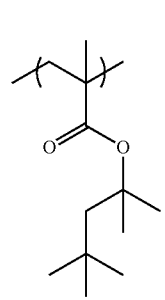 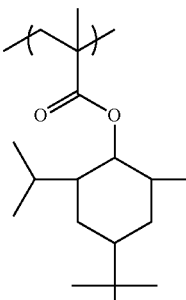 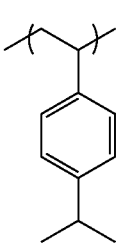
-continued
(D-15)
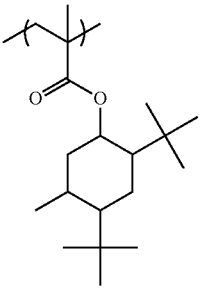 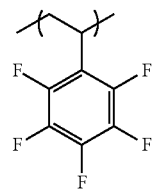 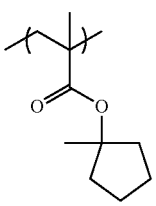
(D-16)
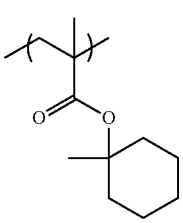 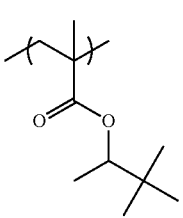 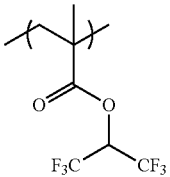
TABLE 2
| Resin | Composition | Mw | Mw/Mn |
|---|---|---|---|
| C-1 | 50/50 | 9600 | 1.74 |
| C-2 | 60/40 | 34500 | 1.43 |
| C-3 | 30/70 | 19300 | 1.69 |
| C-4 | 90/10 | 26400 | 1.41 |
| C-5 | 100 | 27600 | 1.87 |
| C-6 | 80/20 | 4400 | 1.96 |
| C-7 | 100 | 16300 | 1.83 |
| C-8 | 5/95 | 24500 | 1.79 |
| C-9 | 20/80 | 15400 | 1.68 |
| C-10 | 50/50 | 23800 | 1.46 |
| C-11 | 100 | 22400 | 1.57 |
| C-12 | 10/90 | 21600 | 1.52 |
| C-13 | 100 | 28400 | 1.58 |
| C-14 | 50/50 | 16700 | 1.82 |
| C-15 | 100 | 23400 | 1.73 |
| C-16 | 60/40 | 18600 | 1.44 |
| C-17 | 80/20 | 12300 | 1.78 |
| C-18 | 40/60 | 18400 | 1.58 |
| C-19 | 70/30 | 12400 | 1.49 |
| C-20 | 50/50 | 23500 | 1.94 |
| C-21 | 10/90 | 7600 | 1.75 |
| C-22 | 5/95 | 14100 | 1.39 |
| C-23 | 50/50 | 17900 | 1.61 |
| C-24 | 10/90 | 24600 | 1.72 |
| C-25 | 50/40/10 | 23500 | 1.65 |
| C-26 | 60/30/10 | 13100 | 1.51 |
| C-27 | 50/50 | 21200 | 1.84 |
| C-28 | 10/90 | 19500 | 1.66 |
TABLE 3
| Resin | Composition | Mw | Mw/Mn |
|---|---|---|---|
| D-1 | 50/50 | 16500 | 1.72 |
| D-2 | 10/50/40 | 18000 | 1.77 |
| D-3 | 5/50/45 | 27100 | 1.69 |
| D-4 | 20/80 | 26500 | 1.79 |
| D-5 | 10/90 | 24700 | 1.83 |
| D-6 | 10/90 | 15700 | 1.99 |
| D-7 | 5/90/5 | 21500 | 1.92 |
| D-8 | 5/60/35 | 17700 | 2.10 |
| D-9 | 35/35/30 | 25100 | 2.02 |
| D-10 | 70/30 | 19700 | 1.85 |
| D-11 | 75/25 | 23700 | 1.80 |

TABLE 3-continued

| Resin | Composition | Mw | Mw/Mn |
|---|---|---|---|
| D-12 | 10/90 | 20100 | 2.02 |
| D-13 | 5/35/60 | 30100 | 2.17 |
| D-14 | 5/45/50 | 22900 | 2.02 |
| D-15 | 15/75/10 | 28600 | 1.81 |
| D-16 | 25/55/20 | 27400 | 1.87 |

<Basic Compound>

From the viewpoint of diminishing any performance change over time from exposure to baking, it is preferred for the actinic-ray- or radiation-sensitive resin composition of the present invention to contain a basic compound. Useful basic compounds are not particularly limited. For example, appropriate use can be made of compounds of categories (1) to (5) below.

(1) Basic Compound (N)

As preferred basic compounds, there can be mentioned the compounds (N) with structures of the following formulae (A) to (E).

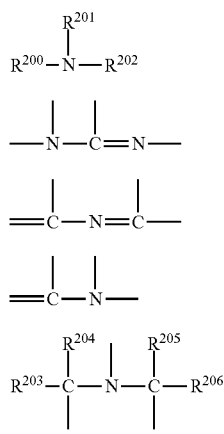

In general formulae (A) and (E), $R^{200}$, $R^{201}$ and $R^{202}$ may be identical to or different from each other, and each represent a hydrogen atom, an alkyl group (preferably having 1 to 20 carbon atoms), a cycloalkyl group (preferably having 3 to 20 carbon atoms) or an aryl group (having 6 to 20 carbon atoms). $R^{201}$ and $R^{202}$ may be bonded to each other to thereby form a ring.

$R^{203}$, $R^{204}$, $R^{205}$ and $R^{206}$ may be identical to or different from each other, and each represent an alkyl group having 1 to 20 carbon atoms.

With respect to the above alkyl group, as a preferred substituted alkyl group, there can be mentioned an aminoalkyl group having 1 to 20 carbon atoms, a hydroxyalkyl group having 1 to 20 carbon atoms or a cyanoalkyl group having 1 to 20 carbon atoms.

In general formulae (A) and (E), it is more preferred for the alkyl groups to be unsubstituted.

As preferred basic compounds (N), there can be mentioned guanidine, aminopyrrolidine, pyrazole, pyrazoline, piperazine, aminomorpholine, aminoalkylmorpholines, piperidine and the like. As further preferred compounds (N), there can be mentioned compounds (N) with an imidazole structure, a diazabicyclo structure, an onium hydroxide structure, an onium carboxylate structure, a trialkylamine structure, an aniline structure or a pyridine structure; alkylamine derivatives containing a hydroxyl group and/or an ether bond; aniline derivatives containing a hydroxyl group and/or an ether bond; and the like.

As the compounds (N) with an imidazole structure, there can be mentioned imidazole, 2,4,5-triphenylimidazole, benzimidazole, 2-phenylbenzimidazole and the like. As the compounds (N) with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like. As the compounds (N) with an onium hydroxide structure, there can be mentioned tetrabutylammonium hydroxide, a triarylsulfonium hydroxide, phenacylsulfonium hydroxide, and sulfonium hydroxides containing a 2-oxoalkyl group, such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. The compounds (N) with an onium carboxylate structure correspond to the compounds (N) with an onium hydroxide structure wherein the anion moiety is a carboxylate, and as such, there can be mentioned, for example, an acetate, adamantane-1-carboxylate, a perfluoroalkyl carboxylate and the like. As the compounds (N) with a trialkylamine structure, there can be mentioned tri(n-butyl)amine, tri(n-octyl)amine and the like. As the aniline compounds (N), there can be mentioned 2,6-diisopropylaniline, N,N-dimethylaniline, N,N-dibutylaniline, N,N-dihexylaniline and the like. As the alkylamine derivatives containing a hydroxyl group and/or an ether bond, there can be mentioned ethanolamine, diethanolamine, triethanolamine, N-phenyldiethanolamine, tris(methoxyethoxyethyl)amine and the like. As the aniline derivatives containing a hydroxyl group and/or an ether bond, there can be mentioned N,N-bis(hydroxyethyl)aniline and the like.

As preferred basic compounds (N), there can further be mentioned an amine compound containing a phenoxy group, an ammonium salt compound containing a phenoxy group, an amine compound containing a sulfonic ester group and an ammonium salt compound containing a sulfonic ester group. As examples of these compounds, there can be mentioned the compounds (C1-1) to (C3-3) shown as examples in Section [0066] of U.S. Patent Application Publication No. 2007/0224539 A1.

The following compounds are also preferred basic compounds (N).

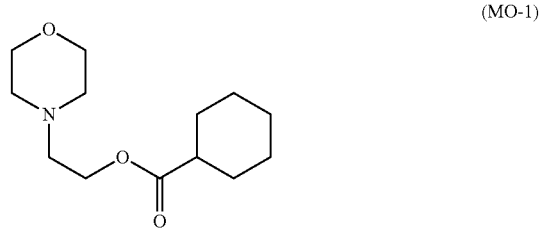

(MO-1)

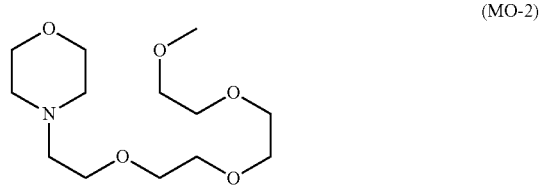

(MO-2)

-continued

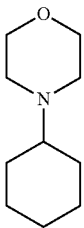
(MO-3)

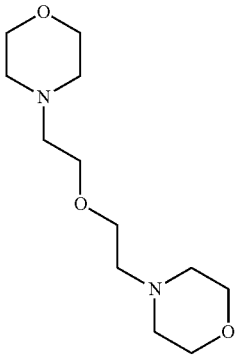
(MO-4)

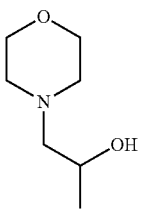
(MO-5)

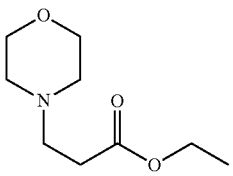
(MO-6)

Besides the foregoing compounds, as basic compounds (N), use can be made of the compounds described in sections [0180] to [0225] of JP-A-2011-22560, sections [0218] to [0219] of JP-A-2012-137735 and sections [0416] to [0438] of International Publication pamphlet WO 2011/158687 A1, etc. The basic compound (N) may be a basic compound or ammonium salt compound whose basicity is lowered upon exposure to actinic rays or radiation.

One type of basic compound (N) may be used alone, or two or more types thereof may be used in combination.

It is optional for the composition of the present invention to contain a basic compound (N). When a basic compound (N) is contained, the content thereof is generally in the range of 0.001 to 10 mass %, preferably 0.01 to 5 mass %, based on the total solids of the actinic-ray- or radiation-sensitive resin composition.

With respect to the ratio of the acid generator to basic compound (N) used in the composition, it is preferred for the acid generator/basic compound (molar ratio) to fall within the range of 2.5 to 300. The reason is as follows. It is preferred for the molar ratio to be 2.5 or higher from the viewpoint of sensitivity and resolving power. It is preferred for the molar ratio to be 300 or below from the viewpoint of inhibiting any resolution deterioration due to thickening of resist pattern over time from exposure to baking treatment.

The acid generator/basic compound (N)(molar ratio) is more preferably in the range of 5.0 to 200, furthermore preferably 7.0 to 150.

(2) Basic compound and ammonium salt compound (E) that when exposed to actinic rays or radiation, exhibit lowered basicity It is preferred for the actinic-ray- or radiation-sensitive resin composition of the present invention to contain a basic compound or ammonium salt compound (hereinafter also referred to as "compound (E)") that when exposed to actinic rays or radiation, exhibits a lowered basicity.

It is preferred for the compound (E) to be a compound (E-1) containing a basic functional group or ammonium group and a group that when exposed to actinic rays or radiation, produces an acid functional group. Namely, it is preferred for the compound (E) to be a basic compound containing a basic functional group and a group that when exposed to actinic rays or radiation, produces an acid functional group, or an ammonium salt compound containing an ammonium group and a group that when exposed to actinic rays or radiation, produces an acid functional group.

As the compounds each exhibiting a lowered basicity, produced by the decomposition of compound (E) or compound (E-1) upon exposure to actinic rays or radiation, there can be mentioned the compounds of general formulae (PA-I), (PA-II) and (PA-III) below. The compounds of general formulae (PA-II) and (PA-III) are especially preferred from the viewpoint of the higher-order simultaneous attainment of excellent effects concerning LWR, local pattern dimension uniformity and DOF.

First, the compounds of general formula (PA-I) will be described.

$$Q\text{-}A_1\text{-}(X)n\text{-}B\text{---}R \quad (PA\text{-}I)$$

In general formula (PA-I), $A_1$ represents a single bond or a bivalent connecting group.

Q represents —SO$_3$H or —CO$_2$H. Q corresponds to the acid functional group produced upon exposure to actinic rays or radiation.

X represents —SO$_2$— or —CO—, and n is 0 or 1.

B represents a single bond, an oxygen atom or —N(Rx)-.

Rx represents a hydrogen atom or a monovalent organic group.

R represents a monovalent organic group containing a basic functional group, or a monovalent organic group containing an ammonium group.

Now, the compounds of general formula (PA-II) will be described.

$$Q_1\text{-}X_1\text{---}NH\text{---}X_2\text{-}Q_2 \quad (PA\text{-}II)$$

In general formula (PA-II), each of $Q_1$ and $Q_2$ independently represents a monovalent organic group, provided that either $Q_1$ or $Q_2$ contains a basic functional group. $Q_1$ and $Q_2$ may be bonded to each other to thereby form a ring, the formed ring containing a basic functional group.

Each of $X_1$ and $X_2$ independently represents —CO— or —SO$_2$—.

In the formula, —NH— corresponds to the acid functional group produced upon exposure to actinic rays or radiation.

Below, the compounds of general formula (PA-III) will be described.

$$Q_1\text{-}X_1\text{---}NH\text{---}X_2\text{-}A_2\text{-}(X_3)_m\text{---}B\text{-}Q_3 \quad (PA\text{-}III)$$

In general formula (PA-III), each of $Q_1$ and $Q_3$ independently represents a monovalent organic group, provided that either $Q_1$ or $Q_3$ contains a basic functional group. $Q_1$ and $Q_3$ may be bonded to each other to thereby form a ring, the formed ring containing a basic functional group.

Each of $X_1$, $X_2$ and $X_3$ independently represents —CO— or —SO$_2$—.

$A_2$ represents a bivalent connecting group.

B represents a single bond, an oxygen atom or —N(Qx)-.

Qx represents a hydrogen atom or a monovalent organic group.

When B is —N(Qx)-, $Q_3$ and Qx may be bonded to each other to thereby form a ring, and m is 0 or 1.

In the formula, —NH— corresponds to the acid functional group produced upon exposure to actinic rays or radiation.

Particular examples of the compounds (E) that produce the compounds of general formula (PA-I) upon exposure to actinic rays or radiation are shown below, which in no way limit the scope of the present invention.

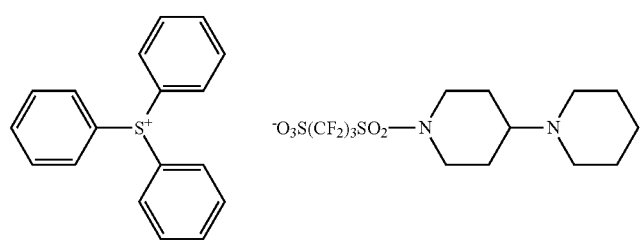

(PA-1)

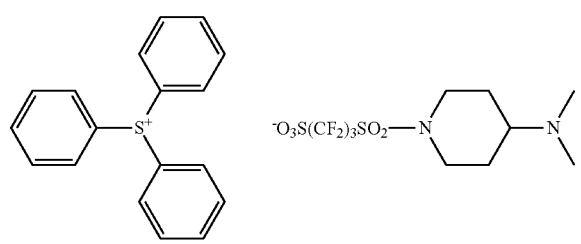

(PA-2)

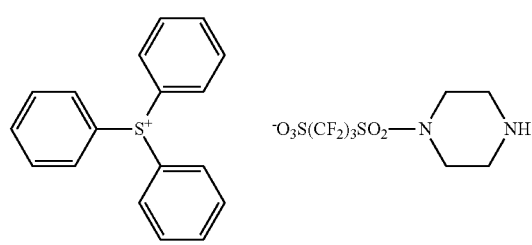

(PA-3)

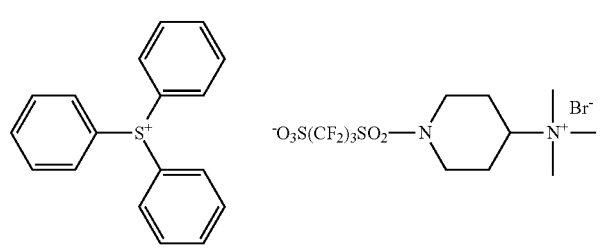

(PA-4)

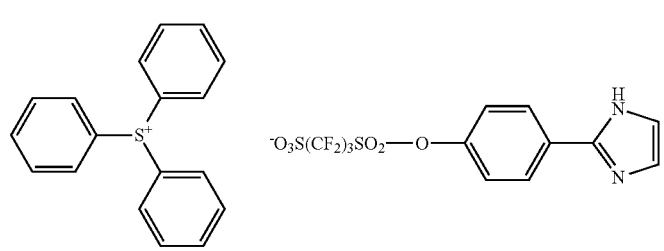

(PA-5)

(PA-6)
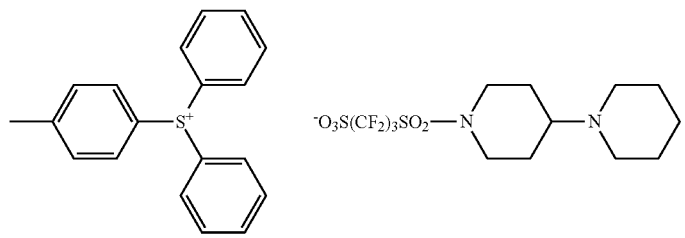
(PA-7)
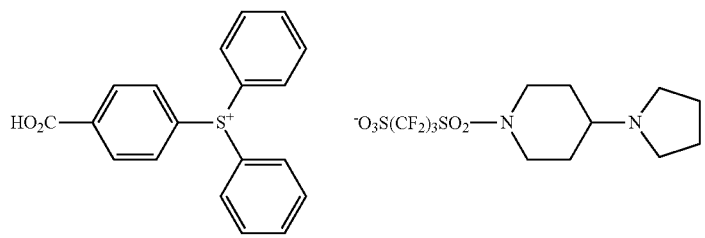
(PA-8)
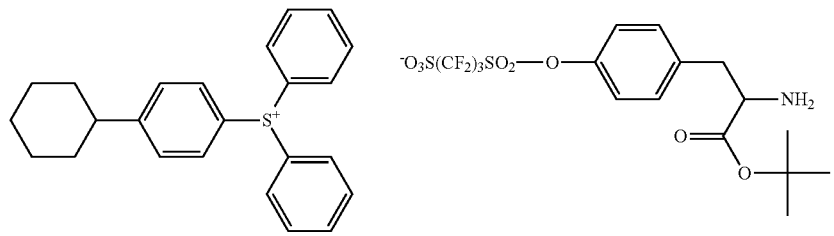
(PA-9)
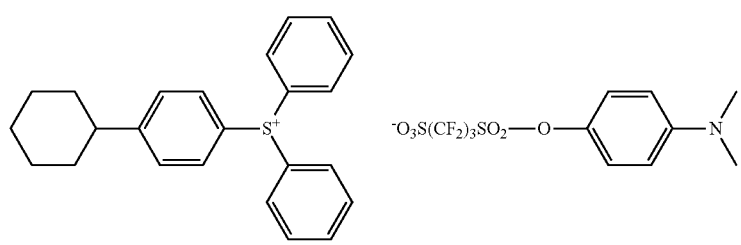
(PA-10)
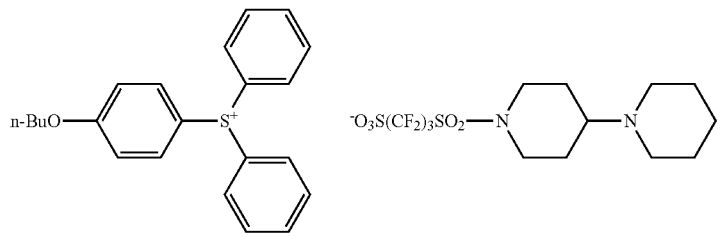
(PA-11)
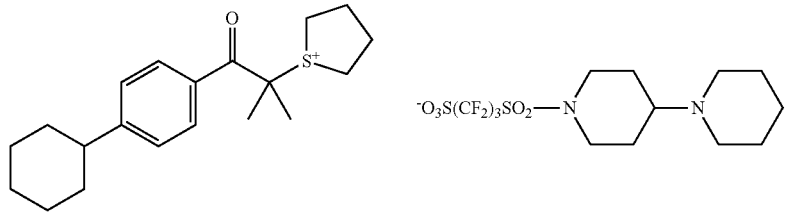
(PA-12)
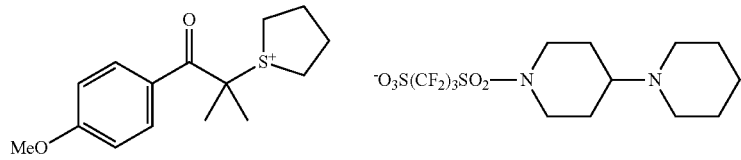

-continued
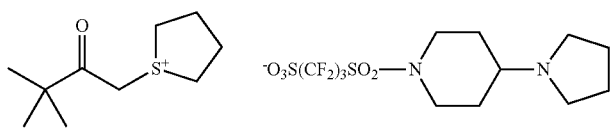 (PA-13)
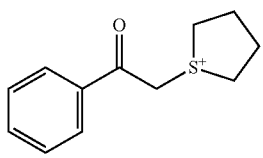 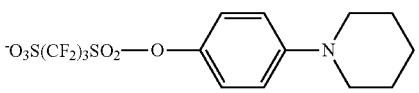 (PA-14)
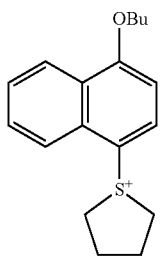 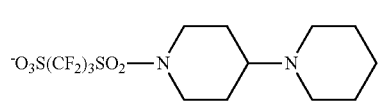 (PA-15)
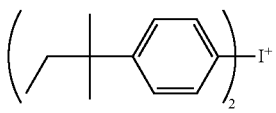 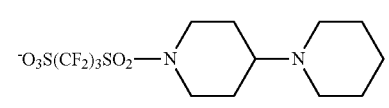 (PA-16)
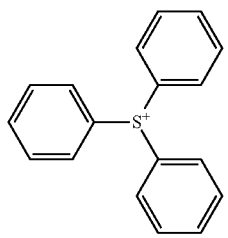 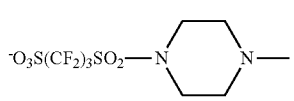 (PA-17)
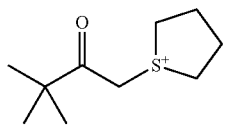 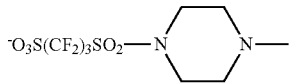 (PA-18)
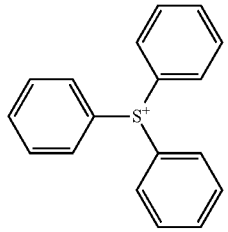 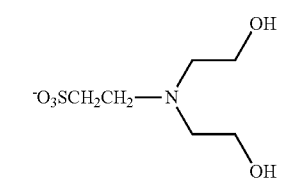 (PA-19)
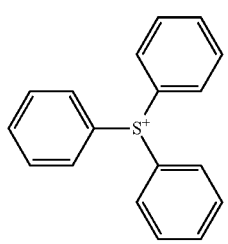 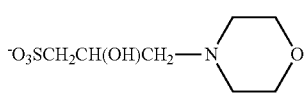 (PA-20)

-continued

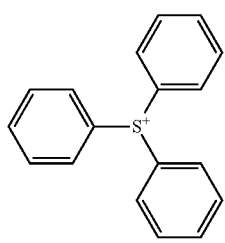 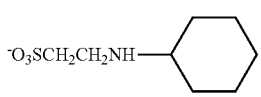 (PA-21)

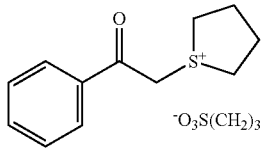 (PA-22)

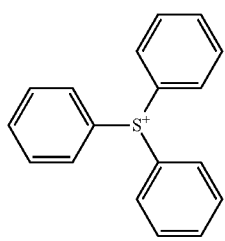 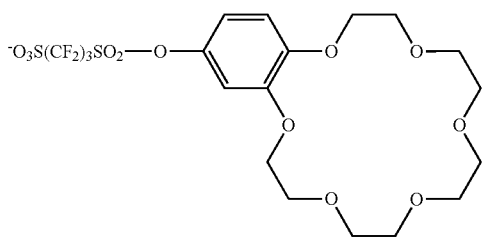 (PA-23)

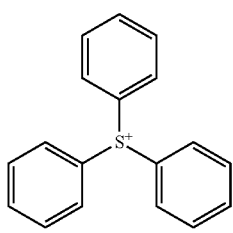 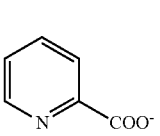 (PA-24)

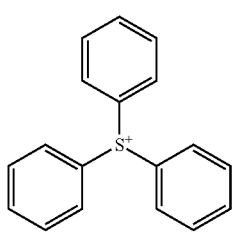 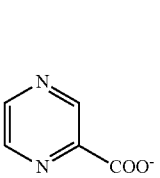 (PA-25)

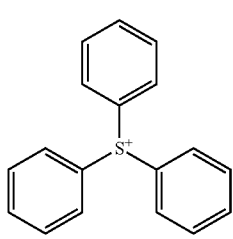 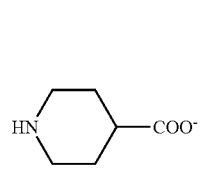 (PA-26)

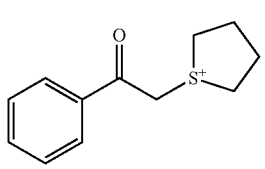 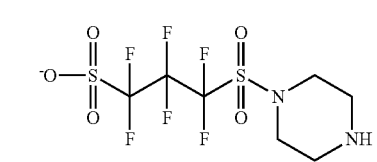 (PA-27)

These compounds can be easily synthesized from the compounds of general formula (PA-I), or a lithium, sodium or potassium salt thereof, and a hydroxide, bromide or chloride of iodonium or sulfonium, etc. by the salt exchange method described in Jpn. PCT National Publication No. H11-501909 and JP-A-2003-246786. Also, the synthesis can be performed in accordance with the method described in JP-A-H7-333851.

Particular examples of the compounds (E) that produce the compounds of general formulae (PA-II) and (PA-III) upon exposure to actinic rays or radiation are shown below, which in no way limit the scope of the present invention.
(PA-28)
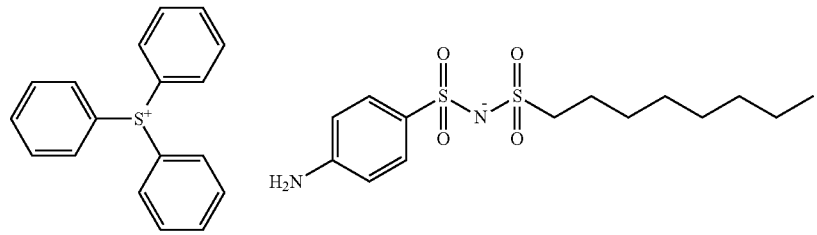
(PA-29)
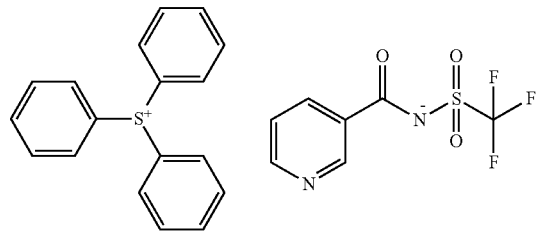
(PA-30)
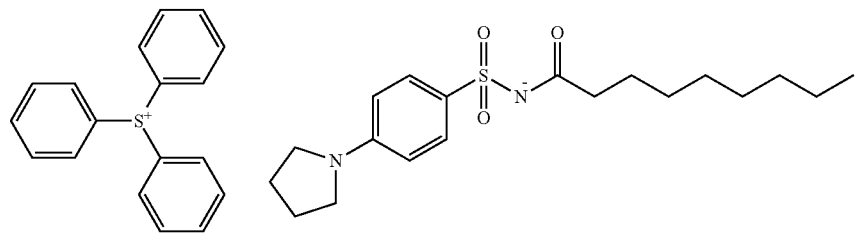
(PA-31)
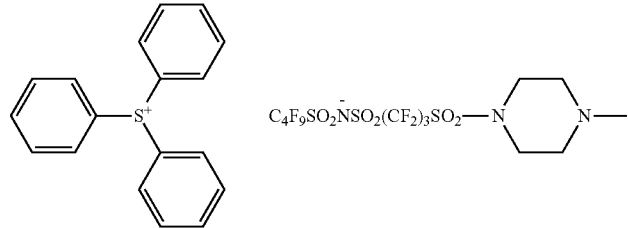
(PA-32)
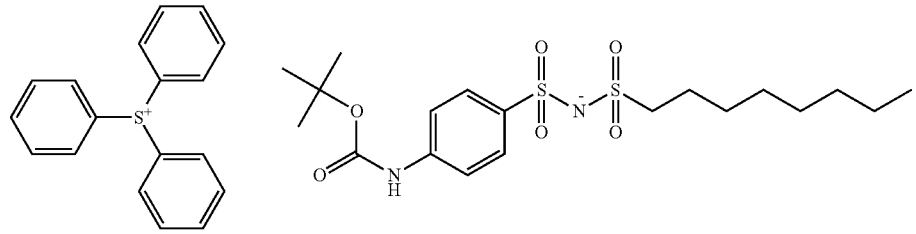
(PA-33)
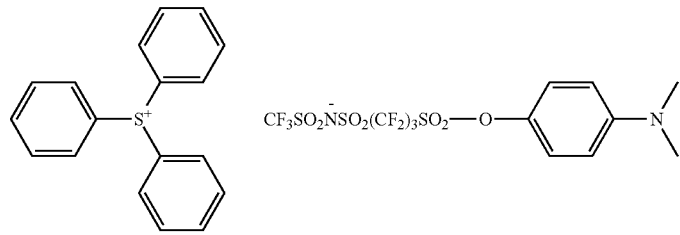

-continued
| | |
|---|---|
| 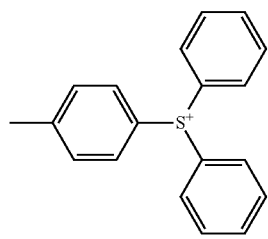 | 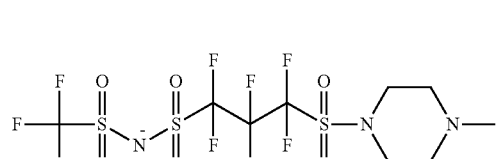 (PA-34) |
| 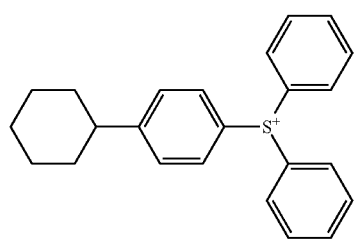 | 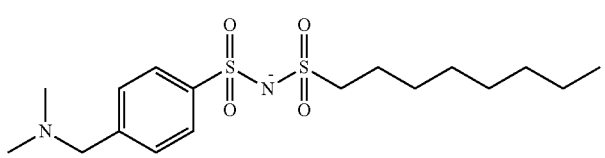 (PA-35) |
| 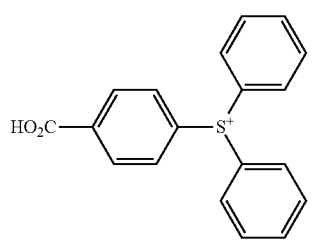 | 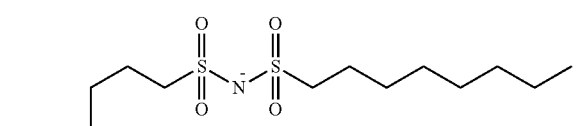 (PA-36) |
| 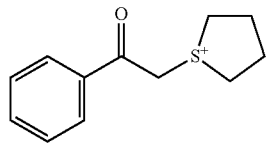 | 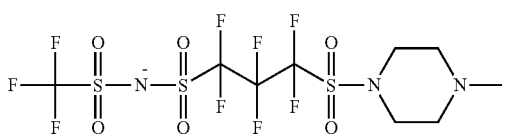 (PA-37) |
| 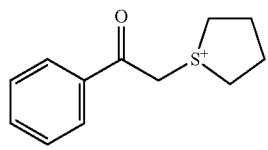 | 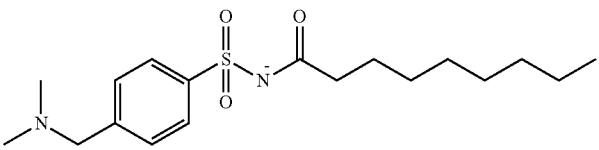 (PA-38) |
| 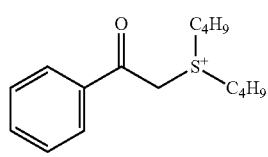 | 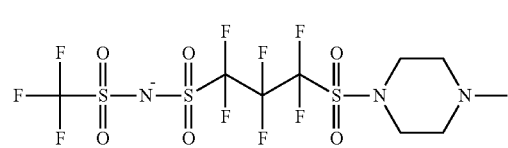 (PA-39) |
| 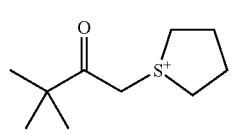 | 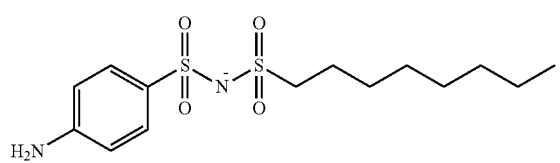 (PA-40) |
| 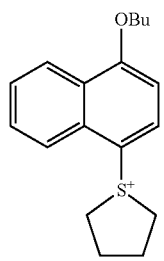 | 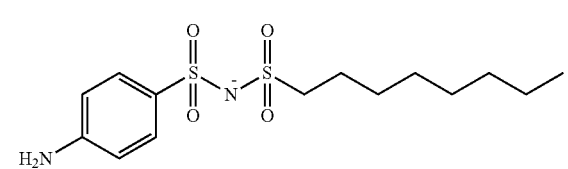 (PA-41) |

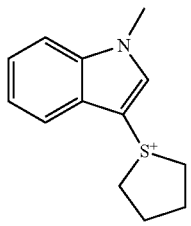 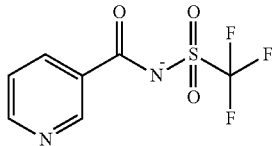
(PA-42)
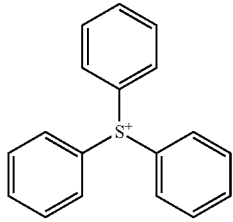 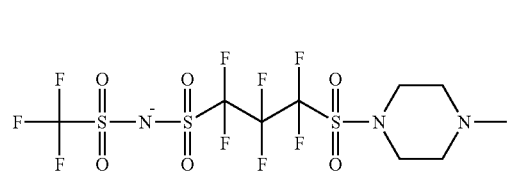
(PA-43)
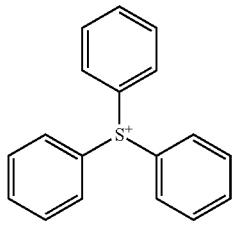 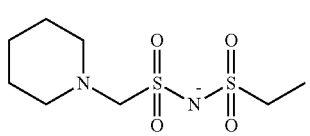
(PA-44)
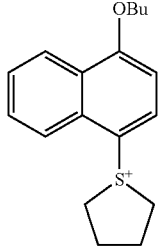 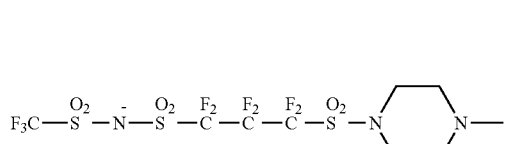
(PA-45)
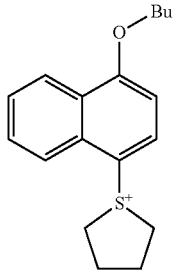 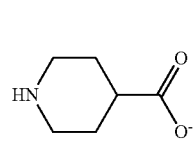
(PA-46)
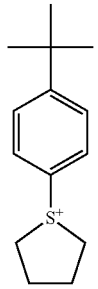 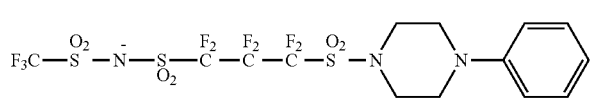
(PA-47)

-continued
(PA-48)
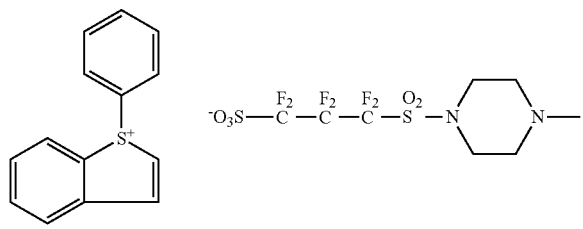
(PA-49)
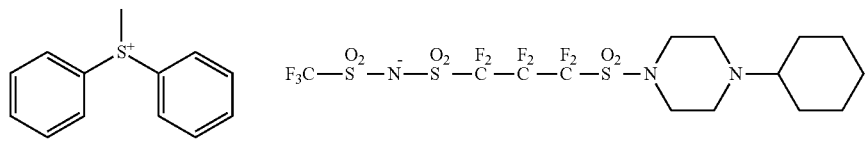
(PA-50)
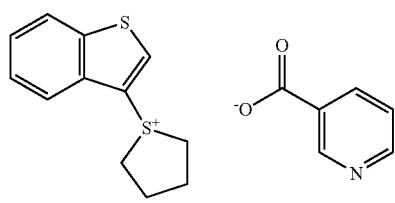
(PA-51)
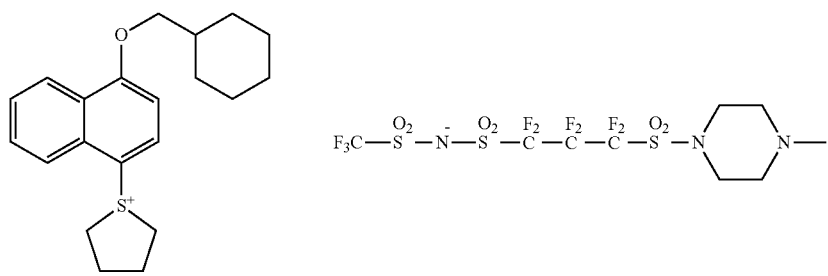
(PA-52)
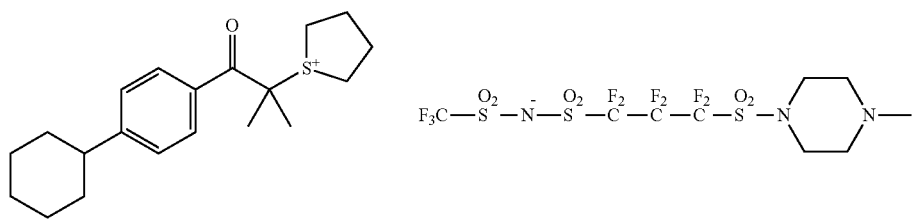
(PA-53)
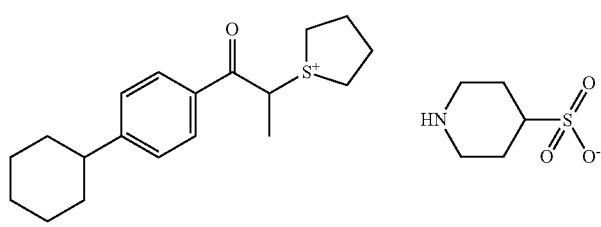
(PA-54)
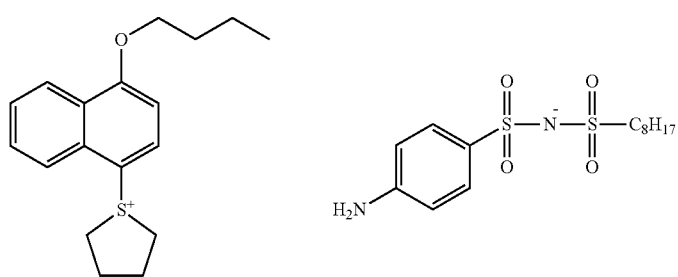

(PA-55)
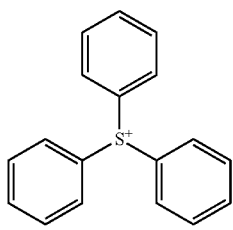 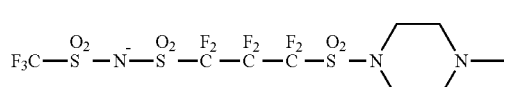
(PA-56)
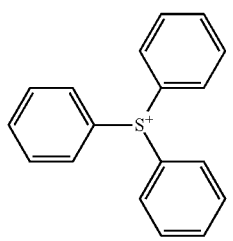 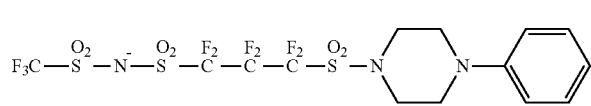
(PA-57)
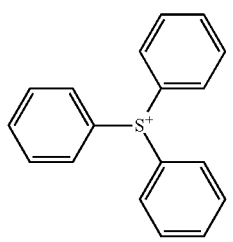 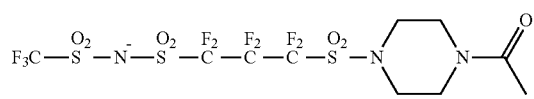
(PA-58)
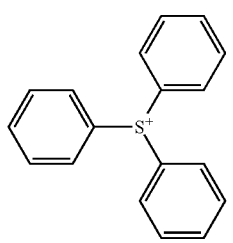 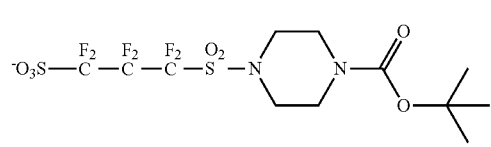
(PA-59)
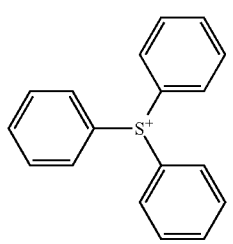 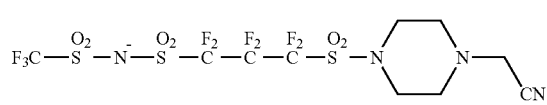
(PA-60)
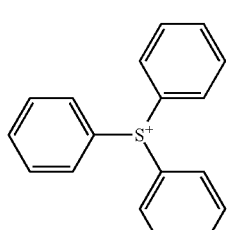 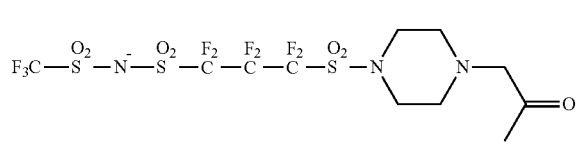

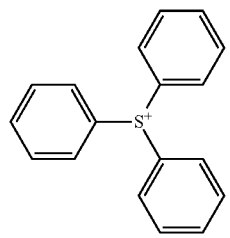 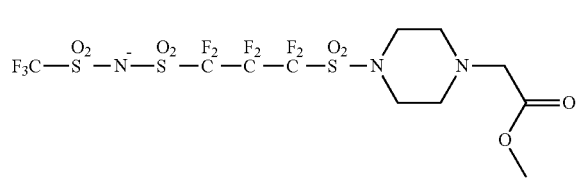 (PA-61)
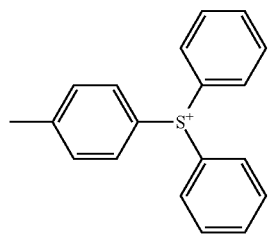 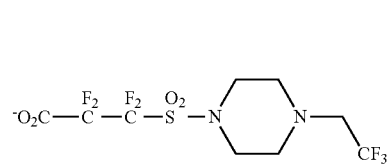 (PA-62)
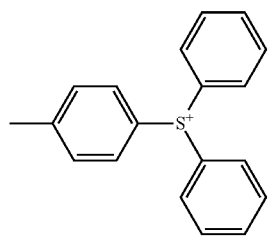 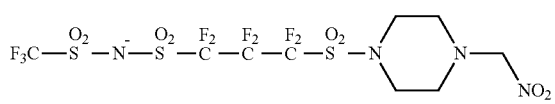 (PA-63)
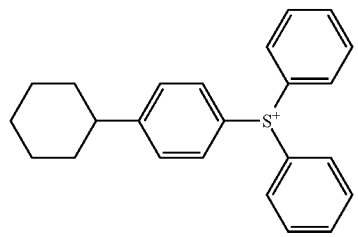 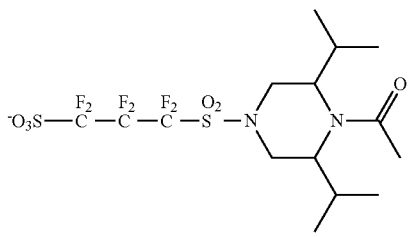 (PA-64)
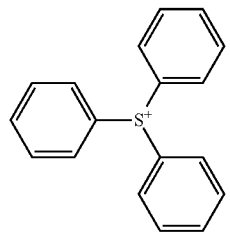 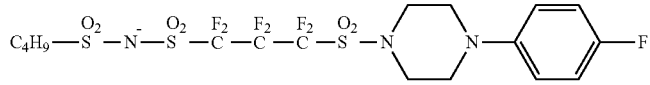 (PA-65)
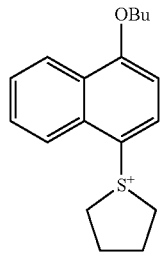 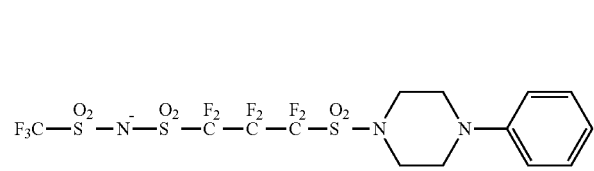 (PA-66)

-continued (PA-67)
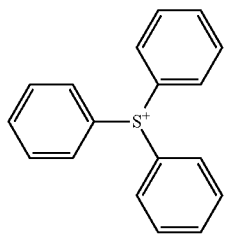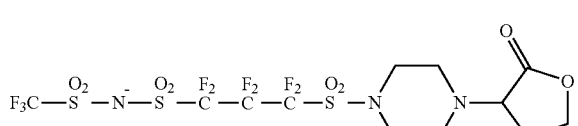

(PA-68)
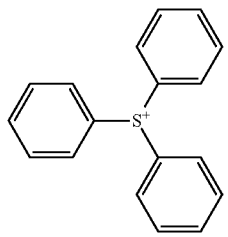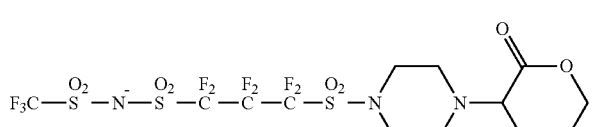

(PA-69)
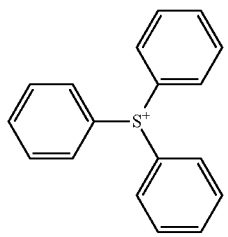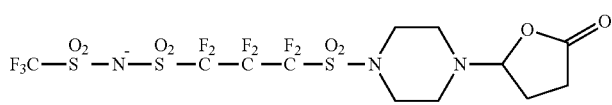

In particular, the synthesis of the compounds (E) can be performed in accordance with, for example, the synthetic examples described in JP-A's 2006-330098 and 2011-100105.

The molecular weight of the compounds (E) is preferably in the range of 500 to 1000.

It is optional for the actinic-ray- or radiation-sensitive resin composition of the present invention to contain the compound (E). When the compound (E) is contained, the content thereof based on the solids of the actinic-ray- or radiation-sensitive resin composition is preferably in the range of 0.1 to 20 mass %, more preferably 0.1 to 10 mass %.

As a form of the compound (E), there can be mentioned a compound (E-2) that when exposed to actinic rays or radiation, is decomposed to thereby produce an acid (weak acid) of strength of a degree at which the acid decomposition of acid-decomposable groups of the resin (A) is not realized.

As this compound, there can be mentioned, for example, an onium salt (preferably a sulfonium salt) of a carboxylic acid containing no fluorine atom, an onium salt (preferably a sulfonium salt) of a sulfonic acid containing no fluorine atom, or the like. As preferred cation structures of the sulfonium salts, there can be mentioned the sulfonium cation structures set forth above in connection with the acid generator (B).

The compound (E-2) is, for example, any of the compounds mentioned in section [0170] of WO 2012/053527 A and sections [0268] to [0269] of JP-A-2012-173419.

(3) Low-molecular compound (F) containing a nitrogen atom and containing a group leaving under the action of an acid The composition of the present invention may contain a low-molecular compound (hereinafter also referred to as "compound (F)") containing a nitrogen atom and containing a group leaving under the action of an acid.

The group leaving under the action of an acid is not particularly limited. However, the group is preferably an acetal group, a carbonate group, a carbamate group, a tertiary ester group, a tertiary hydroxyl group or a hemiaminal ether group, most preferably a carbamate group or a hemiaminal ether group.

The molecular weight of the compound (F) containing a group leaving under the action of an acid is preferably in the range of 100 to 1000, more preferably 100 to 700 and most preferably 100 to 500.

It is preferred for the compound (F) to be an amine derivative in which the group leaving under the action of an acid is contained on its nitrogen atom.

The compound (F) may contain a carbamate group in which a protective group is provided on its nitrogen atom. The protective group as a constituent of the carbamate group can be expressed by general formula (d-1) below.

(d-1)
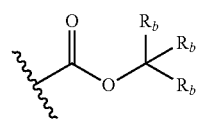

In general formula (d-1), each of Rb's independently represents a hydrogen atom, an alkyl group (preferably 1 to 10 carbon atoms), a cycloalkyl group (preferably 3 to 30 carbon atoms), an aryl group (preferably 3 to 30 carbon atoms), an aralkyl group (preferably 1 to 10 carbon atoms) or an alkoxyalkyl group (preferably 1 to 10 carbon atoms). Rb's may be connected to each other to thereby form a ring.

Each of the alkyl groups, cycloalkyl groups, aryl groups and aralkyl groups represented by Rb's may be substituted with a functional group, such as a hydroxyl group, a cyano group, an amino group, a pyrrolidino group, a piperidino group, a morpholino group or an oxo group, as well as an alkoxy group or a halogen atom. With respect to the alkoxyalkyl groups represented by Rb's, the same substitution can be performed.

Each of Rb's is preferably a linear or branched alkyl group, a cycloalkyl group or an aryl group, more preferably a linear or branched alkyl group or a cycloalkyl group.

As the ring formed by the mutual connection of two Rb's, there can be mentioned an alicyclic hydrocarbon group, an aromatic hydrocarbon group, a heterocyclic hydrocarbon group, any of derivatives from these, or the like.

Nonlimiting particular structures of the groups of general formula (d-1) are as disclosed in section [0466] of US Patent Application Publication No. 2012/0135348 A1.

It is especially preferred for the compound (F) to have any of structures of general formula (6) below.

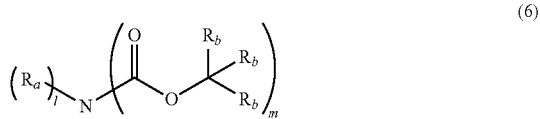

(6)

In general formula (6), Ra represents a hydrogen atom, an alkyl group, a cycloalkyl group, an aryl group or an aralkyl group. When l is 2, two Ra's may be identical to or different from each other. Two Ra's may be connected to each other to thereby form a heterocycle in cooperation with the nitrogen atom in the formula. The heterocycle may contain a heteroatom other than the nitrogen atom in the formula.

Rb's are as defined above in connection with general formula (d-1). Preferred examples are also the same.

In the formula, l is an integer of 0 to 2, and m is an integer of 1 to 3, provided that l+m=3.

In general formula (6), the alkyl group, cycloalkyl group, aryl group and aralkyl group represented by Ra may be substituted with the groups set forth above as being introducible in the alkyl group, cycloalkyl group, aryl group and aralkyl group represented by Rb.

Preferred examples of the alkyl groups, cycloalkyl groups, aryl groups and aralkyl groups represented by Ra (these alkyl groups, cycloalkyl groups, aryl groups and aralkyl groups may be substituted with the above-mentioned groups) can be the same as set forth above in connection with Rb.

As the heterocycle formed by the mutual connection of Ra's, preferably having up to 20 carbon atoms, there can be mentioned, for example, a group derived from a heterocyclic compound, such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline or 1,5,9-triazacyclododecane; a group as obtained by substituting the above heterocyclic-compound-derived group with at least one, or at least one type, of linear or branched-alkane-derived group, cycloalkane-derived group, aromatic-compound-derived group, heterocyclic-compound-derived group and functional group, such as a hydroxyl group, a cyano group, an amino group, a pyrrolidino group, a piperidino group, a morpholino group or an oxo group; or the like.

Nonlimiting particular examples of the compounds (F) especially preferred in the present invention are as disclosed in section [0475] of US Patent Application Publication No. 2012/0135348 A1.

The compounds of general formula (6) can be synthesized in accordance with the processes described in JP-A's 2007-298569 and 2009-199021, etc.

In the present invention, one type of low-molecular compound (F) may be used alone, or two or more types thereof may be used in combination.

The content of compound (F) in the actinic-ray- or radiation-sensitive resin composition of the present invention is preferably in the range of 0.001 to 20 mass %, more preferably 0.001 to 10 mass % and further more preferably 0.01 to 5 mass %, based on the total solids of the composition.

(4) Onium Salt

Moreover, the composition of the present invention may comprise any of onium salts of general formulae (6A) and (6B) below as a basic compound. It can be expected that these onium salts control the diffusion of generated acid in a resist system in relation to the acid strength of photoacid generators generally used in resist compositions.

(6A)

(6B)

In general formula (6A),

Ra represents an organic group, provided that any one in which the carbon atom directly bonded to the carboxylic acid group in the formula is substituted with a fluorine atom is excluded.

$X^+$ represents an onium cation.

In general formula (6B),

Rb represents an organic group, provided that any one in which the carbon atom directly bonded to the sulfonic acid group in the formula is substituted with a fluorine atom is excluded.

$X^+$ represents an onium cation.

It is preferred for the organic group represented by Ra or Rb to be one containing a carbon atom as an atom directly bonded to the carboxylic acid group or sulfonic acid group in the formula. In that instance, for the realization of an acid relatively weak as compared to the acids generated from above photoacid generators, the carbon atom directly bonded to the sulfonic acid group carboxylic acid group is in no event substituted with a fluorine atom.

As the organic groups represented by Ra and Rb, there can be mentioned, for example, an alkyl group having 1 to 20 carbon atoms, a cycloalkyl group having 3 to 20 carbon atoms, an aryl group having 6 to 30 carbon atoms, an aralkyl group having 7 to 30 carbon atoms, a heterocyclic group having 3 to 30 carbon atoms and the like. In these groups, the hydrogen atoms may be partially or entirely replaced.

As substituents introducible in the above alkyl group, cycloalkyl group, aryl group, aralkyl group and heterocyclic group, there can be mentioned, for example, a hydroxyl group, a halogen atom, an alkoxy group, a lactone group, an alkylcarbonyl group and the like.

As the onium cations represented by $X^+$ in general formulae (6A) and (6B), there can be mentioned a sulfonium cation, an ammonium cation, an iodonium cation, a phosphonium cation, a diazonium cation and the like. Of these, a sulfonium cation is preferred.

The sulfonium cation is preferably, for example, an arylsulfonium cation containing at least one aryl group, more preferably a triarylsulfonium cation. A substituent may be introduced in the aryl group, and the aryl group is preferably a phenyl group.

As preferred examples of the sulfonium cations and iodonium cations, there can be mentioned the above-mentioned sulfonium cation structures in general formula (ZI) and iodonium structures in general formula (ZII) with respect to the compound (B).

Specific structures of the onium salts of general formulae (6A) and (6B) are shown below.

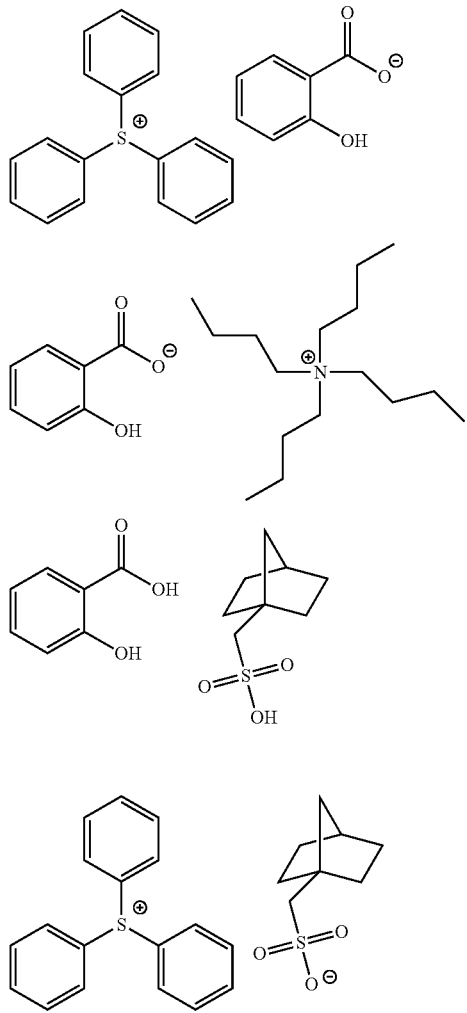

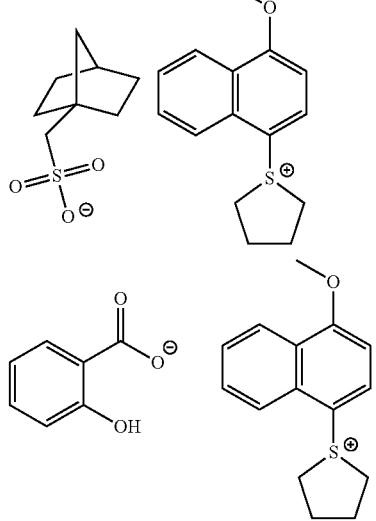

(5) Betaine Compound

Furthermore in the composition of the present invention, preferred use can be made of a compound (hereinafter also referred to as "betaine compound") containing both an onium salt structure and an acid anion alkyl group in its molecule, such as any of compounds included in formula (I) in JP-A-2012-189977, compounds of formula (I) in JP-A-2013-6827, compounds of formula (I) in JP-A-2013-8020 and compounds of formula (I) in JP-A-2012-252124. As the onium salt structure, there can be mentioned a sulfonium, iodonium or ammonium structure. A sulfonium or iodonium salt structure is preferred. The acid anion structure is preferably a sulfonate anion or a carboxylate anion. Examples of these compounds are shown below.

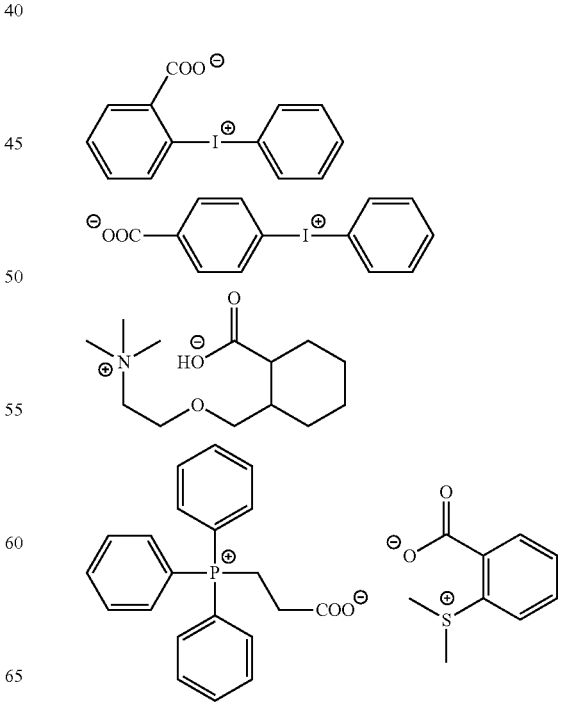

-continued

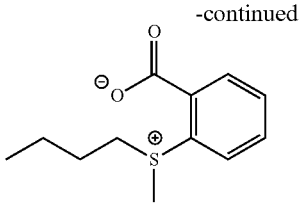

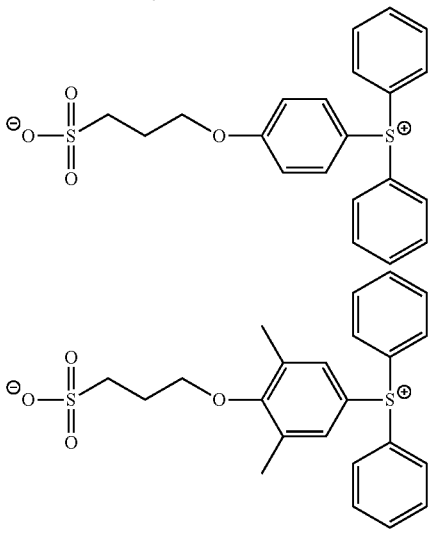

<Solvent>

As solvents that can be used in the preparation of the actinic-ray- or radiation-sensitive resin composition of the present invention, there can be mentioned, for example, organic solvents, such as an alkylene glycol monoalkyl ether carboxylate, an alkylene glycol monoalkyl ether, an alkyl lactate, an alkyl alkoxypropionate, a cyclolactone (preferably having 4 to 10 carbon atoms), an optionally cyclized monoketone compound (preferably having 4 to 10 carbon atoms), an alkylene carbonate, an alkyl alkoxyacetate and an alkyl pyruvate.

As particular examples of these solvents, there can be mentioned those set forth in sections [0441] to [0455] of US Patent Application Publication No. 2008/0187860.

In the present invention, a mixed solvent comprised of a mixture of a solvent containing a hydroxyl group in its structure and a solvent containing no hydroxyl group may be used as the organic solvent.

Compounds set forth above by way of example can be appropriately selected as the solvent containing a hydroxyl group and solvent containing no hydroxyl group. The solvent containing a hydroxyl group is preferably an alkylene glycol monoalkyl ether, an alkyl lactate or the like, more preferably propylene glycol monomethyl ether (PGME, also known as 1-methoxy-2-propanol) or ethyl lactate. The solvent containing no hydroxyl group is preferably an alkylene glycol monoalkyl ether acetate, an alkyl alkoxypropionate, an optionally cyclized monoketone compound, a cyclolactone, an alkyl acetate or the like. Of these, propylene glycol monomethyl ether acetate (PGMEA, also known as 1-methoxy-2-acetoxypropane), ethyl ethoxypropionate, 2-heptanone, γ-butyrolactone, cyclohexanone and butyl acetate are especially preferred. Propylene glycol monomethyl ether acetate, ethyl ethoxypropionate and 2-heptanone are most preferred.

The mixing ratio (mass) of a solvent containing a hydroxyl group and a solvent containing no hydroxyl group is in the range of 1/99 to 99/1, preferably 10/90 to 90/10 and more preferably 20/80 to 60/40. A mixed solvent containing 50 mass % or more of solvent containing no hydroxyl group is especially preferred from the viewpoint of uniform coatability.

The solvent preferably contains propylene glycol monomethyl ether acetate, being preferably a solvent comprised only of propylene glycol monomethyl ether acetate (PGMEA), or a mixed solvent comprised of two or more types of solvents in which propylene glycol monomethyl ether acetate (PGMEA) is contained. Nonlimiting preferred particular examples of such mixed solvents include a mixed solvent comprising PGMEA and a ketone solvent (cyclohexanone, 2-heptanone or the like), a mixed solvent comprising PGMEA and a lactone solvent (γ-butyrolactone or the like), a mixed solvent comprising PGMEA and PGME, a mixed solvent comprising three solvents, namely, PGMEA, a ketone solvent and a lactone solvent, a mixed solvent comprising three solvents, namely, PGMEA, PGME and a lactone solvent and a mixed solvent comprising three solvents, namely, PGMEA, PGME and a ketone solvent.

<Surfactant>

It is optional for the actinic-ray- or radiation-sensitive resin composition of the present invention to further contain a surfactant. When a surfactant is contained, it is preferred for the same to contain any one, or two or more, of fluorinated and/or siliconized surfactants (fluorinated surfactant, siliconized surfactant and surfactant containing both fluorine and silicon atoms).

The actinic-ray- or radiation-sensitive resin composition of the present invention when containing the surfactant can, in the use of an exposure light source of 250 nm or below, especially 220 nm or below, produce a resist pattern of less adhesion and development defects with favorable sensitivity and resolution.

As the fluorinated and/or siliconized surfactants, there can be mentioned those described in section [0276] of US Patent Application Publication No. 2008/0248425. For example, there can be mentioned Eftop EF301 and EF303 (produced by Shin-Akita Kasei Co., Ltd.), Florad FC 430, 431 and 4430 (produced by Sumitomo 3M Ltd.), Megafac F171, F173, F176, F189, F113, F110, F177, F120 and R08 (produced by DIC Corporation), Surflon S-382, SC101, 102, 103, 104, 105, 106 and KH-20 (produced by Asahi Glass Co., Ltd.), Troy Sol S-366 (produced by Troy Chemical Co., Ltd.), GF-300 and GF-150 (produced by TOAGOSEI CO., LTD.), Sarfron S-393 (produced by SEIMI CHEMICAL CO., LTD.), Eftop EF121, EF122A, EF122B, RF122C, EF125M, EF135M, EF351, EF352, EF801, EF802 and EF601 (produced by JEMCO INC.), PF636, PF656, PF6320 and PF6520 (produced by OMNOVA SOLUTIONS, INC.), and FTX-204G, 208G, 218G, 230G, 204D, 208D, 212D, 218D and 222D (produced by NEOS). Further, polysiloxane polymer KP-341 (produced by Shin-Etsu Chemical Co., Ltd.) can be employed as a siliconized surfactant.

As the surfactant, besides the above generally known surfactants, use can be made of a surfactant based on a polymer containing a fluoroaliphatic group derived from a fluoroaliphatic compound produced by a telomerization technique (also known as a telomer process) or an oligomerization technique (also known as an oligomer process). The fluoroaliphatic compound can be synthesized by the process described in JP-A-2002-90991.

As the relevant surfactants, there can be mentioned Megafac F178, F-470, F-473, F-475, F-476 or F-472 (produced by DIC Corporation), a copolymer from an acrylate (or methacrylate) containing a $C_6F_{13}$ group and a poly(oxyalkylene)

acrylate (or methacrylate), a copolymer from an acrylate (or methacrylate) containing a $C_3F_7$ group, polyoxyethylene) acrylate (or methacrylate) and poly(oxypropylene)acrylate (or methacrylate), and the like.

Moreover, in the present invention, use can be made of surfactants other than the fluorinated and/or siliconized surfactants, described in section [0280] of US Patent Application Publication No. 2008/0248425.

These surfactants may be used either individually or in combination.

When the actinic-ray- or radiation-sensitive resin composition contains a surfactant, the amount of surfactant used is preferably in the range of 0.0001 to 2 mass %, more preferably 0.0005 to 1 mass %, based on the total mass of the actinic-ray- or radiation-sensitive resin composition (excluding the solvent).

When the amount of surfactant added is controlled at 10 ppm or less based on the total mass of the actinic-ray- or radiation-sensitive resin composition (excluding the solvent), the localization of the resin (HR) in the surface layer is promoted to thereby cause the surface of the resist film to be highly hydrophobic, so that the water tracking property in the stage of liquid-immersion exposure can be enhanced.

The composition of the present invention can be prepared by appropriate mixing of individual components as described above. The preparation may comprise the operation of reducing metal impurities in the composition to a ppb level by means of an ion exchange membrane, the operation of filtering impurities, such as various particles, by means of an appropriate filter, the operation of deaeration, etc. With respect to the particulars of these operations, reference can be made to, for example, JP-A's 2012-88574, 2010-189563, 2001-12529, 2001-350266, 2002-99076, H5-307263 and 2010-164980, WO 2006/121162 A and JP-A's 2010-243866 and 2010-020297.

It is preferred for the water content of the composition of the present invention to be low. In particular, the water content based on the total mass of the composition is preferably 2.5 mass % or less, more preferably 1.0 mass % or less and further more preferably 0.3 mass % or less.

<Method of Forming Pattern>

Now, the method of forming a pattern according to the present invention will be described.

The method of forming a pattern according to the present invention comprises at least the operations of:

(i) forming a film (resist film) comprising the actinic-ray- or radiation-sensitive resin composition of the present invention, (ii) exposing the film to actinic rays or radiation, and (iii) developing the exposed film with a developer.

In the operation (ii) above, the exposure may be a liquid-immersion exposure.

The pattern forming method of the present invention preferably comprises a baking operation (iv) conducted after the exposing operation (ii).

The pattern forming method of the present invention may comprise a plurality of exposing operations (ii).

The pattern forming method of the present invention may comprise a plurality of baking operations (iv).

The resist film of the present invention is one formed from the above actinic-ray- or radiation-sensitive resin composition of the present invention. In particular, the film is preferably one formed by coating a substrate with the actinic-ray- or radiation-sensitive resin composition. The thickness of the film is not particularly limited. Typically, the thickness is regulated so as to fall within the range of about 25 to 500 nm. In the pattern forming method of the present invention, the operation of forming the film of the actinic-ray- or radiation-sensitive resin composition on a substrate, the operation of exposing the film to light, and the operation of developing the exposed film can be performed using generally known methods.

The pattern forming method preferably comprises the operation of prebake (PB) performed after the film formation but prior to the exposing operation.

Also, the pattern forming method preferably comprises the operation of post-exposure bake (PEB) performed after the exposing operation but prior to the developing operation.

In both PB and PEB, the baking is preferably performed at 70 to 130° C., more preferably 80 to 120° C.

The baking time is preferably in the range of 30 to 300 seconds, more preferably 30 to 180 seconds and further more preferably 30 to 90 seconds.

The baking can be performed by means provided in the common exposure/development equipment. The baking can also be performed using a hot plate or the like.

The baking accelerates the reaction in exposed areas, so that the sensitivity and pattern profile can be enhanced.

The wavelength of light source for use in the exposure apparatus in the present invention is not particularly limited. Use can be made of infrared rays, visible light, ultraviolet rays, far ultraviolet rays, extreme ultraviolet light, X-rays, electron beams, etc. Use is made of far ultraviolet rays of wavelength preferably 250 nm or shorter, more preferably 220 nm or shorter and most preferably 1 to 200 nm, such as a KrF excimer laser (248 nm), an ArF excimer laser (193 nm) and an $F_2$ excimer laser (157 nm), X-rays, EUV (13 nm), electron beams, etc. A KrF excimer laser, an ArF excimer laser, EUV and electron beams are preferred. An ArF excimer laser is more preferred.

A technique of liquid immersion exposure can be employed in the exposing operation according to the present invention. The technique of liquid immersion exposure can be combined with a super-resolution technology, such as a phase shift method or a modified illumination method.

When the liquid immersion exposure is performed, the operation of washing the film surface with an aqueous chemical liquid may be carried out (1) after the film formation on the substrate but prior to the operation of exposure, and/or (2) after the operation of exposing the film to light via the immersion liquid but before the operation of baking the film.

The immersion liquid is preferably comprised of a liquid being transparent in exposure wavelength, whose temperature coefficient of refractive index is as low as possible so as to ensure minimization of any distortion of optical image projected on the film. Especially in the use of an ArF excimer laser (wavelength: 193 nm) as an exposure light source, it is preferred to use water from not only the above viewpoint but also the viewpoint of easy procurement and easy handling.

In the use of water as the immersion liquid, an additive (liquid) capable of not only decreasing the surface tension of water but also increasing an interface activating power may be added in a slight proportion. It is preferred for this additive to be one that does not dissolve the resist layer on the wafer and is negligible with respect to its influence on the optical coat applied to an under surface of lens element.

The additive is preferably, for example, an aliphatic alcohol exhibiting a refractive index approximately equal to that of water, such as methyl alcohol, ethyl alcohol, isopropyl alcohol or the like. The addition of an alcohol exhibiting a refractive index approximately equal to that of water is advantageous in that even when the alcohol component is evaporated from water to thereby cause a change of content concentration, any change of refractive index of the liquid as a whole can be minimized.

On the other hand, when a substance being opaque in 193 nm light or an impurity whose refractive index is greatly different from that of water is mingled in the immersion water, a distortion of optical image projected on the resist is invited. Accordingly, it is preferred to use distilled water as the immersion water. Furthermore, use may be made of pure water having been filtered through an ion exchange filter or the like.

Desirably, the electrical resistance of the water used as the immersion liquid is 18.3 MΩcm or higher, and the TOC (organic matter concentration) thereof is 20 ppb or below. Prior deaeration of the water is desired.

The lithography performance can be enhanced by raising the refractive index of the immersion liquid. From this viewpoint, an additive suitable for refractive index increase may be added to the water, or heavy water ($D_2O$) may be used in place of the water.

The receding contact angle of the resist film formed from the actinic-ray- or radiation-sensitive resin composition of the present invention is 70° or greater at 23±3° C. in 45±5% humidity, which is appropriate in the exposure via the liquid immersion medium. The receding contact angle is preferably 75° or greater, more preferably 75 to 85°.

When the receding contact angle is extremely small, the resist film cannot be appropriate in the exposure via the liquid immersion medium, and the effect of suppressing any residual water (watermark) defect cannot be satisfactorily exerted. For the realization of desirable receding contact angle, it is preferred to incorporate the above-mentioned hydrophobic resin (HR) in the actinic-ray- or radiation-sensitive resin composition. Alternatively, the receding contact angle may be increased by forming a coating layer (known as "top coat") of hydrophobic resin composition on the resist film.

In the operation of liquid immersion exposure, it is needed for the immersion liquid to move on the wafer while tracking the movement of an exposure head involving high-speed scanning on the wafer and thus forming an exposure pattern. Therefore, the contact angle of the immersion liquid with respect to the resist film in a dynamic condition is important, and it is required for the resist to be capable of tracking the high-speed scanning of the exposure head without leaving any droplets.

The substrate for film formation in the present invention is not particularly limited. Use can be made of any of an inorganic substrate of silicon, SiN, $SiO_2$, TiN or the like, a coated inorganic substrate such as SOG and substrates commonly employed in a semiconductor production process for an IC or the like, a circuit board production process for a liquid crystal, a thermal head or the like and other photoapplication lithography processes. Further, according to necessity, an antireflection film may be provided between the resist film and the substrate. Any of heretofore known organic and inorganic antireflection films can be appropriately used as the antireflection film.

In the pattern forming method of the present invention, the developing operation (iii) comprises the development (iii-1) with a developer comprising an organic solvent. The developing operation may further comprise the development (iii-2) with an alkali developer. In that instance, the sequence of developments (iii-1) and (iii-2) is not critical. Preferably, however, the development (iii-2) with an alkali developer is conducted in advance. When both the developments (iii-1) and (iii-2) are conducted, as mentioned with reference to, for example, FIGS. 1 to 11 in U.S. Pat. No. 8,227,183 B, a pattern of resolution corresponding to twice the frequency of optical aerial image can be obtained.

As the developer (hereinafter also referred to as an organic developer) for use in the operation (iii-1) of developing with a developer comprising an organic solvent to be performed in the pattern forming method of the present invention, use can be made of a polar solvent, such as a ketone solvent, an ester solvent, an alcohol solvent, an amide solvent or an ether solvent, and a hydrocarbon solvent.

As the ketone solvent, there can be mentioned, for example, 1-octanone, 2-octanone, 1-nonanone, 2-nonanone, acetone, 2-heptanone(methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, propylene carbonate or the like.

As the ester solvent, there can be mentioned, for example, methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl 3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate or the like.

As the alcohol solvent, there can be mentioned, for example, an alcohol, such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol or n-decanol; a glycol solvent, such as ethylene glycol, diethylene glycol or triethylene glycol; a glycol ether solvent, such as ethylene glycol monomethyl ether, propylene glycol monomethyl ether, ethylene glycol monoethyl ether, propylene glycol monoethyl ether, diethylene glycol monomethyl ether, triethylene glycol monoethyl ether or methoxymethylbutanol; or the like.

As the ether solvent, there can be mentioned, for example, not only any of the above-mentioned glycol ether solvents but also dioxane, tetrahydrofuran or the like.

As the amide solvent, there can be mentioned, for example, N-methyl-2-pyrrolidone, N,N-dimethylacetamide, N,N-dimethylformamide, hexamethylphosphoric triamide, 1,3-dimethyl-2-imidazolidinone or the like.

As the hydrocarbon solvent, there can be mentioned, for example, an aromatic hydrocarbon solvent, such as toluene or xylene, or an aliphatic hydrocarbon solvent, such as pentane, hexane, octane or decane.

In particular, it is preferred for the organic developer to be a developer comprising at least one organic solvent selected from the group consisting of ketone solvents and ester solvents. Developers comprising butyl acetate as an ester solvent and methylamyl ketone (2-heptanone) as a ketone solvent are especially preferred.

Two or more of these solvents may be mixed together before use. Alternatively, each of the solvents may be used in a mixture with a solvent other than those mentioned above or water. However, from the viewpoint of the fullest exertion of the effects of the present invention, it is preferred for the water content of the whole developer to be less than 10 mass %. More preferably, the developer contains substantially no water.

Namely, the amount of organic solvent used in the organic developer is preferably in the range of 90 to 100 mass %, more preferably 95 to 100 mass %, based on the whole amount of the developer.

The vapor pressure of the organic developer at 20° C. is preferably 5 kPa or below, more preferably 3 kPa or below and most preferably 2 kPa or below. When the vapor pressure of the organic developer is 5 kPa or below, the evaporation of the developer on a substrate or in a development cup can be suppressed, so that the temperature uniformity within the plane of the wafer can be enhanced to thereby improve the dimensional uniformity within the plane of the wafer.

According to necessity, an appropriate amount of surfactant can be added to the organic developer.

The surfactant is not particularly limited. For example, use can be made of any of ionic and nonionic fluorinated and/or siliconized surfactants and the like. As such fluorinated and/or siliconized surfactants, there can be mentioned, for example, those described in JP-A's S62-36663, S61-226746, S61-226745, S62-170950, S63-34540, H7-230165, H8-62834, H9-54432 and H9-5988 and U.S. Pat. Nos. 5,405,720, 5,360,692, 5,529,881, 5,296,330, 5,436,098, 5,576,143, 5,294,511 and 5,824,451. Nonionic surfactants are preferred. Although nonionic surfactants are not particularly limited, using a fluorinated surfactant or siliconized surfactant is more preferred.

The amount of surfactant added is generally in the range of 0.001 to 5 mass %, preferably 0.005 to 2 mass % and more preferably 0.01 to 0.5 mass % based on the whole amount of the developer.

Nitrogen-containing compounds as described in sections [0032] to [0063] of JP-A-2013-11833 can be incorporated in the organic developer.

As the development method, use can be made of, for example, a method in which the substrate is dipped in a tank filled with a developer for a given period of time (dip method), a method in which a developer is puddled on the surface of the substrate by its surface tension and allowed to stand still for a given period of time to thereby effect development (puddle method), a method in which a developer is sprayed onto the surface of the substrate (spray method), or a method in which a developer is continuously discharged onto the substrate being rotated at a given speed while scanning a developer discharge nozzle at a given speed (dynamic dispense method).

With respect to the above various development methods, when the operation of discharging a developer toward a resist film through a development nozzle of a development apparatus is included, the discharge pressure of discharged developer (flow rate per area of discharged developer) is, for example, preferably 2 ml/sec/mm$^2$ or below, more preferably 1.5 ml/sec/mm$^2$ or below and further more preferably 1 ml/sec/mm$^2$ or below. There is no particular lower limit of the flow rate. However, from the viewpoint of through-put, it is preferred for the flow rate to be 0.2 ml/sec/mm$^2$ or higher. The particulars thereof are described in, for example, sections 0022 to 0029 of JP-A-2010-232550.

The operation of developing with a developer comprising an organic solvent may be followed by the operation of discontinuing the development by replacement with another solvent.

When the pattern forming method of the present invention comprises the development (iii-2) with an alkali developer, the useful alkali developers are not particularly limited. General use is made of a 2.38 mass % aqueous tetramethylammonium hydroxide solution. Solutions of other concentrations (for example, lower concentration) can also be used. Appropriate amounts of an alcohol and a surfactant may be added to an alkaline aqueous solution before the use thereof.

The alkali concentration of the alkali developer is generally in the range of 0.1 to 20 mass %.

The pH value of the alkali developer is generally in the range of 10.0 to 15.0.

Pure water is used as the rinse liquid for use in the rinse treatment performed after the alkali development. Before the use thereof, an appropriate amount of surfactant may be added thereto.

Further, the development operation or rinse operation may be followed by the operation of removing any portion of developer or rinse liquid adhering onto the pattern by use of a supercritical fluid.

The operation (iii-1) of developing with a developer comprising an organic solvent is preferably followed by the operation of rinsing with a rinse liquid. The rinse liquid is not particularly limited as long as it does not dissolve the resist pattern, and solutions comprising common organic solvents can be used as the same. It is preferred for the rinse liquid to be one comprising at least one organic solvent selected from the group consisting of a hydrocarbon solvent, a ketone solvent, an ester solvent, an alcohol solvent, an amide solvent and an ether solvent.

Particular examples of the hydrocarbon solvent, ketone solvent, ester solvent, alcohol solvent, amide solvent and ether solvent are the same as set forth above in connection with the developer comprising an organic solvent.

The operation (iii-1) of developing with the developer comprising an organic solvent is more preferably followed by the operation of rinsing with a rinse liquid comprising at least one organic solvent selected from the group consisting of a ketone solvent, an ester solvent, an alcohol solvent and an amide solvent; further more preferably followed by the operation of rinsing with a rinse liquid comprising an alcohol solvent or an ester solvent; especially preferably followed by the operation of rinsing with a rinse liquid comprising a monohydric alcohol; and most preferably followed by the operation of rinsing with a rinse liquid comprising a monohydric alcohol having 5 or more carbon atoms.

As the monohydric alcohol for use in the rinse operation, there can be mentioned a linear, branched or cyclic monohydric alcohol. In particular, use can be made of 1-hexanol, 2-hexanol, 4-methyl-2-pentanol, 1-pentanol, 3-methyl-1-butanol or the like.

Two or more of these components may be mixed together before use. Also, they may be mixed with other organic solvents before use.

The water content of the rinse liquid is preferably 10 mass % or below, more preferably 5 mass % or below and most preferably 3 mass % or below. Favorable development performance can be attained by controlling the water content of the rinse liquid at 10 mass % or below.

With respect to the rinse liquid for use after the operation of developing with a developer comprising an organic solvent, the vapor pressure thereof at 20° C. is preferably in the range of 0.05 to 5 kPa, more preferably 0.1 to 5 kPa and most preferably 0.12 to 3 kPa. When the vapor pressure of the rinse liquid is in the range of 0.05 to 5 kPa, not only can the temperature uniformity within the plane of the wafer be enhanced but also the swell attributed to the penetration of the rinse liquid can be suppressed to thereby improve the dimensional uniformity within the plane of the wafer.

An appropriate amount of surfactant may be added to the rinse liquid before use.

In the rinse operation, the wafer having undergone the development with a developer comprising an organic solvent is rinsed with the above rinse liquid comprising an organic solvent. The method of rinse treatment is not particularly limited. For example, use can be made of any of a method in which the rinse liquid is continuously applied onto the substrate being rotated at a given speed (spin application method), a method in which the substrate is dipped in a tank filled with the rinse liquid for a given period of time (dip method) and a method in which the rinse liquid is sprayed onto the surface of the substrate (spray method). Preferably, the rinse treatment is carried out according to the spin application method, and thereafter the substrate is rotated at a rotating speed of 2000 to 4000 rpm to thereby remove the rinse liquid from the top of the substrate. Also, preferably, a baking operation (post-bake) is carried out subsequent to the rinse operation. Any inter-pattern and intra-pattern remaining developer and rinse liquid are removed by carrying out the bake. The bake operation subsequent to the rinse operation is generally performed at 40 to 160° C., preferably 70 to 95° C., for a period of 10 seconds to 3 minutes, preferably 30 to 90 seconds.

In the organic developer, alkali developer and/or rinse liquid for use in the present invention, it is preferred to lessen the amount of impurities, such as various particulates and metal elements. For obtaining such chemicals in which the amount of impurities is less, it is preferred to carry out impurity reduction by producing chemicals in a clean room and, for example, filtering chemicals through any of various filters, such as a Teflon (registered trademark) filter, a polyolefin filter and an ion exchange filter. With respect to metal elements, the concentration of each of the metal elements Na, K, Ca, Fe, Cu, Mg, Mn, Li, Al, Cr, Ni and Zn is preferably 10 ppm or less, more preferably 5 ppm or less.

The storage container for developers and rinse liquids is not particularly limited. Appropriate use can be made of containers of a polyethylene resin, a polypropylene resin, a polyethylene-polypropylene resin, etc. being applied to electronic material usage. From the viewpoint of reducing the amount of impurities leached from a container, it is preferred to select a container in which the amount of components leached from the inside wall of the container into chemicals is less. As such a container, there can be mentioned, for example, a container whose inside wall is comprised of a perfluororesin (e.g., FluoroPurePFA combination drum (liquid-contact inside surface: PFA resin lining) manufactured by Entegris, Inc. or a steel-made drum can (liquid-contact inside surface: zinc phosphate coating) manufactured by JFE Steel Corporation).

The pattern obtained by the method of the present invention is typically used, for example, as a mask in the etching step for semiconductor production and may also be used as a core material (core) in the spacer process disclosed in JP-A-3-270227 and JP-A-2013-164509. Furthermore, the pattern can also be suitably used for guide pattern formation in DSA (Directed Self-Assembly) (see, for example, ACS Nano, Vol. 4, No. 8, pp. 4815-4823). In addition, the pattern can be applied to various uses.

Furthermore, the present invention relates to a process for manufacturing an electronic device in which the above-described negative pattern forming method of the present invention is included, and relates to an electronic device manufactured by the process.

The electronic device of the present invention can be appropriately mounted in electrical and electronic equipments (household electronic appliance, OA/media-related equipment, optical apparatus, telecommunication equipment and the like).

EXAMPLES

The present invention will be described in greater detail below by way of its examples. However, the gist of the present invention is in no way limited to these examples.

Synthetic Example

Synthesis of Resin A-1

In a nitrogen gas stream, 130.9 parts by mass of cyclohexanone was heated at 80° C. While agitating the liquid, a solution comprised of a mixture of 14 parts by mass of monomer of structural formula M-1 below, 10.7 parts by mass of monomer of structural formula M-2 below, 24.7 parts by mass of monomer of structural formula M-3 below, 16.5 parts by mass of monomer of structural formula M-4 below, 243 parts by mass of cyclohexanone and 1.45 parts by mass of dimethyl 2,2'-azobisisobutyrate [V-601, produced by Wako Pure Chemical Industries, Ltd.] was dropped thereinto over a period of six hours. After the completion of the dropping, the mixture was further agitated at 80° C. for two hours. The thus obtained reaction liquid was allowed to stand still to cool, re-precipitated in hexane/ethyl acetate (mass ratio: 9:1) and filtered. The thus obtained solid was dried in vacuum, thereby obtaining 48.4 parts by mass of resin A-1 according to the present invention.

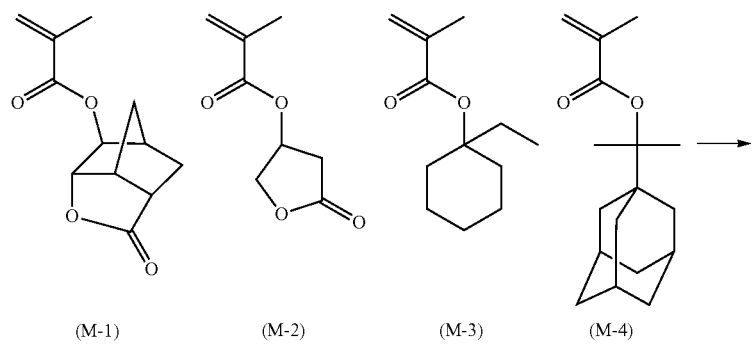

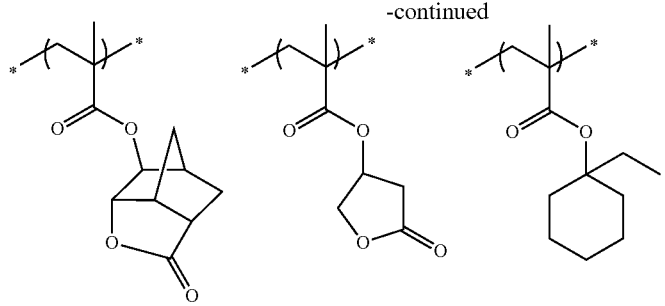

With respect to the obtained resin, it was found by GPC (carrier: tetrahydrofuran (THF)) measurement that the weight average molecular weight (Mw: polystyrene-equivalent) was 14,000 and the polydispersity index (Mw/Mn) was 1.72. The component ratio determined by $^1$H-NMR under the following conditions was 20/20/40/20.

Analytical method: $^1$H-NMR method.

Preparation of sample: A solution obtained by dissolving 25 mg of polymer (powder resulting from drying after re-precipitation) in 0.5 ml of acetone-d6 for NMR was used in NMR measurement.

Measuring conditions: measuring nucleus: H nucleus, observation width: 20 ppm, and measuring temperature: 40° C.

Cumulative number: 64 times.

Internal standard: tetramethylsilane (TMS).

<Resins (A)>

Resins A-2 to A-16, A-22 and A-24 were synthesized in the same manner as described above. Further, for comparison and blend purposes, resins A-17 to A-21 were synthesized in the same manner. With respect to each of the resins A-2 to A-24 including the resin A-1, the individual repeating unit ratios (molar ratios, corresponding in order from left), weight average molecular weight and polydispersity index are given below.

(A-1)

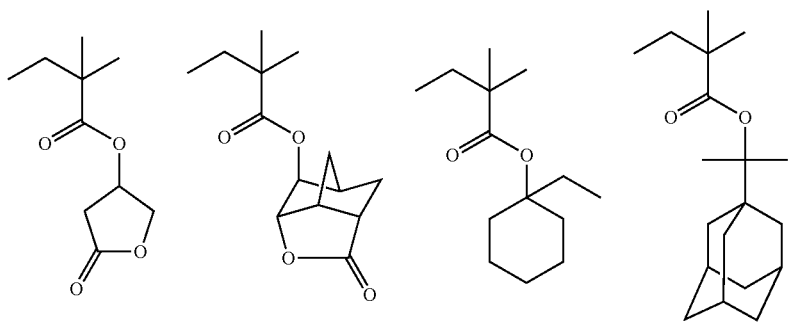

20/20/40/20,
Mw 14000,
Mw/Mn 1.72

(A-2)

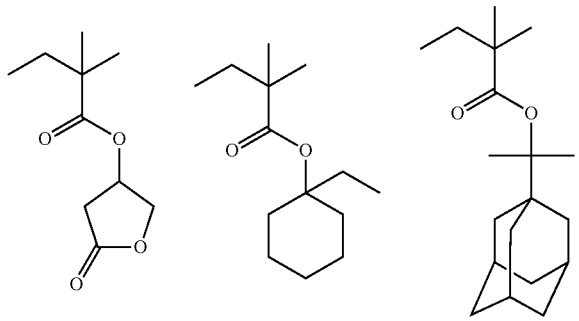

40/50/10,
Mw 14000,
Mw/Mn 1.88

(A-3)
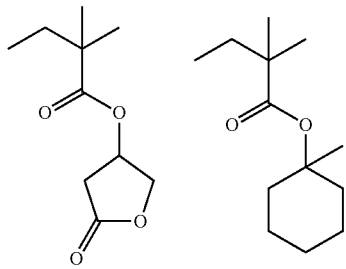
60/40,
Mw 14000,
Mw/Mn 1.69
(A-4)
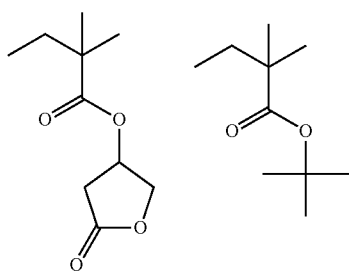
50/50,
Mw 16000,
Mw/Mn 1.82
(A-5)
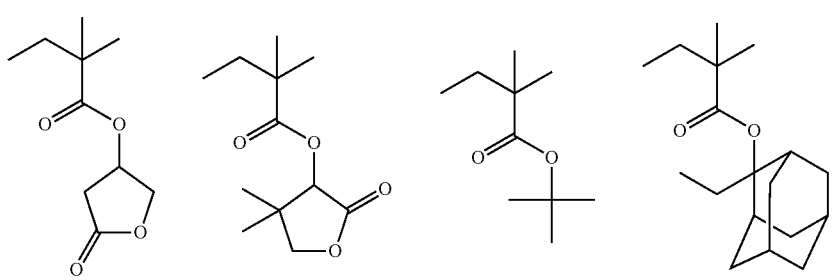
9/31/40/20,
Mw 18000,
Mw/Mn 1.66
(A-6)
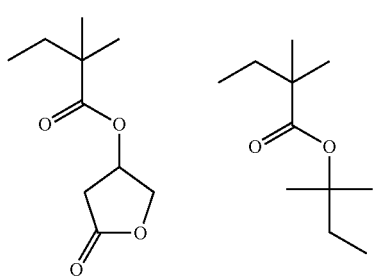
70/30,
Mw 15000,
Mw/Mn 1.77

-continued
(A-7)
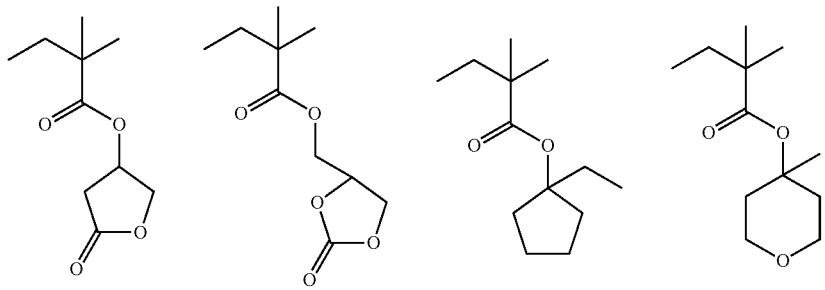
25/25/40/10
Mw 10000,
Mw/Mn 1.75
(A-8)
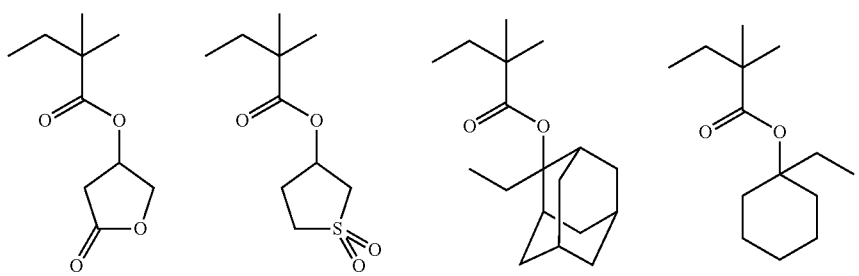
20/20/40/20
Mw 13000,
Mw/Mn 1.71
(A-9)
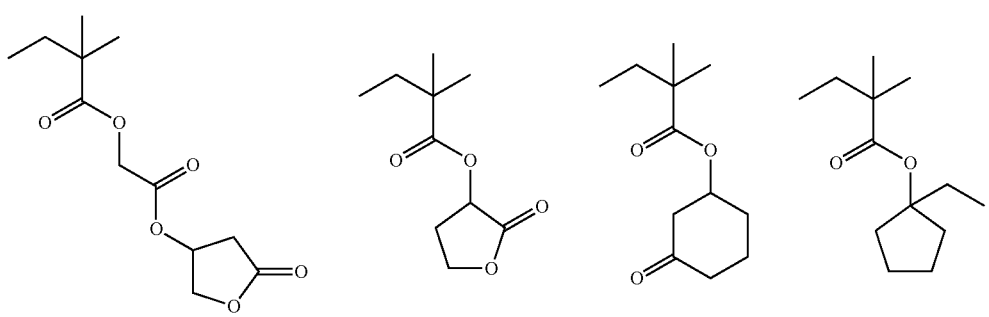
20/10/10/60
Mw 9500,
Mw/Mn 1.72
(A-10)
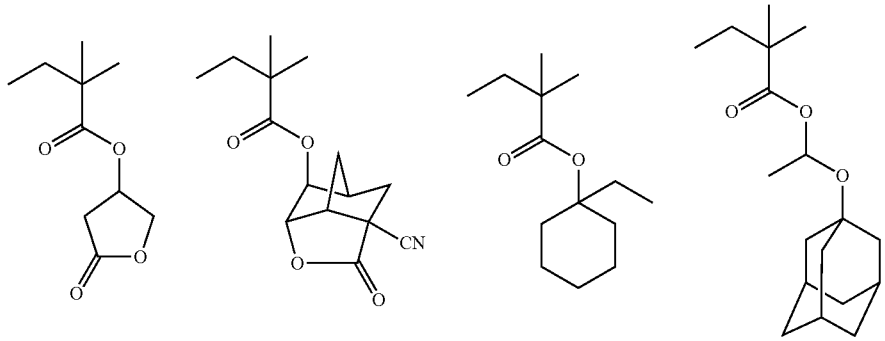
20/30/40/10
Mw 12000,
Mw/Mn 1.68

(A-11)
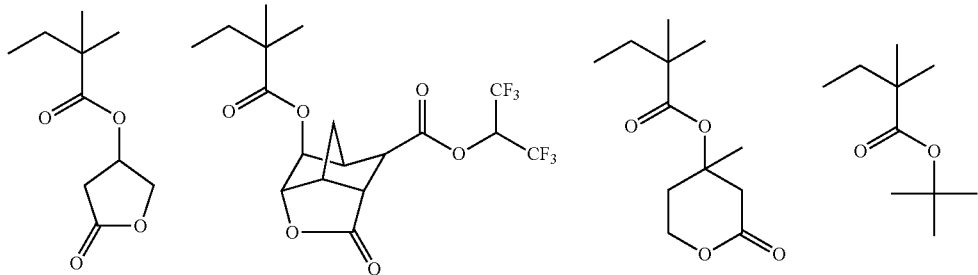
30/10/10/50
Mw 10500,
Mw/Mn 1.77
(A-12)
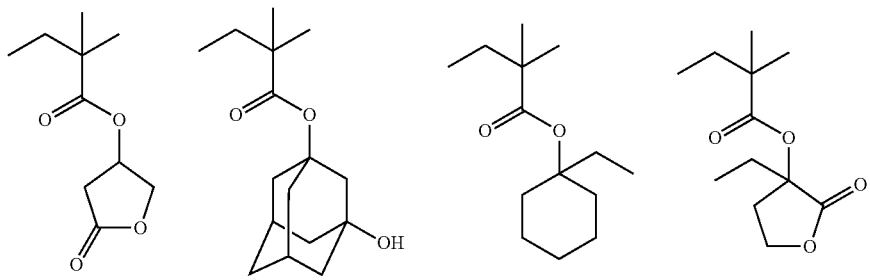
20/5/40/35
Mw 10000,
Mw/Mn 1.75
(A-13)
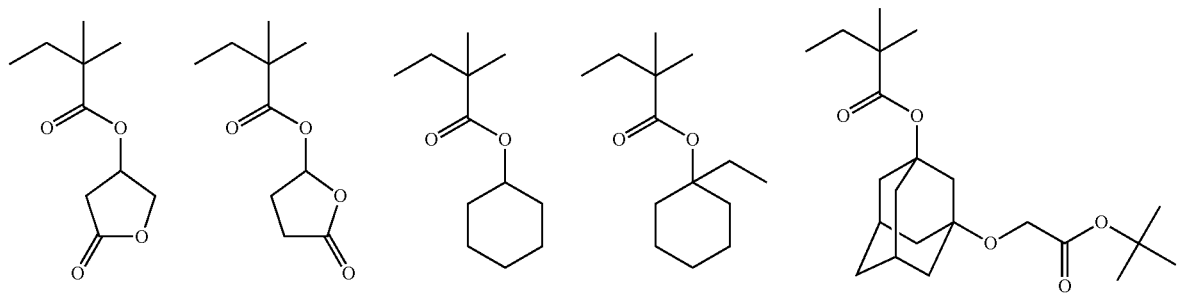
20/10/5/50/15
Mw 18700,
Mw/Mn 1.72
(A-14)
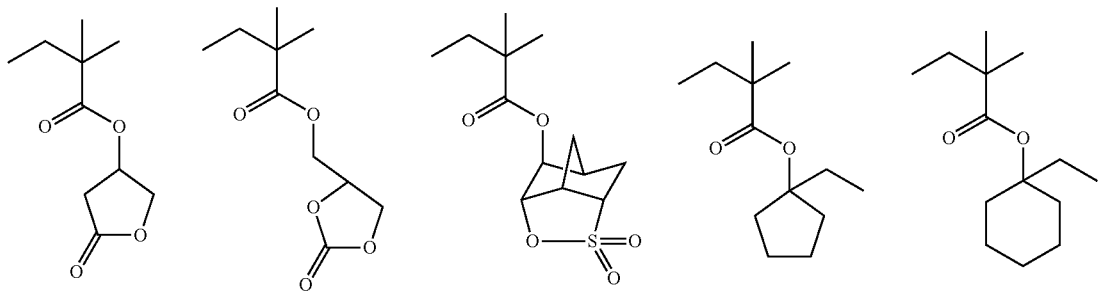
20/10/20/30/20
Mw 8700,
Mw/Mn 1.65

-continued
(A-15)
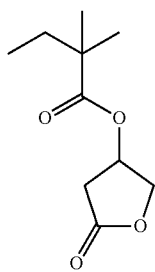 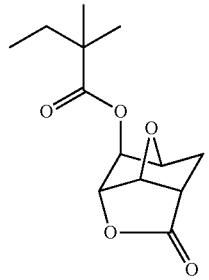 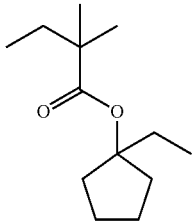 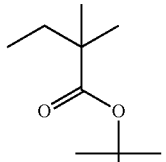 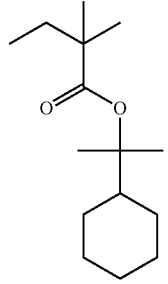
20/30/20/10/20
Mw 12200,
Mw/Mn 1.75
(A-16)
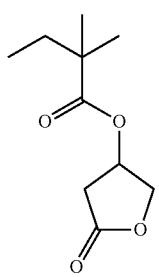 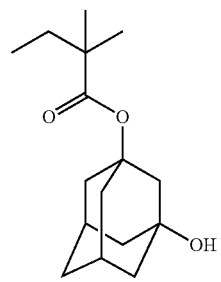 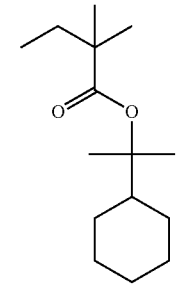 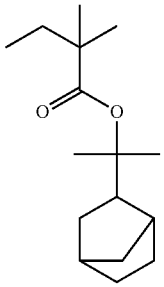
50/10/5/35,
Mw 5500,
Mw/Mn 1.75
(A-17)
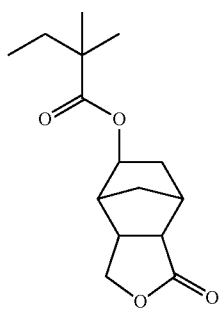 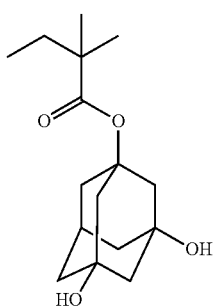 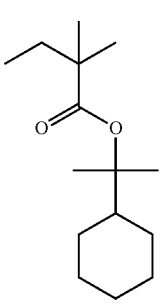 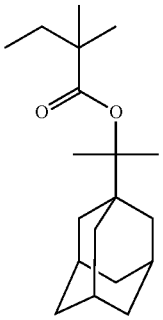
40/10/40/10,
Mw 11000,
Mw/Mn 1.73
(A-18)
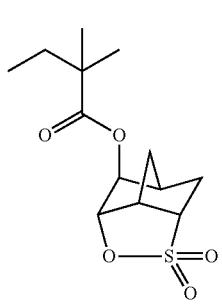 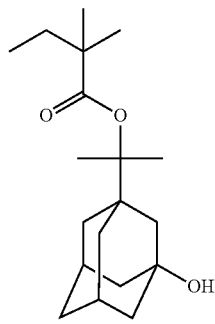 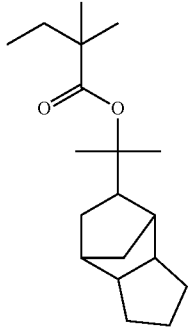 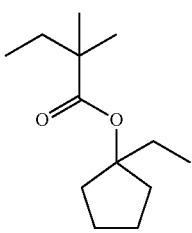
30/15/5/50,
Mw 10000,
Mw/Mn 1.81

-continued
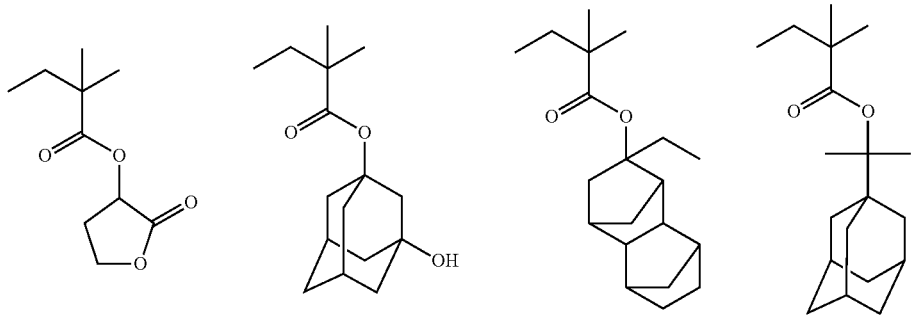
30/20/40/10,
Mw 9800,
Mw/Mn 1.66
(A-19)
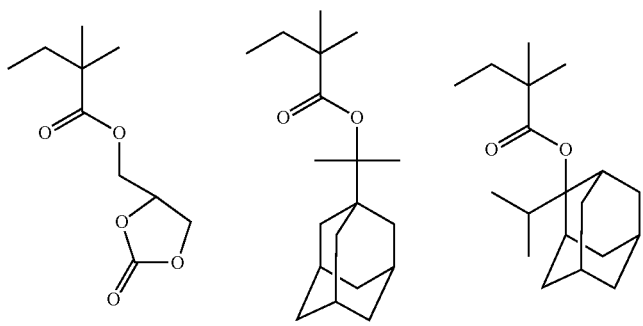
30/40/30,
Mw 8300,
Mw/Mn 1.79
(A-20)
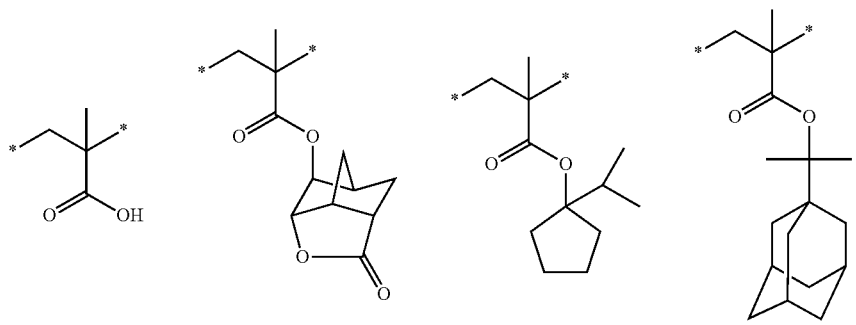
10/30/40/20,
Mw 12000,
Mw/Mn 1.71
(A-21)

(A-22)
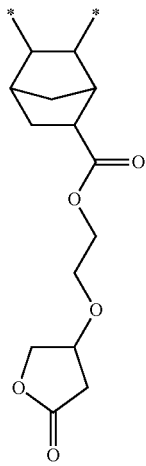 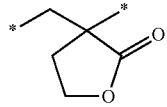 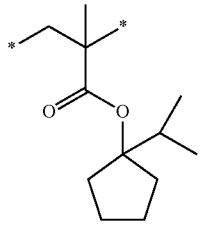 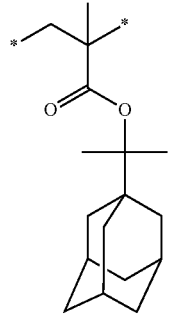
20/20/40/20,
Mw 11000,
Mw/Mn 1.77
(A-23)
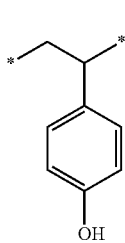 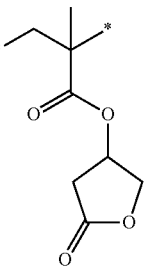 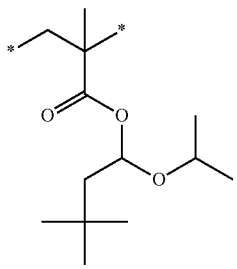
30/10/40/,
Mw 10000,
Mw/Mn 1.65
(A-24)
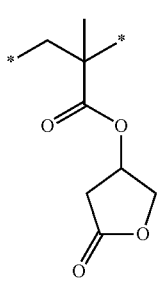 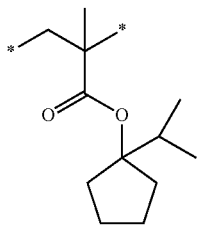 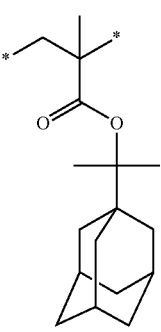
40/40/20/,
Mw 14000,
Mw/Mn 1.69

<Hydrophobic Resin (HR)>
Hydrophobic resins (HR) indicated in the following Table were selected from among those set forth above as specific examples, and used.
<Acid Generator>
The following compounds were used as acid generators.
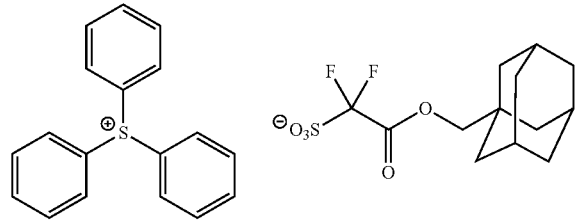
(B-1)
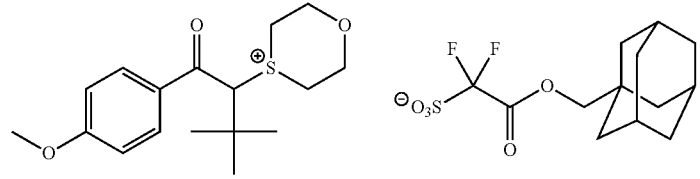
(B-2)
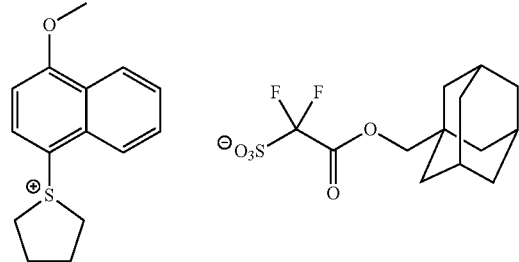
(B-3)
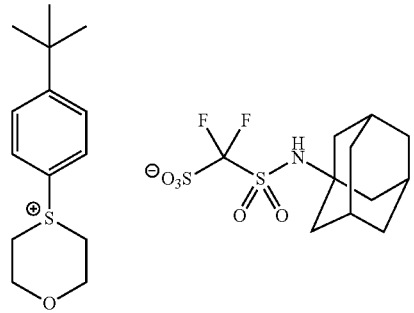
(B-4)
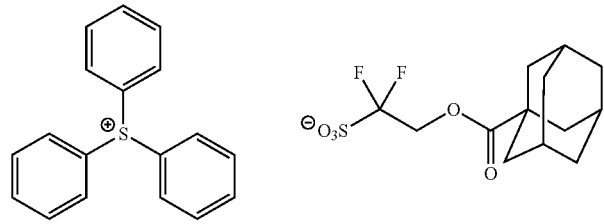
(B-5)
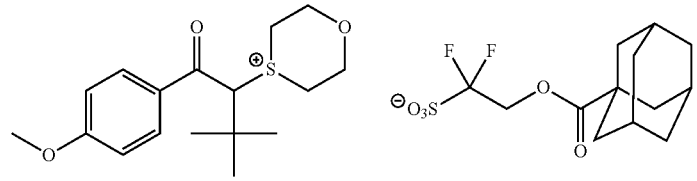
(B-6)

(B-7)
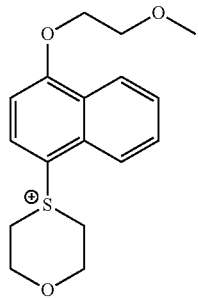 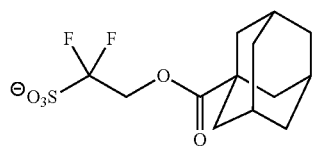
(B-8)
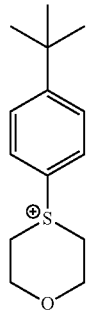 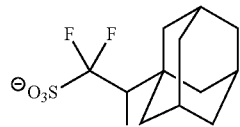
(B-9)
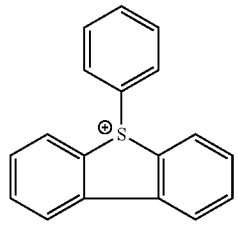 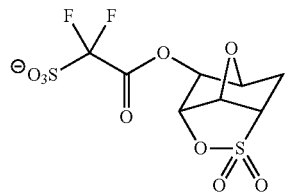
(B-10)
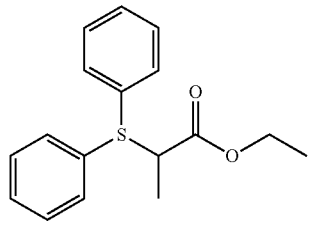 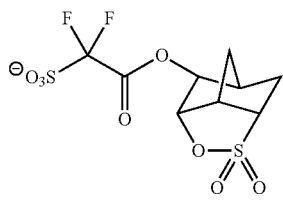
(B-11)
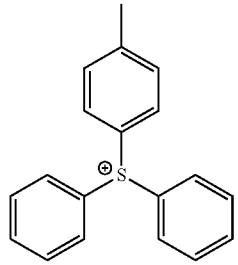 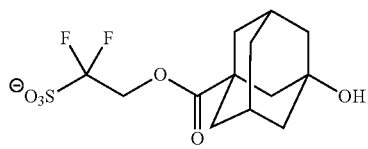
(B-12)
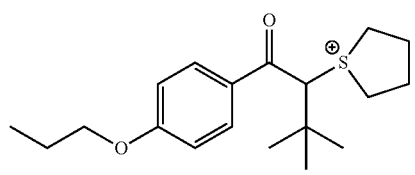 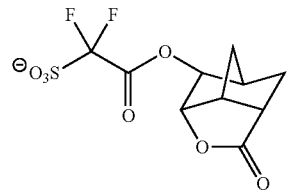

-continued
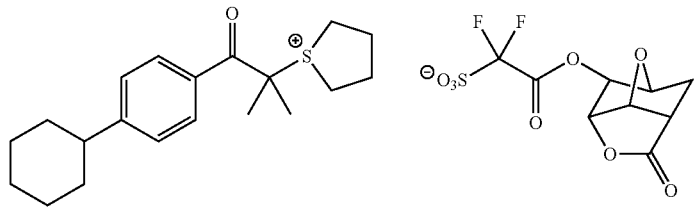 (B-13)
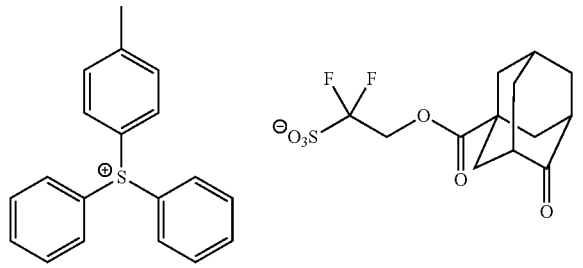 (B-14)
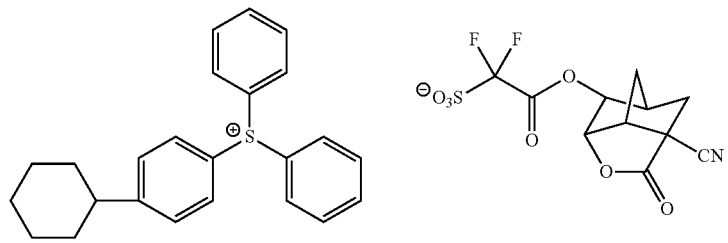 (B-15)
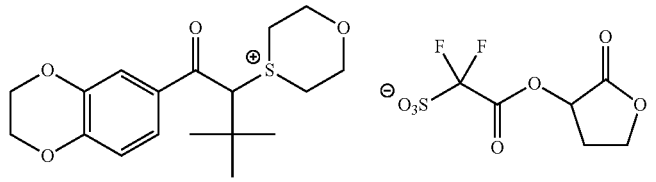 (B-16)
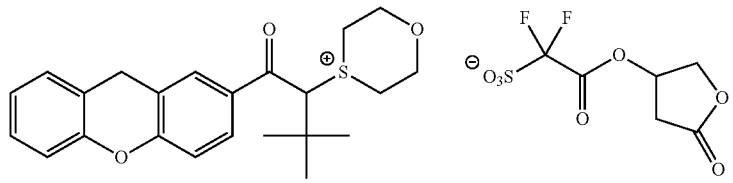 (B-17)
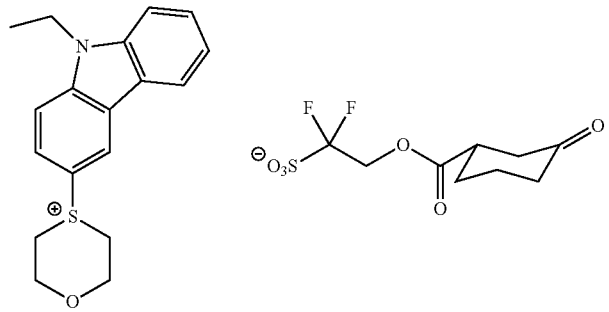 (B-18)

-continued
(B-19)
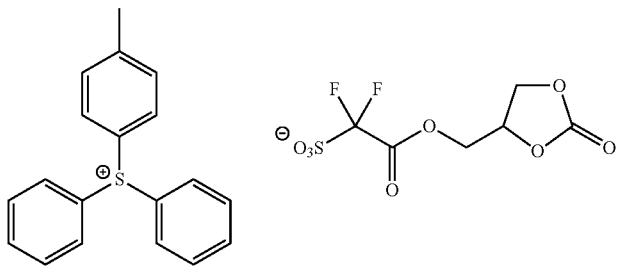
(B-20)
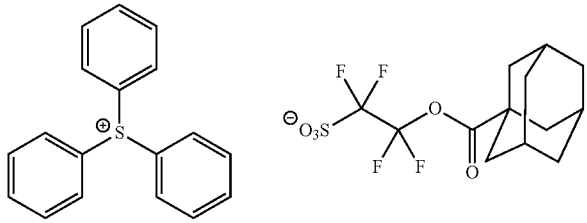
(B-21)
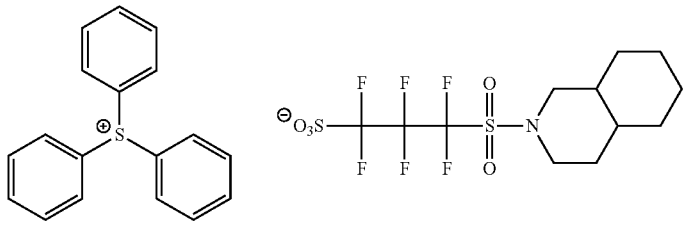
(B-22)
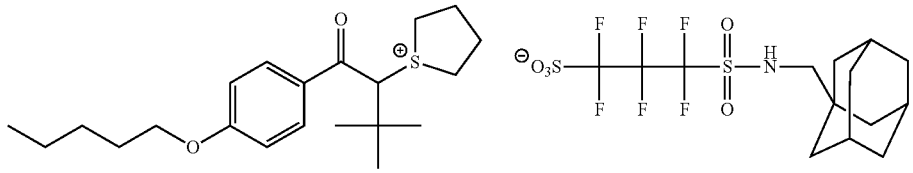
(B-23)
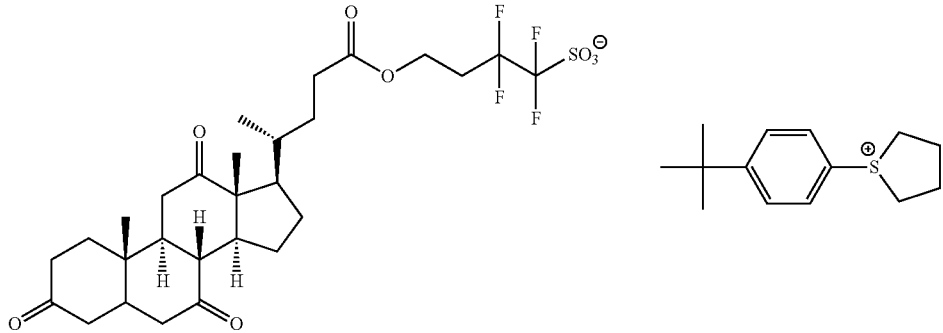
(B-24)
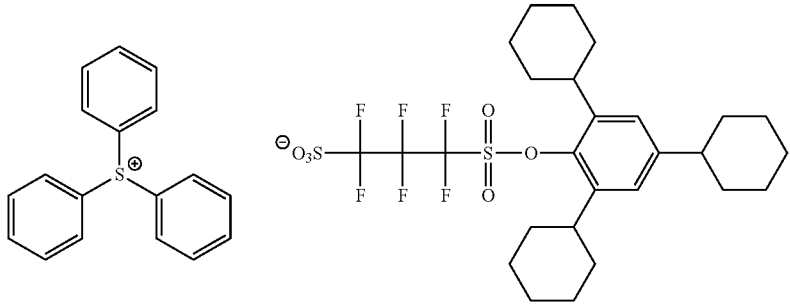

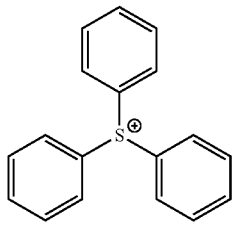 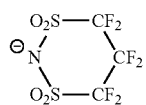 (Z-23)
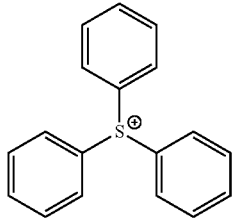 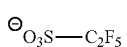 (Z-33)
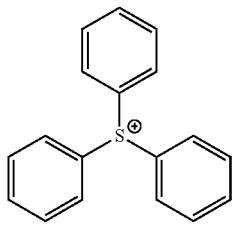 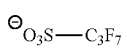 (z-109)
<Basic Compound>
The following compounds were used as basic compounds.
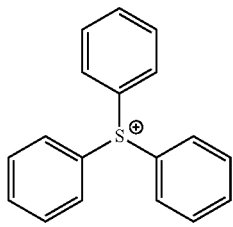 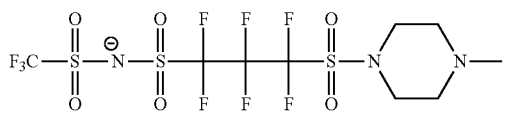 N-1
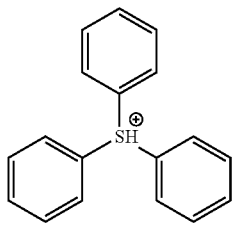 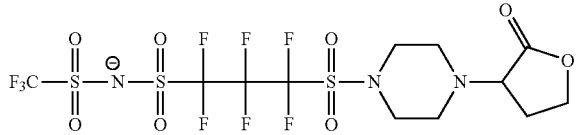 N-2
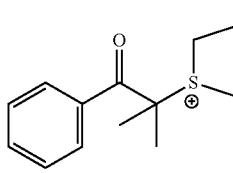 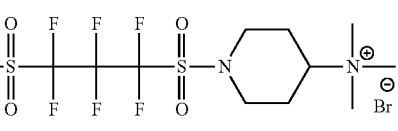 N-3

-continued
N-4
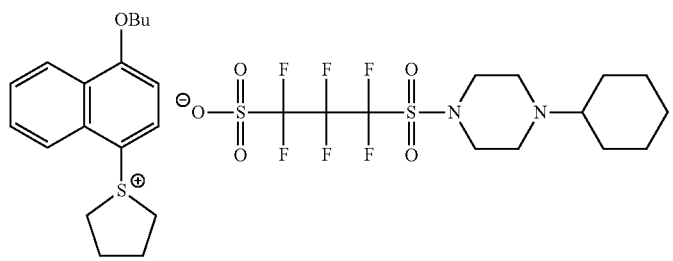
N-5
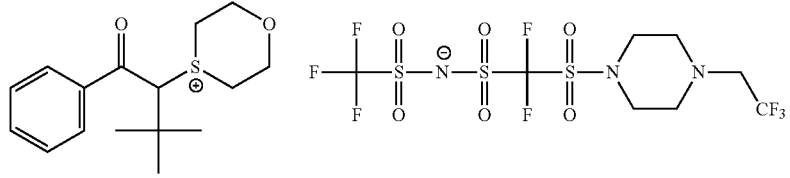
N-6
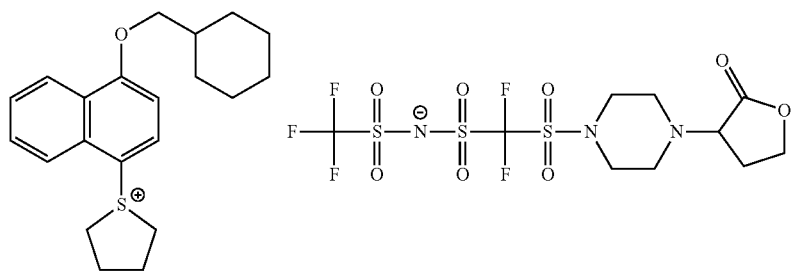
N-7
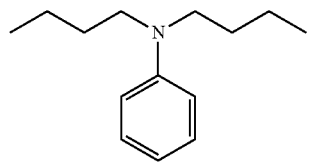
N-8
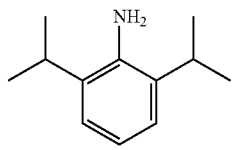
N-9
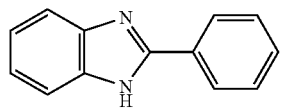
N-10
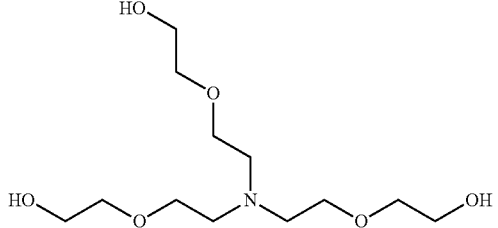
N-11
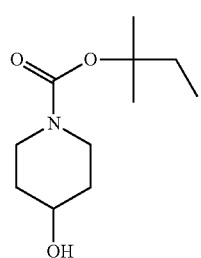
N-12
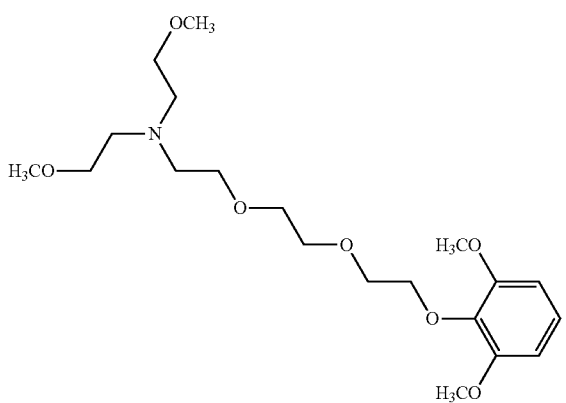

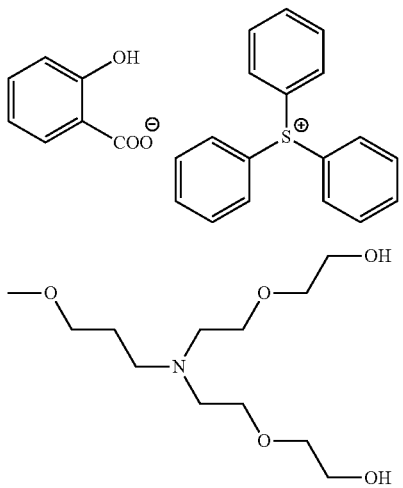

N-13

(N-14)

(N-15)

<Surfactant>

The following surfactants were used.

W-1: Megafac F176 (produced by DIC Corporation, fluorinated),

W-2: Megafac R08 (produced by DIC Corporation, fluorinated and siliconized),

W-3: polysiloxane polymer KP-341 (produced by Shin-Etsu Chemical Co., Ltd., siliconized), W-4: Troy Sol S-366 (produced by Troy Chemical Co., Ltd.), W-5: KH-20 (produced by Asahi Glass Co., Ltd.), and W-6: PolyFox PF-6320 (produced by OMNOVA SOLUTIONS, INC., fluorinated).

<Solvent>

The following solvents were used.

SL-1: propylene glycol monomethyl ether acetate (PGMEA),

SL-2: propylene glycol monomethyl ether propionate,

SL-3: 2-heptanone,

SL-4: ethyl lactate,

SL-5: propylene glycol monomethyl ether (PGME),

SL-6: cyclohexanone,

SL-7: γ-butyrolactone, and

SL-8: propylene carbonate.

<Developer>

The following developers were used.

SG-1: butyl acetate,

SG-2: methyl amyl ketone, and

SG-3: ethyl 3-ethoxy-propionate.

<Rinse Liquid>

The following rinse liquid was used.

SR-1: 4-methyl-2-pentanol.

<ArF Liquid Immersion Exposure>

<Preparation of Resist>

Individual components indicated in Table below were dissolved in solvents indicated in the same table in a solid content of 3.8 mass % and passed through a polyethylene filter of 0.03 μm pore size, thereby obtaining actinic-ray- or radiation-sensitive resin compositions (resist compositions).

(Formation of Line-and-Space Pattern)

An organic antireflection film ARC29SR (produced by Nissan Chemical Industries, Ltd.) was applied onto a silicon wafer and baked at 205° C. for 60 seconds, thereby forming a 95 nm-thick antireflection film on the silicon wafer. Each of the prepared actinic-ray- or radiation-sensitive resin compositions was applied thereonto by means (RF3 manufactured by Sokudo Co., Ltd., rotating speed depending on the viscosity of resist) and baked (prebaked: PB) at 100° C. for 60 seconds, thereby forming a 100 nm-thick resist film.

Each of the obtained resist films was patternwise exposed to light by means of an ArF excimer laser liquid immersion scanner (manufactured by ASML, XT1700i, NA1.20, C-Quad 20, outer sigma 0.90, inner sigma 0.80, XY deflection). A 6% half-tone mask of line size=45 nm and line:space=1:1 was used as a rectile, and ultrapure water was used as the immersion liquid. Thereafter, the exposed film was baked (post-exposure baked: PEB) at 95° C. for 60 seconds. The film after PEB was developed by puddling with an organic solvent developer for a development time as indicated in Table below, and rinsed by puddling with a rinse liquid for a rinse time as indicated in Table below while rotating the wafer at a rotating speed of 500 rpm. Thereafter, the rinsed film was spin dried at 2500 rpm and baked (post-baked) at 90° C. for 60 seconds to thereby attain complete drying thereof. Thus, a 1:1 line and space resist pattern of 45 nm space width was obtained.

(Formation of Contact Hole Pattern)

An organic antireflection film ARC29SR (produced by Nissan Chemical Industries, Ltd.) was applied onto a silicon wafer and baked at 205° C. for 60 seconds, thereby forming a 95 nm-thick antireflection film on the silicon wafer. Each of the prepared actinic-ray- or radiation-sensitive resin compositions was applied thereonto by means (RF3 manufactured by Sokudo Co., Ltd., rotating speed depending on the viscosity of resist) and baked (prebaked: PB) at 100° C. for 60 seconds, thereby forming a 100 nm-thick resist film.

Each of the obtained resist films was patternwise exposed to light by means of an ArF excimer laser liquid immersion scanner (manufactured by ASML, XT1700i, NA1.20, C-Quad 20, outer sigma 0.80, inner sigma 0.70, XY deflection). A 6% half-tone mask of square array with 45 nm hole size and 90 nm inter-hole pitch was used as a rectile, and ultrapure water was used as the immersion liquid. Thereafter, the exposed film was baked (post-exposure baked: PEB) at 95° C. for 60 seconds. The film after PEB was developed by puddling with an organic solvent developer for a development time as indicated in Table below, and rinsed by puddling with a rinse liquid for a rinse time as indicated in Table below while rotating the wafer at a rotating speed of 500 rpm. Thereafter, the rinsed film was spin dried at 2500 rpm and baked (post-baked) at 90° C. for 60 seconds to thereby attain complete drying thereof. Thus, a contact hole resist pattern of 45 nm hole size and 90 nm inter-hole pitch was obtained.

TABLE 4

|  | Developer | Development time (s) | Rinse liquid | Development time (s) |
|---|---|---|---|---|
| Recipe 1 | Butyl acetate | 30 | 4-methyl-2-pentanol | 10 |
| Recipe 2 | Butyl acetate | 30 | 4-methyl-2-pentanol | 60 |
| Recipe 3 | Butyl acetate | 30 | — | — |
| Recipe 4 | Butyl acetate | 60 | 4-methyl-2-pentanol | 30 |
| Recipe 5 | Methyl amyl ketone | 30 | — | — |
| Recipe 6 | Ethyl-3-ethoxy-propionate | 30 | 4-methyl-2-pentanol | 30 |

[LWR/nm]

Each of the 45 nm 1:1 line and space patterns in resist films obtained by the above-mentioned line and space pattern forming method was observed from above by means of a scanning electron microscope (model S9380II manufactured by Hitachi, Ltd.). The space widths were measured at arbitrary points, and the dispersion of measurement of space widths (nm) was evaluated in terms of 3σ. The smaller the value thereof, the more favorable the performance exhibited. Evaluation results are listed in Tables below.

[Pattern Collapse/nm]

Patterns were formed in exposure amounts smaller than the exposure amount providing the 45 nm 1:1 line and space pattern in resist film obtained by the above-mentioned line and space pattern forming method. The patterns were observed from above by means of a scanning electron microscope (model S9380II manufactured by Hitachi, Ltd.), and the critical pattern collapse space width was defined as the space width (nm) allowing pattern resolution without any collapse. The greater the value thereof, the finer the pattern resolved without any collapse, namely, the more effective the suppression of pattern collapse. Evaluation results are listed in Tables below.

[Pattern Shape]

The shape of cross section of each of the 45 nm 1:1 line and space patterns in resist films obtained by the above-mentioned line and space pattern forming method was observed by means of a cross-section SEM (model S-4800, manufactured by Hitachi, Ltd.). The ratio between top portion and bottom portion (namely, [pattern width at bottom portion]/[pattern width at top portion]) was evaluated. The closer to 1 the value thereof, the higher the rectangularity of the shape, ensuring higher performance. The ratio of 0.95 to below 1.05 was rated as A, the ratios of 0.90 to below 0.95 and 1.05 to below 1.10 as B, the ratios of 0.85 to below 0.90 and 1.10 to below 1.15 as C, and the ratios of below 0.85 and 1.15 or above as D. Evaluation results are listed in Tables below.

[CDU/nm]

Each of the 45 nm hole patterns in resist films obtained by the above-mentioned contact hole pattern forming method was observed from above by means of a scanning electron microscope (model S9380II manufactured by Hitachi, Ltd.). The hole sizes were measured at arbitrary points, and the dispersion of measurement of hole size lengths (nm) was evaluated in terms of 3σ. The smaller the value thereof, the more favorable the performance exhibited. Evaluation results are listed in Tables below.

[Circularity]

Each of the 45 nm hole patterns in resist films obtained by the above-mentioned contact hole pattern forming method was observed and photographed from above by means of a scanning electron microscope (model S9380II manufactured by Hitachi, Ltd.). On the photographic image, the circularity (inner diameter, 3σ) of the shape of each of the contact holes was calculated by use of Offline CD Measurement Software (compiled by Hitachi, Ltd). The smaller the value thereof, the higher the circularity. The circularity value of below 2.0 was rated as A, the circularity value of 2.0 to below 2.5 as B, the circularity value of 2.5 to below 3.0 as C, and the circularity value of 3.0 or above as D. Evaluation results are listed in Tables below.

TABLE 5

| Ex. | Resin(A) [g] | Compd. (B) [g] | Basic compd. [g] | Resin(HR) [g] | Solvent [mass ratio] | Surfactant [g] |
|---|---|---|---|---|---|---|
| Resist 1 | A-1 [10] | B-1 [1.42] | N-11 [0.14] | C-3 [0.50] | SL-1/SL-5 [60/40] | W-1 [0.003] |
| Resist 2 | A-2 [10] | B-1/B-2 [0.8/1] | N-13 [0.14] | HR-51 [0.20] | SL-2 [100] | W-3 [0.003] |
| Resist 3 | A-3 [10] | B-3 [1.82] | N-1 [0.86] | HR-53 [0.30] | SL-1/SL-5 [60/40] | W-1 [0.003] |
| Resist 4 | A-4 [10] | B-4 [1.58] | N-7 [0.15] | HR-62 [0.20] | SL-1/SL-6 [80/20] | W-2 [0.001] |
| Resist 5 | A-5 [10] | B-5 [1.29] | N-9 [0.08] | C-3 [0.40] | SL-1 [100] | — |
| Resist 6 | A-6 [10] | B-6 [1.98] | N-9 [0.16] | C-14 [0.40] | SL-1/SL-5 [60/40] | W-1 [0.003] |
| Resist 7 | A-7 [10] | B-7 [1.60] | N-3 [0.84] | D-5 [0.15] | SL-1/SL-5/SL-6 [60/20/20] | W-2 [0.003] |
| Resist 8 | A-8 [10] | B-8 [1.80] | N-7 [0.14] | HR-53 [0.10] | SL-1/SL-5 [60/40] | W-1 [0.003] |
| Resist 9 | A-9 [10] | B-1/B-9/B-17 [0.6/0.3/0.6] | N-2 [0.54] | HR-47 [0.12] | SL-5/SL-6 [30/70] | — |
| Resist 10 | A-10 [10] | B-10 [1.22] | N-6/N-10 [0.31/0.08] | D-5 [0.30] | SL-1/SL-6 [90/10] | W-4 [0.002] |
| Resist 11 | A-11 [10] | B-11 [1.40] | N-12 [0.08] | HR-47 [0.08] | SL-1/SL-7 [95/5] | W-1 [0.003] |
| Resist 12 | A-12 [10] | B-12 [1.98] | N-4 [0.86] | HR-47 [0.08] | SL-1/SL-5 [70/30] | W-5 [0.003] |

TABLE 5-continued

| Ex. | Resin(A) [g] | Compd. (B) [g] | Basic compd. [g] | Resin(HR) [g] | Solvent [mass ratio] | Surfactant [g] |
|---|---|---|---|---|---|---|
| Resist 13 | A-13 [10] | B-13 [2.00] | N-6 [0.14] | HR-47 [0.08] | SL-1/SL-5 [60/40] | W-4 [0.003] |
| Resist 14 | A-14 [10] | B-14/B-16 [0.8/1.2] | N-2 [0.64] | HR-26 [0.08] | SL-1/SL-3 [80/20] | W-1 [0.003] |
| Resist 15 | A-15 [10] | B-15 [1.32] | N-8 [0.14] | C-14 [0.38] | SL-1/SL-5 [60/40] | W-2 [0.003] |
| Resist 16 | A-16 [10] | B-16 [1.86] | N-1 [1.04] | C-14 [1.10] | SL-1/SL-5 [70/30] | W-3 [0.001] |
| Resist 17 | A-2 [10] | B-17/B-19 [0.7/1.5] | N-4 [0.16] | HR-62/HR-24 [0.10/0.03] | SL-1/SL-8 [95/5] | — |
| Resist 18 | A-6 [10] | B-18 [1.04] | N-3 [0.14] | C-3 [1.03] | SL-1 [100] | W-1 [0.003] |
| Resist 19 | A-7 [10] | B-19 [0.83] | N-4/N-8 [0.04/0.04] | C-14 [0.50] | SL-1/SL-5 [60/40] | W-6 [0.003] |
| Resist 20 | A-4 [10] | B-20 [1.89] | N-11 [0.16] | D-5 [0.30] | SL-1/SL-4 [80/20] | W-1 [0.003] |
| Resist 21 | A-1/A-5 [7/3] | B-2 [2.12] | N-9 [0.14] | C-3 [0.45] | SL-1/SL-5 [60/40] | — |
| Resist 22 | A-5 [10] | B-6 [2.00] | N-13 [0.14] | C-3 [0.50] | SL-1/SL-5 [60/40] | W-1 [0.003] |
| Resist 23 | A-9 [10] | B-7/B-13 [0.8/1] | N-9 [0.14] | D-5 [0.37] | SL-1 [100] | W-6 [0.003] |
| Resist 24 | A-10 [10] | B-1 [1.00] | N-5/N-7 [0.4/0.08] | HR-62 [0.13] | SL-1/SL-5 [70/30] | W-1 [0.003] |
| Resist 25 | A-11 [10] | B-5 [1.24] | N-13 [0.14] | HR-47 [0.08] | SL-1/SL-7 [95/5] | W-3 [0.003] |
| Resist 26 | A-1 [10] | B-13/B-17 [0.6/1.2] | N-10 [0.14] | C-14/HR-24 [0.10/0.03] | SL-1 [100] | W-1 [0.003] |
| Resist 27 | A-14 [10] | B-6 [1.89] | N-1 [0.50] | C-14 [0.37] | SL-1/SL-5 [60/40] | W-5 [0.003] |
| Resist 28 | A-8 [10] | B-11/B-6 [0.7/1.4] | N-9 [0.18] | C-14 [0.40] | SL-1/SL-4 [80/20] | W-4 [0.003] |
| Resist 29 | A-5 [10] | B-17/B-23 [1.0/1.2] | N-2 [0.54] | C-14 [0.45] | SL-1/SL-5 [60/40] | — |
| Resist 30 | A-15 [10] | B-16 [1.50] | N-9 [0.08] | C-14 [0.37] | SL-1/SL-5 [60/40] | W-1 [0.003] |
| Resist 31 | A-17 [10] | B-21 [1.42] | N-9 [0.14] | HR-47 [0.08] | SL-1/SL-5 [60/40] | W-1 [0.003] |
| Resist 32 | A-17 [10] | B-22 [1.80] | N-9 [0.14] | HR-47 [0.08] | SL-1/SL-5 [60/40] | W-1 [0.003] |
| Resist 33 | A-18 [10] | B-20 [1.42] | N-9 [0.14] | HR-47 [0.08] | SL-1/SL-5 [60/40] | W-1 [0.003] |
| Resist 34 | A-19 [10] | B-21 [1.42] | N-9 [0.14] | C-3 [0.40] | SL-1/SL-5 [60/40] | W-1 [0.003] |
| Resist 35 | A-20 [10] | B-22 [1.80] | N-9 [0.14] | C-3 [0.40] | SL-1/SL-5 [60/40] | W-1 [0.003] |
| Resist 36 | A-22 [10] | B-2/B-23 [1.5/0.4] | N-13 [0.14] | C-3 [0.40] | SL-1/SL-5 [60/40] | W-1 [1.003] |
| Resist 37 | A-3/A-21 [5/5] | z109 [1.80] | N-13 [0.14] | C-3 [0.40] | SL-1/SL-5 [60/40] | W-1 [2.003] |
| Resist 38 | A-5 [10] | B-6/z23 [1/0.7] | N-9 [0.14] | C-3 [0.40] | SL-1/SL-5 [60/40] | W-1 [3.003] |
| Resist 39 | A-7 [10] | B-3/z33 [1/0.7] | N-2 [0.14] | C-3 [0.40] | SL-1/SL-5 [60/40] | W-1 [4.003] |
| Resist 40 | A-23 [10] | B-24 [2.56] | N-24 [0.25] | — | SL-1/SL-5 [70/30] | W-6 [0.001] |
| Resist 41 | A-24 [10] | B-5 [1.3] | N-2 [1.25] | D-5 [0.3] | SL-1/SL-4 [80/20] | — |

TABLE 6

| | | | LWR (nm) | Collapse (nm) | Shape | CDU (nm) | Circularity |
|---|---|---|---|---|---|---|---|
| Ex. 1 | Resist 1 | Recipe 1 | 3.5 | 56 | B | 2.2 | B |
| Ex. 2 | | Recipe 2 | 3.9 | 57 | B | 2.4 | B |
| Ex. 3 | | Recipe 3 | 3.7 | 56 | B | 2.3 | B |
| Ex. 4 | | Recipe 4 | 3.8 | 58 | B | 2.4 | B |
| Ex. 5 | | Recipe 5 | 3.6 | 56 | B | 2.1 | B |
| Ex. 6 | | Recipe 6 | 3.6 | 55 | B | 2.2 | B |
| Ex. 7 | Resist 2 | Recipe 1 | 3.4 | 63 | A | 1.7 | A |
| Ex. 8 | | Recipe 2 | 3.4 | 61 | A | 1.9 | A |
| Ex. 9 | | Recipe 3 | 3.3 | 64 | A | 1.8 | A |
| Ex. 10 | | Recipe 4 | 3.4 | 60 | A | 1.8 | A |
| Ex. 11 | | Recipe 5 | 3.3 | 62 | A | 1.9 | A |
| Ex. 12 | | Recipe 6 | 3.3 | 63 | A | 1.8 | A |
| Ex. 13 | Resist 3 | Recipe 1 | 3.5 | 55 | B | 2.1 | B |
| Ex. 14 | | Recipe 2 | 3.9 | 58 | B | 2.4 | B |
| Ex. 15 | | Recipe 3 | 3.6 | 55 | B | 2.1 | B |
| Ex. 16 | | Recipe 4 | 3.8 | 59 | B | 2.3 | B |
| Ex. 17 | | Recipe 5 | 3.6 | 57 | B | 2.1 | B |
| Ex. 18 | | Recipe 6 | 3.7 | 56 | B | 2 | B |

TABLE 6-continued

| | | | LWR (nm) | Collapse (nm) | Shape | CDU (nm) | Circularity |
|---|---|---|---|---|---|---|---|
| Ex. 19 | Resist 4 | Recipe 1 | 4.2 | 56 | B | 2.7 | B |
| Ex. 20 | | Recipe 2 | 4.3 | 58 | B | 2.5 | B |
| Ex. 21 | | Recipe 3 | 4 | 55 | B | 2.6 | B |
| Ex. 22 | | Recipe 4 | 4.1 | 59 | B | 2.7 | B |
| Ex. 23 | | Recipe 5 | 4.3 | 57 | B | 2.6 | B |
| Ex. 24 | | Recipe 6 | 4.2 | 55 | B | 2.5 | B |
| Ex. 25 | Resist 5 | Recipe 1 | 3.5 | 56 | B | 2.2 | B |
| Ex. 26 | | Recipe 2 | 3.9 | 56 | B | 2.3 | B |
| Ex. 27 | | Recipe 3 | 3.5 | 56 | B | 2.2 | B |
| Ex. 28 | | Recipe 4 | 3.9 | 56 | B | 2.4 | B |
| Ex. 29 | | Recipe 5 | 3.6 | 57 | B | 2 | B |
| Ex. 30 | | Recipe 6 | 3.6 | 56 | B | 2.1 | B |
| Ex. 31 | Resist 6 | Recipe 1 | 3.2 | 63 | A | 1.6 | A |
| Ex. 32 | | Recipe 2 | 3.3 | 62 | A | 1.6 | A |
| Ex. 33 | | Recipe 3 | 3.1 | 60 | A | 1.7 | A |
| Ex. 34 | | Recipe 4 | 3.2 | 60 | A | 1.8 | A |
| Ex. 35 | | Recipe 5 | 3.3 | 61 | A | 1.7 | A |
| Ex. 36 | | Recipe 6 | 3.3 | 63 | A | 1.8 | A |
| Ex. 37 | Resist 7 | Recipe 1 | 3.6 | 59 | B | 2.1 | B |
| Ex. 38 | | Recipe 2 | 3.9 | 56 | B | 2.2 | B |
| Ex. 39 | | Recipe 3 | 3.7 | 58 | B | 2.1 | B |
| Ex. 40 | | Recipe 4 | 3.9 | 57 | B | 2.4 | B |
| Ex. 41 | | Recipe 5 | 3.6 | 58 | B | 2.4 | B |
| Ex. 42 | | Recipe 6 | 3.7 | 59 | B | 2.3 | B |
| Ex. 43 | Resist 8 | Recipe 1 | 4.2 | 57 | B | 2.6 | B |
| Ex. 44 | | Recipe 2 | 4.2 | 56 | B | 2.6 | B |
| Ex. 45 | | Recipe 3 | 4.3 | 57 | B | 2.7 | B |
| Ex. 46 | | Recipe 4 | 4.4 | 56 | B | 2.7 | B |
| Ex. 47 | | Recipe 5 | 4.3 | 57 | B | 2.6 | B |
| Ex. 48 | | Recipe 6 | 4.2 | 56 | B | 2.6 | B |
| Ex. 49 | Resist 9 | Recipe 1 | 3.6 | 55 | B | 2.3 | B |
| Ex. 50 | | Recipe 2 | 3.5 | 57 | B | 2.2 | B |
| Ex. 51 | | Recipe 3 | 3.6 | 55 | B | 2 | B |
| Ex. 52 | | Recipe 4 | 3.7 | 56 | B | 2.2 | B |
| Ex. 53 | | Recipe 5 | 3.5 | 58 | B | 2 | B |
| Ex. 54 | | Recipe 6 | 3.9 | 57 | B | 2.4 | B |
| Ex. 55 | Resist 10 | Recipe 1 | 4 | 57 | B | 2.6 | B |
| Ex. 56 | | Recipe 2 | 4.1 | 58 | B | 2.5 | B |
| Ex. 57 | | Recipe 3 | 4.1 | 57 | B | 2.6 | B |
| Ex. 58 | | Recipe 4 | 4.3 | 59 | B | 2.7 | B |
| Ex. 59 | | Recipe 5 | 4 | 58 | B | 2.5 | B |
| Ex. 60 | | Recipe 6 | 4.2 | 57 | B | 2.6 | B |
| Ex. 61 | Resist 11 | Recipe 1 | 4.3 | 56 | B | 2.7 | B |
| Ex. 62 | | Recipe 2 | 4.2 | 57 | B | 2.6 | B |
| Ex. 63 | | Recipe 3 | 4.3 | 57 | B | 2.8 | B |
| Ex. 64 | | Recipe 4 | 4.3 | 58 | B | 2.6 | B |
| Ex. 65 | | Recipe 5 | 4.1 | 55 | B | 2.9 | B |
| Ex. 66 | | Recipe 6 | 4.2 | 55 | B | 2.8 | B |
| Ex. 67 | Resist 12 | Recipe 1 | 4.2 | 58 | B | 2.8 | B |
| Ex. 68 | | Recipe 2 | 4.3 | 58 | B | 2.7 | B |
| Ex. 69 | | Recipe 3 | 4.2 | 57 | B | 2.7 | B |
| Ex. 70 | | Recipe 4 | 4.3 | 58 | B | 2.6 | B |
| Ex. 71 | | Recipe 5 | 4.1 | 57 | B | 2.5 | B |
| Ex. 72 | | Recipe 6 | 4.3 | 57 | B | 2.7 | B |
| Ex. 73 | Resist 13 | Recipe 1 | 3.3 | 59 | B | 1.8 | B |
| Ex. 74 | | Recipe 2 | 3.4 | 59 | B | 1.7 | B |
| Ex. 75 | | Recipe 3 | 3.3 | 58 | B | 1.8 | B |
| Ex. 76 | | Recipe 4 | 3.2 | 57 | B | 1.7 | B |
| Ex. 77 | | Recipe 5 | 3.3 | 57 | B | 1.8 | B |
| Ex. 78 | | Recipe 6 | 3.4 | 59 | B | 1.8 | B |
| Ex. 79 | Resist 14 | Recipe 1 | 3.5 | 55 | B | 2 | B |
| Ex. 80 | | Recipe 2 | 3.8 | 56 | B | 2.2 | B |
| Ex. 81 | | Recipe 3 | 3.5 | 58 | B | 2 | B |
| Ex. 82 | | Recipe 4 | 3.7 | 56 | B | 2.2 | B |
| Ex. 83 | | Recipe 5 | 3.5 | 55 | B | 2.3 | B |
| Ex. 84 | | Recipe 6 | 3.6 | 56 | B | 2.3 | B |
| Ex. 85 | Resist 15 | Recipe 1 | 3.7 | 59 | B | 2.2 | B |
| Ex. 86 | | Recipe 2 | 3.5 | 57 | B | 2.1 | B |
| Ex. 87 | | Recipe 3 | 3.5 | 57 | B | 2 | B |
| Ex. 88 | | Recipe 4 | 3.5 | 56 | B | 2.1 | B |
| Ex. 89 | | Recipe 5 | 3.7 | 58 | B | 2.2 | B |
| Ex. 90 | | Recipe 6 | 3.8 | 59 | B | 2.2 | B |
| Ex. 91 | Resist 16 | Recipe 1 | 4.4 | 50 | C | 2.9 | C |
| Ex. 92 | | Recipe 2 | 4.3 | 50 | C | 2.9 | C |
| Ex. 93 | | Recipe 3 | 4.4 | 51 | C | 2.9 | C |
| Ex. 94 | | Recipe 4 | 4.4 | 50 | C | 2.8 | C |
| Ex. 95 | | Recipe 5 | 4.3 | 51 | C | 2.9 | C |
| Ex. 96 | | Recipe 6 | 4.4 | 50 | C | 2.8 | C |
| Ex. 97 | Resist 17 | Recipe 1 | 3.2 | 63 | A | 1.7 | A |
| Ex. 98 | | Recipe 2 | 3.2 | 63 | A | 1.8 | A |
| Ex. 99 | | Recipe 3 | 3.1 | 60 | A | 1.7 | A |
| Ex. 100 | | Recipe 4 | 3.3 | 61 | A | 1.7 | A |
| Ex. 101 | | Recipe 5 | 3.2 | 61 | A | 1.8 | A |
| Ex. 102 | | Recipe 6 | 3.2 | 60 | A | 1.7 | A |
| Ex. 103 | Resist 18 | Recipe 1 | 4.1 | 58 | B | 2.2 | B |
| Ex. 104 | | Recipe 2 | 4.2 | 56 | B | 2 | B |
| Ex. 105 | | Recipe 3 | 4.2 | 58 | B | 2.3 | B |
| Ex. 106 | | Recipe 4 | 4.1 | 56 | B | 2.1 | B |
| Ex. 107 | | Recipe 5 | 4.2 | 55 | B | 2.1 | B |
| Ex. 108 | | Recipe 6 | 4.1 | 57 | B | 2.2 | B |
| Ex. 109 | Resist 19 | Recipe 1 | 3.5 | 58 | B | 2.4 | B |
| Ex. 110 | | Recipe 2 | 3.5 | 57 | B | 2.3 | B |
| Ex. 111 | | Recipe 3 | 3.6 | 58 | B | 2.4 | B |
| Ex. 112 | | Recipe 4 | 3.6 | 58 | B | 2.4 | B |
| Ex. 113 | | Recipe 5 | 3.5 | 57 | B | 2.3 | B |
| Ex. 114 | | Recipe 6 | 3.6 | 58 | B | 2.4 | B |
| Ex. 115 | Resist 20 | Recipe 1 | 4 | 53 | C | 2.5 | C |
| Ex. 116 | | Recipe 2 | 3.9 | 52 | C | 2.6 | C |
| Ex. 117 | | Recipe 3 | 4..1 | 54 | C | 2.5 | C |
| Ex. 118 | | Recipe 4 | 4 | 53 | C | 2.4 | C |
| Ex. 119 | | Recipe 5 | 4 | 52 | C | 2.5 | C |
| Ex. 120 | | Recipe 6 | 3.9 | 54 | C | 2.5 | C |
| Ex. 121 | Resist 21 | Recipe 1 | 3.5 | 58 | B | 2.2 | B |
| Ex. 122 | | Recipe 2 | 3.6 | 57 | B | 2.1 | B |
| Ex. 123 | | Recipe 3 | 3.6 | 58 | B | 2 | B |
| Ex. 124 | | Recipe 4 | 3.5 | 57 | B | 2.2 | B |
| Ex. 125 | | Recipe 5 | 3.6 | 56 | B | 2.1 | B |
| Ex. 126 | | Recipe 6 | 3.6 | 58 | B | 2.2 | B |
| Ex. 127 | Resist 22 | Recipe 1 | 3.4 | 62 | A | 1.7 | A |
| Ex. 128 | | Recipe 2 | 3.3 | 60 | A | 1.8 | A |
| Ex. 129 | | Recipe 3 | 3.3 | 61 | A | 1.7 | A |
| Ex. 130 | | Recipe 4 | 3.3 | 60 | A | 1.8 | A |
| Ex. 131 | | Recipe 5 | 3.4 | 61 | A | 1.7 | A |
| Ex. 132 | | Recipe 6 | 3.4 | 60 | A | 1.7 | A |
| Ex. 133 | Resist 23 | Recipe 1 | 3.4 | 61 | B | 1.8 | B |
| Ex. 134 | | Recipe 2 | 3.3 | 61 | B | 1.7 | B |
| Ex. 135 | | Recipe 3 | 3.2 | 61 | B | 1.7 | B |
| Ex. 136 | | Recipe 4 | 3.4 | 60 | B | 1.8 | B |
| Ex. 137 | | Recipe 5 | 3.3 | 61 | B | 1.8 | B |
| Ex. 138 | | Recipe 6 | 3.3 | 61 | B | 1.8 | B |
| Ex. 139 | Resist 24 | Recipe 1 | 3.6 | 57 | B | 2.3 | B |
| Ex. 140 | | Recipe 2 | 3.5 | 57 | B | 2.3 | B |
| Ex. 141 | | Recipe 3 | 3.6 | 56 | B | 2.2 | B |
| Ex. 142 | | Recipe 4 | 3.5 | 57 | B | 2.3 | B |
| Ex. 143 | | Recipe 5 | 3.7 | 57 | B | 2.3 | B |
| Ex. 144 | | Recipe 6 | 3.7 | 56 | B | 2.2 | B |
| Ex. 145 | Resist 25 | Recipe 1 | 4 | 59 | B | 2.6 | B |
| Ex. 146 | | Recipe 2 | 4.1 | 58 | B | 2.7 | B |
| Ex. 147 | | Recipe 3 | 4.2 | 58 | B | 2.6 | B |
| Ex. 148 | | Recipe 4 | 4.2 | 58 | B | 2.6 | B |
| Ex. 149 | | Recipe 5 | 4.1 | 57 | B | 2.7 | B |
| Ex. 150 | | Recipe 6 | 4.2 | 57 | B | 2.6 | B |
| Ex. 151 | Resist 26 | Recipe 1 | 3.6 | 55 | B | 2.3 | B |
| Ex. 152 | | Recipe 2 | 3.7 | 56 | B | 2.4 | B |
| Ex. 153 | | Recipe 3 | 3.6 | 57 | B | 2.4 | B |
| Ex. 154 | | Recipe 4 | 3.7 | 55 | B | 2.3 | B |
| Ex. 155 | | Recipe 5 | 3.7 | 56 | B | 2.3 | B |
| Ex. 156 | | Recipe 6 | 3.7 | 56 | B | 2.3 | B |
| Ex. 157 | Resist 27 | Recipe 1 | 3.3 | 62 | A | 1.9 | A |
| Ex. 158 | | Recipe 2 | 3.3 | 61 | A | 1.8 | A |
| Ex. 159 | | Recipe 3 | 3.4 | 63 | A | 1.9 | A |
| Ex. 160 | | Recipe 4 | 3.3 | 61 | A | 1.8 | A |
| Ex. 161 | | Recipe 5 | 3.2 | 60 | A | 1.7 | A |
| Ex. 162 | | Recipe 6 | 3.4 | 60 | A | 1.9 | A |
| Ex. 163 | Resist 28 | Recipe 1 | 3.4 | 60 | A | 1.8 | A |
| Ex. 164 | | Recipe 2 | 3.3 | 60 | A | 1.8 | A |
| Ex. 165 | | Recipe 3 | 3.3 | 61 | A | 1.8 | A |
| Ex. 166 | | Recipe 4 | 3.4 | 60 | A | 1.9 | A |
| Ex. 167 | | Recipe 5 | 3.4 | 61 | A | 1.9 | A |
| Ex. 168 | | Recipe 6 | 3.4 | 61 | A | 1.9 | A |
| Ex. 169 | Resist 29 | Recipe 1 | 4.3 | 51 | C | 2.8 | C |
| Ex. 170 | | Recipe 2 | 4.3 | 50 | C | 2.8 | C |

TABLE 6-continued

|  |  | LWR (nm) | Collapse (nm) | Shape | CDU (nm) | Circularity |
|---|---|---|---|---|---|---|
| Ex. 171 |  | Recipe 3 | 4.4 | 51 | C | 2.9 | C |
| Ex. 172 |  | Recipe 4 | 4.3 | 51 | C | 2.8 | C |
| Ex. 173 |  | Recipe 5 | 4.3 | 51 | C | 2.8 | C |
| Ex. 174 |  | Recipe 6 | 4.3 | 51 | C | 2.8 | C |
| Ex. 175 | Resist 30 | Recipe 1 | 3.6 | 57 | B | 2.3 | B |
| Ex. 176 |  | Recipe 2 | 3.6 | 56 | B | 2.3 | B |
| Ex. 177 |  | Recipe 3 | 3.7 | 57 | B | 2.3 | B |
| Ex. 178 |  | Recipe 4 | 3.6 | 55 | B | 2.4 | B |
| Ex. 179 |  | Recipe 5 | 3.7 | 57 | B | 2.4 | B |
| Ex. 180 |  | Recipe 6 | 3.7 | 55 | B | 2.4 | B |
| Comp. Ex. 1 | Resist 31 | Recipe 1 | 5.1 | 54 | C | 3.7 | C |
| Comp. Ex. 2 |  | Recipe 2 | 4.7 | 48 | D | 3.3 | D |
| Comp. Ex. 3 |  | Recipe 3 | 4.4 | 50 | D | 3.2 | D |
| Comp. Ex. 4 |  | Recipe 4 | 4.7 | 48 | D | 3.4 | D |
| Comp. Ex. 5 |  | Recipe 5 | 4.8 | 48 | D | 3.4 | D |
| Comp. Ex. 6 |  | Recipe 6 | 4.9 | 50 | D | 3.6 | D |
| Comp. Ex. 7 | Resist 32 | Recipe 1 | 4.6 | 48 | C | 3 | D |
| Comp. Ex. 8 |  | Recipe 2 | 4.9 | 45 | D | 3.4 | D |
| Comp. Ex. 9 |  | Recipe 3 | 4.5 | 47 | C | 3.1 | C |
| Comp. Ex. 10 |  | Recipe 4 | 5 | 45 | D | 3.5 | D |
| Comp. Ex. 11 |  | Recipe 5 | 5.6 | 45 | D | 3.9 | D |
| Comp. Ex. 12 |  | Recipe 6 | 5.3 | 45 | D | 3.8 | D |
| Comp. Ex. 13 | Resist 33 | Recipe 1 | 4.7 | 45 | D | 3.8 | D |
| Comp. Ex. 14 |  | Recipe 2 | 4.9 | 42 | D | 3.7 | D |
| Comp. Ex. 15 |  | Recipe 3 | 4.8 | 47 | D | 3.5 | D |
| Comp. Ex. 16 |  | Recipe 4 | 4.8 | 41 | D | 3.9 | D |
| Comp. Ex. 17 |  | Recipe 5 | 5.4 | 47 | D | 4 | D |
| Comp. Ex. 18 |  | Recipe 6 | 5.1 | 40 | D | 3.7 | D |
| Comp. Ex. 19 | Resist 34 | Recipe 1 | 4.6 | 45 | C | 3.2 | D |
| Comp. Ex. 20 |  | Recipe 2 | 5.3 | 45 | D | 3.4 | D |
| Comp. Ex. 21 |  | Recipe 3 | 4.4 | 50 | C | 3.3 | D |
| Comp. Ex. 22 |  | Recipe 4 | 5 | 40 | D | 3.5 | D |
| Comp. Ex. 23 |  | Recipe 5 | 5.3 | 49 | D | 3.9 | D |
| Comp. Ex. 24 |  | Recipe 6 | 5.3 | 46 | D | 3.8 | D |
| Comp. Ex. 25 | Resist 35 | Recipe 1 | 5 | 45 | D | 3.8 | D |
| Comp. Ex. 26 |  | Recipe 2 | 5.6 | 40 | D | 3.9 | D |
| Comp. Ex. 27 |  | Recipe 3 | 5.1 | 43 | D | 3.7 | D |
| Comp. Ex. 28 |  | Recipe 4 | 5.5 | 40 | D | 3.9 | D |
| Comp. Ex. 29 |  | Recipe 5 | 4.7 | 46 | D | 3.4 | D |
| Comp. Ex. 30 |  | Recipe 6 | 4.9 | 41 | D | 3.5 | D |

It is apparent from the results listed in the above Tables that the negative patterns obtained by the pattern forming method of the present invention excel in the LWR, pattern collapse, pattern shape, CDU and circularity performances.

It is also apparent that performance variations are less even when the type of solvent and time applied are changed in the development and rinse operations.

The same evaluation as in Example 1 and the like was conducted with the use of resist 41. In this evaluation as well, a favorable result could be obtained.

Further, the same evaluation as in Example 1 recipe 1 was conducted except that a small amount of tri-n-octylamine was added to the developer (butyl acetate). In this evaluation as well, a favorable negative pattern could be obtained.

Still further, the same evaluations as mentioned above were conducted according to recipe 1 with the use of resists 36 to 39. Favorable pattern formation could be realized.

Resist 40 was formed into a film on a substrate, exposed to EUV light and developed with butyl acetate. The same evaluation as mentioned above was conducted. In that instance as well, favorable pattern formation could be realized.

With reference to Example 7 of U.S. Pat. No. 8,227,183, resist 1 was formed into a film, exposed through a line and space mask pattern to light and subjected to both butyl acetate development and alkali development. As a result, a pattern of pitch being ½ of that of the mask pattern could be formed.

What is claimed is:

1. A method of forming a pattern, comprising:
    (a) forming a film of an actinic-ray- or radiation-sensitive resin composition,
    (b) exposing the film to light, and
    (c) developing the exposed film with a developer comprising an organic solvent to thereby form a negative pattern,
    wherein the actinic-ray- or radiation-sensitive resin composition comprises:
    (A) a resin whose solubility in the developer comprising an organic solvent is lowered when acted on by an acid, which resin contains a repeating unit with any of lactone structures of general formula (1) below, and
    (B) a compound that when exposed to actinic rays or radiation, generates an acid,

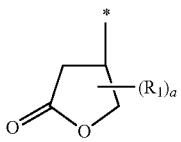

(1)

in which
    $R_1$ represents an alkyl group, a cycloalkyl group, an alkoxy group, an aryloxy group, an aralkyloxy group, an alkoxycarbonyl group, a carboxyl group, a halogen atom, a hydroxyl group, a cyano group or an acid-decomposable group, provided that when there are a plurality of $R_1$s, they may be identical to or different from each other, and
    a is an integer of 0 to 4.

2. The method according to claim 1, wherein the compound (B) contains any of anions of general formula (2) below,

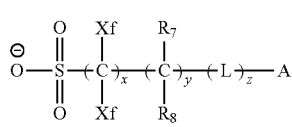

(2)

in which each of Xf's independently represents a fluorine atom or an alkyl group substituted with at least one fluorine atom, each of $R_7$ and $R_8$ independently represents a hydrogen atom, a fluorine atom, an alkyl group or an alkyl group substituted with at least one fluorine atom, provided that when there are a plurality of $R_7$s and $R_8$s, $R_7$s, and $R_8$s, may be identical to or different from each other, L represents a bivalent connecting group, provided that when there are a plurality of L's, they may be identical to or different from each other, A represents an organic group containing a cyclic structure, and x is an integer of 1 to 20, y an integer of 0 to 10 and z an integer of 0 to 10.

3. The method according to claim 1, wherein the compound (B) contains an anion, the anion containing two or three fluorine atoms.

4. The method according to claim 1, wherein the resin (A) contains any of repeating units of general formula (3) below in an amount of 0 to 5 mol % based on all repeating units,

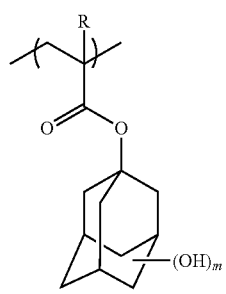

(3)

in which m is an integer of 1 to 3, and R represents a hydrogen atom or an alkyl group.

5. The method according to claim 1, wherein the resin (A) further contains a repeating unit (LC) with a lactone structure different from the lactone structures of general formula (1), or a repeating unit (SU) with a sultone structure.

6. The method according to claim 5, wherein the repeating unit (LC) contains a lactone-containing polycyclic structure, or the repeating unit (SU) contains a sultone-containing polycyclic structure.

7. The method according to claim 1, wherein the resin (A) further contains any of repeating units of general formula (aI) below,

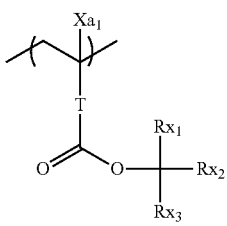

(aI)

in which $Xa_1$ represents a hydrogen atom, an alkyl group, a cyano group or a halogen atom, T represents a single bond or a bivalent connecting group, and each of $Rx_1$ to $Rx_3$ independently represents an alkyl group or a cycloalkyl group, provided that two of $Rx_1$ to $Rx_3$ may be bonded to each other to thereby form a cyclic structure.

8. The method according to claim 7, wherein any of repeating units of general formula (aI) is contained in an amount of 30 to 80 mol % based on all repeating units constituting the resin (A).

9. The method according to claim 7, wherein any of repeating units of general formula (aI) is contained in an amount of 50 to 70 mol % based on all repeating units constituting the resin (A).

10. The method according to claim 1, wherein the resin (A) contains no repeating units containing a hydroxyl group.

11. The method according to claim 1, wherein resin (A) contains, as the repeating unit containing an acid-decomposable group, any of repeating units of general formula (aII) below and a repeating unit (aIII) containing an acid-decomposable moiety containing a polycyclic structure, which the acid-decomposable moiety has 10 to 20 carbon atoms,

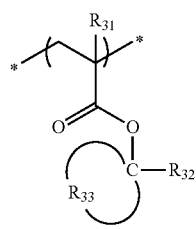

(aII)

in which $R_{31}$ represents a hydrogen atom or an alkyl group, $R_{32}$ represents a methyl group, an ethyl group, an n-propyl group, an isopropyl group, an n-butyl group, an isobutyl group or a sec-butyl group, and $R_{33}$ represents an atomic group required for forming a monoalicyclic hydrocarbon structure in cooperation with the carbon atom to which $R_{32}$ is bonded, provided that in the alicyclic hydrocarbon structure, the carbon atoms constructing the ring may partially be replaced by a heteroatom or a group containing a heteroatom, and that the sum of carbon atoms in $R_{32}$ and $R_{33}$ is up to 8.

* * * * *